(12) United States Patent
Triendl et al.

(10) Patent No.: US 12,211,592 B2
(45) Date of Patent: Jan. 28, 2025

(54) MACHINE LEARNING BASED METHODS OF ANALYSING DRUG-LIKE MOLECULES

(71) Applicant: KUANO LTD., London (GB)

(72) Inventors: Hagen Triendl, London (GB); Matthias Bal, London (GB); Jarvist Moore Frost, London (GB); Lawrence Phillips, London (GB); Agisilaos Chantzis, London (GB); Graham Simpson, London (GB); Vic Stojevic, London (GB); Noor Shaker, London (GB); Michael Craig, London (GB); Usman Bashir, London (GB); Mariana Assmann, London (GB)

(73) Assignee: KUANO LTD., London (GB)

( * ) Notice: Subject to any disclaimer, the term of this patent is extended or adjusted under 35 U.S.C. 154(b) by 889 days.

(21) Appl. No.: 17/606,960

(22) PCT Filed: Jul. 17, 2019

(86) PCT No.: PCT/GB2019/052000
§ 371 (c)(1),
(2) Date: Oct. 27, 2021

(87) PCT Pub. No.: WO2020/016579
PCT Pub. Date: Jan. 23, 2020

(65) Prior Publication Data
US 2022/0383992 A1  Dec. 1, 2022

(30) Foreign Application Priority Data

| Jul. 17, 2018 | (GB) | 1811656 |
| Oct. 19, 2018 | (GB) | 1817045 |
| Oct. 29, 2018 | (GB) | 1817646 |
| Nov. 7, 2018 | (GB) | 1818154 |
| Mar. 22, 2019 | (GB) | 1903945 |

(Continued)

(51) Int. Cl.
*G16C 20/70* (2019.01)
*G06N 3/02* (2006.01)
(Continued)

(52) U.S. Cl.
CPC ............ *G16C 20/70* (2019.02); *G06N 3/02* (2013.01); *G06N 10/20* (2022.01); *G16C 20/50* (2019.02)

(58) Field of Classification Search
None
See application file for complete search history.

(56) References Cited

U.S. PATENT DOCUMENTS

2021/0081804 A1* 3/2021 Stojevic ................. G16B 5/20

FOREIGN PATENT DOCUMENTS

| WO | WO-2012177108 A2 * | 12/2012 | ............... G06N 3/12 |
| WO | 2018220368 A1 | 12/2018 | |

OTHER PUBLICATIONS

WO2012177108A2 translation (Year: 2012).*
(Continued)

*Primary Examiner* — Lina Cordero
(74) *Attorney, Agent, or Firm* — Saul Ewing LLP

(57) ABSTRACT

There is provided a method for a machine learning based method of analysing drug-like molecules by representing the molecular quantum states of each drug-like molecule as a quantum graph, and then feeding that quantum graph as an input to a machine learning system.

27 Claims, 88 Drawing Sheets

(30) Foreign Application Priority Data

Mar. 22, 2019 (GB) .................................... 1903995
Apr. 26, 2019 (GB) .................................... 1905870

(51) Int. Cl.
*G06N 10/20* (2022.01)
*G16C 20/50* (2019.01)

(56) References Cited

OTHER PUBLICATIONS

Grégoire Montavon et al 2013 New J. Phys. 15 095003 (Year: 2013).*

Chen, Hongming, et al., "The rise of deep learning in drug discovery," Drug Discovery Today, vol. 23, No. 6, pp. 1241-1250 (Jan. 31, 2018) XP055994738.

Gilmer, Justin, et al., "Neural Message Passing for Quantum Chemistry," retrieved from the Internet: URL:https://arxiv.org/pdf/1704.01212.pdf; (Apr. 4, 2017) XP055700744.

Matta, Cherif, "Modeling biophysical and biological properties from the characteristics of the molecular electron density, electon localization and delocalization matrices, and the electrostatic potential," J. Computational Chemistry, vol. 35, No. 16, pp. 1165-1198, Jun. 15, 2014.

Mayr, Andreas, et al., "Large-scale comparison of machine learning methods for drug target prediction on ChEMBL," Chemical Science, vol. 9, No. 24, pp. 5441-5451 (Jan. 1, 2018) XP055699857.

Wu, Zhenquin, et al., "MoleculeNet: a benchmark for molecular machine learning," Chemical Science, vol. 0, No. 2. pp. 513-530 (Jan. 1, 2018) XP055699866.

* cited by examiner

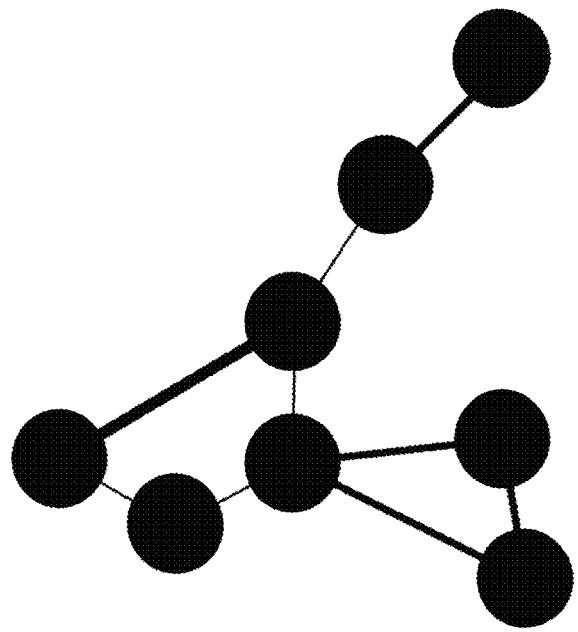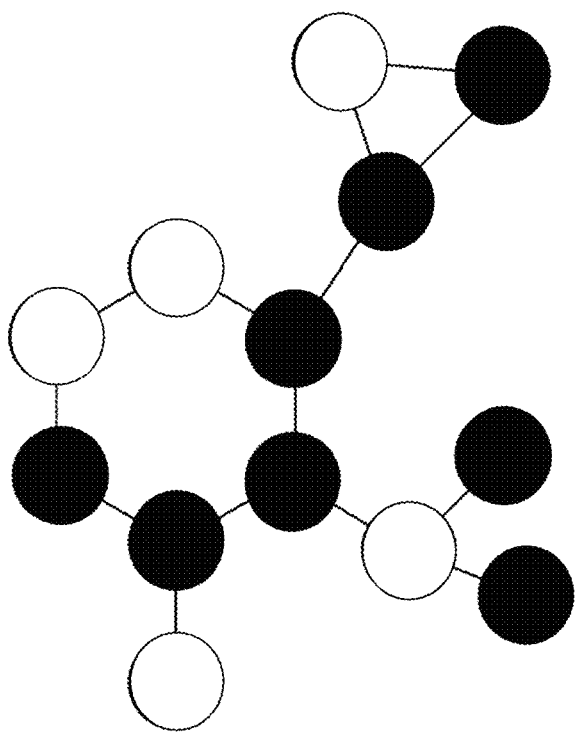
FIGURE 4

| Model | RMSE results on | | | ROC-AUC results on | |
|---|---|---|---|---|---|
| | ESOL | Lipophilicity | BBBP | HIV |
| RF | 1.07 ± 0.19 | 0.876 ± 0.040 | 0.714 ± 0.000 | 0.698 ± 0.037 |
| Multitask | 1.12 ± 0.15 | 0.859 ± 0.013 | 0.688 ± 0.005 | 0.756 ± 0.000 |
| XGBoost | 0.912 ± 0.000[a] | 0.799 ± 0.054 | 0.696 ± 0.000 | |
| KRR | 1.53 ± 0.06 | 0.899 ± 0.043 | | |
| GC | 0.648 ± 0.019[a] | 0.655 ± 0.036 | 0.690 ± 0.009 | 0.763 ± 0.016 |
| DAG | 0.82 ± 0.08 | 0.835 ± 0.039 | | |
| Weave | 0.553 ± 0.035[a] | 0.715 ± 0.035 | 0.671 ± 0.014 | 0.703 ± 0.039 |
| MPNN | 0.58 ± 0.03 | 0.719 ± 0.031 | | |
| Logreg | | | 0.699 ± 0.002 | 0.702 ± 0.018 |
| KernelSVM | | | 0.729 ± 0.000 | 0.792 ± 0.000 |
| IRV | | | 0.700 ± 0.000 | 0.737 ± 0.000 |
| Bypass | | | 0.702 ± 0.006 | 0.693 ± 0.026 |
| Chemception (B. Goh et al., 2017c; Goh et al., 2018) | | | | 0.752 |
| Smiles2vec (B. Goh et al., 2017a) | 0.63 | | | 0.8 |
| ChemNet (B. Goh et al., 2017b) | | | | 0.8 |
| Dummy super node GC (Li et al., 2017a) | | | | 0.766 |
| Bypass | | | | |
| EAGCN (Shang et al., 2018) | | 0.61 ± 0.02 | | 0.83 ± 0.01 |
| Mol2vec (Jaeger et al., 2018) | 0.79 | | | |
| Outer RNN (Urban et al., 2018) | 0.62 | 0.64 | | |
| PotentialNet (Feinberg et al., 2018) | 0.490 ± 0.014 | | | |
| SA-BiLSTM (Zheng et al., 2019) | | | | 0.83 ± 0.02 |
| RNN encoder (Winter et al., 2019) | 0.58 | 0.62 | 0.74 | |
| NoPool | 0.410 ± 0.023 | 0.551 ± 0.010 | 0.846 ± 0.011 | 0.825 ± 0.008 |
| SimplePooling (0.9) | 0.410 ± 0.018 | 0.536 ± 0.009 | 0.839 ± 0.022 | 0.824 ± 0.014 |
| SimplePooling (0.8) | 0.417 ± 0.027 | 0.542 ± 0.013 | 0.869 ± 0.010 | 0.816 ± 0.020 |
| SimplePooling (0.7) | 0.485 ± 0.020 | 0.563 ± 0.016 | 0.859 ± 0.009 | 0.825 ± 0.015 |
| SimplePooling (0.6) | 0.413 ± 0.021 | 0.622 ± 0.030 | 0.852 ± 0.006 | 0.840 ± 0.019 |
| SimplePooling (0.5) | 0.437 ± 0.016 | 0.637 ± 0.027 | 0.851 ± 0.012 | 0.822 ± 0.019 |
| CoarseGrainPooling (0.9) | 0.420 ± 0.015 | 0.517 ± 0.005 | 0.852 ± 0.010 | 0.834 ± 0.015 |
| CoarseGrainPooling (0.8) | 0.430 ± 0.019 | 0.529 ± 0.020 | 0.853 ± 0.009 | 0.833 ± 0.009 |
| CoarseGrainPooling (0.7) | 0.472 ± 0.013 | 0.530 ± 0.005 | 0.856 ± 0.012 | 0.830 ± 0.007 |
| CoarseGrainPooling (0.6) | 0.495 ± 0.053 | 0.536 ± 0.026 | 0.838 ± 0.020 | 0.824 ± 0.026 |
| CoarseGrainPooling (0.5) | 0.412 ± 0.031 | 0.535 ± 0.009 | 0.858 ± 0.023 | 0.826 ± 0.010 |

FIGURE 5

| Dataset | Model | Keep ratio | Node Channels | Edge Channels |
|---|---|---|---|---|
| ESOL | NoPooling | | [128, 128] | [128, 128] |
| | CoarseGrainPooling | 0.9 | [128, 128] | [256, 256] |
| | | 0.8 | [128, 128] | [64, 64] |
| | | 0.7 | [512, 512, 512] | [128, 128, 128] |
| | | 0.6 | [256, 256, 256] | [128, 128, 128] |
| | | 0.5 | [128, 128] | [64, 64] |
| | SimplePooling | 0.9 | [256, 256] | [128, 128] |
| | | 0.8 | [256, 256, 256] | [256, 256, 256] |
| | | 0.7 | [128, 128, 128] | [128, 128, 128] |
| | | 0.6 | [512, 512] | [128, 128] |
| | | 0.5 | [256, 256] | [256, 256] |
| Lipophilicity | NoPooling | | [256, 256, 256] | [64, 64, 64] |
| | CoarseGrainPooling | 0.9 | [256, 256] | [128, 128] |
| | | 0.8 | [256, 256] | [64, 64] |
| | | 0.7 | [256, 256] | [64, 64] |
| | | 0.6 | [256, 256] | [256, 256] |
| | | 0.5 | [512, 512] | [64, 64] |
| | SimplePooling | 0.9 | [512, 512] | [64, 64] |
| | | 0.8 | [128, 128] | [128, 128] |
| | | 0.7 | [256, 256] | [128, 128] |
| | | 0.6 | [512, 512] | [128, 128] |
| | | 0.5 | [256, 256] | [128, 128] |
| BBBP | NoPooling | | [128, 128] | [256, 256] |
| | CoarseGrainPooling | 0.9 | [256, 256] | [256, 256] |
| | | 0.8 | [512, 512] | [256, 256] |
| | | 0.7 | [128, 128, 128] | [128, 128, 128] |
| | | 0.6 | [256, 256] | [64, 64] |
| | | 0.5 | [256, 256, 256] | [64, 64, 64] |
| | SimplePooling | 0.9 | [128, 128, 128] | [256, 256, 256] |
| | | 0.8 | [512, 512] | [128, 128] |
| | | 0.7 | [256, 256] | [64, 64] |
| | | 0.6 | [512, 512] | [256, 256] |
| | | 0.5 | [128, 128, 128] | [64, 64, 64] |
| HIV | All models | | [512, 512, 512] | [128, 128, 128] |

FIGURE 7

| pooling | Multi-task | | | Single-task |
|---|---|---|---|---|
| ratio | $R^2$ on PCE | $R^2$ on GAP | $R^2$ on HOMO | $R^2$ on PCE |
| none | 0.862 ± 0.005 | 0.967 ± 0.001 | 0.981 ± 0.000 | 0.866 ± 0.003 |
| 0.9 | 0.863 ± 0.003 | 0.966 ± 0.001 | 0.981 ± 0.000 | 0.862 ± 0.002 |
| 0.8 | 0.860 ± 0.003 | 0.966 ± 0.001 | 0.981 ± 0.001 | 0.859 ± 0.004 |
| 0.7 | 0.856 ± 0.003 | 0.964 ± 0.001 | 0.980 ± 0.001 | 0.855 ± 0.004 |
| 0.6 | 0.854 ± 0.007 | 0.962 ± 0.002 | 0.979 ± 0.001 | 0.853 ± 0.003 |
| 0.5 | 0.844 ± 0.003 | 0.955 ± 0.002 | 0.974 ± 0.001 | 0.833 ± 0.007 |
| | RMSE on PCE | RMSE on GAP | RMSE on HOMO | RMSE on PCE |
| none | 0.217 ± 0.004 | 0.177 ± 0.002 | 0.134 ± 0.001 | 0.215 ± 0.002 |
| 0.9 | 0.217 ± 0.002 | 0.180 ± 0.002 | 0.134 ± 0.001 | 0.218 ± 0.002 |
| 0.8 | 0.220 ± 0.002 | 0.179 ± 0.002 | 0.135 ± 0.003 | 0.220 ± 0.003 |
| 0.7 | 0.179 ± 0.097 | 0.148 ± 0.080 | 0.112 ± 0.060 | 0.223 ± 0.003 |
| 0.6 | 0.224 ± 0.005 | 0.190 ± 0.005 | 0.143 ± 0.004 | 0.225 ± 0.003 |
| 0.5 | 0.232 ± 0.002 | 0.208 ± 0.004 | 0.159 ± 0.003 | 0.239 ± 0.005 |

FIGURE 8

| | | | |
|---|---|---|---|
| 22008 | 6069 | 40682 | |
| 38392 | 23310 | 20171 | |
| 24753 | 36163 | 16733 | |
| 27331 | 39719 | 50555 | |
| 46756 | 32657 | 20593 | |
| 8367 | 49998 | 49719 | |

FIGURE 9

|  |  |  |
|---|---|---|
| 22098 | 6069 | 40662 |
| 38392 | 25310 | 20171 |
| 24753 | 36163 | 16733 |
| 27331 | 39719 | 50555 |
| 46756 | 32657 | 20593 |
| 8367 | 49998 | 49719 |

FIGURE 10

| 22993 | 6069 | 40682 |
|---|---|---|
| 38392 | 23310 | 20171 |
| 24753 | 36163 | 16733 |
| 27331 | 39719 | 50555 |
| 46756 | 32657 | 20593 |
| 8367 | 49998 | 49719 |

FIGURE 11

Section 4 equations and schematics $$H(\mathbf{R},\mathbf{r})\Psi(\mathbf{R},\mathbf{r}) = E(\mathbf{R})\Psi(\mathbf{R},\mathbf{r}), \quad (1)$$

$$H(\mathbf{R},\mathbf{r}) = -\frac{1}{2}\sum_{i=1}^{N}\nabla_i^2 - \frac{1}{2}\sum_{A=1}^{M}\frac{1}{M_A}\nabla_A^2 - \sum_{i=1}^{N}\sum_{A=1}^{M}\frac{Z_A}{r_{iA}} + \sum_{i=1}^{N}\sum_{j>i}^{N}\frac{1}{r_{ij}} + \sum_{A=1}^{M}\sum_{B>A}^{M}\frac{Z_A Z_B}{R_{AB}}, \quad (2)$$

$$H_{\text{elec}}(\mathbf{R},\mathbf{r})\lambda(\mathbf{R},\mathbf{r}) = E_{\text{elec}}(\mathbf{R})\lambda(\mathbf{R},\mathbf{r}) \quad (3)$$

$$H_{\text{elec}}(\mathbf{R},\mathbf{r}) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

FIGURE 12

$$\Psi(x_1, x_2, \ldots, x_N) = \frac{1}{\sqrt{N!}} \begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$\equiv |\chi_1, \chi_2, \cdots, \chi_N\rangle; \quad (6)$$

where the $\chi_i(x), \forall i \in \{1, 2, \ldots, N\}$ are a set of one-electron spin-orbital wave functions.

FIGURE 13

$$|\Psi_{CI}\rangle = C_0 \left|\substack{\rightarrow \\ \leftarrow \\ \rightarrow \\ \leftarrow \\ \rightarrow \\ \leftarrow}\right\rangle + \sum_{ia} C_i^a \left|\substack{\rightarrow^a \\ \\ \rightarrow \\ \leftarrow \\ \rightarrow_i \\ \leftarrow}\right\rangle + \sum_{ijab} C_{ij}^{ab} \left|\substack{\downarrow^b \ \uparrow^a \\ \\ \rightarrow \\ \leftarrow_i \\ \rightarrow_j \\ \leftarrow}\right\rangle + \ldots \quad (8)$$

$$|\Psi_{CI}\rangle = (1 + T_1 + T_2 + \ldots)|\Psi_{HF}\rangle. \quad (9)$$

$$|\Psi_{CC}\rangle = e^{T_1 + T_2 + \ldots}|\Psi_{HF}\rangle \quad (10)$$

FIGURE 15

$$\rho = |\Psi(x_1, x_2, \ldots, x_N)\rangle \langle \Psi(x_1, x_2, \ldots, x_N)|, \quad (11)$$

$$\rho^{(1)}(x_1, x_1') = N \int \Psi^*(x_1', x_2, \ldots, x_N) \Psi(x_1, x_2, \ldots, x_N) \, dx_2 \ldots dx_N. \quad (12)$$

$$\rho^{(1)}(x_1) = N \int \Psi^*(x_1, x_2, \ldots, x_N) \Psi(x_1, x_2, \ldots, x_N) \, dx_2 \ldots dx_N. \quad (13)$$

$$P^{(1)}(r_1) = \int \rho^{(1)}(r_1; s_1) \, ds_1. \quad (14)$$

$$\rho^{(2)}(x_1, x_2; x_1', x_2') = N(N-1) \int \Psi^*(x_1', x_2', \ldots, x_N) \Psi(x_1, x_2, \ldots, x_N) \, dx_3 \ldots dx_N. \quad (15)$$

$$\rho^{(2)}(x_1, x_2) = N(N-1) \int \Psi^*(x_1, x_2, \ldots, x_N) \Psi(x_1, x_2, \ldots, x_N) \, dx_3 \ldots dx_N. \quad (16)$$

FIGURE 18

$$\rho^{(1)}(\mathbf{x}_1, \mathbf{x}_1') = \sum_{i,j} \rho_{ij}^{(1)} \phi_i(\mathbf{x}_1) \phi_j^*(\mathbf{x}_1'). \quad (17)$$

$$\rho^{(1)}(\mathbf{x}_1, \mathbf{x}_1') = \sum_i n_i \phi_i^{NSO}(\mathbf{x}_1) \phi_j^{*NSO}(\mathbf{x}_1'). \quad (18)$$

$$P^{(1)}(\mathbf{r}_1, \mathbf{r}_1') = \sum_i n_i \phi_i^{NO}(\mathbf{r}_1) \phi_j^{*NO}(\mathbf{r}_1'). \quad (19)$$

$$\nabla \rho(\mathbf{r}) \cdot \mathbf{n}(\mathbf{r}) = 0, \quad (21)$$

FIGURE 19

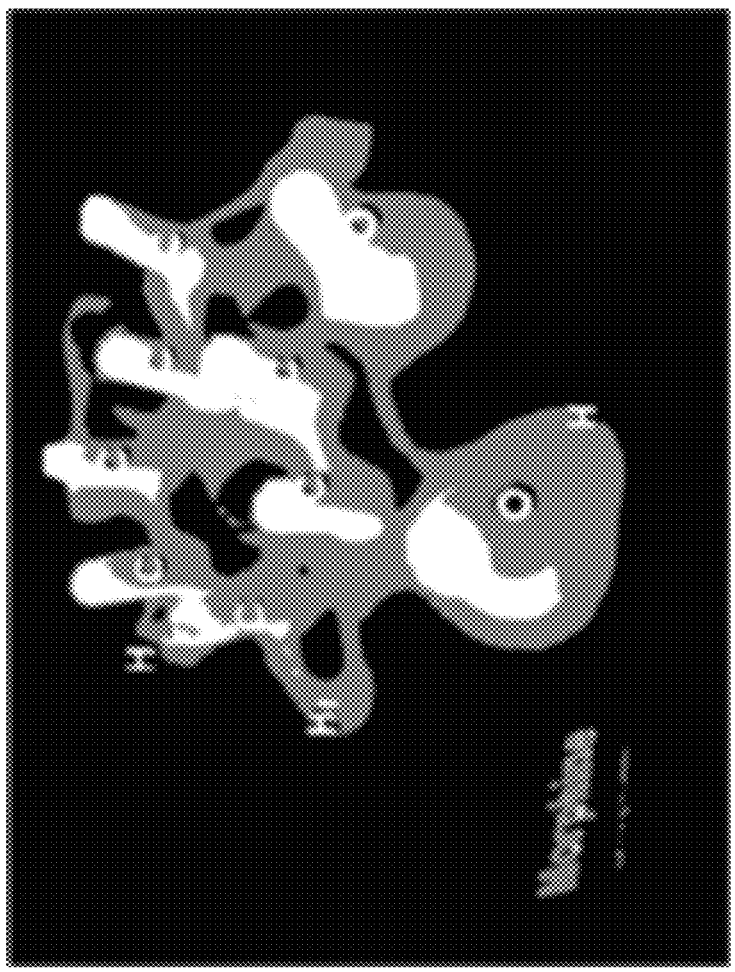
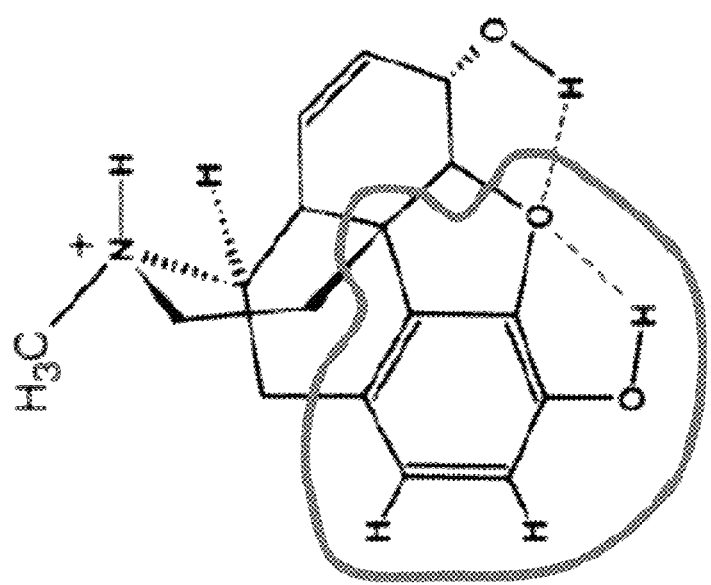
FIGURE 20

$$\rho(\mathbf{r}) = \sum_i n_i |\phi_i(\mathbf{r})|^2 = \sum_i n_i \left| \sum_j C_{j,i} \aleph_j(\mathbf{r}) \right|^2 \quad (22)$$

$$\pi(\mathbf{r}_1, \mathbf{r}_2) = N(N-1) \int \int \ldots \int |\Psi(x_1, x_2, \ldots, r_N)|^2 d\sigma_1 d\sigma_2 dx_3 x_4 \ldots x_N \quad (23)$$

$$\pi^{\sigma_1 \sigma_2}(\mathbf{r}_1, \mathbf{r}_2) = \rho^{\sigma_1}(\mathbf{r}_1) \rho^{\sigma_2}(\mathbf{r}_2) + \Gamma_{XC}^{\sigma_1 \sigma_2}(\mathbf{r}_1, \mathbf{r}_2). \quad (24)$$

$$\Gamma_{XC}^{\sigma,tot}(\mathbf{r}_1, \mathbf{r}_2) = \Gamma_{XC}^{\sigma\alpha}(\mathbf{r}_1, \mathbf{r}_2) + \Gamma_{XC}^{\sigma\beta}(\mathbf{r}_1, \mathbf{r}_2). \quad (25)$$

$$\Gamma_{XC}^{\alpha,tot}(\mathbf{r}_1, \mathbf{r}_2) = \Gamma_{XC}^{\alpha\alpha}(\mathbf{r}_1, \mathbf{r}_2) = -\sum_{i \in \alpha} \sum_{i \in \alpha} \phi_i^*(\mathbf{r}_1) \phi_j^*(\mathbf{r}_2) \phi_i(\mathbf{r}_1) \phi_j(\mathbf{r}_2) \quad (26)$$

FIGURE 22

$$\Gamma_{XC}^{\alpha,tot}(\mathbf{r}_1, \mathbf{r}_2) \approx -\sum_{i \in \alpha}\sum_{j \in \alpha} \sqrt{\eta_i \eta_j}\, \phi_i^*(\mathbf{r}_1)\phi_j^*(\mathbf{r}_2)\phi_i(\mathbf{r}_1)\phi_j(\mathbf{r}_2) \quad (27)$$

$$I_{AB} = \int w_A(\mathbf{r}) w_B(\mathbf{r}) P(\mathbf{r})\, d\mathbf{r}. \quad (28)$$

$$w_A(\mathbf{r}) = 1 \quad \text{if } \mathbf{r} \in \Omega_A. \quad (29)$$
$$w_A(\mathbf{r}) = 0 \quad \text{if } \mathbf{r} \notin \Omega_A. \quad (30)$$

$$0 \leq w_A(\mathbf{r}) \leq 1, \quad \forall A \in \{1, 2, \ldots, N_{atoms}\}. \quad (31)$$
$$\sum_B w_B(\mathbf{r}) = 1. \quad (32)$$

$$S_{ij}(\Omega) = \int_\Omega d\mathbf{r}\, \phi_i(\mathbf{r})\phi_j(\mathbf{r}). \quad (33)$$

FIGURE 23

$$\epsilon = \frac{\sum_{i,j}\left(\left[\sum_A S(\Omega_A)\right]_{ij} - 1_{ij}\right)}{N_{atoms}} \quad (34)$$

$$DLI^\alpha(\Omega_A \to \Omega_B) = -\int_{\Omega_A}\int_{\Omega_B} \Gamma_{XC}^{\alpha,tot}(r_1, r_2)dr_1 dr_2 \quad (35)$$

$$DLI^\alpha(\Omega_A, \Omega_B) = DLI^\alpha(\Omega_A \to \Omega_B) + DLI^\alpha(\Omega_B \to \Omega_A) = -2\int_{\Omega_A}\int_{\Omega_B} \Gamma_{XC}^{\alpha,tot}(r_1, r_2)dr_1 dr_2 \quad (36)$$

$$LI^\alpha(\Omega_A) = -\int_{\Omega_A}\int_{\Omega_A} \Gamma_{XC}^{\alpha,tot}(r_1, r_2)dr_1 dr_2 = DLI^\alpha(\Omega_A, \Omega_A)/2. \quad (37)$$

FIGURE 24

$$N^\alpha_{\Omega_A} = \text{LI}^\alpha(\Omega_A) + \frac{1}{2}\sum_{B\neq A}\text{DLI}^\alpha(\Omega_A, \Omega_B) \quad (38)$$

$$= \text{LI}^\alpha(\Omega_A) + \sum_{B\neq A}\text{DLI}^\alpha(\Omega_A \to \Omega_B) \quad (39)$$

$$= -\int_{\Omega_A}\int \Gamma^{\alpha,\text{tot}}_{\text{XC}}(\mathbf{r}_1, \mathbf{r}_2)\mathrm{d}\mathbf{r}_1\mathrm{d}\mathbf{r}_2 = \int_{\Omega_A}\rho^\alpha(\mathbf{r})\mathrm{d}\mathbf{r} \quad (40)$$

$$\text{DLI}(\Omega_A, \Omega_B) = 2\sum_i\sum_j \sqrt{\eta_i\eta_j}\, S_{ij}(\Omega_A)S_{ij}(\Omega_B), \quad (41)$$

$$\text{LI}(\Omega_A) = \sum_i\sum_j \sqrt{\eta_k\eta_j}\, S_{ij}(\Omega_A)S_{ij}(\Omega_A), \quad (42)$$

FIGURE 25

$$S(\mathbf{r}) = \frac{1}{2(3\pi^2)^{1/3}} \frac{|\nabla \rho(\mathbf{r})|}{\rho(\mathbf{r})^{4/3}} \quad (46)$$

FIGURE 34

| | Nuclei | Bonds | Weak interaction region | Boundary of molecule |
|---|---|---|---|---|
| $\|\nabla\rho(r)\|$ | Large | 0 - Minor | 0 - Small | Very small - Small |
| $\rho(r)$ | Large | Medium | Small | 0 - Small |
| RDG(r) | Medium | 0 - Minor | 0 - Medium | Medium - Very large |

FIGURE 35

$$\rho(\mathbf{r}) = \sum_a \rho_a^{\text{free}}(\mathbf{r} - \mathbf{R}_a) \quad (50)$$

$$V(\mathbf{r}) = \sum_a \frac{Z_a}{|\mathbf{r} - \mathbf{R}_a|} - \int d\mathbf{r}' \frac{\rho(\mathbf{r})}{|\mathbf{r} - \mathbf{r}'|} \quad (51)$$

FIGURE 39

$$|\Psi_{CAS-CI}\rangle = \sum_{n_1,\ldots,n_L} C_{n_1,\ldots,n_L} |n_1 n_2 \ldots n_L\rangle, \quad (52)$$

FIGURE 43

$$\epsilon = |||\Psi\rangle - |\tilde{\Psi}\rangle||^2 = 1 - \sum_{\alpha=1}^{D} w_\alpha, \quad (53)$$

FIGURE 45

$$S_i = -\sum_{\alpha=1}^{4} w_{\alpha,i} \ln w_{\alpha,i}, \quad (54)$$

$$S_{ij} = -\sum_{\alpha=1}^{16} w_{\alpha,ij} \ln w_{\alpha,ij}, \quad (55)$$

$$I_{ij} = \frac{1}{2}(S_i + S_j - S_{ij})(1 - \delta_{ij}). \quad (56)$$

FIGURE 47

| Training set size (#samples) | 20 | 40 | 80 | 160 |
|---|---|---|---|---|
| Edge Complex | 0.377±0.07 | 0.447±0.049 | 0.523±0.035 | 0.589±0.02 |
| Edge Ligand Based | 0.172±0.36 | 0.431±0.032 | 0.531±0.026 | 0.58±0.029 |
| Edge Ligand Only (scatter max) | 0.36±0.05 | 0.436±0.067 | 0.526±0.029 | 0.599±0.023 |
| Pocket Attention Pair Message | -0.094±0.417 | 0.205±0.135 | 0.451±0.068 | 0.526±0.044 |
| Pocket Gating Pair Message | 0.351±0.078 | 0.433±0.059 | 0.509±0.037 | 0.595±0.034 |
| Edge Ensemble Ligand Only (10 poses per eg) | 0.29±0.14 | 0.36±0.08 | 0.47±0.04 | 0.5±0.04 |
| Edge Ensemble Ligand Only (2 poses per eg) | 0.39±0.06 | 0.44±0.06 | 0.53±0.03 | 0.57±0.02 |
| Edge Ensemble Pocket (2 poses per eg) | 0.13±0.18 | 0.32±0.07 | 0.43±0.05 | 0.54±0.05 |

FIGURE 65

| Client Split | 20 | 40 | 80 | 160 |
|---|---|---|---|---|
| Ege Ligand Based | 0.036±0.152 | 0.161±0.165 | 0.419±0.059 | 0.494±0.017 |
| Edge Ligand Only | 0.195±0.118 | 0.29±0.172 | 0.407±0.033 | 0.521±0.024 |
| Pair Message Complex | -1.16±1.28 | 0.248±0.183 | 0.432±0.065 | 0.486±0.049 |
| Pocket Attention Pair Message | -0.532±0.566 | 0.009±0.174 | 0.271±0.104 | 0.384±0.039 |
| Pocket Gating Pair Message | -25.25±6.55 | -6.81±3.40 | 0.006±0.269 | 0.451±0.052 |
| Edge Ensemble Ligand Only (10 poses per eg) | 0.13±0.288 | 0.22±0.11 | 0.29±0.07 | 0.32±0.03 |
| Edge Ensemble Ligand Only (2 poses per eg) | 0.21±0.34 | 0.37±0.077 | 0.45±0.074 | 0.50±0.02 |

FIGURE 73

| Training set size (#samples) | 20 | 40 | 80 | 160 |
|---|---|---|---|---|
| Edge Ligand Only (scatter max) | 0.36±0.05 | 0.436±0.067 | 0.526±0.029 | 0.599±0.023 |
| Edge Ensemble Ligand Only (2 poses per eg) | 0.39±0.06 | 0.44±0.06 | 0.53±0.03 | 0.57±0.02 |

FIGURE 82

```
from sklearn.metrics import r2_score, mean_squared_error,
mean_absolute_error
from rdkit import Chem
from rdkit.Chem import Descriptors
from GTN.utils.misc import parse_smiles_csv csv_path = '/home/mcbal/gtn_data/ligand-based/log_P/logp_avdeef.csv'
raw_data = parse_smiles_csv(csv_path, target_fields='target')

gts, preds = [], []
for k, v in raw_data.items():
    mol = Chem.MolFromSmiles(v['smiles'])
    if mol is not None:
        gts.append(v['target'])
        preds.append(Descriptors.MolLogP(Chem.MolFromSmiles(v['smiles'])))

metrics = {}
metrics['r2'] = r2_score(gts, preds, multioutput='raw_values')
metrics['mse'] = mean_squared_error(gts, preds,
multioutput='raw_values')
metrics['mae'] = mean_absolute_error(gts, preds,
multioutput='raw_values')
print(metrics)
```

FIGURE 84

```
import os
import json
import glob
from math import sqrt root_path = '/home/mcbal/Desktop/logp_train_eval_other/'
datasets = ['logp_avdeef', 'logp_martel']
results = {d: {} for d in datasets} glob_pattern = os.path.join(root_path,
'**/other_dataset_results.json')
for filename in glob.iglob(glob_pattern, recursive=True):
    model_id =
os.path.basename(os.path.dirname(os.path.dirname(filename)))
    sub_results = json.load(open(filename))
    for d in sub_results.keys():  # loop over datasets
        prevshit = results[d].get(model_id, [])
        prevshit.append(float(sub_results[d]['results']['mse']))
        results[d].update({model_id: prevshit})

for d in results.keys():  # loop over datasets
    for m in results[d].keys():  # loop over models
        results[d][m] = sqrt(sum(results[d][m]) /
float(len(results[d][m])))
print(results)
```

FIGURE 85

| Developability Property | Pharma interest | Experiment | Models | Data-sets |
|---|---|---|---|---|
| Melting point | Medium - Relating to solubility | Relatively cheap experiment but need pure material | predictors poor - RMSE 30degC | Lots in public |
| Solubility | High - critical for ADME | Cheap experiment but lots of flavours need pure material | poor predictors, complex thermodynamic, kinetic | Lots in public |
| Lipophilicity (logP, logD) | High - critical for ADME | Experiment - cheap using HPLC columns | good predictors | Lots in public |
| pKa | High- critical for PK | Experiment - requires a fair amount of material | poor predictors for accurate prediction | Fewer accurate measured |
| permeability | High - critical for ADME | Experiment - cheap for simple but more complex expensive e.g. BBBP | good predictors for simple AMP, poor for BBBP | Some datasets, need some proprietary e.g. ATOM |
| mutagenicity/ carcinogenicity | Medium - important but generally later stage | Expensive Ames experiment but later stage | reasonable predictors but later stage so most compounds tested; complex problem | Lots |
| IR/NMR spectra predictions | Low - mainly for characterisation, identity, purity during synthesis | Cheap Experiment, | good predictors | lots |
| Metabolic | High - critical in all | Expensive In vitro/In vivo | Some predictors but very | Not comprehensive |

FIGURE 86

MACHINE LEARNING BASED METHODS OF ANALYSING DRUG-LIKE MOLECULES

CROSS REFERENCE TO RELATED APPLICATIONS

This application claims the priority of International Application No. PCT/GB2019/052000, filed on Jul. 17, 2019, which claims priority to GB Applications Nos. 1811656.6, filed Jul. 17, 2018; 1817045.6, filed Oct. 19, 2018; 1817646.1, filed Oct. 29, 2018; 1818154.5, filed Nov. 7, 2018; 1903945.2, filed Mar. 22, 2019; 1903995.7, filed Mar. 22, 2019; and 1905870.0, filed Apr. 26, 2019, the entire contents of which are fully incorporated herein by reference.

BACKGROUND OF THE INVENTION

1. Field of the Invention

The field of the invention relates to machine learning based methods of analysing drug-like molecules and of modelling a thermodynamic ensemble or representation of a drug-like molecule.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Background of the Invention

Traditional approaches to in saw drug discovery have been hampered by incomplete and inaccurate representations of molecules, leading to poorly performing predictive models of efficacy and safety and inability to fully probe all of the drug-like chemical space.

Discovery of small molecule drugs continues to be the life-blood of the pharmaceutical industry, despite challenge from biopharmaceutical and more recently, cell-based medicines. However, increasing costs due to extended timelines and higher rates of failure/attrition; decreasing profitability due to smaller, more stratified patient populations; and fewer well-validated drug targets to impact diseases which have an unmet need, threaten the industry's sustainability. As legacy approaches to discovering new drugs are drying-up, so-called "Eroom's Law" is observed: a staggering drop in R&D drug development efficiencies by a factor of one half every nine years.

The drug discovery process takes around 15 years and it costs $2.9 Bn to take a drug from conception to market. The process involved in identifying a suitable clinical candidate with a balanced safety profile is experimental in nature and fraught with failure for a variety of reasons, with the likelihood of approval for molecules entering Phase 1 clinical trials and progressing to market is only 10.4% (M. Hay, D. W. Thomas, J. L. Craighead, C. Economides, J. Rosenthal, Nature Biotechnology, 32, pages 40-51 (2014)). This means that the costs of these failures need to be absorbed in the total cost of the successful medicines. New approaches to dramatically reduce the timelines and costs are needed right across the industry.

1. The search problem: There are an estimated $10^{60}$ possible small drug-like molecules. A brute force search through this astronomically large space is not feasible and traditional methods are not capable of efficiently sampling and exploring drug-like space. Moreover, any successful drug needs to satisfy a large number of desirable properties (low toxicity, high binding affinity to the target protein, solubility, etc.), and the challenge of simultaneously satisfying these significantly compounds the search problem.

2. The representation problem: An accurate simulation of small molecule drugs, in particular of their physchem properties as well as the processes central to determining a drug's efficacy and safety, such as binding to target and off-target proteins, requires both an understanding of the conformation relevant to the process, as well as a sufficiently fine grained quantum mechanical description of the system. Adequately representing the ensemble of conformers is a complex problem, and obtaining accurate representations can incur exponential computational costs for particularly challenging conformations, due to fundamental limitations of classical computers.

Latter stages of the drug discovery process require an understanding of biology at cellular scales and beyond, and computational methods are thus faces with the problem of large scale complexity in addition to the representation problem. A comprehensive solution would require a deeper computational and theoretical grasp of incredibly complex emergent phenomena, a prospect that is currently far from feasible. Current computational approaches are crude at best and have limited applicability, and thus latter stages of drug discovery remain experimentally driven.

All stages of drug discovery, but most significantly hit-to-lead and lead optimization, are further impacted by the search problem—the challenge of identifying novel candidate drugs from the astronomically large space of possible candidates.

Current machine learning approaches often used SMILES (Simplified Molecular Input Line Entry System) representation of molecules, which encode molecule structures using text data, as input data.

Over the last few years, using chemical graph representation of molecules as input to machine learning models has also been popular, where molecules are represented as graph. In the simplest form of the graph representation, nodes encode atom, and edges encode chemical bond types (such as single bond, double bond etc), respectively. More generally, any desired per atom and per node features can be included. However, standard chemical graphs are 19th century constructs, which while amazingly useful, are not quantitatively correct, and the division of chemical bonds into single, double, aromatic, is only a rough approximation of reality.

The present invention addresses the above vulnerabilities and also other problems not described above.

Reference may also be made to GB1811656.6, GB1817045.6, GB1817646.1, GB1818154.5, GB1903945.2, GB1903995.7 and GB1905870.0, the contents of which are hereby incorporated by reference.

SUMMARY OF THE INVENTION

The invention is a machine learning based method of analysing drug-like molecules by representing the molecular quantum states of each drug-like molecule as a quantum graph, and then feeding that quantum graph as an input to a machine learning system.

Optional features in an implementation of the invention include any one or more of the following:

A quantum graph or Q-graph is a molecular graph representation of a drug-like molecule obtained from quantum mechanical calculations.

A quantum graph is a molecular graph representation in which each node corresponds to an orbital and the edges correspond to a type of quantum correlation between these orbitals.

A quantum graph depends on the conformational state of a drug-like molecule.

Quantum graphs for multiple conformational states or thermodynamic ensemble for each drug-like molecule are fed as an input to the machine learning system.

For every conformational state of a drug-like molecule, a different Q-graph is created.

For every conformational state in a thermodynamic ensemble of a drug-like molecule, a different Q-graph is created.

Different quantum graphs can be combined, such as concatenated, or averaged over, in order to obtain a more expressive object that is fed into the machine learning system.

A quantum graph represents conformations of ligands and protein pockets, and the machine learning system determines a specific property such as binding affinity binding affinity, lipophilicity, thermodynamic solubility, kinetic solubility, melting point or pKA, in order to identify candidate, small drug like molecules.

The identified candidate, small drug like molecules are input to a machine learning platform that optimizes the selection of candidates across multiple parameters.

The machine learning system is supervised, semi-supervised or unsupervised.

the machine learning system is specifically a supervised system where the input consists of a set of Q-graph objects obtained from an ensemble of conformations of ligand in solution, ensemble of ligand in the protein pocket, where both pocket and ligand are represented as a large graph.

The large graph includes water molecules and/or other residues.

The machine learning system is one or more of the following: generative model, generative adversial network, GAN on graph data, autoencoder, RNN, monte carlo tree search model, ising model, restricted Boltzmann machine trained in an unserpervised manner, graph model, graph to graph autoencoder.

A training dataset made up of multiple quantum graphs is used.

Another aspect of the invention is a machine learning based method of modelling a thermodynamic ensemble or representation of a drug-like molecule, in which a sample of a thermodynamic ensemble or representation is synthetically generated and inputted into a machine learning system, the thermodynamic ensemble or representation being a molecular orbital representation or quantum graph representation of the drug-like molecule.

Optional features in an implementation of the invention include any one or more of the following:

every element of the thermodynamic ensemble can be represented as a quantum graph or tensor network, or molecular orbital representation.

a quantum graph is a molecular graph representation of a molecule obtained from quantum mechanical calculations.

a quantum graph is a molecular graph representation in which each node corresponds to a molecular orbital and the edges correspond to a type of quantum correlation between these orbitals.

a quantum graph depends on the conformational state of a molecule.

Molecular orbital representation is a tensor network representation of molecular quantum states of a drug like molecule.

the synthetic generation of one or more samples of thermodynamic ensembles or representations is based on a thermodynamic quantity.

the machine learning system is configured to output a thermodynamic quantity based on an approximate expectation value over the entire or a representative set of the modelled thermodynamic ensemble or representation.

the machine learning system is configured to learn the distribution of Boltzmann weights of the entire or a representative set of the thermodynamic ensemble or representation of the molecule.

determining the cost function or backpropagation of the machine learning system is based on a thermodynamic quantity to be outputted by the system.

the size of the synthetically generated sample of the thermodynamic ensemble or representation is tuned depending on a downstream application.

the machine learning system is a graph convolutional neural network.

the generated sample of thermodynamic ensemble or representation is inputted as a molecular graph such as a quantum graph.

the machine learning system is configured to output any quantity that is a function of a thermodynamic ensemble or representation, such as binding affinity, lipophilicity, thermodynamic solubility, kinetic solubility, melting point or protonation.

the machine learning system is used to predict ligand protein binding affinity, and in which synthetically generated samples of the thermodynamic ensemble or representation of the ligand in solution, of the protein in solution, and of the ligand-protein complex are inputted into the machine learning system.

the machine learning system is used to predict ligand protein inhibition concentration, and in which synthetically generated samples of the thermodynamic ensemble or representation of the ligand in solution and of the ligand-protein complex are inputted into the machine learning system.

the machine learning system is used to predict lipophilicity of a drug-like molecule, and in which synthetically generated samples of the thermodynamic ensemble or representation of the unionized and/or ionized state of the molecule in octanol, and in water are inputted into the machine learning system.

the machine learning system is used to predict thermodynamic solubility of the drug-like molecule, and in which synthetically generated samples of the thermodynamic ensemble or representation of the solid state of the molecule and of the dissolved state of the molecule are inputted into the machine learning.

the machine learning system is used to predict kinetic solubility of the drug-like molecule, and in which synthetically generated samples of the thermodynamic ensemble or representation of the amorphous solid state of the molecule and of the dissolved state of the molecule are inputted into the machine learning.

the machine learning system is used to predict melting point of the drug-like molecule, and in which synthetically generated samples of the thermodynamic ensemble or representation of the solid state of the molecule and of the molecule in octanol are inputted into the machine learning.

the machine learning system is used to predict pKa of the drug-like molecule and in which synthetically generated samples of the thermodynamic ensemble or representation of the small drug-like molecule in the appropriate environment, such as water or pocket on a target protein, are inputted into the machine learning.

the machine learning system uses GAN or VAE, or GCPN style models.

the machine learning system uses generative models to learn new thermodynamic ensemble or thermodynamic ensemble for which data is not available.

the machine learning system implements weight sharing method when multiple generated samples of thermodynamic ensembles or representations are inputted into the machine learning system.

docking is used to generate the sample of thermodynamic ensemble or representation.

docking enhanced by molecular dynamics is used to generate the sample of thermodynamic ensemble or representation.

Another aspect of the invention is a graph-based machine learning method of predicting chemical properties of a molecule or class molecules in which input graphs representing molecules are fed into a graph convolutional neural network that implements graph pooling layers that have been trained for usefulness or relevance with regards to the chemical properties.

Optional features in an implementation of the invention include any one or more of the following:

the input graphs are represented with a sparse representation using node and edge feature vectors.

Edge feature vectors represent different bond types or distances between atoms.

input graphs are quantum graphs.

a quantum graph is a molecular graph representation of a drug-like molecule obtained from quantum mechanical calculations.

a quantum graph is a molecular graph representation of a molecule in which each node corresponds to a molecular orbital and the edges correspond to a type of quantum correlation between these orbitals.

a quantum graph depends on the conformational state of a molecule.

during a graph pooling step, the nodes in the input graphs are selected based on their usefulness or relevance with regards to the chemical property that is predicted.

the convolutional neural network learns which nodes needs to be selected.

during a graph pooling step, the nodes in the input graphs are selected by determining a gating for each node feature vector.

In which effective edge feature vectors between selected nodes are updated or created using a pooling algorithm.

effective edge feature vectors are updated or created based on atom features.

the pooling algorithm computes an effective edge feature vector by summing all edge feature vectors along the paths connecting pairs of selected nodes and by reducing any overlapping effective edge feature vectors.

the pooling algorithm uses multiple neural networks to compute effective edge-feature vectors.

each convolutional layer apart from the final convolutional layer is followed by a pooling layer.

a graph gathering layer is used following a pooling layer n order to map node and edge feature vectors into a global feature vector.

a dual-message graph-convolutional layer that supports both node and edge feature vectors is implemented.

an input graph representing a molecule encodes any chemical properties of the molecule such as atom type, node degree or bond type.

the method is used to predict one or more of the following: binding affinity, lipophilicity, thermodynamic solubility, kinetic solubility, melting point or pKA.

BRIEF DESCRIPTION OF THE FIGURES

Aspects of the invention will now be described, by way of example(s), with reference to the following Figures, which each show features of the invention:

FIG. 4 shows a schematic of a graph pooling step.

FIG. 5 shows a table with literature results for the MoleculeNet benchmarks comparing RMSE and ROC-AUC results, on a range of models.

FIG. 7 shows a table summarising the graph-convolutional model hyperparameters used.

FIG. 8 shows multi-task and single-task test set evaluation R2 results.

FIG. 9 shows the original molecular graphs before pooling.

FIG. 10 shows the coarse-grained graphs after pooling layer 1.

FIG. 11 shows the coarse-grained graphs after pooling layer 2.

FIG. 12 shows equations (1) to (4) of Section 4.

FIG. 13 shows equations (5) to (6) of Section 4.

FIG. 15 shows equations (8) to (10) of Section 4.

FIG. 18 shows equations (11) to (16) of Section 4.

FIG. 19 shows equations (17) to (19) and (21) of Section 4.

FIG. 20 shows a Morphine molecule (left) with relief map of electron density in the plane of the aromatic ring (right).

FIG. 22 shows equations (22) to (26).

FIG. 23 shows equations (27) to (33) of Section 4.

FIG. 24 shows equations (34) to (37) of Section 4.

FIG. 25 shows equations (38) to (42) of Section 4.

FIG. 34 shows equation (46) of Section 4.

FIG. 35 shows a table with density gradient, density, and reduced density gradient values. (from the Multiwfn manual).

FIG. 39 shows equations (50) and (51) of Section 4.

FIG. 43 reproduces equation (52) of Section 4.

FIG. 45 reproduces equation (53) of Section 4.

FIG. 47 shows equations (54)-(56) of Section 4.

FIG. 65 shows the results for the dataset size experiment on a dataset.

FIG. 73 shows another table of results for the experiment based on the client split.

FIG. 82 shows a table of results for the edge ligand only and edge ensemble ligand only experiments.

FIG. 84 shows the RD Kit baseline script.

FIG. 85 shows the filter other_dataset_results.json script.

FIG. 86 shows a table summarising pharma applications of quantum and conformational features.

DETAILED DESCRIPTION

Figure 1:
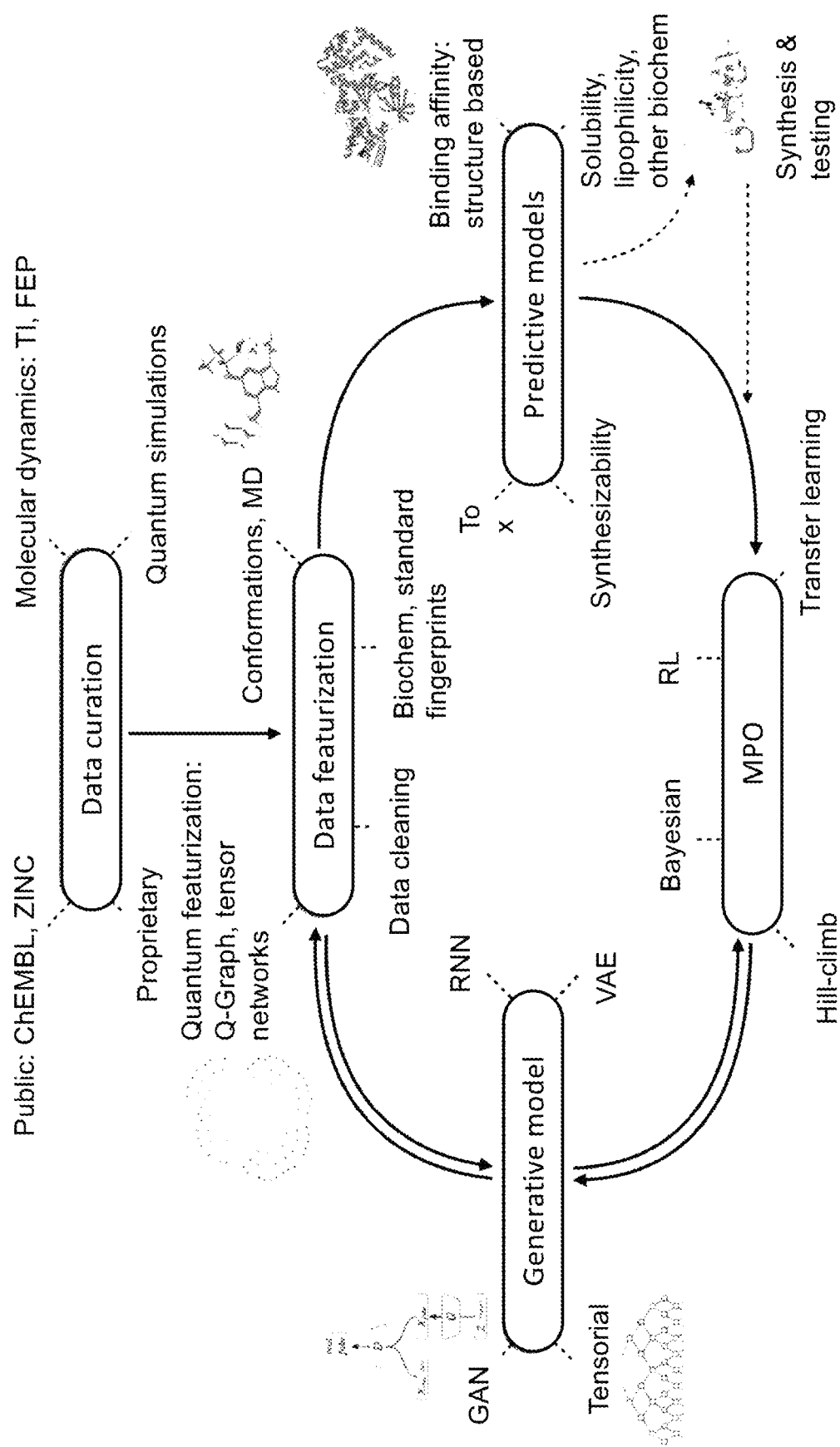
FIG. 1 shows a diagram of the GTN platform.

Key features of this invention will be described in one of the following sections and appendices:

Section 1: Overview of small molecule drug discovery
Section 2: Quantum graph
Section 3: Sparse hierarchical representation learning on molecular graphs
Section 4: Graph featurization and quantum chemistry
Section 5: Structure based model overview
Section 6: Conformations in statistical mechanics and thermodynamics of binding
Section 7: Machine learning on thermodynamic ensembles
Section 8: Conformational searching methods for machine learning
Section 9: DFTB quantum features
Appendix A: Models and modules
Appendix B: Exploring Novel IP Space: new candidates for CDK9
Appendix C: Advanced predictive models from quantum observables
Appendix D: Experiment P450 site of metabolism
Appendix E: Experiments on conformational ensemble ML Appendix F: Ligand-based models—pharma applications of quantum and conformational features
Appendix G: QTAIM code
Appendix H: Quantum mechanics and entanglement
Appendix I: Key Features Section 1: Overview of Small Molecule Drug Discovery GTN's technology is based on the premise that in order to go beyond the capabilities of current drug discovery methods, a successful approach to the search problem must also address the representation problem. Our solution is based on a multidisciplinary approach that combines advanced quantum mechanical representations of molecules and their conformational ensembles, together with state of the art machine learning, in particular, deep generative models capable of efficiently sampling chemical space. We believe that this is the key to begin reversing the negative trends that are currently holding back the drug discovery process.

Specifically, to generate truly novel molecules and to accurately predict their properties, a machine learning method needs to have the capacity to handle advanced quantum mechanical and conformational descriptions of molecules as input data, and to ultimately capture complex properties involving highly entangled quantum mechanical states. Engineering this requires designing custom methods to featurize molecular input data, as well as custom machine learning networks. The general solution is expected to be unfeasible on classical computers, requiring access to scalable quantum computers. Based on ideas from quantum physics, GTN's technology is pushing classically feasible methods to their limits, and is by design portable to quantum computers, when these become available.

Our starting point is based on current state-of-the-art machine learning approaches to molecular prediction, which utilise graph convolutional networks where molecular data is represented simply in terms of standard chemical graphs. GTN's models extend, and go beyond graph based models, and utilise descriptors based directly on the quantum wavefunctions of the molecules. The approach is inspired by a recent surge in research on the boundary between machine learning and quantum mechanics, in large part formulated using the technology of graphs and tensor networks (A tensor network provides a way of decomposing a general full rank tensor description of a quantum state into smaller 'building block').

The components of the platform are depicted in FIG. 1 in which the following acronyms are used: MPO="Multi-parameter optimization", TI="Thermodynamic integration" FEP="Free energy perturbation", MD="Molecular dynamics", RL="Reinforcement learning", RNN="Recurrent neural network", GAN="Generative adversarial network", VAE="Variational auto-encoder".

Data curation: Both generative and predictive machine learning methods are only as good as the quality of the data upon which they are trained. Our custom database combines a carefully curated selection of data from publicly available sources such as ChEMBL, ZINC, and PDB, as well as data scraped from published patents.

It is useful to make a distinction between ligand-only and structure-based data. The former contains assay or physchem property data, without reference to a target protein structure, while the latter includes information on ligand and protein conformations as well as corresponding affinity data. Moreover, molecular datasets can be used in an unsupervised learning setting, without reference to any measurements, for example when training baseline generative models, or as part of semi-supervised learning. Structure-based data is scarce as it is obtained from expensive crystallography experiments, and for this reason our database is augmented using methods such as free energy perturbation (FEP), or thermodynamic integration (TI) (R. Abel, L. Wang, E. D. Harder, B. J. Berne and R. A. Friesner Accounts of Chemical Research, 50, 1625 (2017), 2. Z. Cournia, B. Allen and W. Sherman Journal of Chemical Information and Modeling, 57, 2911 (2017), 3. S. Wan, A. P. Bhati, S. J. Zasada, I. Wall, D. Green, P. Bamborough and P. V. Coveney Journal of Chemical Theory and Computation, 13, 784 (2017)), which are capable of generating binding affinities and poses of closely related ligands, provided an experimentally obtained starting point.

Figure 2:
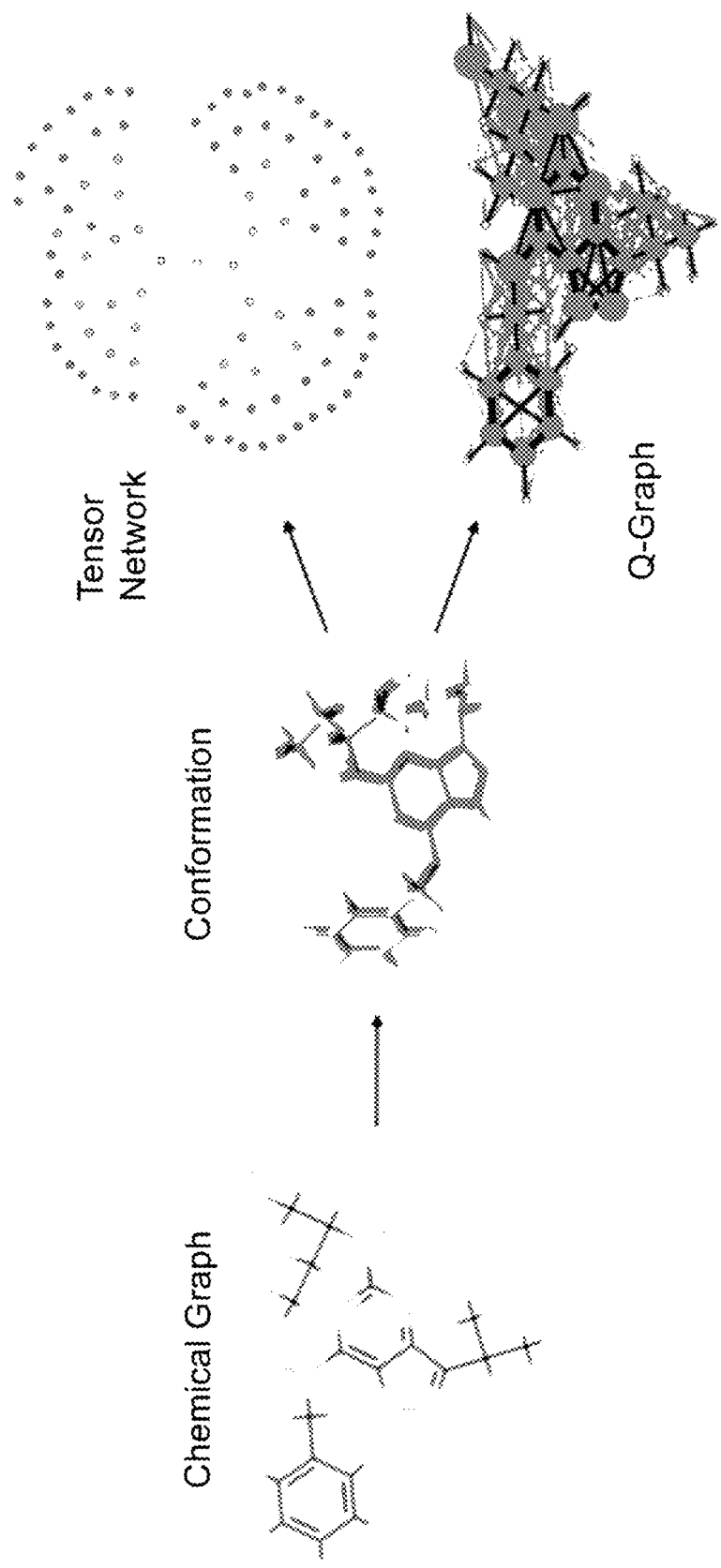
FIG. 2 shows the conformation of small molecule 404 in pocket of PDB 3pj8 structure.

Data featurization: The module contains a large number of components, from standard data cleaning workflows, to domain specific methods, such as algorithms for sampling conformational ensembles, and for adding hydrogens and water molecules to crystallography data. GTN's proprietary methods for conformational and quantum featurization play a central role in the pipeline. Depending on the demands of the problem, feautrization can be based on descriptors that encode simple 3D geometric information (conformation), our Q-Graph approach, or custom tensor network based methods as shown in FIG. 2. The latter two depend on sophisticated compact representations of the full quantum mechanical wavefunction, and form the core part of GTN's efforts to build the world's first database of quantum featurised molecules specifically for machine learning purposes.

FIG. 2 illustrates the conformation of small molecule 404 in pocket of PDB 3pj8 structure: molecular graph, Q-Graph, and a tree-tensor network representation of the quantum state in orbital space. The nodes of the tensor network graph represent non-local molecular orbitals rather than atomic positions.

Predictive models: Predictive models relevant for small-molecule pharmaceutical applications can be divided into two classes: ligand- and structure-based models, depending on what type of data they are trained on. Clearly, models trained using a combination of the two types of datasets is also possible.

Figure 3A:
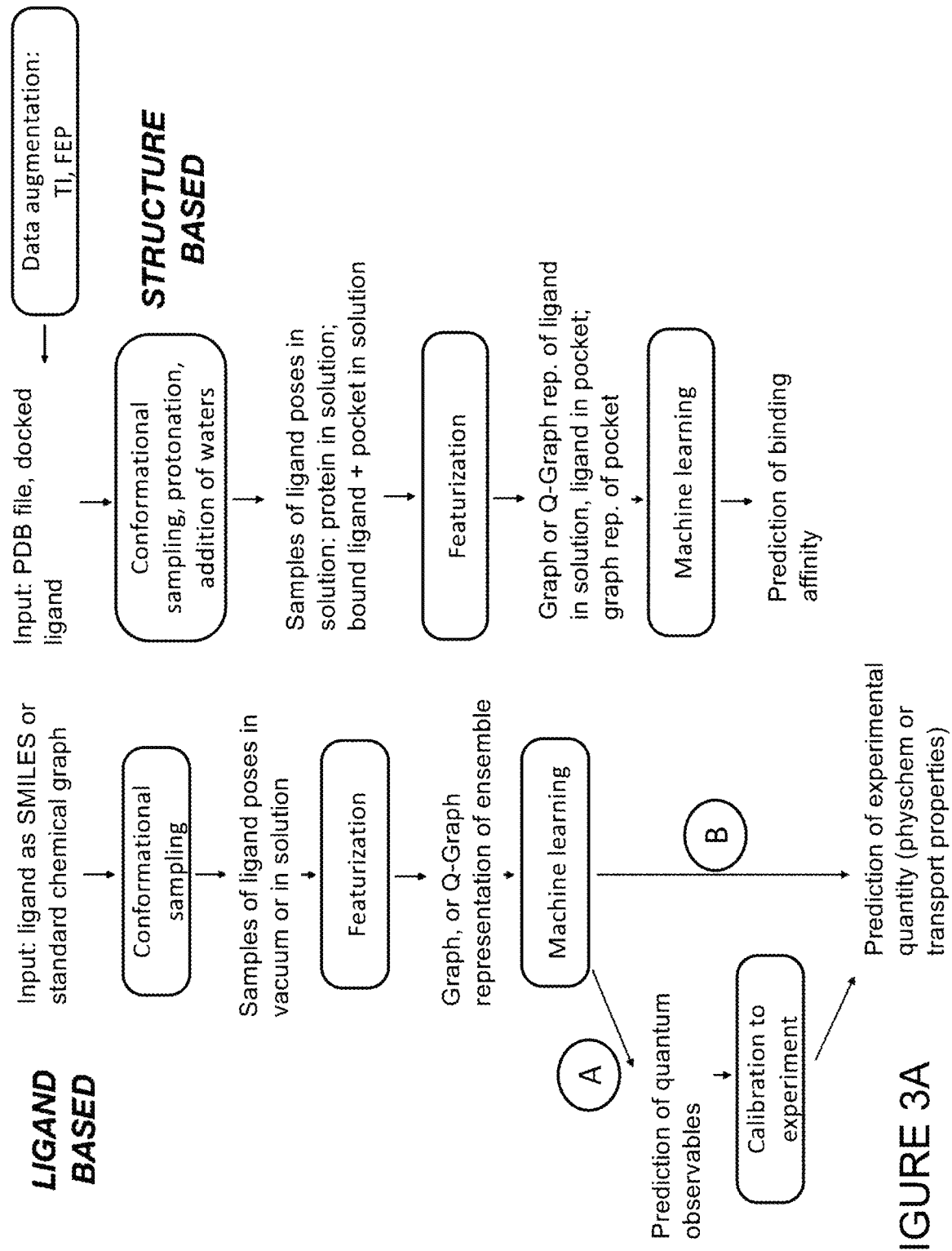
FIG. 3A shows a diagram comparing ligand based and structure based typical scenario.

FIG. 3A shows a schematic diagram depicting typical workflows for ligand-based and structure-based model side by side. Data curation, data processing, and predictive modules of the GTN Platform (FIG. 1), all feature in the two depicted workflows. Two approaches for designing ligand based models are shown. For case A) the ML algorithm first predicts a set of quantum observables, which are then correlated to the experimental quantity of interest. In B) the model is trained on experimental data directly. Structure based workflow is distinguished by the fact that, at present, binding affinities for realistic systems can not be feasibly approximated using de novo molecular dynamics or QM/MM methods. On the other hand, for a number of physchem observables it is often possible to perform de novo calculations of theoretically derived quantum mechanical observables that closely correlate to experimentally measured quantities. In pharma, this is the case for a large number of properties relevant to lead optimisation of high-quality, efficacious and safe clinical candidates (Properties relating to drug absorption (melting point [62], solubility [63], pKa [64], lipophilicity [65], permeability [66]), distribution (non-specific binding to plasma proteins and tissue [67]), metabolism (oxidative metabolism [68]), excretion (drug transporter activity [69]) and toxicity (Ames mutagenicity [70], formation of reactive metabolites [71], ADMET [72]), and there are many relevant applications in materials science (For example, photovoltaic and OLED efficiencies [42-43]). Because of this, in the context of many ligand-based models, it is natural to split the machine learning algorithm into a part that predicts a relevant QM observable, for which training data can be obtained synthetically using sophisticated and often costly QM calculations, and a part that subsequently correlates these observables with experimentally obtained data, using a supervised learning step (path A in FIG. 3A).

GTN's custom featurization based on accurate representations of conformations and quantum mechanics of the system, such as our Q-Graph approach, can benefit predictive models in an impressive manner. The capacity of Q-Graph features to predict quantum mechanical observables is demonstrated in the Quantum Observables case study, surpassing state-of-art results by a significant margin, especially in scenarios when only a small amount of data is available. Conformational and quantum featurisation is also helping us beat traditional approaches by 5-20% in prediction of physicochemical properties, toxicity measures, site of metabolism prediction, as well as binding affinity classification. In addition, we have applied multi-task models across similar targets (e.g. kinases, GPCRs), as well as transfer learning approaches, which allows for accurate predictions against targets with limited data, a common situation faced in drug discovery projects. Our structure based models are currently based on descriptors derived from a single, or a small number of, conformations, and are already beating state of the art models [41]. We are advancing these by incorporating features that utilise both quantum mechanical descriptors and information about the conformational ensembles—both for the ligand in solution, and for the ligand-protein complex.

Molecular generative models: Inspired by standard deep generative models, such as GANs, variational autoencoders [27, 32], and also graph-based generative models such as GCPN [arxiv: 1806.02473], GTN is developing generative models to incorporate conformational and quantum mechanical representations of molecules.

Deep generative models provide a means to search the intractable space of drug-like molecules, and are capable of dealing with the peculiar, high-dimensional space of chemical structures without feature engineering [31]. One can obtain a reliable model of drug-like space by training an RNN on SMILES, a linearized representation of chemical graphs [44]. In order to incorporate advanced features, GTN is starting from molecular generative models that are able to learn directly from graphs rather than from their linearized forms [45-48]. These models allow for the construction of GANs and VAEs for molecules, providing a continuous representation of drug-like space which is useful for gradient based MPO methods. We also utilise GCPN style models [arxiv:1806.02473]], which work well with reinforcement learning methods.

Multi-parameter optimization (MPO): In order to discover promising candidates, GTN's predictive and generative models are used in conjunction with a variety of optimization techniques. Candidates proposed by a generative model are scored by a set of predictive models; the scores are then fed back to the generative model which updates its behaviour such that it becomes more likely to generate interesting molecules. This general approach is highly flexible and can be leveraged for de-novo design, lead optimization, and fast-follower design, among others.

In the de-novo scenario, a generative model is trained to produce molecules that are predicted to be active, as well as having desirable DMPK and physchem properties. A combination of DMPK, physchem, and activity predictions plays the role of a reward function in a reinforcement learning setting, guiding the agent (in this case the generative model) to maximize reward by producing molecules that are predicted to fit a desired profile [50, 51]. Another successful approach is to iteratively train a generative model on a high-scoring subset of its output [44]. Finally, when obtaining predictions is computationally expensive, requiring for instance costly featurization, we make use of Bayesian optimization, which seeks to minimize the number of predictions needed to discover an optimal molecule [49]. This is performed in the latent space learned by a GAN or VAE, which will have a much lower dimensionality than molecular space, and is endowed with semantic structure which facilitates optimization [53] (A potential problem, well-known in RL but endemic to all three of the above techniques, is reward hacking [54], which we mitigate by modulating predictions using custom built Bayesian uncertainty estimates). Since these optimization procedures do not directly encourage the generative model to produce molecules that are similar to the training data, they are able to explore uncharted regions of chemical space and produce novel IP.

As well as de-novo design, the platform is capable of generating optimized proposals based on a set of known actives. By using a small set of similar molecules as fine-tuning data for transfer learning [52, 55], we arrive at models that produce countless variations on the theme described by that set. Properties of interest, such as activity against a particular target, are captured by the model and appear in the molecules that it generates. After transfer learning, the model may be refined further by using techniques similar to those leveraged for de-novo design, allowing us to produce a large number of proposals which are similar to a small initial set in terms of structure and binding, but which have enhanced physchem properties.

Quantum Inspired Machine Learning

GTN is aiming to reverse the negative trends in the hit-to-lead and lead optimisation phases of drug discovery, by building a technology uniquely capable of addressing the representation and search challenges.

Key to addressing the representation problem lies in combining data driven methods, based on machine learning, with de novo methods, which attempt to build models from first principles. De novo models attempt to deal with the representation challenge head on, the principal advantage being full control of the system under study. Unfortunately, for many problems relevant to the pharmaceutical industry the associated computational costs are prohibitively high (This is both due to the representation and large scale complexity problems, and is illustrated by the fact that one-third of the world's supercomputer time is being used for applications in chemistry and materials science [20].). Furthermore, a large class of problems is believed to be fundamentally intractable on classical computers, and it is expected that de novo methods will only be able to tackle these once scalable quantum computation becomes available. Machine learning based approaches do not suffer from such limitations, but are a lot less flexible than de novo models as they depend on experimentally available data, and can only generalize to a limited extent beyond the dataset they are trained on. In addition, machine learning methods have largely been developed for image, text, or time series data, so most available approaches are not well suited for molecular data.

Our solution to the representation problem is to combine the best of de novo and machine learning worlds, by developing advanced quantum mechanical and thermodynamic representations of molecules specifically for machine learning. Our approach is inspired by a recent surge in research on the boundary between machine learning, many-body quantum mechanics simulations, and quantum computing, in large part formulated using the technology of tensor networks.

Figure 3B:
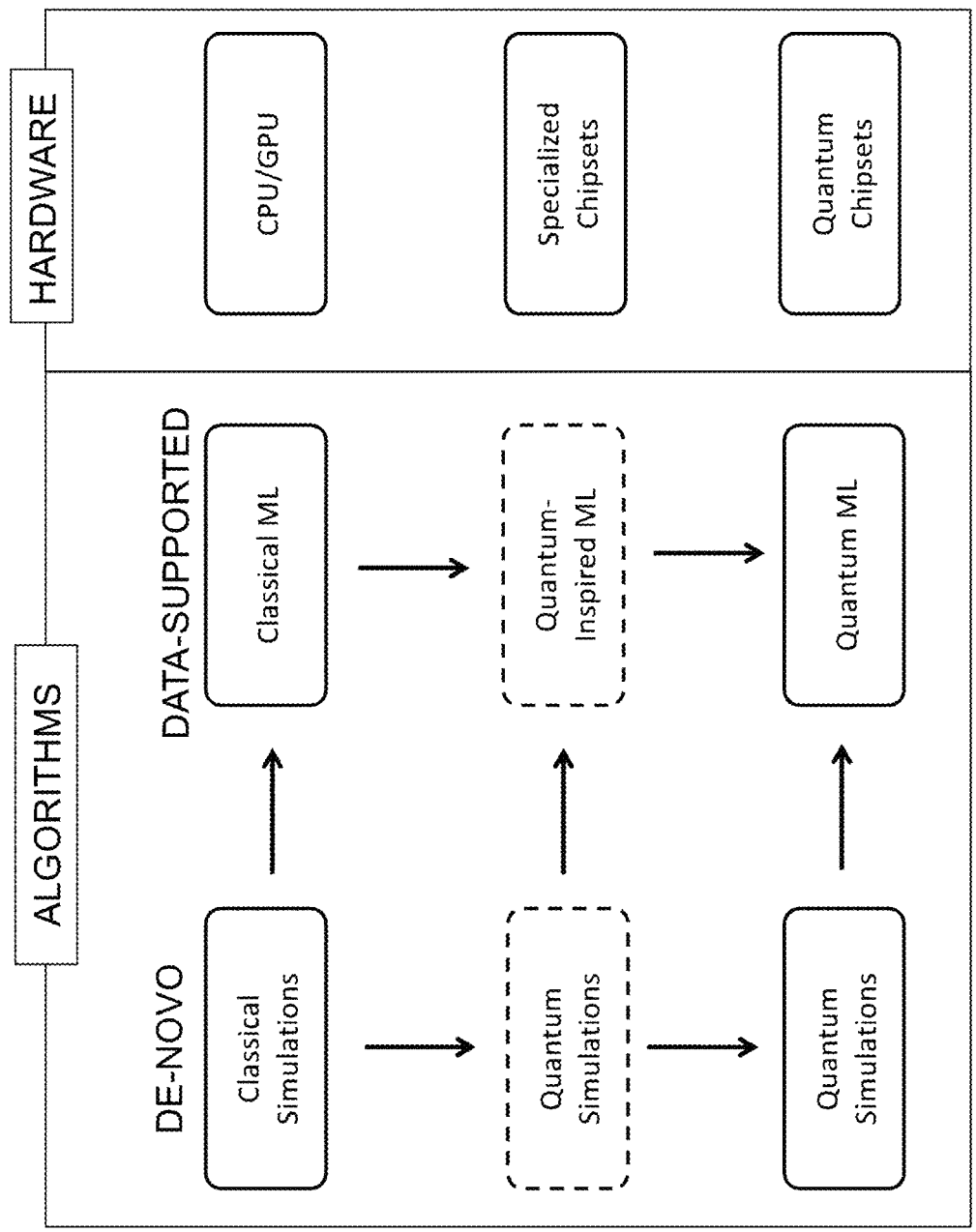
FIG. 3B shows a diagram illustrating the quantum-Inspired Machine Learning in the context of currently available classical, and future quantum-computing enabled technologies.

Our approaches are quantum computing ready—and as such will be capable of tackling the most challenging aspects of the representation problem once robust quantum computers are available at large enough scales—but are designed to run optimally on current classical hardware, and leverage the latest in modern CPU/GPU and custom chipset designs. For this reason we refer to the set of methodologies comprising our platform as Quantum-Inspired Machine Learning (QIML). The position of GTN's platform in today's machine learning, de novo, and quantum computing technology landscape is depicted in FIG. 3B. FIG. 3B shows a diagram illustrating the quantum-Inspired Machine Learning in the context of currently available classical, and future quantum-computing enabled technologies.

In addition to addressing the representation problem, our QIML technology forms a crucial component necessary to successfully tackle the two core aspects of the search problem:

Size of the search space: There are an estimated $10^{60}$ possible small drug-like molecules. A comprehensive search through this astronomically large space is not feasible, and available sampling methods are highly inefficient.

Multi-Parameter Optimisation (MPO): A high quality drug candidate needs to have optimal properties across a large number of parameters (such as binding affinity to the target protein, favorable toxicity and ADME properties); optimising over high dimensional parameter spaces is extremely challenging.

In order to efficiently sample drug-like chemical space, GTN has developed custom deep generative models for molecular data. Generative models, in general, aim to capture the statistical distribution of a certain data set by training in an unsupervised manner, in order to then generate completely novel, hitherto unseen, data samples. The capacity of deep generative models to generalise beyond the training set has been impressively demonstrated over the past few years; the advent of Generative Adversarial Networks [26, 27] in particular has opened the way to ambitious applications, enabling the generation of novel images [28], pieces of music and art [29, 30]. In order to achieve similarly impressive capabilities for small molecule drug discovery GTN is building QIML enabled generative machine learning models, that is, generative models that are custom designed to work with advanced molecular descriptors. In order to tackle the MPO challenge, we have developed reinforcement learning (RL) based optimisation methods, by building on technologies that have revolutionised difficult optimisation problems in other industries and tailoring these to our QIML based generative models.

A further challenge, which touches on both of the aspects of the search problem outlined above, is that proposed drugs need to be easily synthesizable. This can be achieved either by building predictive models for synthesis, and integrating these into the MPO methods, or by building synthesizability constraints directly into the generative models.

Positioning in the Pharma Industry: Sweet-Spot Applications

The aim of GTN's technology is to achieve two interdependent objectives 1) to develop better drugs—more potent, less toxic, and more resistant to mutations of the target protein than what the traditional discovery process is capable of yielding—and 2) to accelerate the speed and efficiency of drug discovery. These correspond to two largely independent directions that need to be pursued in order to build up the technology: 1) relies on advancing the precision of both de novo and predictive ML modelling for physicochemical properties and mechanisms of drug action, Quantum-Inspired (QI) Modelling for short; 2) is more dependent on ML Engineering, that is, the challenge of applying predictive, generative, and MPO technologies at scale and in a maximally automated manner across drug discovery projects. These two directions are brought together in our QIML Platform.

Figure 3C:
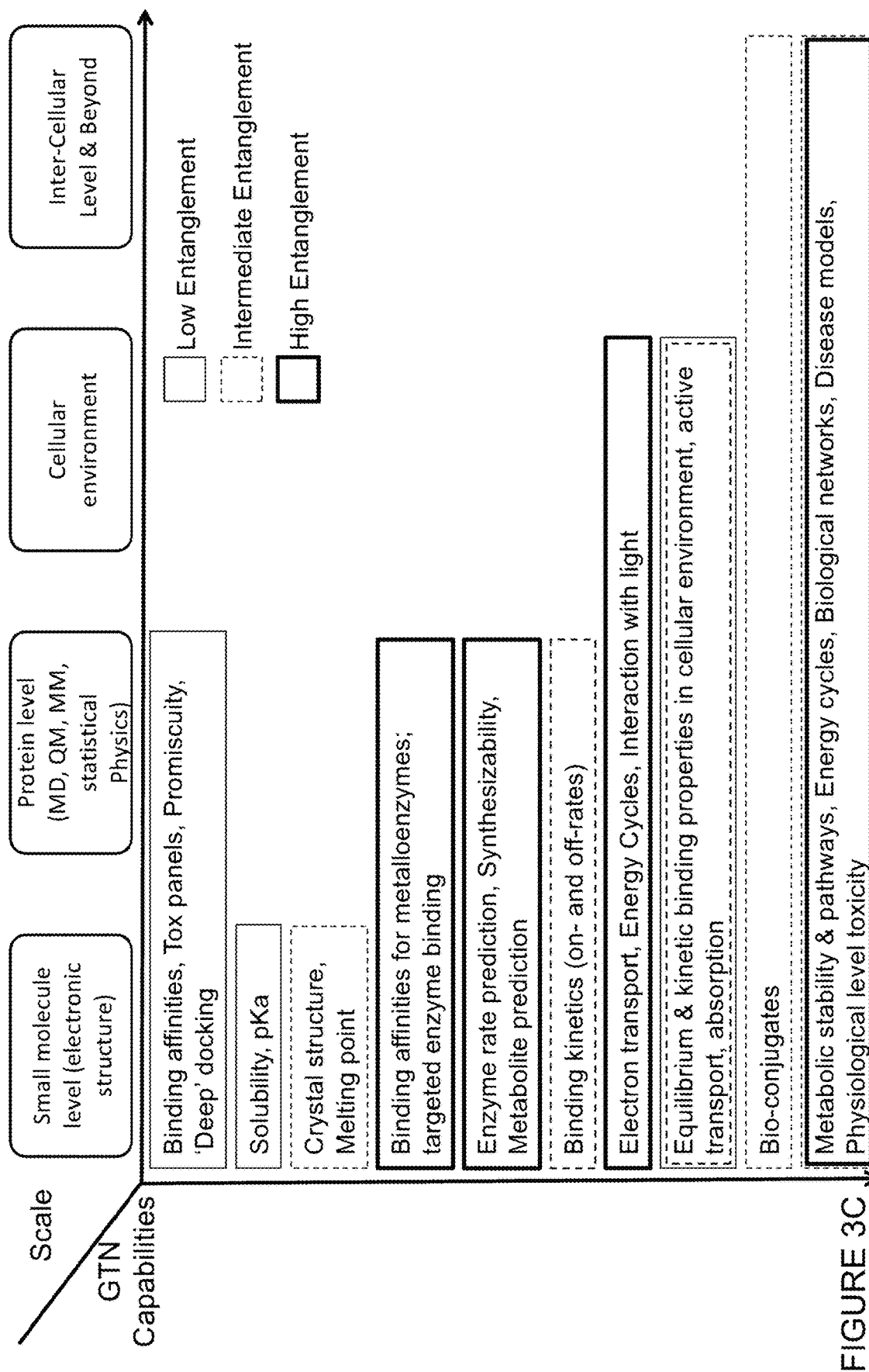
FIG. 3C shows a diagram illustrating the impact of GTN's technology on key drug discovery challenges.

FIG. 3C shows a diagram illustrating the impact of GTN's technology on key drug discovery challenges.

FIG. 3C depicts a wide spectrum of properties associated with binding affinity and ADMET that need to be modelled accurately as part of any effort contributing to the development of high quality drug candidates, and places these in the context of GTN's QI Modelling capabilities. The prioritisation overall reflects the fact that smaller scales, namely those at which the representation and search problems dominate the computational challenge, yield the most exciting applications for our models. An additional quantity, that of entanglement (Entanglement is a measure of the non-locality of the electron wavefunction and serves as a good metric for the computational complexity of the problem. It is expected that a solution to the highly entangled problems in FIG. 3B, at least in a de novo setting, will only be possible on a quantum chipset), is used to help focus down further towards specific sweet-spot applications, that is, disruptive problems that GTN's QIML technology can successfully tackle in reasonable time-frames.

Entanglement (see "Appendix H: Quantum mechanics and entanglement") measures the computational challenge of modelling the quantum mechanical aspects of a particular property, and is a metric of central importance since simulations of highly entangled systems, both in a de novo and a machine learning setting form a core expertise of our team, and at the same time high entanglement flags some of the most important and challenging problems for drug discovery.

An important class of sweet-spot problems for GTN's technology involves enzyme catalysis, as highlighted in FIG. 3C. Enzymes are crucial to biological functions. From a drug discovery perspective they are important both as drug targets (one third of approved drugs act as enzyme inhibitors (Robertson J G. Enzymes as a special class of therapeutic target: clinical drugs and modes of action. Curr Opin Struct Biol. 2007; 17:674-79) and in terms of their impact on ADMET, especially through their role in metabolism processes. The catalysis process often involves highly entangled states, and a deeper understanding of these promises to revolutionise key aspects of drug discovery. Capturing the entangled states of a small molecule in an active site as a target enzyme protein is performing its biological function, and using this information to guide the search for drug candidates, opens up a path towards developing medicines that work at drastically lower doses, are selective with respect to other proteins in the same class, and offer superior resistance to mutations of the target protein (Schramm, Vern L., Enzymatic Transition States, Transition-State Analogs, Dynamics, Thermodynamics, and Lifetimes, Annual Review of Biochemistry, Vol. 80; 703-732. [37] R. Lonsdale, J. N. Harvey, A. Mulholland, A practical guide to modelling enzyme-catalysed reactions, Chem. Soc. Rev., 2012, 41, 3025-3038). In working towards such 'magic bullet' drugs, GTN integrates protein function analysis, based on QI Modelling, with generative and MPO methods, and develops predictive models for enzymes that are already beating best available results.

The incorporation of key technologies pertaining to both target selection and later stages of drug discovery into the GTN platform is part of our future plans. Integration of wet lab experiments is currently enabled through partners and CROs, and is designed to maximally benefit our QI Models by leveraging custom active learning methods. We plan to progressively bring the most impactful wet lab experiments in-house.

References for Section 1

[2] R. P. Feynman, International Journal of Theoretical Physics 21, 467 (1982).
[3] J. Hachmann, J. J. Dorando, M. Aviles, and G. K.-L. Chan, The Journal of Chemical Physics 127, 134309 (2007).
[4] K. H. Marti, B. Bauer, M. Reiher, M. Troyer, and F. Verstraete, New Journal of Physics 12, 103008 (2010).
[5] G. K.-L. Chan and S. Sharma, Annual Review of Physical Chemistry 62, 465 (2011), pMID: 21219144.
[6] R. Orús, Annals of Physics 349, 117 (2014), arXiv: 1306.2164 [cond-mat.str-el].
[7] I. Kassal, J. D. Whitfield, A. Perdomo-Ortiz, M.-H. Yung, and A. Aspuru-Guzik, Annual Review of Physical Chemistry 62, 185 (2011), pMID: 21166541.
[8] P. J. D. Crowley, T. Duric, W. Vinci, P. A. Warburton, and A. G. Green, Phys. Rev. A 90, 042317 (2014), arXiv: 1405.5185 [quant-ph].
[9] S. Sharma and A. Alavi, J. Chem. Phys. 143, 102815 (2015), arXiv:1509.00216 [physics.chem-ph].
[10] Y. S. et al, Molecular Physics 113, 184 (2015).
[11] A. Cavalli, P. Carloni, and M. Recanatini, Chemical Reviews 106, 3497 (2006), pMID: 16967914.
[12] R. Dilip, "Quantum computing to create better drugs," http://princetoninnovation.org/magazine/2017/02/18/quantum-computing-create-better-drugs/.
[13] Accenture, "Consortium applies quantum computing to drug discovery for neurological diseases," https://www.dddmag.com/news/2017/06/consortium-applies-quantum-computing-drug-discovery-neurologicaldiseases/.
[14] A. Kandala, A. Mezzacapo, K. Temme, M. Takita, J. M. Chow, and J. M. Gambetta, ArXiv e-prints (2017), arXiv: 1704.05018 [quant-ph].
[15] M. Reiher, N. Wiebe, K. M. Svore, D. Wecker, and M. Troyer, Proceedings of the National Academy of Science 114, 7555 (2017), arXiv:1605.03590 [quant-ph].
[16] J. Olson, Y. Cao, J. Romero, P. Johnson, P.-L. Dallaire-Demers, N. Sawaya, P. Narang, I. Kivlichan, M. Wasielewski, and A. Aspuru-Guzik, ArXiv e-prints (2017), arXiv:1706.05413 [quant-ph].
[17] F. Verstraete, V. Murg, and J. Cirac, Advances in Physics 57, 143 (2008).
[18] Stoudenmire, "List of physics and machine learning papers," https://physicsml.github.io/pages/papers.html.
[19] E. Miles Stoudenmire and D. J. Schwab, ArXiv e-prints (2016), arXiv:1605.05775 [stat.ML].
[20] G. Carleo and M. Troyer, ArXiv e-prints (2016), arXiv:1606.02318 [cond-mat.dis-nn].
[21] D. Draxler, J. Haegeman, T. J. Osborne, V. Stojevic, L. Vanderstraeten, and F. Verstraete, Physical Review Letters 111, 020402 (2013), arXiv:1212.1114 [quant-ph].
[22] V. Stojevic, P. Crowley, T. Duric, C. Grey, and A. G. Green, Phys. Rev. B 94, 165135 (2016), arXiv: 1604.07210 [quant-ph].
[23] A. G. Green, C. A. Hooley, J. Keeling, and S. H. Simon, ArXiv e-prints (2016), arXiv:1607.01778 [cond-mat.str-el].
[24] C. M. Bishop, Pattern Recognition and Machine Learning (Information Science and Statistics) (Springer-Verlag New York, Inc., Secaucus, N.J., USA, 2006).
[25] N. Shaker, J. Togelius, and M. J. Nelson, Procedural Content Generation in Games, Computational Synthesis and Creative Systems (Springer, 2016).
[26] I. J. Goodfellow, J. Pouget-Abadie, M. Mirza, B. Xu, D. Warde-Farley, S. Ozair, A. Courville, and Y. Bengio, ArXiv eprints (2014), arXiv:1406.2661 [stat.ML].
[27] A. Radford, L. Metz, and S. Chintala, ArXiv e-prints (2015), arXiv:1511.06434 [cs.LG].
[28] K. Gregor, I. Danihelka, A. Graves, D. Jimenez Rezende, and D. Wierstra, ArXiv e-prints (2015), arXiv: 1502.04623 [cs.CV].
[29] A. van den Oord, S. Dieleman, H. Zen, K. Simonyan, O. Vinyals, A. Graves, N. Kalchbrenner, A. Senior, and K. Kavukcuoglu, ArXiv e-prints (2016), arXiv:1609.03499 [cs.SD].
[30] H. Zhang, T. Xu, H. Li, S. Zhang, X. Wang, X. Huang, and D. Metaxas, ArXiv e-prints (2016), arXiv: 1612.03242 [cs.CV].
[31] R. Gómez-Bombarelli, J. Duvenaud, J. M. Hernández-Lobato, J. Aguilera-Iparraguirre, T. D. Hirzel, R. P. Adams, and A. Aspuru-Guzik, ArXiv e-prints (2016), arXiv:1610.02415 [cs.LG].
[32] S. R. Bowman, L. Vilnis, O. Vinyals, A. M. Dai, R. Jozefowicz, and S. Bengio, ArXiv e-prints (2015), arXiv: 1511.06349 [cs.LG].
[33] D. Duvenaud, D. Maclaurin, J. Aguilera-Iparraguirre, R. Gómez-Bombarelli, T. Hirzel, A. Aspuru-Guzik, and R. P. Adams, ArXiv e-prints (2015), arXiv:1509.09292 [cs.LG].
[34] S. Kearnes, K. McCloskey, M. Berndl, V. Pande, and P. Riley, Journal of Computer-Aided Molecular Design 30, 595 (2016), arXiv:1603.00856 [stat.ML]. [35] T. N. Kipf and M. Welling, ArXiv e-prints (2016), arXiv:1609.02907 [cs.LG].
[35] Justin Gilmer, Samuel S. Schoenholz, Patrick F. Riley, Oriol Vinyals and George E. Dahl "Neural Message Passing for Quantum Chemistry", Journal: CoRR, arXiv: 1704.01212 [cs.LG].
[36] PandeLabs, "Deepchem library," https://github.com/deepchem/deepchem.
[37] M. A. et al, "Tensorflow: Large-scale machine learning on heterogeneous distributed systems," (2015).
[38] Z. Wu, B. Ramsundar, E. N. Feinberg, J. Gomes, C. Geniesse, A. S. Pappu, K. Leswing, and V. Pande, ArXiv eprints (2017), arXiv:1703.00564 [cs.LG].
[39] A. Hallam, E. Grant, V. Stojevic, S. Severini, and A. G. Green, ArXiv e-prints (2017), arXiv:1711.03357.
[40] Grant, Edward; Benedetti, Marcello; Cao, Shuxiang; Hallam, Andrew; Lockhart, Joshua; Stojevic, Vid; Green, Andrew G.; Severini, Simone, "Hierarchical quantum classifiers", arXiv:1804.03680, accepted in njp Quantum Information.
[41] Feinberg, Evan N.; Sur, Debnil; Husic, Brooke E.; Mai, Doris; Li, Yang; Yang, Jianyi; Ramsundar, Bharath; Pande, Vijay S, "Spatial Graph Convolutions for Drug Discovery", arXiv:1803.04465.
[42] Benjamin Sanchez-Lengeling, Alan Aspuru-Guzik, "Inverse molecular design using machine learning: Generative models for matter engineering", Science 27 Jul. 2018: Vol. 361, Issue 6400, pp. 360-365

[43] R. Gómez-Bombarelli, T. Hirzel, A. Aspuru-Guzik, et al, "Design of efficient molecular organic light-emitting diodes by a high-throughput virtual screening and experimental approach", Nature Materials volume 15, pages 1120-1127 (2016)

[44] Daniel Neil, Marwin Segler, Laura Guasch, Mohamed Ahmed, Dean Plumbley, Matthew Sellwood, Nathan Brown, ICLR 2018

[45] Wengong Jin, Regina Barzilay, Tommi Jaakkola, ArXiv e-prints (2018), arXiv:1802.04364

[46] Nicola De Cao, Thomas Kipf, ArXiv e-prints (2018), arXiv:1805.11973

[47] Yujia Li, Oriol Vinyals, Chris Dyer, Razvan Pascanu, Peter Battaglia, ArXiv e-prints (2018), arXiv:1803.03324

[48] Qi Liu, Miltiadis Allamanis, Marc Brockschmidt, Alexander L. Gaunt, ArXiv e-prints (2018), arXiv:1805.09076

[49] Peter I. Frazier, ArXiv e-prints (2018), arXiv:1807.02811

[50] Sutton and Barto, "Reinforcement Learning: An Introduction" (2018)

[51] Volodymyr Mnih, Koray Kavukcuoglu, David Silver, Alex Graves, Ioannis Antonoglou, Addn Wierstra, Martin Riedmiller, ArXiv e-prints (2013), arXiv:1312.5602

[52] Marwin H S. Segler, Thierry Kogej, Christian Tyrchan, Mark O. Waller, "Generating Focussed Molecule Libraries for Drug Discovery with Recurrent Neural Networks", arXiv:1701.01329

[53] Tom White, ArXiv e-prints (2016), arXiv:1609.04468 "Deep Reinforcement Learning Doesn't Work Yet" Alex Irpan (2018), alexirpan.com

[55] Jason Yosinski, Jeff Clune, Yoshua Bengio, Hod Lipson, ArXiv e-prints (2014), arXiv:1411.1792

[56] 1) WO2011026904 A1, 2) J. Med. Chem., 2018, 61 (4), 1664-1687, 3) Curr. Med. Chem., 2011, 18 (3), 342-358 DTNN reference: Schutt, K. T., Arbabzadah, F., Chmiela, S., Muller, K. R., & Tkatchenko, A. (2017). Quantum-chemical insights from deep tensor neural networks. Nature communications, 8, 13890.

[57] CDK9 biology; De Falco & Giordano, 2002, Cancer Biology and Therapy July-August; 1(4):342-7; Boffo et al., 2018, Journal of Experimental and Clinical Cancer Research doi: 10.1186/s13046-018-0704-8

[58] 1. R. Abel, L. Wang, E. D. Harder, B. J. Berne and R. A. Friesner Accounts of Chemical Research, 50, 1625 (2017), 2. Z. Cournia, B. Allen and W. Sherman Journal of Chemical Information and Modeling, 57, 2911 (2017), 3. S. Wan, A. P. Bhati, S. J. Zasada, I. Wall, D. Green, P. Bamborough and P. V. Coveney Journal of Chemical Theory and Computation, 13, 784 (2017).

[59] R. Ramakrishnan, P. O. Dral, M. Rupp, O. A. von Lilienfeld, Quantum chemistry structures and properties of 134 kilo molecules, Scientific Data 1, 140022, 2014. [bibtex]

[60] L. Ruddigkeit, R. van Deursen, L. C. Blum, J.-L. Reymond, Enumeration of 166 billion organic small molecules in the chemical universe database GDB-17, J. Chem. Inf. Model. 52, 2864-2875, 2012.

[61] van der Maaten, L. J. P.; Hinton, G. E. (November 2008). "Visualizing Data Using t-SNE" (PDF). Journal of Machine Learning Research. 9: 2579-2605.

[62] Tetko, I. V., Sushko, Y., Novotarskyi, S., Patiny, L., Kondratov, I., Pet enko, A. E., Charochkina, L. and Asiri, A. M., 2014. How accurately can we predict the melting points of drug-like compounds?. Journal of chemical information and modeling, 54(12), pp. 3320-3329.

[63] Bergstrom, C. A., & Larsson, P. (2018). Computational prediction of drug solubility in water-based systems: Qualitative and quantitative approaches used in the current drug discovery and development setting. International journal of pharmaceutics, 540(1-2), 185-193.

[64] Jensen, J. H., Swain, C. J., & Olsen, L. (2017). Prediction of pKa Values for Druglike Molecules Using Semiempirical Quantum Chemical Methods. The Journal of Physical Chemistry A, 121(3), 699-707.

[65] Kujawski, J., Popielarska, H., Myka, A., Drabińska, B., & Bernard, M. K. (2012). The log P parameter as a molecular descriptor in the computer-aided drug design—an overview. Computational Methods in Science and Technology, 18(2), 81-88.

[66] Bennion, B. J., Be, N. A., McNerney, M. W., Lao, V., Carlson, E. M., Valdez, C. A., . . . & Carpenter, T. S. (2017). Predicting a drug's membrane permeability: a computational model validated with in vitro permeability assay data. The Journal of Physical Chemistry B, 121(20), 5228-5237.

[67] Rimac, H., Debeljak, ., Šakić, D., Weitner, T., Gabričević, M., Vrček, V., . . . & Bojić, M. (2016). Structural and electronic determinants of flavonoid binding to human serum albumin: an extensive ligand-based study. RSC Advances, 6(79), 75014-75022.

[68] Lonsdale, R., Fort, R. M., Rydberg, P., Harvey, J. N., & Mulholland, A. J. (2016). Quantum mechanics/molecular mechanics modeling of drug metabolism: Mexiletine N-hydroxylation by cytochrome P450 1A2. Chemical research in toxicology, 29(6), 963-971.

[69] Agrawal, M., Kumar, A., & Gupta, A. (2017). Conformational stability, spectroscopic signatures and biological interactions of proton pump inhibitor drug lansoprazole based on structural motifs. RSC Advances, 7(66), 41573-41584.

[70] McCarren, P., Springer, C., & Whitehead, L. (2011). An investigation into pharmaceutically relevant mutagenicity data and the influence on Ames predictive potential. Journal of Cheminformatics, 3, 51. http://doi.org/10.1186/1758-2946-3-51

[71] Hughes, T. B., Dang, N. L., Miller, G. P., & Swamidass, S. J. (2016). Modeling reactivity to biological macromolecules with a deep multitask network. ACS central science, 2(8), 529-537.

[72] F Silva-Júnior, E., M Aquino, T., & X Araujo-Junior, J. (2017). Quantum Mechanical (QM) Calculations Applied to ADMET Drug Prediction: A Review. Current drug metabolism, 18(6), 511-526.

[73] M. Hay, D. W. Thomas, J. L. Craighead, C. Economides, J. Rosenthal, Nature Biotechnology, 32, pages 40-51

Section 2: Quantum Graph

Quantum Description of Molecules into Graph Structure Representation

The idea is to construct a so called quantum chemical graph or quantum graph or Q-graph, which is a graph based description of the molecule that utilises information obtained directly from quantum mechanical calculations (such as DFT or DMRG), and use this as input to machine learning algorithms, potentially for many conformational states (e.g. for a description of a thermodynamic ensemble).

In one iteration, Q-graph is similar to a standard chemical graph in that the graph nodes correspond to atoms in the molecule. The distinction is that the q-graph is derived directly from quantum mechanical correlation functions, with bond features given by so-called de-localisation indices (DLI), and atom features by localisation indices (LI). Unlike the standard chemical graph, the q-graph is not a heuristic construct.

One q-graph construction is part of the so-called QTAIM method—details are given in section 3.1 of "Section 4: Graph Featurization and Quantum Chemistry". The QTAIM method incorporates a partitioning of the electron density, obtained directly from a QM method, into volumes associated with each atom. This Voronoi style partitioning is then used to obtain the DLI and LI indices.

In another iteration, Q-graphs can be defined directly on the space of orbitals. Thus, each node can correspond to an orbital, and the graph can correspond to any type of quantum correlation between these orbitals. One could for example use graphs defined in "Section 4: Graph featurization and quantum chemistry" which forms part of this specification. The issue here is to make sure that the same types of orbitals are used across the dataset, as otherwise one would not be comparing like-to-like.

Q-graph is in general fully connected (in contrast to for example a standard molecular graph), and also depends on the conformational state of the molecule. This results in a Q-graph representation of molecules in which a measure of the correlation between every pair of atoms present in the molecule, or between every pair of orbital present in its description, is represented. In comparison, with chemical graph representation, an atom is only connected with another atom if a chemical bound exists between the two atoms. Expressed another way, the 'dominant' edges in an atom-based Q-graph correspond to the bonds in a standard chemical graph, at least roughly.

Q-graph can also be used in the ensemble context described in "Section 5: Structure based model overview", where every element of the ensemble is a Q-graph description of the molecule in the" corresponding conformation.

Note that Q-graph methods are not confined to densities, and can be used for number of properties that can be obtained from quantum calculations, e.g. charge distribution. A different method for calculating Q-Graph features is presented in "Appendix D: Experiment P450 site of metabolism".

Note also that relationship between quantum graphs and tensor networks: we can use tensor networks as inputs, where we fix the gauge freedom of the TN, and treat it as a graph, with tensors at nodes and indices specifying various edges; ends open edges can be treated as special nodes (in the usual tensor network formulation, a node corresponds to an atomic or molecular orbital, i.e. it is an open edge of a tensor network, and internal links specify contractions). In this setting ML treats the TN as a graph, and does not explicitly perform contractions, as would be the case in any standard application of TNs. "Appendix D: Experiment P450 site of metabolism" describes how Q-graph is calculated, as well as the specific Graph Convolutional model architecture used in full detail, citing neural network layers that are themselves described in "Appendix A: Models and modules".

Note also that Q-graph can be generalised to mean not just an approximate graph description of the $\rho(x,x)$ and $\rho(x,x')$ density matrix (see "Section 4: Graph featurization and quantum chemistry"), but also a graph description obtained from any QM derived scalar field (and beyond, vector, tensor field).

The process of building Graph Convolutional models is described in details in "Section 3: Sparse hierarchical representation learning on molecular graphs".

Q-Graph results for the QM9 dataset are described in "Appendix C: Advanced predictive models from quantum observables". Here Q-graph has a significant impact on small dataset sizes. The precise featurisation process is described in "Section 4: Graph featurization and quantum chemistry", note that this featurisation is slightly different than the one used in the P450 experiment above.

Additionally, FEP (Free Energy Perturbation), or MMGBSA [https://www.nbci.nlm.nih.gov/pmc/articles/PMC4487606/] calculations may be combined with quantum graph models, in order to augment the dataset of small, drug like molecules.

Using FEP calculations, binding affinities can be predicted for new molecules that are closely related to other molecules with known binding affinities. These new molecules are then used to augment the original training dataset for the ML, and are featurised using Q-graph methods.

Section 3: Sparse Hierarchical Representation Learning on Molecular Graphs

Architectures for sparse hierarchical representation learning have recently been proposed for graph-structured data, but so far assume the absence of edge features in the graph. We close this gap and propose a method to pool graphs with edge features, inspired by the hierarchical nature of chemistry. In particular, we introduce two types of pooling layers compatible with an edge-feature graph-convolutional architecture and investigate their performance for molecules relevant to drug discovery on a set of two classification and two regression benchmark datasets of MoleculeNet. We find that our models significantly outperform previous benchmarks on three of the datasets and reach state-of-the-art results on the fourth benchmark, with pooling improving performance for three out of four tasks, keeping performance stable on the fourth task, and generally speeding up the training process.

Introduction and Related Work

Predicting chemical properties of molecules has become a prominent application of neural networks in recent years. A standard approach in chemistry is to conceptualize groups of individual atoms as functional groups with characteristic properties, and infer the properties of a molecule from a multi-level understanding of the interactions between functional groups. This approach reflects the hierarchical nature of the underlying physics and can be formally understood in terms of renormalization (Lin et al., 2017). It thus seems natural to use machine learning models that learn graph representations of chemical space in a local and hierarchical manner. This can be realized by coarse-graining the molecular graph in a step-wise fashion, with nodes representing effective objects such as functional groups or rings, connected by effective interactions.

Much published work leverages node locality by using graph-convolutional networks with message passing to process local information, see Gilmer et al. (2017) for an overview. In graph classification and regression tasks, usually, only a global pooling step is applied to aggregate node features into a feature vector for the entire graph (Duvenaud et al., 2015; Li et al., 2016; Dai et al., 2016; Gilmer et al., 2017).

Much published work leverages node locality by using graph-convolutional networks with message passing to process local information, see Gilmer et al. (2017) for an overview. In graph classification and regression tasks, usually, only a global pooling step is applied to aggregate node features into a feature vector for the entire graph (Duvenaud et al., 2015; Li et al., 2016; Dai et al., 2016; Gilmer et al., 2017). In some publications (Altae-Tran et al., 2017; Li et al., 2017b) the phrase "pooling layer" has been used to refer to a MAX aggregation step. We reserve the notion of pooling for an operation which creates a true hierarchy of graphs, in line with its usage for images in computer vision.

An alternative is to aggregate node representations into clusters, which are then represented by a coarser graph (Bruna et al., 2013; Niepert et al., 2016; Defferrard et al., 2016; Monti et al., 2017; Simonovsky & Komodakis, 2017; Fey et al., 2018; Mrowca et al., 2018). Early work uses predefined and fixed cluster assignments during training, obtained by a clustering algorithm applied to the input graph. More recently, dynamic cluster assignments are made on learned node features (Ying et al., 2018; Gao & Ji, 2019; Cangea et al., 2018; Gao et al., 2019). A pioneering step in using learnable parameters to cluster and reduce the graph was the DIFFPOOL layer introduced by Ying et al. (2018). Unfortunately, DIFFPOOL is tied to a disadvantageous quadratic memory complexity that limits the size of graphs and cannot be used for large sparse graphs. A sparse, and therefore more efficient, technique has been proposed by Gao & Ji (2019) and further tested and explored by Cangea et al. (2018); Gao et al. (2019).

Sparse pooling layers have so far not been developed for networks on graphs with both node and edge features. This is particularly important for molecular datasets, where edge features may describe different bond types or distances between atoms. When coarsening the molecular graph, new, effective edges need to be created whose edge features represent the effective interactions between the effective nodes. We explore two types of sparse hierarchical representation learning methods for molecules that process edge features differently during pooling: a simple pooling layer simply aggregates the features of the involved edges, while a more physically-inspired coarse-graining pooling layer determines the effective edge features using neural networks.

We evaluate our approach on established molecular benchmark datasets (Wu et al., 2018), in particular on the regression datasets ESOL and lipophilicity and the classification datasets BBBP and HIV, on which various models have been benchmarked (Li et al., 2017a; B. Goh et al., 2017a; b; c; Goh et al., 2018; Shang et al., 2018; B. Goh et al., 2018; Jaeger et al., 2018; Urban et al., 2018; Feinberg et al., 2018; Zheng et al., 2019; Winter et al., 2019). We obtain significantly better results on the datasets ESOL, lipophilicity, and BBBP, and obtain state-of-the-art results on HIV. Simple pooling layers improve results on BBBP and HIV, while coarse grain pooling improves results on lipophilicity. In general pooling layers can keep performance at least stable while speeding up training.

2. Approach 2.1 Model Architecture

We represent input graphs in a sparse representation using node (a) and edge (e) feature vectors $$a_i^{(0)} = a_i, i=1, \ldots, n_{nodes}, \quad (1)$$

$$e_{ij}^{(0)} = e_{ij}, i,j=1, \ldots, n_{nodes} \text{ for } j \in NN(i), \quad (2)$$

where belongs to the set of nearest-neighbours (NN) of i. For chemical graphs we encode the atom type as a one-hot vector and its node degree as an additional entry in $a_i$, while the bond type is one-hot encoded in $e_{ij}$. Framed in the message-passing framework (Gilmer et al., 2017), the graph-convolutional models we use consist of alternating message-passing steps to process information locally and pooling steps that reduce the graph to a simpler sub-graph. Finally, a read-out phase gathers the node features and computes a feature vector for the whole graph that is fed through a simple perceptron layer in the final prediction step.

Dual-message graph-convolutional Since edge features are an important part of molecular graphs, the model architecture is chosen to give more prominence to edge features. We design a dual-message graph-convolutional layer that supports both node and edge features. First, we compute an aggregate message $m_i^{(k+1)}$ to a target node from all neighbouring source nodes $j \in NN(i)$ using a fully-connected neural network $f_w$ acting on the source node features $a_i^{(k)}$ and the edge features $e_{ij}^{(k)}$ of the connecting edge. A self-message $s_i^{(k+1)} = W_s^{(k)} a_i^{(k)} + b_s^{(k)}$ from the original node features is added to the aggregated result. New node features are computed by applying batch norm (BN) and a RELU nonlinearity, i.e.

$$m_i^{(k+1)} = \sum_{j \in N(i)} f w_a\left(a_j^{(k)}, e_{ij}^{(k)}\right), \quad (3)$$

$$\tilde{a}_i^{(k+1)} = ReLU\left(BN\left(m_i^{(k+1)}, s_i^{(k+1)}\right)\right). \quad (4)$$

In contrast to the pair-message graph-convolutional layer of Gilmer et al. (2017), we also update the edge feature with the closest node feature vectors via $$m_{ij}^{(k+1)} = g w_e\left(\tilde{a}_i^{(k+1)} + \tilde{a}_j^{(k+1)}, e_{ij}^{(k)}\right), \quad (5)$$

$$\tilde{e}_{ij}^{(k+1)} = ReLU\left(BN\left(m_{ij}^{(k+1)} + s_{ij}^{(k)}\right)\right). \quad (6)$$

where g is a fully-connected neural network and $s_{ij}^{(k)} = W_e^{(k)} e_{ij}^{(k)} + b_e^{(k)}$ is the edge feature self-message.

Pooling layer Pooling layers, as introduced in Gao & Ji (2019), reduce the number of nodes by a fraction $$\rho = K/n_{nodes}^{(k)} \quad (7)$$

specified as a hyperparameter, via scoring all nodes using a learnable projection vector $p^{(k)}$, and then selecting the K nodes with the highest score $y_i^{(k)}$. In order to make the projection vector $p^{(k)}$ trainable, and thus the node selection differentiable, $p^{(k)}$ is also used to determine a gating for each feature vector via $$y^{(k)} = p^{(k)} \cdot \tilde{a}_i^{(k)}, a_i^{(k)} = \tilde{a}_i^{(k)} \tanh(y_i^{(k)}), \quad (8)$$

where we only keep the top-K nodes and their gated feature vectors $a_i^{(k)}$.

Pooling nodes requires the creation of new, effective edges between kept nodes while keeping the graph sparse. We discuss in Section 3.2.2 how to solve this problem in the presence of edge features.

Gather layer After graph-convolutional and pooling layers, a graph gathering layer is required to map from node and edge features to a global feature vector. Assuming that the dual-message message-passing steps are powerful enough to distribute the information contained in the edge features to the adjacent node features, we gather over node features only by concatenating MAX and SUM, and acting with a tanh non-linearity on the result. All models have an additional linear layer that acts on each node individually before applying the gather layer and a final perceptron layer.

2.2 Pooling with Edge Features

An important step of the pooling process is to create new edges based on the connectivity of the nodes before pooling in order to keep the graph sufficiently connected. For graphs with edge features this process also has to create new edge features. In addition, the algorithm must be parallel for performance reasons.

We tackle these issues by specifying how to combine edge features into an effective edge feature between remaining (kept) nodes. If a single dropped node or a pair of dropped nodes connect two kept nodes, we construct a new edge and drop the linked to the dropped nodes as shown in FIG. 4.

FIG. 4 shows a schematic of a graph pooling step (dark nodes are kept, white nodes are dropped). Dangling nodes are removed, together with their connecting edges. Pairs of edges connecting a dropped node to two kept nodes are coarse-grained to a new edge (heavy lines). New edges can also be constructed between kept nodes connected by two dropped nodes (heaviest line).

We propose two layers to calculate the replacement effective edge feature from the dropped edge features. A simple pooling layer computes an effective edge-feature by summing all edge feature vectors along the paths connecting pairs of kept nodes. When multiple paths between a pair of nodes are simultaneously reduced, this method will generate overlapping effective edge features. We reduce these to a single vector of the sum of overlapping edge feature vectors.

We know however that in chemistry effective interactions are more complex functions of the involved component features. Using this as an inspiration, we propose a more expressive coarse-graining pooling layer, which is obtained by replacing the simple aggregation function with neural networks to compute effective edge features. In particular, we use two fully-connected neural networks. The first network maps the atom and adjoining edge feature vectors of dropped nodes to a single effective-edge feature. The second network calculates effective edge features for kept edges (between kept nodes) to account for an effective coarse-grained interaction compensating for deleted nodes.

We use pooling layers after every convolutional layer except for the final one. For N convolutional layers, the number of nodes thus gets reduced by a factor $\rho^{N-1}$. This compression not only gets rid of irrelevant information but also reduces memory requirements and makes training faster, as we show in the experiments in Sec. 3.3.

3. Experimental Results on MoleculeNet

Model parameters and implementation We use hyperparameter tuning to decide on the number of stacks and channel dimensions of graph-convolutional and pooling layers while keeping the pooling keep ratio defined in equation 7 fixed. All our models were implemented in PyTorch and trained on a single Nvidia Tesla K80 GPU using the ADAM optimizer with a learning rate of 0.0001.

Evaluation on MoleculeNet

With reference to FIG. 5, a table shows literature results for the MoleculeNet benchmarks comparing RMSE and ROC-AUC results, on a range of models. Benchmarks without reference come from Wu et al. (2018), except those values decorated with a, which come from Feinberg et al. (2018). (Bottom) Our model with coarse-grain pooling, simple pooling, and without pooling. The number in brackets specifies the pooling keep ratio $\rho$ of the pooling layer.

We evaluate our models with and without pooling layers on the MoleculeNet benchmark set (Wu et al., 2018). We focus on four different datasets, comprised of the regression benchmarks ESOL (1128 molecules) and Lipophilicity (4200 molecules), where performance was evaluated by RMSE, and the classification benchmarks on the BBBP (2039 molecules) and HIV (41127 molecules) datasets, evaluated via ROC-AUC. Following Wu et al. (2018), we used a scaffold split for the classification datasets as provided by the DeepChem package. Apart from the benchmarks generated in the original paper, various models have been evaluated on these datasets (Li et al., 2017a; B. Goh et al., 2017a; b; c; Goh et al., 2018; Shang et al., 2018; B. Goh et al., 2018; Jaeger et al., 2018; Urban et al., 2018; Feinberg et al., 2018; Zheng et al., 2019; Winter et al., 2019). An overview over the results in the literature can be found in the top of the table in FIG. 5. Our results are the mean of 5 runs over 5 random splits (ESOL, Lipophilicity) or 5 runs over the same scaffold split (BBBP, HIV). The results of our models with and without pooling are displayed in the lower part of the table.

For the regression tasks, we found that our models significantly outperformed previous models for both datasets, with pooling layers keeping performance stable for ESOL and the coarse-grain pooling layer significantly improving results for Lipophilicity (see table in FIG. 5). Regarding classification tasks, we found that our models significantly outpooling performed previous models on BBBP and also exceeded previous benchmarks for the HIV dataset. For both datasets simple pooling layers improved performance. Curiously, the extent to which pooling layers improve performance and which layer is better suited for a particular task strongly depends on the dataset. It seems that simple pooling performs much better for classification tasks while for regression tasks it depends on the dataset.

Figure 6:
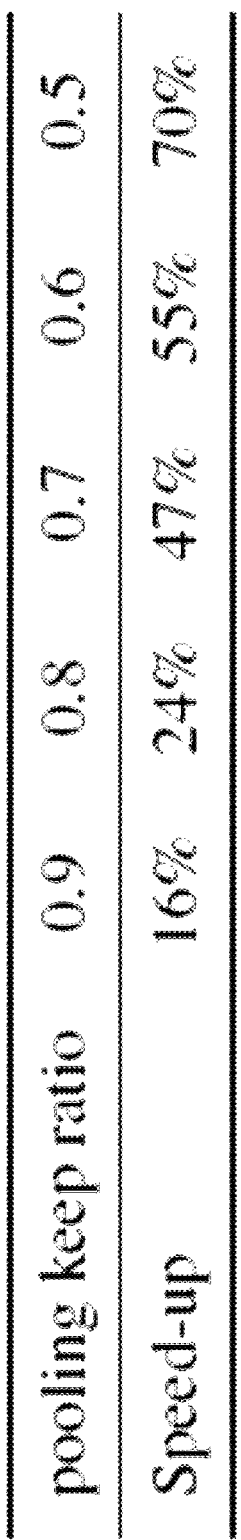
FIG. 6 shows a table with speed-up of pooling runs of the HIV data set using Simple Pooling.

We also measure the speed-up given by pooling layers during the evaluation on the HIV dataset in terms of elapsed real-time, using the simple pooling layer. FIG. 6 shows a table with speed-up of pooling runs of the HIV data set using Simple Pooling. The speed-up is measured as increase in speed in terms of elapsed real time compared to the run without pooling layer. We see significant speed-ups for moderate values of the pooling ratio.

4. Conclusion

We introduce two graph-pooling layers for sparse graphs with node and edge features and evaluate their performance on molecular graphs. While our model without pooling significantly outperforms benchmarks on ESOL, lipophilicity and BBBP and reaches state-of-the-art results on HIV in the MoleculeNet dataset, we find that our pooling methods improve performance and provide a speedup of up to 70% in the training of graph-convolutional neural networks that utilize edge features, along with a reduction in memory requirements.

While all experiments have been performed on datasets comprised of small, druglike molecules, we expect even stronger performance for datasets comprised of larger graphs like protein structures, where pooling can create a large, sequential hierarchy of graphs. More generally, our work may result in more pertinent and information-effective latent space representations for graph-based machine learning models.

5. Supplementary Material 5.1 Model Hyperparameters

With reference to FIG. 7, a table summarises the graph-convolutional model hyperparameters used in this work.

5.2 Material Science Application: Clean Energy Project 2017 Dataset

In this section, we propose a regression benchmark for hierarchical models using the 2017 non-fullerene electron-acceptor update (Lopez et al., 2017) to the Clean Energy Project molecular library (Hachmann et al., 2011). We refer to this dataset as CEP-2017. This dataset was generated by combining molecular fragments from a reference library generating 51256 unique molecules. These molecular graphs were then used as input to density functional theory electronic-structure calculations of quantum-mechanical observables (such as GAP and HOMO). Restrictions of the crowd-sourced computing platform limited these structures to molecules of 306 electrons or less. The direct observables quantities are then used in a physically motivated but empirical Scharber (Scharber et al., 2006) model to predict power conversion efficiency (PCE). This efficiency is the ultimate figure of merit for a new photovoltaic material.

We emphasize that this data, generated with an approximate density functional theory method, and then used in an empirical PCE model, lacks predictive power in terms of design of new materials. However a machine learning model built on this data is likely to be transferable to other molecular datasets built on higher level theory (such as coupled-cluster calculations) or experimental ground truth. As we are anticipating this future application of the method, we use the raw (calc) values rather than the Gaussian process regressed (to a small experimental dataset) values (calib).

The method of construction of the dataset allows us to highlight the coarse-graining interpretation of the pooling layers introduced in the main text, in terms of the explicit combinatorial building blocks of the non-fullerene electron acceptors.

In FIG. 8, we show multi-task and single-task test set evaluation R2 results for the power conversion efficiency (PCE), the band gap (GAP), and the highest occupied molecular orbital (HOMO) energy. We used a dual-message graph-convolutional model with three graph-convolutional layers with node channel dimensions [512, 512, 512] and edge channel dimensions [128, 128, 128] with two interleaved layers of simple pooling. We found our model to be a powerful predictor of both fundamental quantum-mechanical properties (GAP and HOMO), and to a lesser extend the more empirical PCE figure. The inclusion of pooling layers resulted in a significant speedup and only a very mild decay in performance.

5.3 Pooling Layers Illustrations

In FIGS. 9-11 we illustrate the effect of two consecutive pooling layers (each keeping only 50% of the nodes) on a batch of molecules for a DM-SIMPLEPOOLING model trained on a random split of the CEP-2017 dataset introduced in Section 5.2 above. After the first pooling layer (FIG. 10) the model has approximately learned to group rings and identify the backbones or main connected chains of the molecules. After the second pooling layer (FIG. 11) the molecular graphs have been reduced to basic components connected by chains, encoding a coarse-grained representation of the original molecules.

Disconnected parts can be interpreted as a consequence of the aggressive pooling forcing the model to pay attention to the parts it considers most relevant for the task at hand.

References for Section 3

Altae-Tran, H., Ramsundar, B., Pappu, A. S., and Pande, V. S. Low data drug discovery with one-shot learning. American Chemical Society, 3, 2017. URL http://arxiv.org/abs/1611.03199.

B. Goh, G., O. Hodas, N., Siegel, C., and Vishnu, A. Smiles2vec: An interpretable general-purpose deep neural network for predicting chemical properties. 12 2017a. URL https://arxiv.org/abs/1712.02034.

B. Goh, G., Siegel, C., Vishnu, A., and O. Hodas, N. Chemnet: A transferable and generalizable deep neural network for small-molecule property prediction. 12 2017b. URL https://arxiv.org/abs/1712.02734.

B. Goh, G., Siegel, C., Vishnu, A., O. Hodas, N., and Baker, N. Chemception: A deep neural network with minimal chemistry knowledge matches the performance of expert developed qsarqspr models. 06 2017c. URL https://arxiv.org/abs/1706.06689.

B. Goh, G., Siegel, C., Vishnu, A., and Hodas, N. Using rulebased labels for weak supervised learning: A chemnet for transferable chemical property prediction. pp. 302-310, 07 2018. doi: 10.1145/3219819.3219838.

Bruna, J., Zaremba, W., Szlam, A., and LeCun, Y. Spectral networks and locally connected networks on graphs. preprint, 2013. URL http://arxiv.org/abs/1312.6203.

Cangea, C., Velikovi, P., Jovanovi, N., Kipf, T., and Li, P. Towards sparse hierarchical graph classifiers. Workshop on Relational Representation Learning (R2L) at NIPS, 2018. URL http://arxiv.org/abs/1811.01287. Dai, H., Dai, B., and Song, L. Discriminative embeddings of latent variable models for structured data. Proceedings of the International Conference on Machine Learning (ICML), 48, 2016. URL http://arxiv.org/abs/1603.05629.

Defferrard, M., Bresson, X., and Vandergheynst, P. Convolutional neural networks on graphs with fast localized spectral filtering. Advances in Neural Information Processing Systems (NIPS), 29, 2016. URL http://arxiv.org/abs/1606.09375.

Duvenaud, D. K., Maclaurin, D., Iparraguirre, J., Bombarell, R., Hirzel, T., Aspuru-Guzik, A., and Adams, R. P. Convolutional networks on graphs for learning molecular fingerprints. In Cortes, C., Lawrence, N. D., Lee, D. D., Sugiyama, M., and Garnett, R. (eds.), Advances in Neural Information Processing Systems 28, pp. 2224-2232. Curran Associates, Inc., 2015. URL https://arxiv.org/abs/1509.09292.

Feinberg, E. N., Sur, D., Wu, Z., Husic, B. E., Mai, H., Li, Y., Sun, S., Yang, J., Ramsundar, B., and Pande, V. S. Potentialnet for molecular property prediction. ACS Central Science, 4(11):1520-1530, 2018. doi: 10.1021/acscentsci.8b00507. URL https://doi.org/10.1021/acscentsci.8b00507.

Fey, M., Lenssen, J. E., Weichert, F., and Müller, H.Splinecnn: Fast geometric deep learning with continuousb-spline kernels. IEEE/CVF Conference on ComputerVision and Pattern Recognition (CVPR), 2018. URL http://arxiv.org/abs/1711.08920.

Gao, H. and Ji, S. Graph u-net. ICLR 2019 Conference Blind Submission, 2019. URL https://openreview.net/forum?id=HJePRoAct7.

Gao, H., Chen, Y., and Ji, S. Learning graph pooling and hybrid convolutional operations for text representations. preprint, abs/1901.06965, 2019. URL http://arxiv.org/abs/1901.06965.

Gilmer, J., Schoenholz, S. S., Riley, P. F., Vinyals, O., and Dahl, G. E. Neural message passing for quantum chemistry. In ICML 2017. URL http://arxiv.org/abs/1704.01212v2.

Goh, G., Siegel, C., Vishnu, A., Hodas, N., and Baker, N. How much chemistry does a deep neural network need to know to make accurate predictions? In 2018 IEEE Winter Conference on Applications of Computer Vision (WACV), pp. 1340-1349, March 2018. doi: 10.1109/WACV.2018.00151.

Hachmann, J., Olivares-Amaya, R., Atahan-Evrenk, S., Amador-Bedolla, C., S'anchez-Carrera, R. S., Gold-Parker, A., Vogt, L., Brockway, A. M., and Aspuru-Guzik, A. The harvard clean energy project: Large-scale computational screening and design of organic photovoltaics on the world community grid. The Journal of Physical Chemistry Letters, 2(17):2241-2251, aug 2011. doi: 10.1021/jz200866s. URL https://doi.org/10.1021/jz200866s.

Jaeger, S., Fulle, S., and Turk, S. Mol2vec: Unsupervised machine learning approach with chemical intuition. Journal of Chemical Information and Modeling, 58(1):27-35, 2018. doi:10.1021/acs.jcim.7b00616. URL https://doi.org/10.1021/acs.jcim.7b00616. PMID: 29268609.

Li, J., Cai, D., and He, X. Learning graph-level representation for drug discovery. CoRR, abs/1709.03741, 2017a. URL http://arxiv.org/abs/1709.03741.

Li, J., Cai, D., and He, X. Learning graph-level representation for drug discovery. 2017b. URL http://arxiv.org/abs/1709.03741.

Li, Y., Tarlow, D., Brockschmidt, M., and Zemel, R. S. Gated graph sequence neural networks. International Conference on Learning Representations (ICLR), 2016. URL http://arxiv.org/abs/1511.05493.

Lin, H. W., Tegmark, M., and Rolnick, D. Why does deep and cheap learning work so well? Journal of Statistical Physics, 168(6):1223-1247, jul 2017. doi:10.1007/s10955-017-1836-5. URL https://doi.org/10.1007/02Fs10955-017-1836-5.

Lopez, S. A., Sanchez-Lengeling, B., de Goes Soares, J., and Aspuru-Guzik, A. Design principles and top nonfullerene acceptor candidates for organic photovoltaics. Joule, 1(4):857-870, dec 2017. doi: 10.1016/j.joule.2017.10.006. URL https://doi.org/10.1016%2Fj.joule.2017.10.006.

Monti, F., Boscaini, D., Masci, J., Rodol'a, E., Svoboda, J., and Bronstein, M. M. Geometric deep learning on graphs and manifolds using mixture model cnns. IEEE Conference on Computer Vision and Pattern Recognition (CVPR), 2017. URL http://arxiv.org/abs/1611.08402.

Mrowca, D., Zhuang, C., Wang, E., Haber, N., Fei-Fei, L., Tenenbaum, J. B., and Yamins, D. L. K. Flexible neural representation for physics prediction. Advances in Neural Information Processing Systems (NIPS), 31, 2018. URL http://arxiv.org/abs/1806.08047.

Niepert, M., Ahmed, M., and Kutzkov, K. Learning convolutional neural networks for graphs. Proceedings of the International Conference on Machine Learning (ICML), 48, 2016. URL http://arxiv.org/abs/1605.05273.

Scharber, M., Mhlbacher, D., Koppe, M., Denk, P., Waldauf, C., Heeger, A., and Brabec, C. Design rules for donors in bulk-heterojunction solar cells—towards 10% energy-conversion efficiency. Advanced Materials, 18(6):789-794, mar 2006. doi: 10.1002/adma.200501717. URL https://doi.org/10.1002% 2Fadma.200501717.

Shang, C., Liu, Q., Chen, K.-S., Sun, J., Lu, J., Yi, J., and Bi, J. Edge Attention-based Multi-Relational Graph Convolutional Networks. arXiv e-prints, art. arXiv:1802.04944, February 2018. URL https://arxiv.org/pdf/1802.04944v1.pdf Simonovsky, M. and Komodakis, N. Dynamic edge conditioned filters in convolutional neural networks on graphs. 2017 IEEE Conference on Computer Vision and Pattern Recognition (CVPR), pp. 29-38, 2017. URL http://arxiv.org/abs/1704.02901v3.

Urban, G., Subrahmanya, N., and Baldi, P. Inner and outer recursive neural networks for chemoinformatics applications. Journal of Chemical Information and Modeling, 58(2):207-211, 2018. doi: 10.1021/acs.jcim.7b00384. URL https://doi.org/10.1021/acs.jcim.7b00384. PMID: 29320180.

Wu, Z., Ramsundar, B., Feinberg, E. N., Gomes, J., Geniesse, C., Pappu, A. S., Leswing, K., and Pande, V. S. Moleculenet: A benchmark for molecular machine learning. Chemical Science, 2, 2018. URL http://arxiv.org/abs/1703.00564.

Ying, R., You, J., Morris, C., Ren, X., Hamilton, W. L., and Leskovec, J. Hierarchical graph representation learning with differentiable pooling. Advances in Neural Information Processing Systems (NIPS), 31, 2018. URL http://arxiv.org/abs/1806.08804.

Section 4: Graph Featurization and Quantum Chemistry

1. High-Level Overview

According to some, the holy grail of rational drug design would be the advent of large scale quantum computers capable of aiding and guiding scientists at every step in the drug discovery process. These devices would exploit our understanding of quantum mechanics to directly simulate chemical, biochemical, and biological reactions rather than resort to approximations. Since quantum computing in its current form is very much a toy project in its infancy, decades away from any applications, one feels obliged to come up with other strategies in the meantime.

One such strategy involves combining machine learning algorithms with computational chemistry, leveraging recent advances in computational infrastructure. Let us focus on ligand-based drug design in a vacuum for now since structure-based drug design comes with its additional set of complications, assumptions, and approximations. From a physics perspective (In biology, as one goes to larger scales, to cellular scales and beyond, in order to develop fundamental models one needs to understand complex emergent phenomena—in this setting the effectiveness of the thinking proposed here is obscured, which is why the ideas described here are most readily applicable at smaller scales, e.g. at small molecule and protein levels, and for physicochemical properties), the ground state wave function of a molecule in the gas phase contains everything there is to know about that molecule. Feeding molecular wave functions (e.g. their tensor network representations) to a machine learning pipeline makes sense intuitively if the goal is to make the algorithm focus on calculating properties and not on finding the ground state by already providing it with data connected to the ground state wave function. As a midpoint between intractable full many-body wave function descriptions and oversimplified proxies like fingerprints and SMILES strings, we would like to provide algorithms with relevant raw data on correlations and/or electron densities calculated from the wave function using ab initio quantum chemistry methods.

Since machine learning is far from a black box, a delicate balance between letting the algorithm figure out things on its own and steering the learning process by choosing adequate and unbiased representations and features is of paramount importance, especially when the sizes of the datasets are modest.

When we mention the incorporation of quantum chemistry methods, we are talking about the representation/featurisation problem (as opposed to methods used approximate density functional theory (DFT) results like suggested in Google's Neural Message Passing for Quantum Chemistry [Gilmer2017]): how to present the input molecules to a computer, with the most honest representation/featurization being the wave function (or an ensemble of states at finite temperature) and the worst (but most feasible, and often adequate) being oversimplified proxies like fingerprints and SMILES strings.

Since there is more to chemistry than SMILES strings and atom connectivity, one way to improve ad hoc featurization of graph models is by introducing node, edge, or global features derived from approximate molecular wave functions, which supply fine-grained information about the underlying chemistry/physics. This is the basic idea behind Q-gaph. Starting from a molecule's geometry and composition, ab initio quantum chemistry methods try to approximate the molecular wave function in some appropriately chosen orbital basis set. The properties/features we extract from these methods should in some sense be raw, i.e. independent of the method or basis used and as close as possible to the wave function data. The expectation is that this should lead to stronger learning capabilities, better generalization, and improved latent representations without overfitting, which is important for both predictive and generative models.

It is important to stress that the goal in practice is not to obtain the best possible descriptions for every relevant conformation of the molecules in a dataset. That would likely be infeasible for the sizes of the datasets we are interested in. In a realistic setting we need something quick and reasonably accurate to deduce qualitatively correct information about the electronic correlations and (bio) chemically important features, under the implicit assumption that any information on quantum correlations and actual chemistry will be better than just inputting SMILES.

2 Quantum Chemistry 101 (for Physicists)

In this short review, we will focus on ab initio (Density functional theory (DFT) quantum is also sometimes referred to as ab initio even though the approximation of the exchange-correlation functionals of the electron density involve quite a bit of magic. We here focus on ab initio methods based on the molecular wave function) electronic structure of small molecules within the Born-Oppenheimer approximation of the time-independent non-relativistic quantum many-body Schrödinger equation, $$H(R,r)\Psi(R,r) = E(R)\Psi(R,r), \quad (1)$$

with the molecular Hamiltonian $$H(R, r) = -\frac{1}{2}\sum_{i=1}^{N}\nabla_i^2 - \frac{1}{2}\sum_{A=1}^{M}\frac{1}{M_A}\nabla_A^2 - \sum_{i=1}^{N}\sum_{A=1}^{M}\frac{Z_A}{r_{iA}} + \sum_{i=1}^{N}\sum_{j>i}^{N}\frac{1}{r_{ij}} + \sum_{A=1}^{M}\sum_{B>A}^{M}\frac{Z_A Z_B}{R_{AB}}, \quad (2)$$

where $Z_A$, $M_A$, M, and N denote respectively nuclear charges, nuclear masses relative to the electron's mass, the number of nuclei, and the number of electrons. The electronic part of the Schrödinger equation looks like $$H_{elec}(R,r)\chi(R,r) = E_{elec}(R)\chi(R,r) \quad (3)$$

where $$H_{elec}(R, r) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

so that the total energy is simply $$E_{tot} = E_{elec} + E_{nucl}.$$

FIG. 12 reproduces equations (1) to (4).

In practice, one uses a finite set of basis functions to turn the above partial differential equations into algebraic equations amenable to numerical simulation. In electronic structure calculations for condensed-matter physics plane waves are natural whereas in quantum chemistry people are fond of atomic orbitals (Note that basis functions are most often not true atomic orbitals, apart from hydrogen and other one-electron systems. Most basis sets are constructed to model diffusive and polarization contributions). Common basis sets are Gaussian-type orbitals, Slater-type orbitals, or other numerically obtained orbitals. While atomic orbitals contain the electrons of a single atom, molecular orbitals, which surround a number of atoms in a molecule, are said to describe valence electrons shared between atoms. To understand bonding, molecular orbital theory thus approximates the molecular orbitals, which, essentially, correspond to delocalized electrons, as linear combinations of atomic orbitals (LCAO). It is important to remember that molecular orbitals, like much of physics, are just a mathematical constructs whose inferred predicitions approximate reality. They are single-particle wave functions with no real physical meaning in the context of a many-body system. (As one might have already anticipated, the treatment of entanglement in fermionic systems is particularly finicky and subtle. We refer to Ref. [2] for a gentle introduction.)

2.1 Hartree-Fock Method

The Hartree-Fock (HF) method is a variational procedure which approximates energy eigenfunctions of the electronic Schrödinger equation (3) by a single Slater determinant, i.e. an anti-symmetrized product of one-electron wave functions (orbitals), $$\Psi(x_1, x_2, \ldots, x_N) = \frac{1}{\sqrt{N!}}\begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$\equiv |\chi_1, \chi_2, \ldots, \chi_N\rangle, \quad (6)$$

where the $$\chi_i(x), \forall i \in \{1, 2, \ldots N\}$$

are a set of one-electron spin-orbital wave functions. FIG. 13 reproduces equations (5) to (6). These are products of a spatial orbital $\psi_i(r)$ and a spin function $\alpha$ or $\beta$. Note that each electron is actually associated with every orbital (the electrons are indistinguishable) and that the number of electrons N is taken to be equal to the number of orbitals L.

The Fermi correlation due to electron exchange (Pauli exclusion principle) is accounted for via the explicit antisymmetrization. Electrons move independently within molecular orbitals, each of which describes the probability distribution of a single electron. On top of that, the HF approximation also resorts to a mean-field treatment of the interactions among electrons, neglecting the instantaneous electron-electron correlations. Every electron only feels an average contribution of all other electrons.

2.1.1 Self-Consistent Field Algorithm

The starting point of HF calculations is the molecular geometry (3D coordinates) and a finite set of approximate one-electron wave functions (spin-orbitals). For a molecular orbital calculation, the initial one-electron wave functions are typically already a linear combination of atomic orbitals (LCAO). One obtains the optimum set of molecular orbitals by variationally minimizing the energy in what is called a "self-consistent field" or SCF approximation to the many-electron problem. Given a set of molecular orbitals, the energy expectation value is minimized by solving one-particle eigenvalue equations (Hartree-Fock-Roothan generalized eigenvalue equations) for the molecular orbitals. These new eigenfunctions can then be used to recalculate the average field felt by each electron, after which the procedure is repeated until the set of molecular orbitals converges to the so-called Hartree-Fock molecular orbitals.

In practice, there's a number of methods. Restricted Hartree-Fock (RHF) is used for closed-shell molecules at their equilibrium geometry, where electrons occupy orbitals in pairs. Restricted open-shell Hartree-Fock (ROHF) is used for open-shell molecules where the spin parts α and β of the orbitals are constrained to be identical, leading to proper eigenfunctions of the total spin operator but lacking a unique set of molecular orbitals since the form of the Fock matrix is often not unique. Unrestricted Hartree-Fock (UHF) is used for open-shell molecules and uses different molecular orbitals for the α and β electrons, leading a ground state which can be contaminated by excited states since spin is not conserved.

2.1.2 Hartree-Fock Wave Functions

Since the HF algorithm is variational, the HF energy is an upper bound to the true ground state energy of a given molecule, corresponding to the minimal energy for a single Slater determinant. The best possible solution in the HF setting is called the HF limit, where the basis set approaches completeness. On the other hand, dropping the HF approximations of a single Slater determinant and mean-field interactions, we arrive at the full-CI (configuration interaction) limit, which corresponds to the exact solution in a particular basis set up to the Born-Oppenheimer approximation. The exact-CI solution would correspond to doing full-CI in a complete basis set. The energy difference between the HF solution and the exact ground state is sometimes called the electron correlation energy.

The exact ground state corresponding to the full-CI limit will be important to connect quantum chemistry methods to tensor networks (see Sec. D.2 below).

In physics, we would call the wave function obtained from Hartree-Fock a mean-field solution. The probability P(r1; r2) of finding an electron at r1 and r2 is not simply p(r1)p(r2). To deal with this weakness, a lot of post-Hartree-Fock methods have been devised, correcting for the neglected electron-electron correlation in different ways. Still, because HF is so cheap and often qualitatively correct in that it accounts for more than 99% of the total energy, many types of calculations are initialized with a HF calculation. However, since energy differences are often more relevant than absolute energies, the small fraction due to electron correlation can be decisive for the relevant chemistry.

2.2 Post-Hartree-Fock Methods

In general, the exact ground state wave function of the electronic Hamiltonian Eq. (4) entails a superposition of all possible distributions of N electrons over L orbitals, i.e. a linear combination over all possible Slater determinants, which blows up factorially. In this sense, HF boils down to the simplest possible approximation by picking only a single Slater determinant. The occupancy of the HF orbitals is fixed: occupied orbitals are filled with probability 1 and virtual orbitals are empty with probability 1. Post-Hartree-Fock methods improve upon the HF-SCF method by adding the effects of electron correlation, which HF completely neglects apart from the exchange energy resulting from the explicit anti-symmetrization of the wave function. Note that there are many more post-Hartree-Fock methods than the ones we will mention below, including subtle variations and combinations with other methods.

2.2 Post-Hartree-Fock Methods

In general, the exact ground state wave function of the electronic Hamiltonian Eq. (4) entails a superposition of all possible distributions of N electrons over L orbitals, i.e. a linear combination over all possible Slater determinants, which blows up factorially. In this sense, HF boils down to the simplest possible approximation by picking only a single Slater determinant. The occupancy of the HF orbitals is fixed: occupied orbitals are filled with probability 1 and virtual orbitals are empty with probability 1.

Post-Hartree-Fock methods improve upon the HF-SCF method by adding the effects of electron correlation, which HF completely neglects apart from the exchange energy resulting from the explicit anti-symmetrization of the wave function. Note that there are many more post-Hartree-Fock methods than the ones we will mention below, including subtle variations and combinations with other methods.

2.2.1 General Overview

Figure 14:
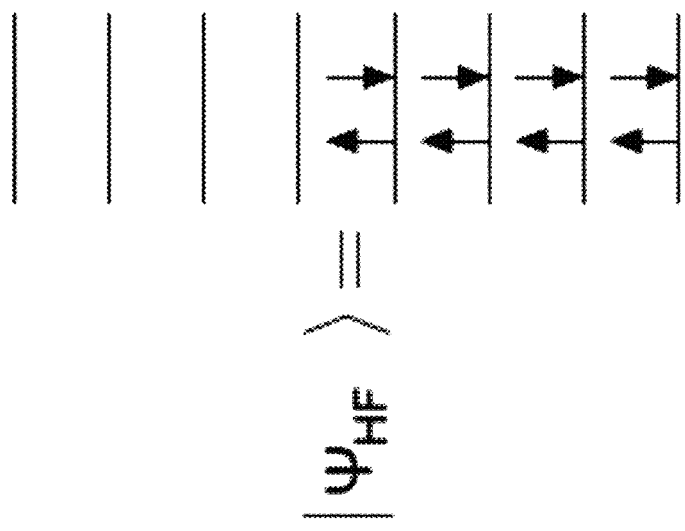
FIG. 14 shows equation (7) of Section 4.

In second quantization (Fock space), orbitals are either doubly, singly, or unoccupied by an electron. Following Ref. [3], we can conceptually regard Hartree-Fock with mostly paired electrons as optimizing occupied (red) and virtual (blue) orbital spaces such that the energy expectation value is minimized (also shown in FIG. 14):

The configuration interaction (CI) method is a post-Hartree-Fock variational method which accounts for electron correlation by using a variational wave function that is a linear combination of configuration state functions (CSFs—configuration state function is a symmetry-adapted linear combination of Slater determinants) built from spin orbitals:

$$|\Psi_{CI}\rangle = (1+T_1+T_2+\ldots)|\Psi_{HF}\rangle. \tag{9}$$

FIG. 15 reproduces (8) to (9).

The first term in the expansion is usually the HF determinant $|\Psi_{HF}\rangle$ and this reference state is assumed to be qualitatively correct and dominant. If the expansion includes all possible CSFs of the appropriate symmetry by exciting all possible electrons to all possible virtual orbitals, then this is a full configuration interaction (full-CI) procedure which exactly solves the electronic Schrödinger equation within the space spanned by the one-particle basis set. Usually though, the series is truncated to single and double excitations, leading to problems with size-consistency (i.e. energies of two systems A and B of a combined system AB with A and B far apart should satisfy E(AB)=E(A)+E(B)). Other methods like coupled cluster (CC) use an exponential trial wave function (also shown in FIG. 15):

$$|\Psi_{CC}\rangle = e^{T_1+T_2+\ldots}|\Psi_{HF}\rangle \tag{10}$$

as an ansatz, which is size-consistent. On the other hand, coupled cluster is not variational.

In practice that doesn't really matter though, since, for properties such as energy, it is known how to truncate the ansatz when examining expectation values. The gold standard of quantum chemistry is often said to be CCSD(T), i.e. coupled cluster which includes singles, doubles, and perturbative triples corrections. Recent advances to improve computational costs of CCSD(T) and to counter the requirements for large basis sets have led to the development of DLPNO-CCSD(T) methods [4, 5], which exploit locality of correlations using strong pair approximations and pair natural orbitals. For nearly degenerate states contributing to the ground state Eq. (8) one should use multi-configurational self-consistent field (MC-SCF) methods (see Sec. 2.2.3). In that case, the Hartree-Fock determinant reference state is qualitatively wrong, since the weight jC0j is not dominant, and so are the resulting CI wave functions and energies. This can happen when the ground state is strongly-correlated and static correlations have to be taken into account.

2.2.2 Static and Dynamic Correlations

Figure 16:
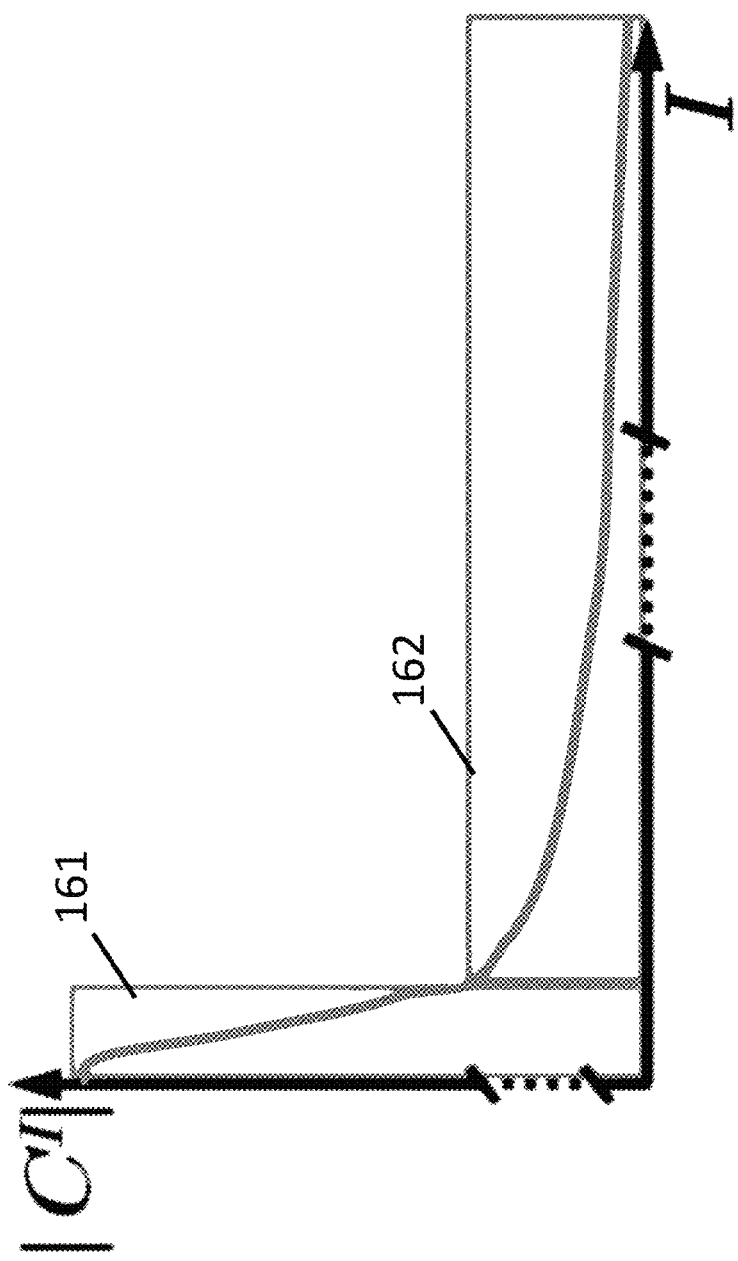
FIG. 16 shows a sketch of configurations and weights in a wave function expansion.

FIG. 16 shows a sketch of configurations and weights in a wave function expansion [6]. The box 161 corresponds to static correlations (moderate number of determinants of large weight contribute), and the box 162 to dynamic correlations (lots of weak excitations contribute).

Electron correlations are often rather artificially divided into two contributions: static and dynamic correlations. The former corresponds to configurations which are nearly degenerate with respect to the reference Slater determinant, while the latter arises from the need of mixing the Hartree-Fock state with a bunch of higher-order excited states. In systems with (strong) static correlation the wave function is said to differ qualitatively from the reference Slater determinant, while strong dynamic correlation implies a wave function which includes a large number of excited determinants, all with comparable, small yet important occupations. An example of a method that recovers primarily dynamic correlation is Møller-Plesset perturbation theory (MPn), while multiconfigurational self-consistent field (MC-SCF) methods primarily take care of static correlations. It is almost impossible to keep dynamic and static correlation effects rigorously separated since, from a physical point of view, they both arise from the very same interactions.

Dynamic correlation can be captured with ab initio post-Hartree-Fock methods. These start from the optimized HF orbitals and the corresponding Slater determinant and build in dynamic correlation on top of that single reference state. Examples include the aforementioned MPn perturbation theory, the configuration interaction (CI) expansion, and coupled cluster (CC) theory. Because these post-Hartree-Fock methods start from a single Slater determinant reference, they have difficulty building in static correlation. It is therefore better to resort to multi-configurational self-consistent field (MC-SCF) methods for systems with pronounced static correlation, e.g. for molecular ground states which are quasi-degenerate with low-lying excited states or in bond breaking situations.

2.2.3 Multi-Configurational Methods

Figure 17:
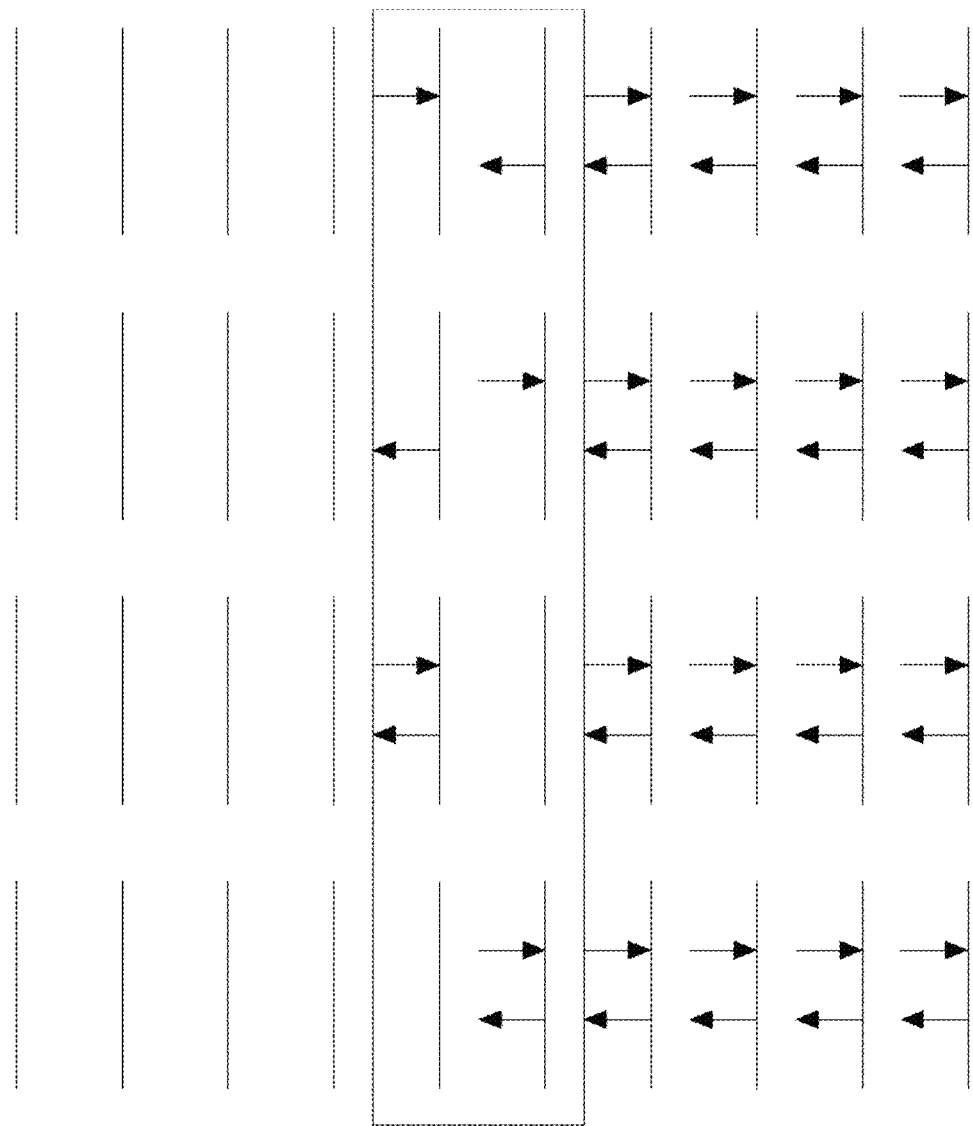
FIG. 17 shows a representation of a MC-SCF approach.

Multi-configurational self-consistent field (MC-SCF) methods come into play when a single electron configuration does no longer provide an adequate description of the electronic structure. An important MC-SCF approach is the complete active space SCF (CAS-SCF) method which can be used to obtain an approximation of the static correlation. In this framework, orbitals can be classified as either occupied (always containing two electrons), active (partially occupied and relevant for the chemistry), and virtual (always empty). See FIG. 17 for an intuitive representation.

From a HF solution, a subset of occupied and virtual orbitals is selected to act as active space. The remaining occupied and virtual orbitals are kept frozen at HF level and the electronic structure in the active space is solved for exactly. The notation CAS(N,L) refers to an active space containing N electrons distributed between all configurations that can be constructed from L molecular orbitals. A CAS-SCF simulation is a two-step process where the energy can be iteratively minimized by doing a full-CI calculation only in the active space (CAS-CI). That information is then used to rotate the occupied and active orbital spaces to minimize the energy even further. Because the many-body Hilbert space grows exponentially with the number of single-particle states, only small active spaces up to 18 electrons in 18 orbitals can be treated with CAS-CI (cf. exact diagonalization). Dynamic correlation is usually small and can be recovered with good accuracy by means of (computationally expensive) perturbative methods on top of the CAS solution which should contain the proper static correlation.

2.2.4 Single-Reference Methods, Multi-Reference Methods, and Jiggly Atoms

When not only the ground state is of importance, as is almost always the case in chemistry, the results of single-reference methods can become particularly tricky to interpret. Different regions of a molecular potential energy surface (PES), which can be parametrized by the coordinates of the nuclei of the jiggly atoms, are often dominated by different determinants. This means that an expansion based on the dominant Slater at one conformation can result in a poor description of the wave function at other conformations. Additionally, let us repeat that the dominant reference function for one electronic state is often not appropriate for describing other electronic (excited) states, even at the same PES point.

2.3 Remarks on Density Matrices, Orbitals, and Wave Functions

2.3.1 Density Matrices

Density matrices are fundamental objects in quantum mechanics. To avoid confusion with the notion of a density matrix as used by physicists, let us explicitly state what is meant by the term in quantum chemistry and electronic structure calculations. In particular, the N-particle density matrix refers to $$\rho = |\Psi(x_1, x_2, \ldots, x_N)\rangle \langle \Psi(x_1, x_2, \ldots, x_N)|, \quad (11)$$

which specifies everything there is to know about the wave function of the system since it gives the probability of the state with a given set of coordinates xi (space and spin) for all electrons in the system. Since most physical operators are not N-electron operators (e.g. the kinetic energy operator is a one-electron operator and the Coulomb interaction is a two-electron operator), we do not require the full N-particle density matrix to calculate energies and local properties. If we trace out all coordinates except for x1, we arrive at the one-particle reduced density matrix (1PDM, ODM, 1RDM, ...)

$$\rho^{(1)}(x_1, x_1') = N \int \Psi^*(x_1', x_2, \ldots, x_N) \Psi(x_1, x_2, \ldots, x_N) dx_2 \ldots dx_N. \quad (12)$$

which is a generalization of the one-electron density $$\rho^{(1)}(x_1) = N \int \Psi^*(x_1, x_2, \ldots, x_N) \Psi(x_1, x_2, \ldots, x_N) dx_2 \ldots dx_N. \quad (13)$$

Integrating the one-electron density over the spin of the first electron yields the following spin-free first-order reduced density matrix, $$\rho^{(1)}(r_1) = \int \rho^{(1)}(r_1; s_1) ds_1. \quad (14)$$

Similarly, we can also define a two-particle reduced density matrix $$\rho^{(2)}(x_1, x_2; x_1', x_2') = N(N-1) \int \Psi^*(x_1', x_2', \ldots, x_N) \Psi(x_1, x_2, \ldots, x_N) dx_3 \ldots dx_N. \quad (15)$$

which is a generalization of the two-electron density $$\rho^{(2)}(x_1, x_2) = N(N-1) \int \Psi^*(x_1, x_2, \ldots, x_N) \Psi(x_1, x_2, \ldots, x_N) dx_3 \ldots dx_N. \quad (16)$$

FIG. 18 reproduces equations (11) to (16).

Determining the one- and two-particle RDMs is enough for the electronic structure problem. In the Hartree-Fock approximation, the one-particle RDM is enough since the two-particle, three-particle, ... density matrices can all be expressed in terms of direct products of the one-particle RDM. For correlated methods however, the $\rho^{(i)}$ density matrices have to be determined separately.

2.3.2 Wave Functions and Relaxed Density Matrices

For wave functions which are exact solutions of the Schrödinger equation, obtaining one-particle RDMs boils down to a pretty straightforward application of quantum mechanics. But quantum chemistry uses incomplete basis sets and a whole host of approximations. Computational methods like HF, CI, MC-SCF, and QC-DMRG do have approximate wave functions associated to them in the sense that their expressions for the energy correspond to the expectation value of the Hamiltonian operator calculated using those approximate wave functions. The one-particle RDM derived from these approximate wave function methods is well-defined and the expectation value of any one-electron property is simply the trace of the density matrix multiplied by the operator representing that property.

However, it is important to stress that other methods (like DFT, MPn, and CC) do not have wave functions at all, not even approximate ones. What this means is that the approximate "wave function" simply does not exist (like in DFT where the quantity of interest is an effective density), or that the energy evaluated in these methods using the corresponding approximate "wave function" does not at all correspond to the expectation value of the Hamiltonian using this same "wave function" (like in MPn and CC methods) [7]. To appreciate this, let us define a response-type density matrix D, defined such that the derivative of the energy E with respect to any one-electron perturbation is xV is E'=Tr(DV); which leads to identical results for methods which optimize the energy with respect to the wave function in terms of molecular orbitals (HF, MCSCF, full-CI). For other approaches solutions, they can differ and one can define both expectation-value and response-type density matrices with different properties. Calculating quantities like dipole moments then gives two different answers for the two kinds of density matrices, namely the expectation value of the dipole operator and the derivative of the energy with respect to the applied electric field (the conjugate operator). The response-type density matrix is often called the relaxed density matrix and does not require a wave function to be defined. For methods without an approximate wave function, one can still construct approximations to the expectation value density matrix, which are then called unrelaxed densities.

2.3.3 Natural Orbitals

The one-particle RDM Eq. (12) can be written in terms of a complete set of spin orbitals $$\rho^{(1)}(x_1, x_1') = \sum_{i,j} \rho_{ij}^{(1)} \phi_i(x_1) \phi_j^*(x_1'). \tag{17}$$

The diagonal elements $\rho_{ii}^{(1)}$ are called orbital occupation numbers. Since a unitary transformation on the set of spin-orbitals leaves the wave function invariant, the matrix $\rho_{ij}^{(1)}$ can be transformed into diagonal form with diagonal elements $0 \leq n_i \leq 1$ corresponding to the occupation numbers of the natural spin-orbitals (NSOs), satisfying $\Sigma_i n_i = N$. The one-particle RDM then becomes $$\rho^{(1)}(x_1, x_1') = \sum_i n_i \phi_i^{NSO}(x_1) \phi_j^{*NSO}(x_1'). \tag{18}$$

Diagonalizing the spin-free first-order RDM yields so-called natural orbitals (NOs), which constitute an orthonormal set of eigenorbitals intrinsic to the N-electron wave function, $$P^{(1)}(r_1, r_1') = \sum_i n_i \phi_i^{NO}(r_1) \phi_j^{*NO}(r_1'). \tag{19}$$

where now $0 \leq n_i \leq 2$. Note that natural orbitals can be generically delocalized.

FIG. 19 reproduces equations (17) to (19).

2.3.4 Orbital Localization

For a given system, the electronic wave function is a vector in the quantum many-body Hilbert space, satisfying the Schrödinger equation Eq. (3). Let us stress again that molecular orbitals are completely fictitious constructs used to piece together a wave function of the molecule. Similarly, atomic orbitals are used merely because they are computationally efficient in trying to construct the molecular orbitals. As we have seen above, solving an energy eigenvalue equation using a set of basis orbitals yields so-called canonical molecular orbitals (CMOs), which represent specific electrons (since they are one-particle wave functions) and can generically be completely delocalized over the entire molecule. One can also consider localized molecular orbitals (LMOs), which are concentrated in a limited spatial region of a molecule and relate MO calculations back to "classical" theories of chemical bonding. These LMOs are obtained from a unitary transformation on a set of delocalized orbitals by optimizing the expectation value of some operator. For closed-shell molecules, the localized and delocalized orbital descriptions are equivalent and represent the same physical state. Different prescriptions (e.g. Foster-Boys, Edmiston-Ruedenberg, Pipek-Mezey) optimize different quantitities and can thus lead to different localized orbitals (these can all be used in the construction of Q-graph representations). This observation underscores the arbitrariness of rotating molecular orbitals and the care which should be taken when attributing any significance to them.

2.3.5 Natural Bond Orbitals (NBOs)

Another approach to localization of molecular orbitals is given by natural bond orbitals (NBOs) which are said to stay closer to the historical picture of chemical bonding by piecing together the wave function in terms of its constituent atomic parts. Given the one-particle RDM, these orbitals are constructed to have maximum electron density in localized regions, corresponding to the best possible Lewis structure, and are part of a sequence of orbital sets related by similarity/unitary transformations $$\text{Atomic orbital} \rightarrow \text{NAO} \rightarrow \text{NHO} \rightarrow \text{NBO} \rightarrow \text{NLMO} \rightarrow \text{Molecular orbital} \tag{20}$$

which includes natural atomic orbitals (NAO), natural hybrid orbitals (NHO), natural bonding orbitals (NBO) and natural (semi-)localized molecular orbitals (NLMO). These natural localized sets of orbitals are in between atomic orbitals and molecular orbitals. Natural atomic orbitals (NAOs) correspond to the effective natural orbitals of an atom in the molecular environment, with core and valence-shell NAOs having significant occupancies. Natural bond orbitals (NBOs) are optimized linear combinations of NAOs which attempt to give the best possible valence bond-type description of the wave function. They are said to be insensitive to variations of basis sets or approximation methods and to reflect the character of the wave function. Finally, the natural localized molecular orbitals (NLMOs) are LMOs which are obtained by optimizing for minimal delocalization of NBOs, to be contrasted with the localization procedures of the previous section which all start from the (delocalized) MOs. An extensive discussion on NBOs and their usage can be found on the website of the proprietary NBO 6.0 software. The free package JANPA can construct natural atomic orbitals (NAOs) but no NHOs or NBOs.

FIG. 20 shows a Morphine molecule (left) with relief map of electron density in the plane of the aromatic ring (right). The local maxima at the nuclei (truncated at $\rho(r)=1$ a.u.) are clearly visible [11].

2.3.6 Quantum Theory of Atoms in Molecules (QTAIM)

The quantum theory of atoms in molecules (QTAIM) by Bader and coworkers [9, 8, 10] uses the electron density $\rho(r)$ (obtained either from measurements or quantum chemistry calculations) to try to address the observation that some properties attributed to atoms and functional groups are transferable from one molecule to another [11]. It defines atoms and bonding in molecules using the topology of the electron density, which is dominated by the electron-nuclear force causing the electron density $\rho(r)$ to exhibit maxima at the nuclear positions. This topology provides the physical basis for QTAIM's partitioning of space into atomic regions. The connectivity of the atomic regions is defined by lines of maximum density linking neighbouring atoms (bond paths). The collection of bond paths linking the nuclei of bonded atoms in an equilibrium geometry, with the associated critical points, is known as the molecular graph [11].

A critical point in the electron density satisfies $\nabla \rho(r))=0$, with the nuclear critical points being ill-defined and leading to cusps. To discriminate between local maxima, minima, or saddle points, the real and symmetric Hessian derivative can be calculated and diagonalized to yield the curvatures $\lambda_1$, $\lambda_2$, and $\lambda_3$. The trace of the Hessian is the Laplacian $\nabla^2 \rho(r) = \lambda_1 + \lambda_2 + \lambda_3$ and is invariant to rotations of the coordinate system. Familiar differential geometry analysis predicts the critical point to be stable if all eigenvalues are non-zero (rank!=3) and further classifies them according to their signature (sigma), which is the sum of the signs of the eigenvalues:

(3;−3): three negative curvatures, p local maximum (nuclear critical point)

(3;−1): two negative curvatures, p maximum in plane and minimum along third perpendicular axis (bond critical point)

(3; 1): two positive curvatures, p minimum in plane and maximum along third perpendicular axis (ring critical point)

(3; 3): three positive curvatures, p local minimum (cage critical point)

The surface bounding an atom in a molecule is one of zero flux in the gradient vector field of the electron density, $$\nabla \rho(r) \cdot n(r) = 0, \quad (21)$$

for all positions r belonging to the surface where n(r) is the normal to the surface. This procedure divides the molecule in atomic basins where the nuclei act as attractors in the sense of dynamical systems. Consequently, the expectation value of an operator averaged over all space is then given by the sum of the expectation values of this operator averaged over all the atoms in the molecule ("atomic additivity"). Note that the partitioning used in QTAIM is in real space rather than in the abstract Hilbert space where the orbital basis set lives.

FIG. 19 reproduces equation (21).

Using the QTAIM formalism, dozens of atomic and bonding descriptors can be defined (see Ref. [11] for a non-exhaustive list). For our graph purposes, the electron localization and delocalization indices (number of electrons localized within a given atom and the number of electron delocalized between two atoms) might prove useful. These features can be obtained from integrals over the exchange-correlation part of the pair density over the atomic basins [11, 13, 15, 14, 12]. The group of Popelier in Manchester has used some of the QTAIM bonding descriptors for force fields and QSAR models for rational drug design. Some freely available software includes DGrid and Multiwfn.

Figure 21:
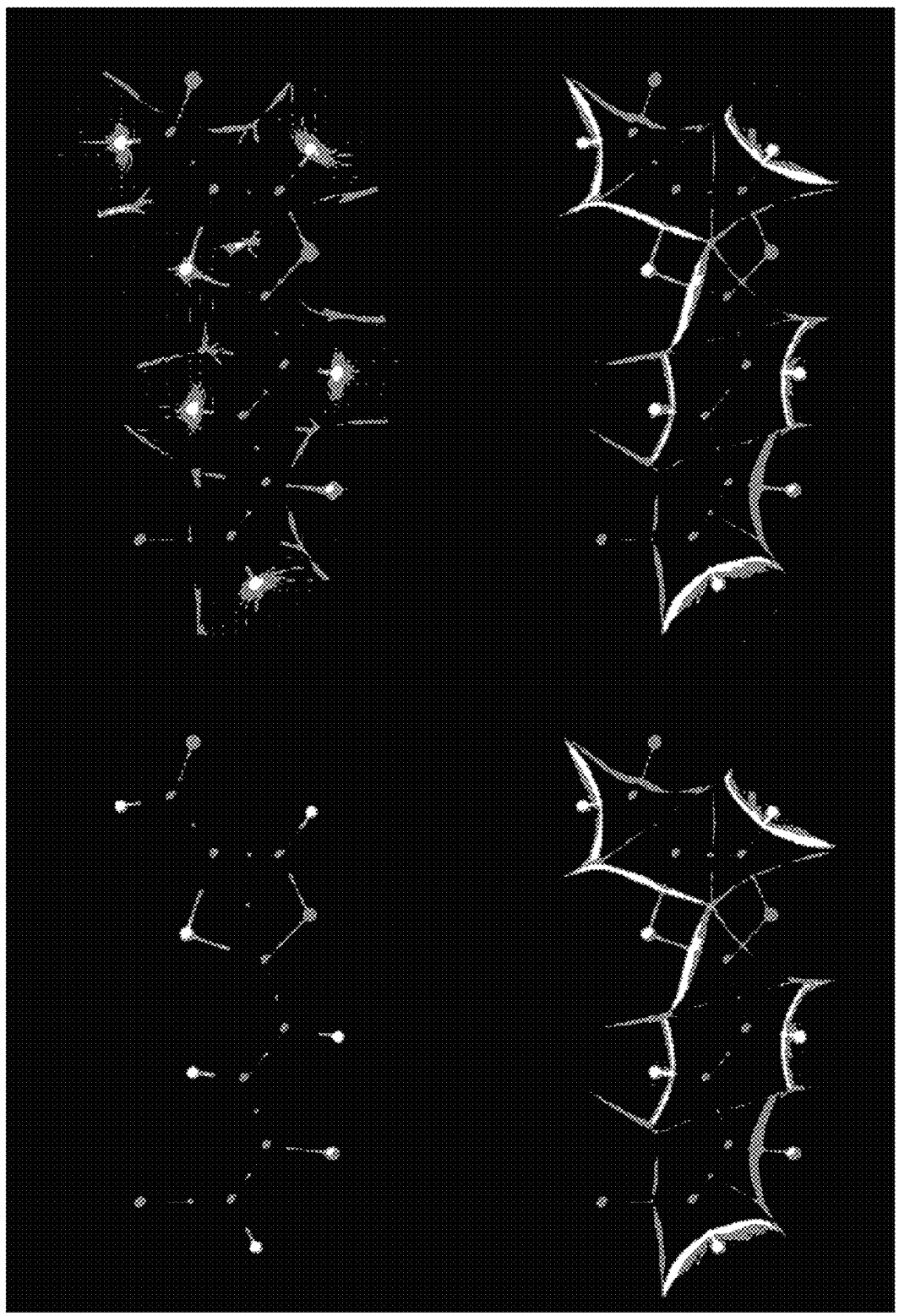
FIG. 21 shows a representation of bond and ring critical points for 5-formyl-2-(3-fluoro-4-bromobutadienyl)thiazole together with gradient field of electron density and the partitioning of real-space into atomic basins.

FIG. 21 shows a representation of bond (green) and ring (red) critical points for 5-formyl-2-(3-fluoro-4-bromobutadienyl)thiazole together with gradient field of electron density and the partitioning of real-space into atomic basins. From the website of the commercial AIMALL software.

2.3.7 NBO Vs. QTAIM

While NBO and QTAIM can provide valuable chemical insight based on respectively the one-particle RDM and the electron density, there is no "better" method and one will never obtain a complete picture by looking at properties of either of these methods. There are lots of articles in the literature defending either NBO or QTAIM as the ultimate diagnostic tool, but, from a physics perspective, both methods can be considered part of the many attempts to fit results from intrinsically quantum mechanical calculations to classical intuition. This is clearly not on exact approach, but is often useful for practical purposes to bridge the gap to machine learning models for molecules defined on graphs (see Sec. 3 below).

3. Enhancing Molecular Graph Models

Just as much as the mathematical description of a molecule is not a SMILES string, it is also not a 2D ball-and-stick graph with individual atoms connected by bonds. Even though chemical bonds are a massively useful approximation, one should keep in mind that feeding bond features (single, double, aromatic, . . . ) into machine learning models might not be the best approach if one wants the model to learn chemistry and functional groups instead of simplified grammar tailored to human intuition. Indeed, there exists no such thing as a single, double, triple, or aromatic bond from a physics perspective; electrons are just more or less likely to be found at a certain location. In particular, the approach breaks down for highly entangled states, such as for transition states in chemical or biological processes (enzyme reactions), or in e.g. metalloproteins.

One application is to enhance molecular graphs for deep learning models with features derived from ab initio quantum chemistry simulations. Rather than familiar molecular descriptors, these features ought to be sufficiently indicative of the electronic correlations and serve as a proxy for the information contained in the wave function. Localized features then facilitate the transformation to atoms (nodes) and bonds (edges) and could be incorporated in the feature vectors of existing graph models. Delocalized features can also be incorporated into a Q-graph, for example a fully connected one, but might be handled more naturally by generalizing graph models to include additional structure. Possible strategies to do so are discussed in Sec.4.1.

3.1 Q-Graph: Electron Density Descriptors 3.1.1 Covalent Interactions: Chemical Bonding A first step would be to change the familiar bond features on the graph's edges to slightly more sophisticated coarse-grained features resulting from a QTAIM analysis, which are based on the electron density $$\rho(r) = \sum_i n_i |\phi_i(r)|^2 = \sum_i n_i \left| \sum_j C_{j,i} \chi_j(r) \right|^2 \quad (22)$$

where $n_i$ is the occupation number of molecular orbital $\phi_i$, $\chi_j$ the basis set functions and C the coefficient matrix of the expansion coefficients of the orbitals in terms of basis functions.

Lots of QTAIM descriptors for biophysical properties and characteristics are enumerated in the review Ref. [12]. In particular, the Localization/Delocalization Indices [11, 13, 15, 14, 12] look very relevant for an immediate translation of electron density information to node/bond features, which can be fed to existing graph convolutional networks.

Derivation DLI/LI (Excerpts from the Multiwfn Manual)

The pair density is defined as $$\pi(r_1, r_2) = N(N-1) \int \int \ldots |\Psi(x_1, x_2, \ldots r_N)|^2 d\sigma_1 d\sigma_2 dx_3 x_4 \ldots x_N \quad (23)$$

where $x=(r;\sigma)$ groups spatial coordinates and spin. The pair density can be rewritten as a sum of an correlated part and a correction term accounting for electron interactions, the exchange-correlation density, $$\pi^{\sigma_1 \sigma_2}(r_1, r_2) = \rho^{\sigma_1}(r_1)\rho^{\sigma_2}(r_2) + \Gamma_{XC}^{\sigma_1 \sigma_2}(r_1, r_2). \quad (24)$$

The total exchange-correlation density for an electron with spin a, irrespective of the spin of the other electron, can be defined as $$\Gamma_{XC}^{\alpha, tot}(r_1, r_2) = \Gamma_{XC}^{\sigma\alpha}(r_1, r_2) + \Gamma_{XC}^{\sigma\beta}(r_1, r_2). \quad (25)$$

For single-determinant wave functions (e.g. Hartree-Fock), the exchange-correlation density for an a electron can be explictly written as $$\Gamma_{XC}^{\alpha, tot}(r_1, r_2) = \Gamma_{XC}^{\alpha\alpha}(r_1, r_2) = -\sum_{i\in\alpha}\sum_{i\in a}\phi_i^*(r_1)\phi_j^*(r_2)\phi_i(r_1)\phi_j(r_2) \quad (26)$$

FIG. 22 reproduces equations (22) to (26).

Where the summation runs over the respective occupied α-spin orbitals. The same expression holds for the β-spin. The cross terms αβ and βα are zero for single-determinant wave functions.

For post-HF wave functions, the two-particle RDM is required which is a notoriously hard/expensive quantity to calculate using ab initio quantum chemistry methods. For this reason, we will evaluate it approximately using natural orbitals (This approximation is not unique (J. Chem. Theory Comput., 6, 2736). Following (Phys. Lett., 105A, 446, also see Mol. Phys., 100, 401), we use $$\Gamma_{XC}^{\alpha, tot}(r_1, r_2) \approx -\sum_{i\in\alpha}\sum_{j\in\alpha}\sqrt{\eta_i\eta_j}\,\phi_i^*(r_1)\phi_j^*(r_2)\phi_i(r_1)\phi_j(r_2) \quad (27)$$

For single-determinant wave functions, the occupations $\eta_i$; $\eta_j$ are binary (0 or 1) so Eq. (26) is recovered with the sum running over the occupied orbitals.

Let us now introduce the notation $A \in \{1, 2, \ldots, N_{atoms}\}$ to label the atoms in a particular molecule. We can then define eighted overlap integrals over space for a particular function P(r), $$I_{AB} = \int w_A(r) w_B(r) P(r) dr, \quad (28)$$

by specifying the weight functions $w_A(r)$ and $w_B(r)$. Let $\Omega_A$ denote the real-space volume surrounding atom A, which we here take to correspond to the volume given by the basin of attraction of the atom obtained from a QTAIM analysis of the electron density. Then the weight function is simply $$w_A(r) = 1 \text{ if } r \in \Omega_A. \quad (29)$$

$$w_A(r) = 0 \text{ if } r \notin \Omega_A. \quad (30)$$

and similar for B. Basically, the QTAIM basins correspond to a discrete partition method where every point is wholly associated to one or the other atom. Fuzzy partition methods (Hirshfeld, Hirshfeld-I, Becke, . . . ) on the other hand, partition molecular space contiguously, so that atomic spaces overlap with each other and any point may be simultaneously attributed to many atoms, with weights normalized to unity, $$0 \leq w_A(r) \leq 1, \forall A \in \{1, 2, \ldots, N_{atoms}\}, \quad (31)$$

$$\sum_B w_B(r) = 1, \quad (32)$$

The most significant advantage of fuzzy partition schemes is that the integration of real-space functions in fuzzy atomic space is much cheaper than in discrete atomic space since no QTAIM analysis is needed. The weight functions are determined from pre-calculated, free atomic densities, similar to promolecular approximations for weak interactions (see later on).

One more ingredient: the atomic overlap matrix (AOM) for molecular orbitals or natural orbitals in atomic spaces has elements $$S_{ij}(\Omega) = \int_\Omega dr \phi_i(r)\phi_j(r). \quad (33)$$

FIG. 23 reproduces equations (27) to (33).

where i,j are orbital indices. Due to the orthonormality of the orbitals in the whole space, the sum of all AOMs, which corresponds to integrating over all of space, should yield an identity matrix. The deviation of this sum from the identity can be used as an error measure for the numerical integration, $$\epsilon = \frac{\sum_{k,j}\left(\left[\sum_A S(\Omega_A)\right]_{ij} - 1_{ij}\right)}{N_{atoms}} \quad (34)$$

The delocalization index corresponding to spin-α electrons which are "shared" (delocalized) between the real-space volumes $\Omega_A$ and $\Omega_B$ surrounding respectively atoms A and B is then defined by $$DLI^\alpha(\Omega_A \to \Omega_B) = -\int_{\Omega_A}\int_{\Omega_B}\Gamma_{XC}^{\alpha, tot}(r_1, r_2) dr_1 dr_2 \quad (35)$$

For A↔B the integral obviously yields the same value, so we define the delocalization index as $$DLI^\alpha(\Omega_A, \Omega_B) = DLI^\alpha(\Omega_A \to \Omega_B) + DLI^\alpha(\Omega_B \to \Omega_A) = -2\int_{\Omega_A}\int_{\Omega_B}\Gamma_{XC}^{\alpha, tot}(r_1, r_2) dr_1 dr_2 \quad (36)$$

The localization indices measure the number of electrons localized in the neighbourhood of each atom, $$LI^\alpha(\Omega_A) = -\int_{\Omega_A}\int_{\Omega_A}\Gamma_{XC}^{\alpha, tot}(r_1, r_2) dr_1 dr_2 = DLI^\alpha(\Omega_A, \Omega_A)/2. \quad (37)$$

FIG. 24 reproduces equations (34) to (37).

Physically, the (de)localization indices are related to the number of α-electrons $N_{\Omega_A}^\alpha$ in real-space volume surrounding atom A, $$N^{\alpha}_{\Omega_A} = LI^{\alpha}(\Omega_A) + \frac{1}{2}\sum_{B \neq A} DLI^{\alpha}(\Omega_A, \Omega_B) \quad (38)$$

$$= LI^{\alpha}(\Omega_A) + \sum_{B \neq A} DLI^{\alpha}(\Omega_A \to \Omega_B) \quad (39)$$

$$= -\int_{\Omega_A}\int \Gamma^{\alpha,tot}_{XC}(r_1, r_2) dr_1 dr_2 = \int_{\Omega_A} \rho^{\alpha}(r) dr \quad (40)$$

The total DLI and LI are obtained by summing α and β contributions. In the closed-shell case these two contributions are equal, so that we find $$DLI(\Omega_A, \Omega_B) = 2\sum_i \sum_j \sqrt{\eta_i \eta_j}\, S_{ij}(\Omega_A) S_{ij}(\Omega_B), \quad (41)$$

$$LI(\Omega_A) = \sum_i \sum_j \sqrt{\eta_i \eta_j}\, S_{ij}(\Omega_A) S_{ij}(\Omega_A), \quad (42)$$

FIG. 25 reproduces equations (38) to (42).

For a comparison of localization and delocalization indices obtained with Hartree-Fock, density functional theory, and conventional post-HF methods, see Refs. [15, 16]; the conclusion is that these descriptors are quite robust and do not strongly depend on the method/basis used. These descriptors have up to now only been fed into QSARlike models [18, 17], which most likely do not rely on graph-based machine learning, rendering this a novel approach worthwhile of consideration.

Figure 26:
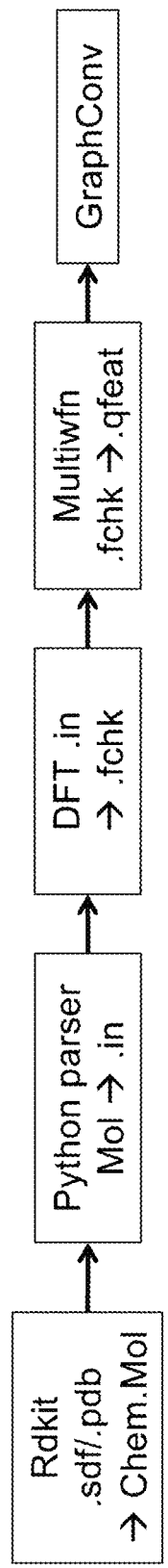
FIG. 26 shows a workflow with a collection of Python and bash scripts direct

A collection of Python and bash scripts direct the following high-level workflow as shown in FIG. 26 where the geometry is first extracted from the .sdf/.pdb file and placed inside an .in input file for ORCA/Psi4, which configures the options of the simulation. Then ORCA/Psi4 runs the specified calculations and spits out a .out log file together with the wave function data in Gaussian checkpoint.fchk format. This data is piped to Multiwfn which calculates the localization indices (a number for the basin around each atom in QTAIM language) and delocalization indices (a symmetric matrix with edge features for the fully-connected graph, the dominant contributions corresponding to the "actual" bonds of the molecular graph, as we will see below).

The final output for every valid molecule is
a number for every node (localization index of the atom/attractor)
a number for every bond (delocalization indices between atoms/attractors)

For more details on the workflow, we refer to the "Appendix G: QTAIM code".

Example 1: Artificial Molecule gdb_34775 from QM9 Dataset

Plotting the calculated delocalization indices versus the adjacency matrix of the rdkit Chem. Mol object for FIG. 27 gives FIG. 28.

Figure 27:
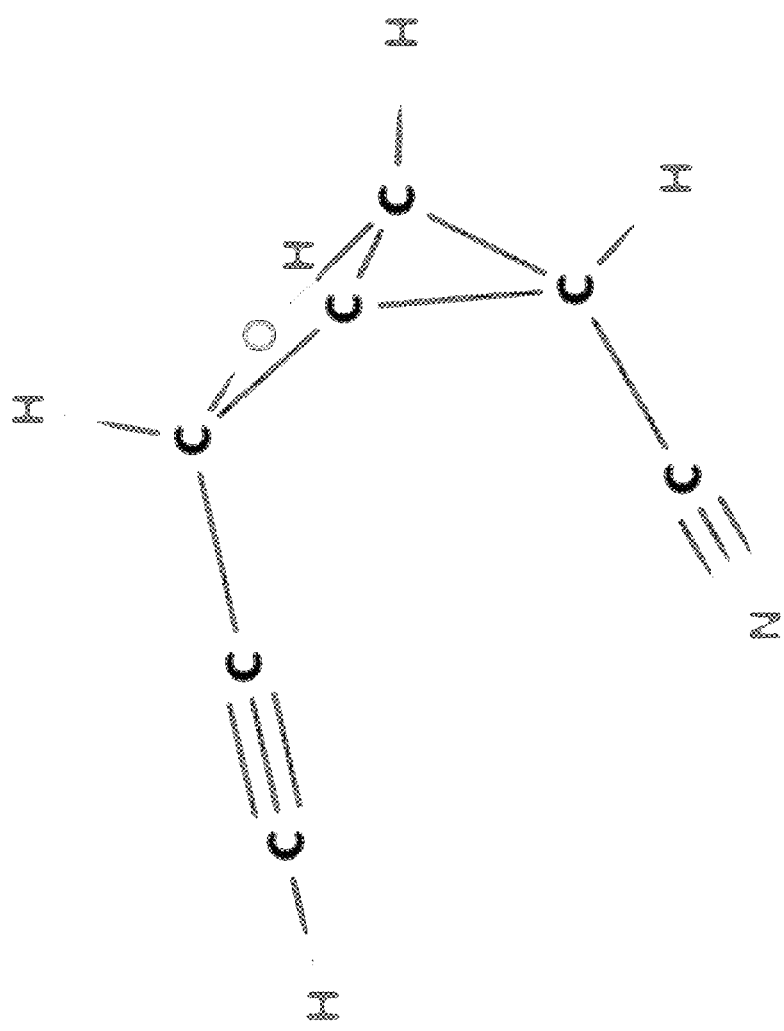
FIG. 27 shows an example of a molecule
Figure 28:
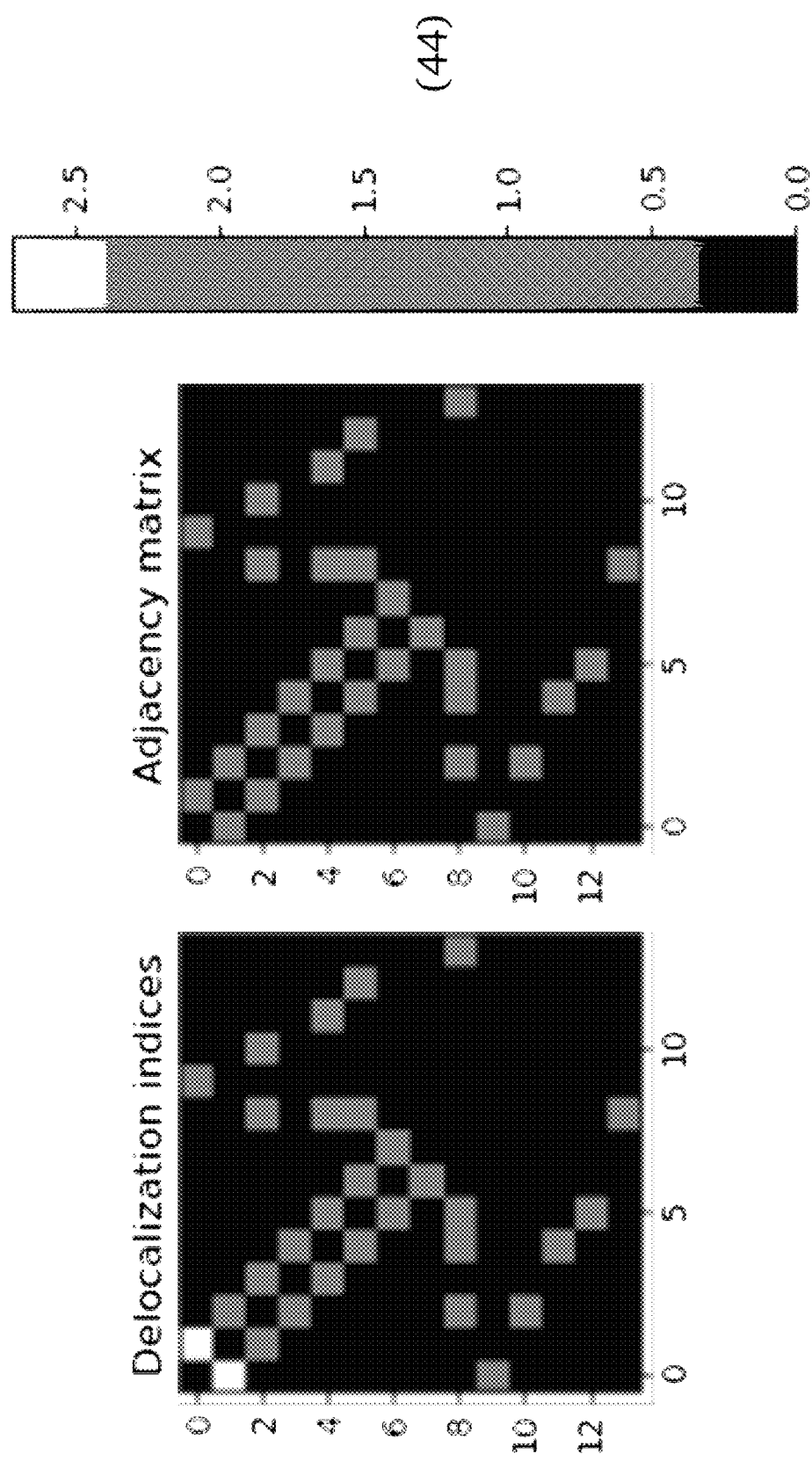
FIG. 28 shows a plot with the calculated delocalization indices versus the adjacency matrix for FIG. 27.

FIG. 28 shows a comparison with calculated delocalization indices versus the adjacency matrix for FIG. 27.

Figure 29:
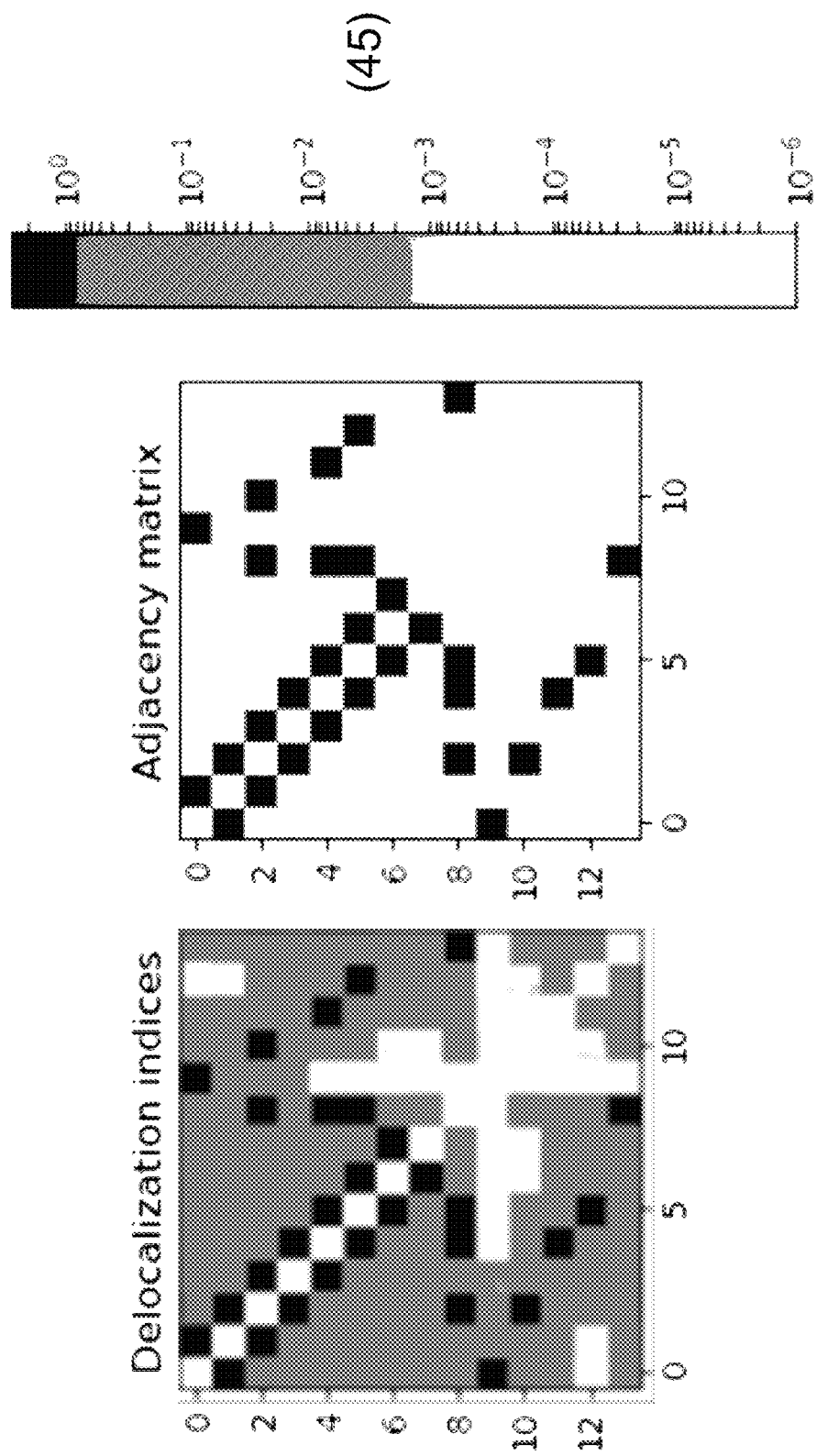
FIG. 29 shows a plot with the calculated delocalization indices versus the adjacency matrix in a logarithmic scale.

We thus get a fully-connected graph, where the signs of the dominant elements of the symmetric delocalization matrix correspond to the adjacency matrix of the associated 2D molecular graph. Do note however that the values of the delocalization indices are all very different from unity. Also, due to the shared colorbar, the fine distinctions of the smaller elements remains largely invisible. So let's check on a logarithmic scale: FIG. 29.

Now it's clear that the delocalization indices encode more information than the mere connectivity of the adjacency matrix.

Example 2: Ligand 404 Bound to Protein 3pj8

More realistic and relevant than the triangles and squares of QM9 are the ligands in in the Protein Data Bank (see Section C PDBbind background information below).

Figure 30:
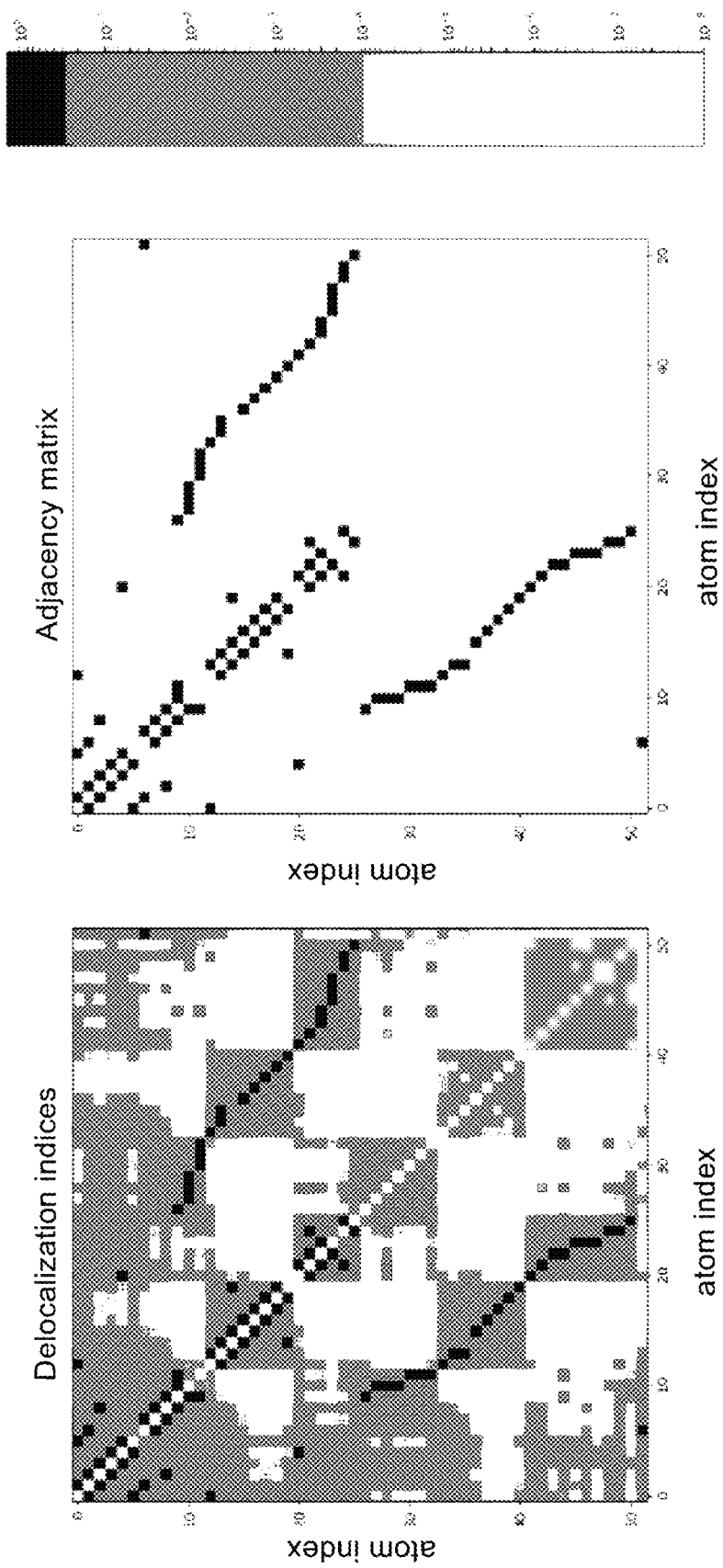
FIG. 30 shows a comparison of the delocalization indices and adjacency matrix for 404 bound to 3pj8.

FIG. 30 shows a comparison of the delocalization indices and adjacency matrix for 404 bound to 3pj8.

We again get a fully-connected graph, where the signs of the dominant elements of the symmetric delocalization matrix correspond to the adjacency matrix of the associated 2D molecular graph. The values of the delocalization indices resemble the adjacency matrix but are all very different from unity. The "boxes" appearing in the plot on the lefthand side are due to the particular ordering of the ligand in the original geometry of the molecule, reflecting stronger correlations among neighbouring atoms or the atoms of functional groups (boxes before index 27 are the carbon/nitrogen rings in the molecule, starting at index 27-52 are all hydrogens attached to the rings).

Figure 31:
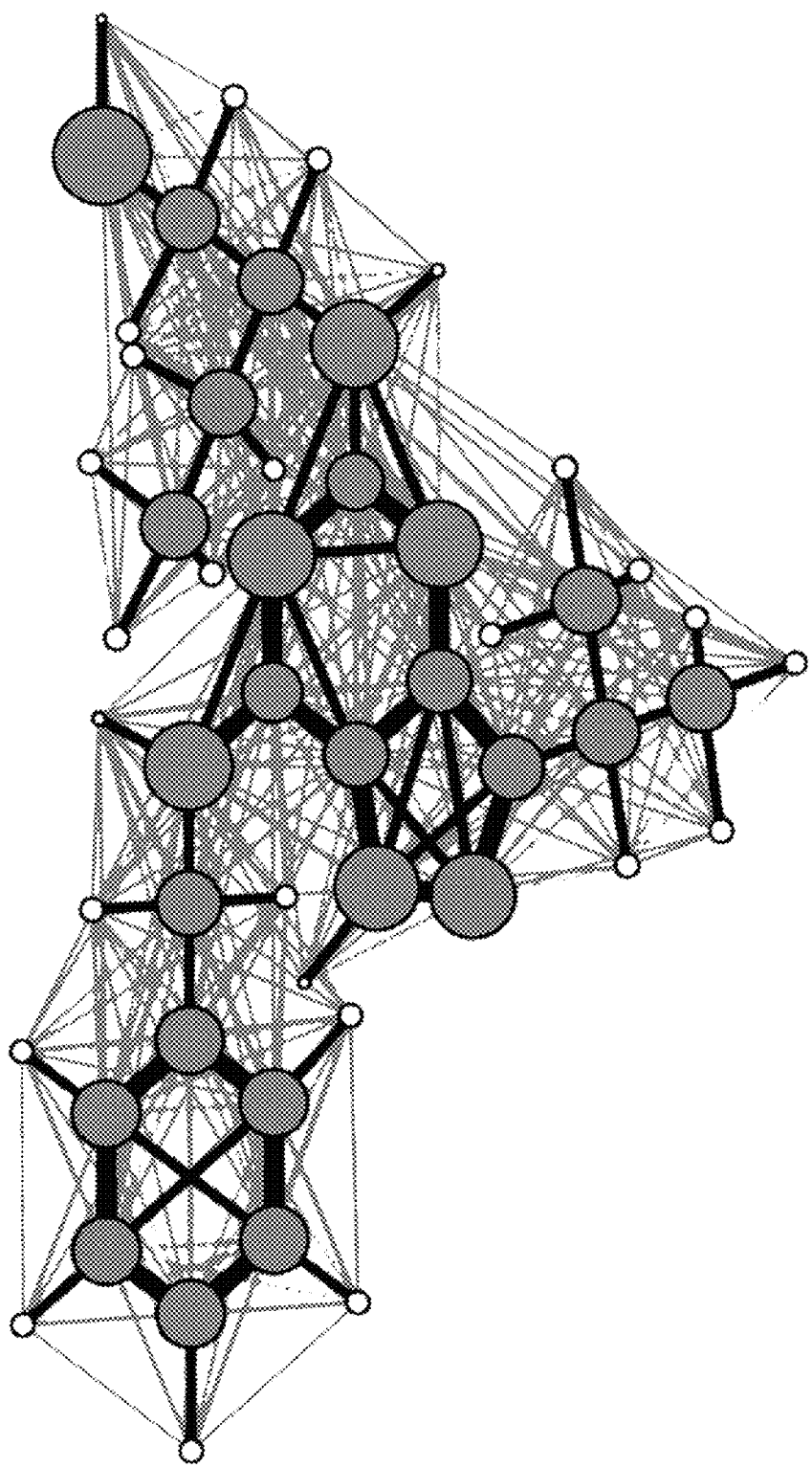
FIG. 31 shows a graph representation of (de)localization indices and chemical bonds.

FIG. 31 shows a graph representation of (de)localization indices and chemical bonds. In the graph representation, the edge weights are based on the DI and the nodes' sizes scale with the magnitude of the corresponding LI. Values of DI have been binned into 5 bins [>1>0:1>0:01>0:001>] from fat/black to thin/gray. The dominant black lines clearly encode the familiar chemical graph.

These features represent a generalization which is a natural step beyond familiar bond features, with the values for the bonds beyond the molecular graph structure encoding a crude representation of the 'delocalization' of electrons.

Distributions of Delocalization Indices Across Datasets

Another way to appreciate that the delocalization indices capture and generalize chemical bonds is by comparing histograms of all DI values across different datasets.

Figure 32:
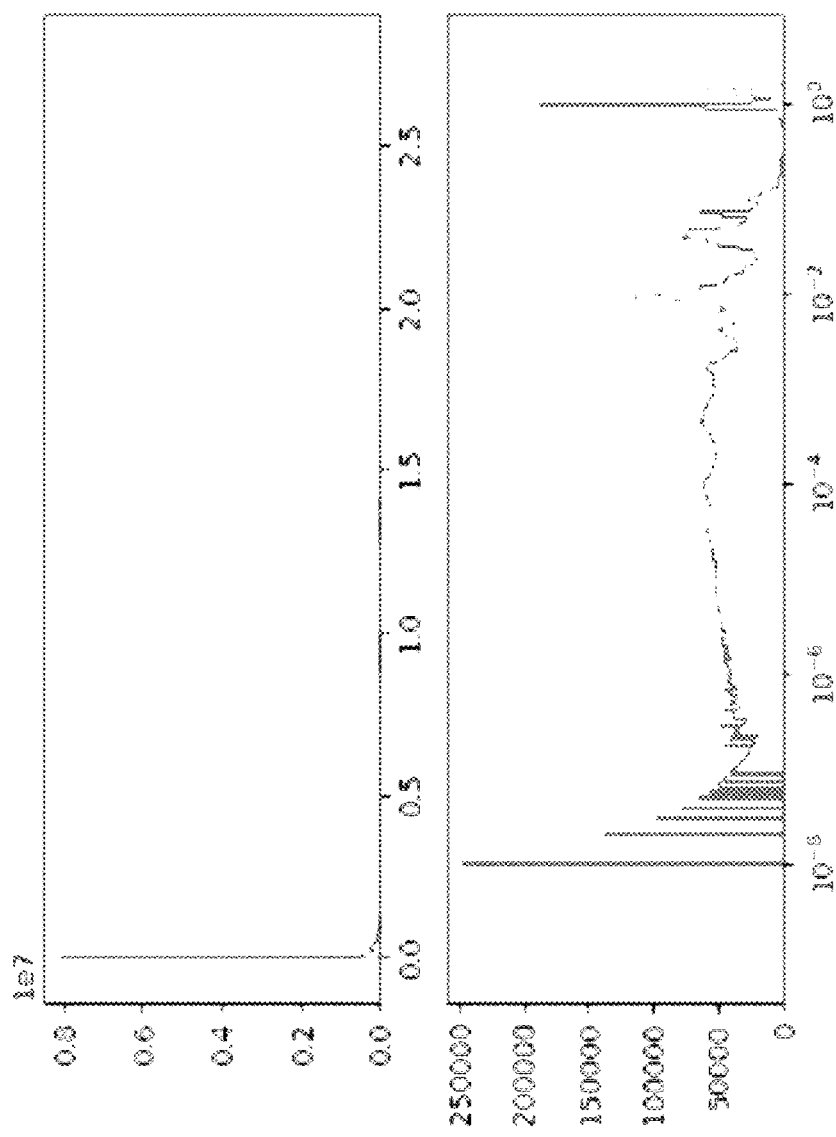
FIG. 32 shows linear and log plots of histograms of all values of the delocalization indices for the ligands in the lipophilicity dataset.

FIG. 32 shows linear and log plots of histograms of all values of the delocalization indices for the ligands in the lipophilicity dataset.

Figure 33:
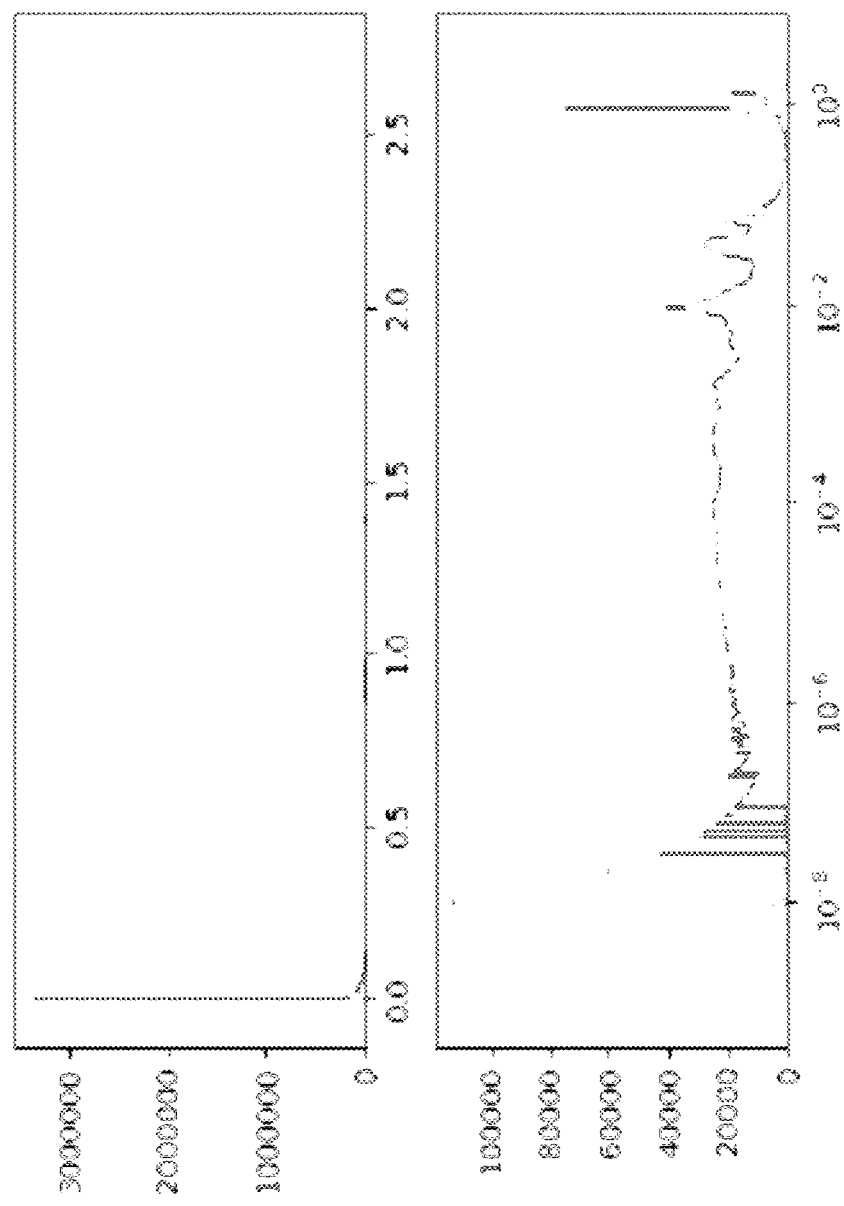
FIG. 33 shows linear and log plots of histograms of all values of the delocalization indices for the ligands in the PDBbind17 subset.

FIG. 33 shows linear and log plots of histograms of all values of the delocalization indices for the ligands in the PDBbind17 subset.

3.1.2 Intermolecular Forces and Non-Covalent Interactions: Hydrogen Bonds and Van Der Waals Forces Molecular structure is governed by covalent, noncovalent, and electrostatic interactions, the latter two of which are the driving force in most biochemical processes. The three-dimensional molecular structure defines covalent bonds; however, noncovalent interactions are hidden within voids in the bonding network [Johnson 2010]. The (de)localization indices of the previous section are well-suited to capture strong, covalent bonds, i.e. the dominant contributions to the familiar chemical graph. However, in applications we care about, like protein-ligand binding, weaker non-covalent interactions are crucial.

The bond strength of hydrogen bonds, steric effects, and van der Waals forces can be assessed using the NCI index, non-covalent interactions index [J. Am. Chem. Soc., 132, 6498 (2010)], which allows a visualization of non-covalent interactions using the electron density and its derivative. Specifically, the reduced density gradient (RDG)

$$S(r) = \frac{1}{2(3\pi^2)^{1/3}} \frac{|\nabla \rho(r)|}{\rho(r)^{4/3}} \quad (46)$$

isolates the regions relevant for weak interactions (namely where the density is small and the RDG is medium).

FIG. 34 reproduces equation (46).

FIG. 35 shows a table with density gradient, density, and reduced density gradient values (from the Multiwfn manual).

Figure 36:
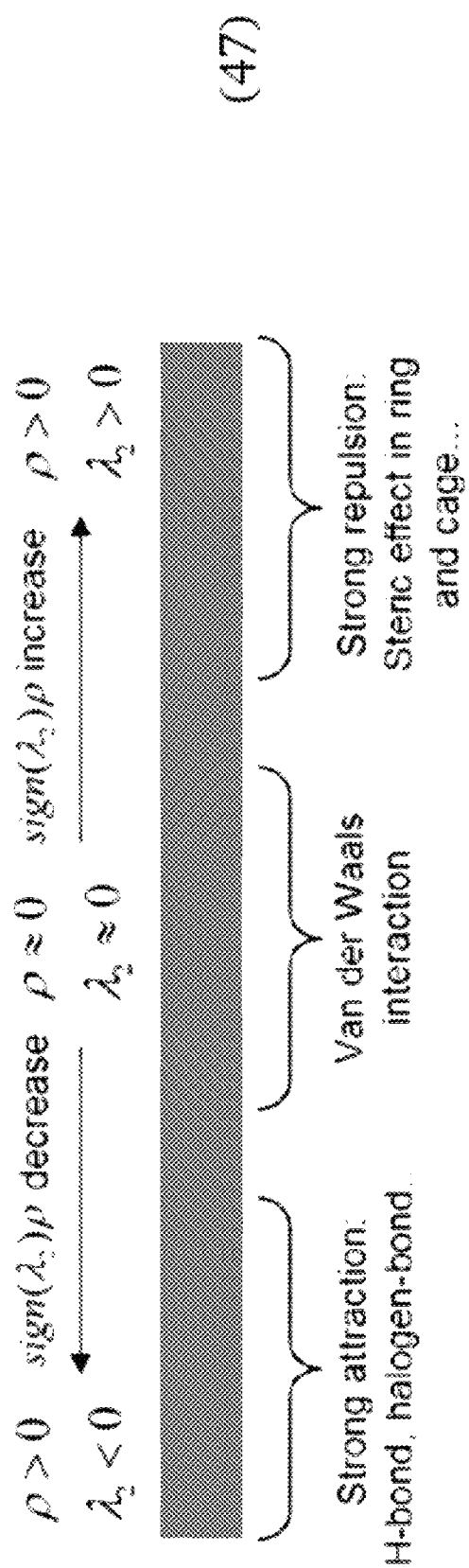
FIG. 36 shows a RDG versus sign($\lambda 2$)$\rho$(r).

The nature of the weak interaction can be determined from the sign of the second largest eigenvalue λ2 of the Hessian of the electron density (see Sec. 2.3.6) as illustrated in FIG. 36.

Figure 37:
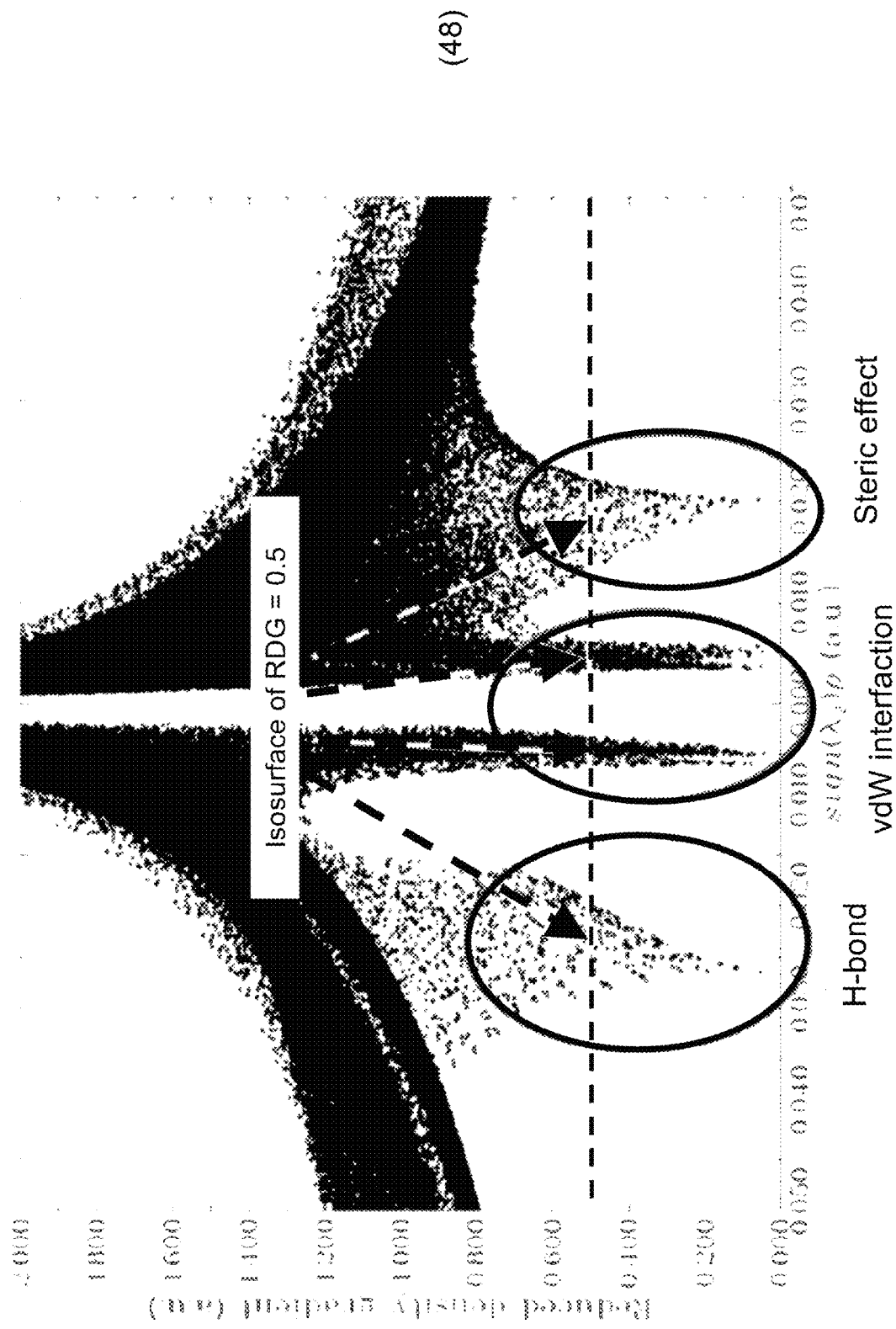
FIG. 37 shows a NCI scatterplot.

Plotting the RDG versus sign(λ2)ρ(r) leads to the following NCI scatterplot with spikes corresponding to points in weak interaction regions: FIG. 37.

Figure 38:
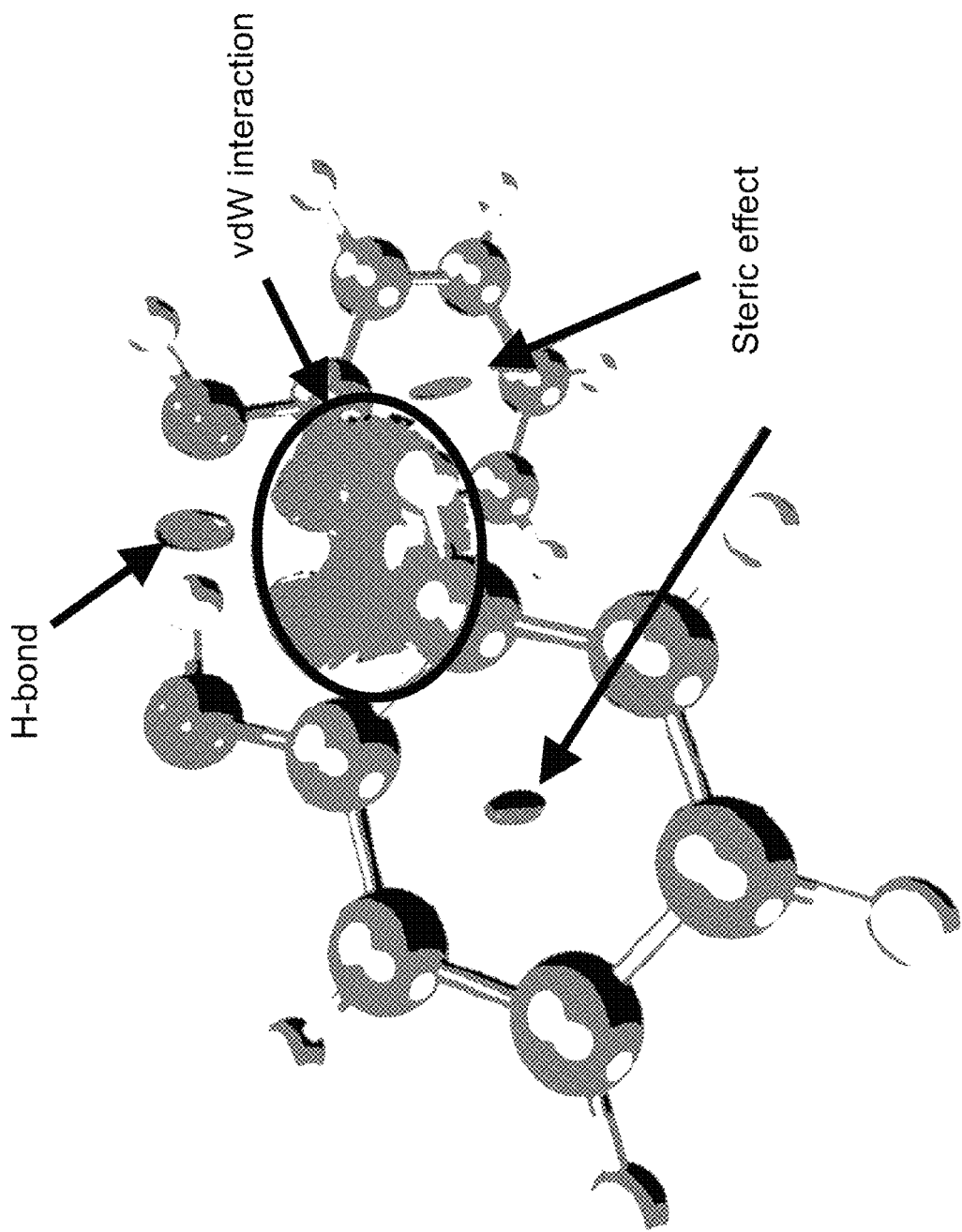
FIG. 38 shows the isosurfaces of the RDG map to different spatial regions.

FIG. 38 shows the isosurfaces of the RDG map to different spatial regions.

Instead of calculating an expensive electron density, the promolecular density $$\rho(r) = \sum_a \rho_a^{free}(r - R_a) \quad (50)$$

where $\rho_\alpha^{free}$ is a pre-calculated, fitted, spherically averaged density of atom (type) a, known to still give reasonable qualitative results. Using promolecular densities allows to calculate weak interaction regions for proteins/pockets.

FIG. 39 reproduces equation (50).

3.1.3 Electrostatic Interactions

Electrostatic Interaction Potential:

$$V(r) = \sum_a \frac{Z_a}{|r - R_a|} - \int dr' \frac{\rho(r)}{|r - r'|} \quad (51)$$

FIG. 39 reproduces equation (51).

Note that for every point an integral over al of space has to be calculated. This can be calculated by most quantum chemistry programs and also from existing electron density data using e.g. the cubegen utility of the Gaussian program (commercial).

4 Beyond Molecular Graph Models 4.1 Electron Density as Point Cloud and Attention Mechanisms Given a previously calculated electron density of an input molecule, attention mechanisms could be used to probe the (local) electron density and allow the ML algorithm to come up with more elaborate edge features for the bonds. This idea is motivated by the artificialness of chemical bonds, which act as edge features in many models and correspond to the roughest possible "binning" of electron correlations. A more natural approach for the mesh-like electron density would be to combine graph models with point cloud models [19] to arrive at an architecture which combines the molecular structure of graphs with density information encoded as point clouds. Recent models like EdgeConv [20] are in between point clouds and graphs in that the graphs do not remain fixed but get dynamically updated. There are lots of potential options to explore in this direction.

The general workflow would be to obtain electron density from DFT calculations for every molecule and feed this "global" data to the ML algorithm rather than coarse-grained quantities like the descriptors of the previous approach. The challenge in this scenario is the following: given a scalar field ρ(x; y; z) which spits out a value related to the probability of an electron at every position, a machine learning algorithm, consisting of for example a graph convolutional network in conjunction with a point cloud based network, can be trained on samples of this "global" data.

A Q-Graph Test Run: Random Subset of 2649 QM9 Molecules

Figure 40:
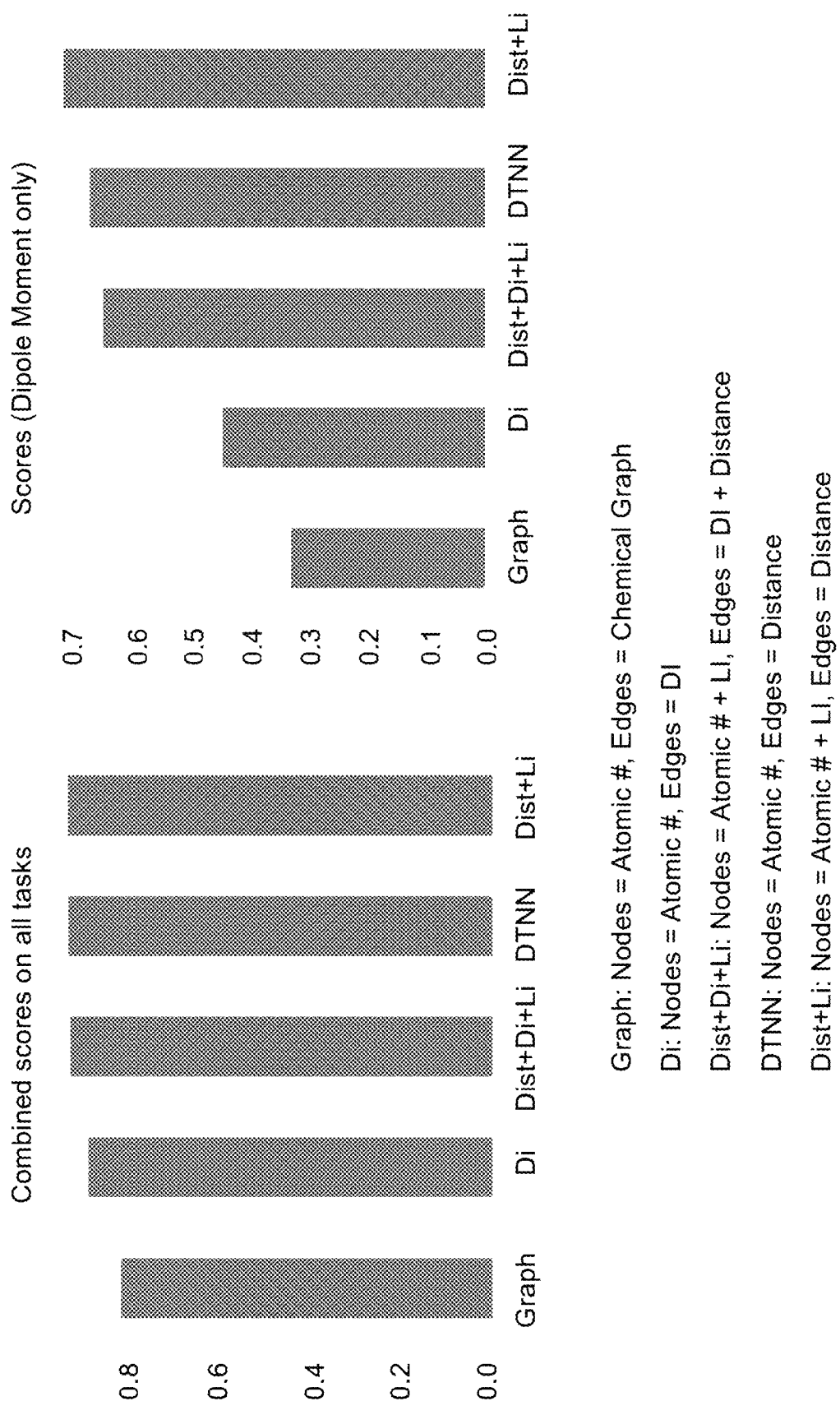
FIG. 40 shows DTTN results.

As a complete toy model test run, we used DFT to extract features for the graph network to model the DFT-calculated tasks of the QM9 dataset. The above method was benchmarked on a random subset of 2649 molecules and compared the features with Euclidean distances as used in the DTNN model, see FIG. 40. The quantum features outperform known models/features especially on difficult tasks such as total dipole moment (μ).

It should be noted however that the values for all of the QM9 tasks were computed at the B3LYP/6-31G(2df,p) level whereas we used the more accurate B3LYP/AUG-CC-PVDZ basis set. This can be seen by plotting the calculated energies for every molecule and the difference with the target of the QM9 dataset (see FIG. 41) and, similarly, for the dipole moments (see FIG. 42). From observing the systematic bias (lower energies and higher values of dipole moments for our calculations), it appears we have actually been training on less accurate values.

Figure 41:
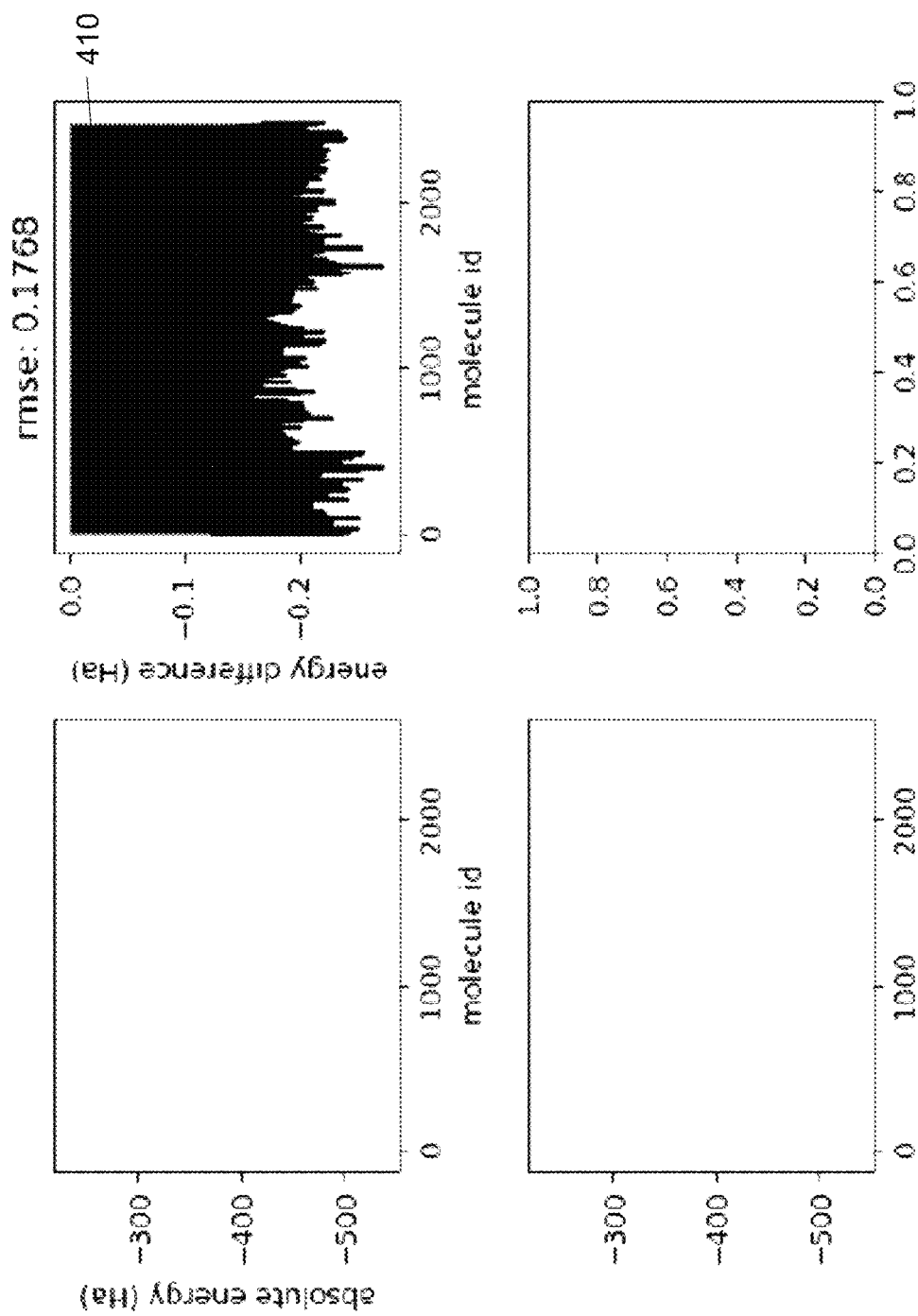
FIG. 41 shows the absolute DFT energies (top-left our results, bottom-left QM9) and energy differences for the random QM9 subset of 2694 molecules.

FIG. 41 shows the absolute DFT energies (top-left our results, bottom-left QM9) and energy differences for the random QM9 subset of 2694 molecules. Absolute energy trends match the original QM9 calculations. Relative differences reveal that the calculations yielded consistently lower energies 410 is when gtn is lower than the tabulated QM9 energy). The large RSME value is thus due to a systematic error of our having used a better basis set.

Figure 42:
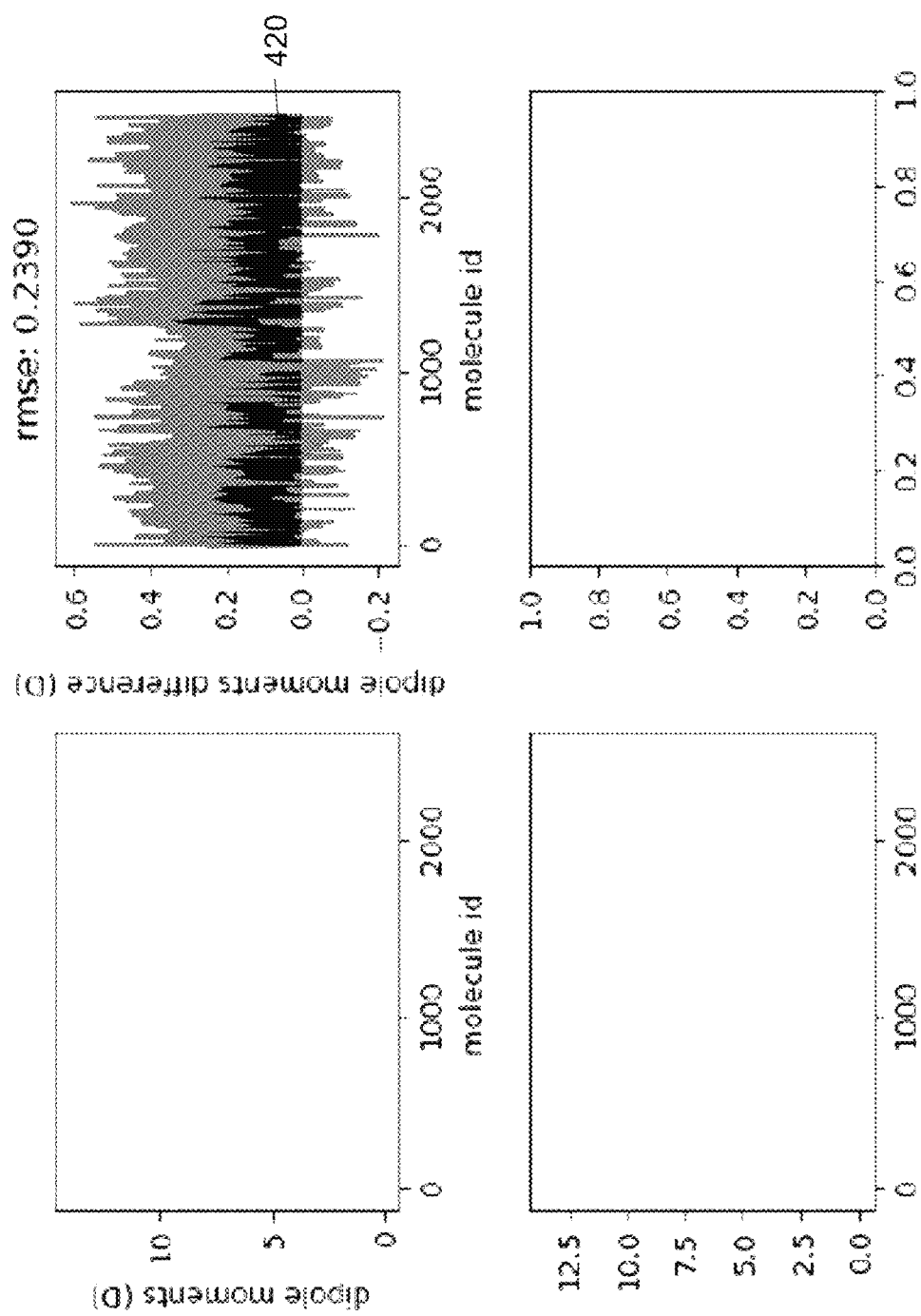
FIG. 42 shows the same global trends for the dipole moments, but an even larger RSME value and lots of fluctuations.

FIG. 42 shows the same global trends for the dipole moments, but an even larger RSME value and lots of fluctuations. Most of the time, our calculated dipole moment is larger (420) than the QM9 one.

C PDBbind Background Information

In general, .pdb files contain atomic coordinates from heavy atoms obtained from crystallographic X-ray/NMR experiments. Information on bonds and hydrogens has to be inferred.

More details on hydrogens in PDB files can be found (https://www.umass.edu/molvis/decatur/pe2.727/protexpl/help_hyd.htm): since X-ray crystallography cannot resolve hydrogen atoms in most protein crystals, most PDB files do not contain hydrogen atoms. Hydrogens are always present in PDB files resulting from more accurate NMR analysis, which determine some hydrogen positions. High resolution protein crystallography (1.2 A or less) can guess some hydrogen positions from the electron density map. Note that, in proteins, the average number of hydrogens per non-hydrogen atom, weighted to take into account the frequencies of amino acids, is 1.01. Thus, hydrogens constitute about 50% of all atoms in a protein. Most macromolecular crystals also do not provide enough resolution to detect hydrogen positions. For example, the X-ray model in PDB file 1hho for oxyhemoglobin (2.1 A resolution) contains no hydrogens, while the X-ray file 1lfa (1.8 A resolution) contains 312 waters each with 2 hydrogens, and 645 protein hydrogens for 2941 non-hydrogen protein atoms, accounting for only 22% of the hydrogens actually present in this protein. The hydrogens are however required for molecular dynamics or any sort of quantum-mechanical calculation. Some crystallographers strip hydrogens out before submitting a PDB file and others leave them in. Since the Protein Data Bank accepts X-ray models either way, according to the preference of the depositor, a very messy database is created and maintained which requires significant pre-processing for almost all purposes. We used the commercial OEChem package by OpenEye in order to tackle these challenges.

D Tensor Networks and Quantum Chemistry

Applying tensor network ideas to quantum chemistry has been initiated in the group of White [21] and has been subsequently developed in the groups of Legeza, Chan, Reiher, and Van Neck during the past 15 years. For a more extensive overview of ab initio DMRG in quantum chemistry, we refer to the introductory chapters of the PhD dissertations of Sebastian Wouters [22] and Johannes Hachmann [6].

D.1 What is a Tensor Network?

Tensor networks are entanglement-based ansatze for ground and excited states of quantum many-body systems. There exist lots of different tensor networks tailored to different kinds of entanglement structure, but they all boil down to the same idea: efficient ways of exploring the "physical" part of an exponentially large many-body Hilbert space. The reason this even works at all can be understood in terms of entanglement area laws and the local nature of interactions. Put differently, a tremendous amount of information in the "mathematical" exponential Hilbert space is completely redundant and superfluous if you are interested in "physical" ground states and low-lying excited states of local Hamiltonians.

D.2 Matrix Product States: QC-DMRG

For our purposes, we will focus on matrix product states (MPS), which is the particular kind of linear ansatz underlying the influential density matrix renormalization group (DMRG) algorithm [https://arxiv.org/abs/1407.2040]. The quantum chemistry version of DMRG (QC-DMRG) naturally emerges when trying to construct a tensor decomposition of the full-CI wave function. Recall that in the CAS-SCF approach, we select an active space of N electrons in L orbitals, on on which a full-CI expansion is applied [23]

$$|\Psi_{CAS-CI}\rangle = \sum_{n_1,\ldots,n_L} C_{n_1,\ldots,n_L}|n_1 n_2 \ldots n_L\rangle, \quad (52)$$

where $|n_1 n_2 n_L\rangle$ is an occupation number vector (Fock space).

FIG. 43 reproduces equation (52).

Figure 44:
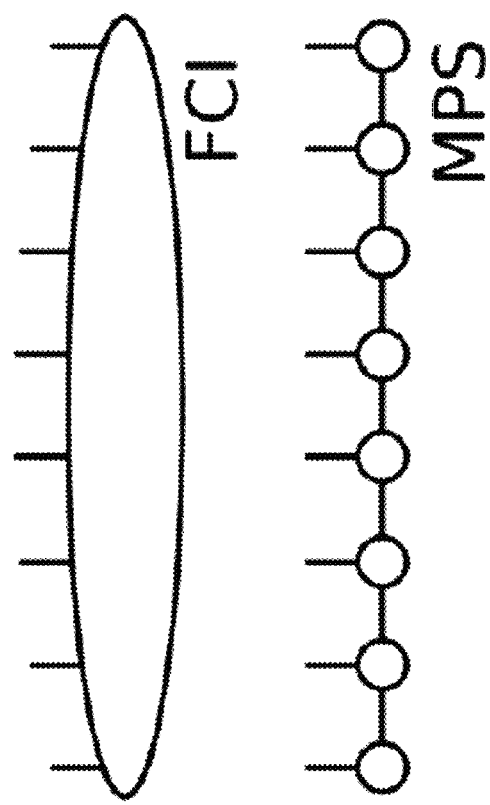
FIG. 44 shows a representation of ansatz in terms of local tensors.

This ansatz scales exponentially since the calculations of the full-CI tensor is limited to CAS(18,18) spaces (cf. exact diagonalization). By doing successive singular value decompositions (SVDs) on the rank-n tensor C, we arrive at an ansatz in terms of local tensors. Pictorially [24], see FIG. 44.

This leads to an ansatz for the wave function where the FCI tensor is rewritten as a contracted matrix product. Unlike most wave function methods in quantum chemistry, the MPS wave function is built directly from these local variational objects (tensors).

Rather than truncating the number of excitations on top of some single reference state, QC-DMRG truncates in a virtual space of bond dimension D (the horizontal legs) containing entanglement degrees of freedom with no preferences towards any particular state, which makes it a natural candidate to study multi-configurational systems where static correlations are important. The error in the MPS wave function can be quantified by the truncation error $$\epsilon = \| |\Psi\rangle - |\tilde{\Psi}\rangle \|^2 = 1 - \sum_{\alpha=1}^{D} w_\alpha, \quad (53)$$

where the target wave function $|\Psi\rangle$ is approximated by $|\tilde{\Psi}\rangle$ and the $\omega_\alpha$ are the eigenvalues of the local reduced density matrix which you throw away. FIG. 45 reproduces equation (53). The DMRG algorithm is an iterative algorithm which optimizes over MPS wave functions to converge to the exact solution of the electronic Schrödinger equation in a given active orbital space with polynomial rather than exponential cost. Unlike traditional CAS-based approaches, DMRG is a local multi-configurational approach which, thanks to its polynomial scaling, can deal with active spaces comprising up to 50 orbitals. In terms of the number of orbitals L (corresponding to the number of lattice sites) and the bond dimension D, the QC-DMRG algorithm has an overall scaling per sweep of $O(L^4 D^2 + L^3 D^2)$ in CPU time, $O(L^2 D^2)$ in memory, and $O(L^3 D^2)$ in disk.

The correlations among the orbitals are characterized by the bond dimension D which sets the number of variational parameters (for $D \to \infty$, the wave function would become exact for a given active space). The one-dimensional nature of the ansatz suggests that it is important to order orbitals along the chain such that strongly-correlated ones are close to each other (otherwise, correlations would have to travel "through" many sites of the chain to communicate). The QC-DMRG algorithm has been combined with CAS-SCF methods to optimize the orbitals themselves, using the QC-DMRG method as an approximate solver in the active space instead of CI. Dynamical correlations can be added on top of the MPS reference wave function by resorting to N-electron valence perturbation theory to second-order (NEVPT2) and complete-active space perturbation theory to second order (CASPT2) [23].

Figure 46:
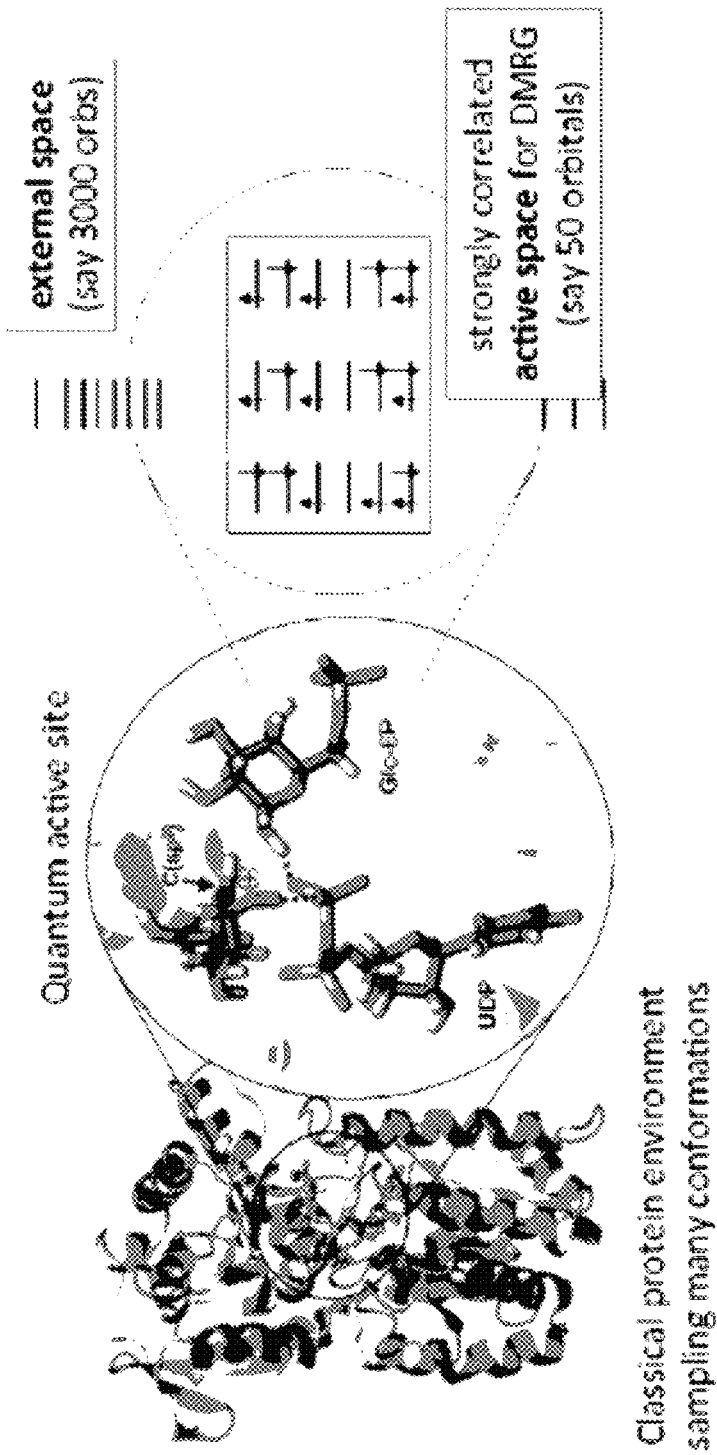
FIG. 46 shows Chan's optimistic idea of DMRG.

Recent applications of QC-DMRG are listed in the review article Ref. [24]. For more details, I recommend the very same review article Ref. [24] by Sebastian Wouters since be uses modern MPS notation rather than old-fashioned DMRG-block style notation. Other reviews are included in the references [25, 26, 27, 23] and another extensive list of references can be found online. A great introductory talk by Chan can be found at [28], reflective of his vision as depicted in FIG. 46.

D.3 Software Packages for QC-DMRG

Options include BLOCK by the Chan group and CHEMPS2 by Sebastian Wouters, both of which are written in C++ with Python wrappers.

D.4 Entanglement Measures

One advantage of QC-DMRG is the easy access to the one-orbital von Neumann entropy $$S_i = -\sum_{\alpha=1}^{4} w_{\alpha,i} \ln w_{\alpha,i}, \quad (54)$$

the two-orbital von Neumann entropy $$S_{ij} = -\sum_{\alpha=1}^{16} w_{\alpha,ij} \ln w_{\alpha,ij}, \quad (55)$$

and the mutual information between a pair of active orbitals $$I_{ij} = \frac{1}{2}(S_i + S_j - S_{ij})(1 - \delta_{ij}) \quad (56)$$

FIG. 47 reproduces equations (54)-(56).

These quantities can be straightforwardly calculated from the tensor network representation of the molecular wave function in orbital space. A correlated wavefunction is required to have non-zero orbital entanglement and correlation. In the case of an uncorrelated wavefunction (for instance, a single Slater determinant) the (orbital) entanglement entropy is zero. These bipartite entanglement measures reveal a lot about the correlations in the quantum state. In particular, calculating these quantities using QC-DMRG, for a given choice of active space orbitals and orbital order, leads to fancy diagrams where the linear, one-dimensional MPS chain are plotted as a circle. Every dot in corresponds to an orbital in the active space. The size of the dots in the second picture also scales with the one-orbital entropy. The color and style of the lines connecting the orbitals denote the value of the mutual information for those two orbitals, binned in large, medium, and small contributions. Stein and Reiher have proposed to use these measures to automate the selection of active orbital spaces in CAS-DMRG by exploiting the capability of QC-DMRG to include up to about one hundred orbitals in the active space to systematically assess and select active orbitals [29].

D.5 Other QC-TNS Ansätze

In the tensor network community, people often study strongly-correlated 2D quantum systems using DMRG/MPS by curling up the 1D ansatz like a snake to cover the 2D lattice, thereby introducing unnatural long-range interactions between neighbouring sites. In many cases, the computational efficiency of MPS (Due to the existence of isometric, canonical forms of the tensors which simplify the contractions (number of matrix multiplications) and also stabilize the eigenvalue problems (conditioning).) outweighs the additional complexity of 2D extensions of the MPS ansatz such as Projected-entangled Pair States (PEPS). Actually, the development of fast and accurate numerical PEPS algorithms for 2D quantum lattice systems is still very much an active area of research. Apart from the linear matrix product state (MPS) ansatz, tree tensor networks (TNS) [30, 31, 32] and other tensor product states like complete graphs [33] have also been considered in the context of quantum chemistry. Even though these alternative ansatze might seem more appealing because trees kind of look like molecules, their numerical efficiency is much lower than that of DMRG.

D.6 Example: N2

A simple molecule with multi-configurational character like N2 suffices to demonstrate the unfavourable properties of QC-DMRG for our purposes. Running a CAS-DMRG simulation with a CAS(10,8) active space with natural orbitals in the active space leads to an energy of $-109{:}103502335253$ Eh with natural orbital occupation numbers (NOONs)

[1.996, 1.990, 1.981, 1.937, 1.937, 0.069, 0.069, 0.021]

single-orbital entropies

[0.0235, 0.0360, 0.1015, 0.2329, 0.2329, 0.2456, 0.2456, 0.1085]

and symmetric mutual information matrix between orbitals i and j.

00.003036 0.000617 0.001916 0.001916 0.004322 0.004322 0.002960

0.003036 0 0.000451 0.003054 0.003054 0.012242 0.012242 0.000762

0.000617 0.000451 00.008947 0.008947 0.009109 0.009109 0.057489

0.001916 0.003054 0.008947 0 0.037332 0.036786 0.153104 0.009804

0.001916 0.003054 0.008947 0.037332 0 0.153104 0.036786 0.009804

0.004322 0.012242 0.009109 0.036786 0.153104 0 0.038169 0.009986

0.004322 0.012242 0.009109 0.153104 0.036786 0.038169 0 0.009986

0.002960 0.000762 0.057489 0.009804 0.009804 0.009986 0.009986 0

If we run the same simulation, but with Edmiston-Ruedenberg localization applied to the active space orbitals, we get the same energy and NOONs but the single-orbital entropies become

[0.8441, 1.3634, 1.3634, 1.3634, 1.3634, 1.3634, 1.3634, 0.8441]

which are close to maximally entangled ($\ln 4 \approx 1.38$), and the mutual information matrix is now 0 0.093808 0.015324 0.013050 0.007883 0.009190 0.046646 0.208481

0.093808 00.018521 0.007623 0.147469 0.085459 0.045329 0.046646

0.015324 0.018521 0 0.018521 0.087071 0.045268 0.148051 0.009190

0.013050 0.007623 0.018521 0 0.172476 0.150280 0.084960 0.007883

0.007883 0.147469 0.087071 0.172476 0 0.018521 0.007623 0.013050

0.009190 0.085459 0.045268 0.150280 0.018521 0 0.018521 0.015324

0.046646 0.045329 0.148051 0.084960 0.007623 0.018521 0 0.093808

0.208481 0.046646 0.009190 0.007883 0.013050 0.015324 0.093808 0

Note that the values, as expected, are completely different because we have picked a different basis for the active space: we did a particular "global" unitary transformation which mixes up all orbitals in going from one basis to the other.

The meaning of entanglement between active space orbitals and, more generally, fermionic entanglement is d in Ref. [2].

D.7 Synopsis of Using TNS for Quantum Chemistry

Higher-dimensional tensor networks (tree tensor networks, projected-entangled pair states, . . . ) are not mature enough yet for real-world applications.

Matrix product states (QC-DMRG) work great for particular kinds of molecules, namely those exhibiting multi-configurational character. They require chemical intuition and expert experience to decide on the choice of active space. As mentioned by the ORCA user guide:

Let us stress again: it is strongly recommended to first LOOK at your orbitals and make sure that the ones that will enter the active space are really the ones that you want to be in the active space! Many problems can be solved by thinking about the desired physical contents of the reference space before starting a CASSCF. A poor choice of orbitals results in poor convergence or poor accuracy of the results! Choosing the active orbitals always requires chemical and physical insight into the molecules thatyou are studying!

For QC-DMRG specifically, there is also the issue of the ordering of the orbitals on the effective one-dimensional chain of orbitals. Finding the optimal ordering is in general NP-hard, so people use heuristics, chemical intuition, or a Fiedler vector ordering obtained from the Laplacian matrix of the graph [26, 24, 27, 34, 23].

The entanglement measures defined for the active space orbitals in QC-DMRG are dependent on the chosen basis. It should also be mentioned that, more generally for all ab initio methods, that canonical, natural, and localized molecular orbitals are fictitious constructs which are all very much tailored to the specific molecule at hand. Approaches based on molecular orbitals (expect maybe for natural bond orbitals, see Sec. 2.3.5) will not lead to features which can be used across a dataset of molecules unless a "common" molecular orbital basis set is used.

REFERENCES FROM SECTION 4

[1] Klaus Capelle. "A bird's-eye view of density-functional theory". In: (November 2002). arXiv: 0211443 [cond-mat]. URL: http://arxiv.org/abs/cond-mat/0211443.

[2] K. Eckert et al. "Quantum Correlations in Systems of Indistinguishable Particles". In: (March 2002). DOI: 10.1006/aphy.2002.6268. arXiv: 0203060 [quant-ph]. URL: http://arxiv.org/abs/quant-ph/0203060%20http://dx.doi.org/10.1006/aphy.2002.6268.

[3] Sebastian Wouters, ed. Workshop on DMRG for quantum chemistry. 2016.

[4] Christoph Riplinger and Frank Neese. "An efficient and near linear scaling pair natural orbital based local coupled cluster method". In: Journal of Chemical Physics 138.3 (May 2013), p. 34106. ISSN: 00219606. DOI: 10.1063/1.4773581. URL: https://aip.scitation.org/doi/figure/10.1063/1.4773581.

[5] Christoph Riplinger et al. "Natural triple excitations in local coupled cluster calculations with pair natural orbitals". In: Journal of Chemical Physics 139.13 (May 2013), p. 134101. ISSN: 00219606. DOI: 10.1063/1.4821834. URL: https://aip.scitation.org/doi/abs/10.1063/1.4821834.

[6] Johannes Hachmann. "Ab initio density matrix renormalization group methodology and computational transition metal chemistry". In: Cornell University February (2009). URL: http://ecommons.cornell.edu/handle/1813/14774.

[7] Alex Granovsky. Re: relaxed/unrelaxed density excited state properties. URL: http://classic.chem.msu.su/cgi-bin/ceilidh.exe/gran/gamess/forum/?C34df668afbHW-7216-1405+00.htm (visited on May 29, 2018).

[8] Richard F. W. Bader. "Atoms in Molecules". In: Encyclopedia of Computational Chemistry. Chichester, UK: John Wiley & Sons, Ltd, April 2002. DOI: 10.1002/0470845015.caa012. URL: http://doi.wiley.com/10.1002/0470845015.caa012.

[9] Richard F. W. Bader. "A quantum theory of molecular structure and its applications". In: Chemical Reviews 91.5 (July 1991), pp. 893-928. ISSN: 0009-2665. DOI: 10.1021/cr00005a013. URL: http://pubs.acs.org/doi/abs/10.1021/cr00005a013.

[10] Richard F. W. Bader. "Everyman's Derivation of the Theory of Atoms in Molecules". In: (2007). DOI: 10.1021/JP073213K. URL: https://pubs.acs.org/doi/abs/10.1021/jp073213k.

[11] Chérif F. Matta and Russell J. Boyd. "An Introduction to the Quantum Theory of Atoms in Molecules". In: The Quantum Theory of Atoms in Molecules. Weinheim, Germany: Wiley-VCH Verlag GmbH & Co. KGaA, pp. 1-34. DOI: 10.1002/9783527610709.ch1. URL: http://doi.wiley.com/10.1002/9783527610709. ch1.

[12] Chérif F. Matta. "Modeling biophysical and biological properties from the characteristics of the molecular electron density, electron localization and delocalization matrices, and the electrostatic potential". In: Journal of Computational Chemistry 35.16 (June 2014), pp. 1165-1198. ISSN: 1096987X. DOI: 10.1002/jcc.23608. URL: http://doi.wiley.com/10.1002/jcc.23608%20http://www.ncbi.nlm.nih.gov/pubmed/24777743%20http://www.pubmedcentral.nih.gov/articlerender.fcgi?artid=PMC4368384.

[13] Xavier Fradera, Maggie A. Austen, and Richard F. W. Bader. "The Lewis Model and Beyond". In: Journal of Physical Chemistry A 103.2 (1999), pp. 304-314. ISSN: 10895639. DOI: 10.1021/jp983362q. URL: https://pubs.acs.org/doi/abs/10.1021/jp983362q.

[14] Eduard Matito and Miguel Solà. "The role of electronic delocalization in transition metal complexes from the electron localization function and the quantum theory of atoms in molecules viewpoints". In: Coordination Chemistry Reviews 253.5-6 (March 2009), pp. 647-665. ISSN: 00108545. DOI: 10.1016/j.ccr.2008.10.003. URL: https://www.sciencedirect.com/science/article/pii/S0010854508001793?via%7B%5C%%7D3Dihub.

[15] Jordi Poater et al. "The calculation of electron localization and delocalization indices at the Hartree-Fock, density functional and post-Hartree-Fock levels of theory". In: Theoretical Chemistry Accounts 107.6 (June 2002), pp. 362-371. ISSN: 1432881X. DOI: 10.1007/s00214-002-0356-8. URL: http://link.springer.com/10.1007/s00214-002-0356-8.

[16] Yi-Gui Wang, Cherif Matta, and Nick Henry Werstiuk. "Comparison of localization and delocalization indices obtained with Hartree-Fock and conventional correlated methods: Effect of Coulomb correlation". In: Journal of Computational Chemistry 24.14 (November 2003), pp. 1720-1729. ISSN: 0192-8651. DOI:10.1002/jcc.10435. URL: http://doi.wiley.com/10.1002/jcc.10435.

[17] Chérif Matta et al. "Localization-delocalization matrices: bridging QTAIM and chemical graph theory". In: Acta Crystallographica Section A Foundations and Advances 73.a2 (December 2017), pp. C796-C796. ISSN: 2053-2733. DOI: 10.1107/S2053273317087782. URL: http://scripts.iucr.org/cgi-bin/paper?S2053273317087782.

[18] Ovidiu Ivanciuc. "Chemical Graphs, Molecular Matrices and Topological Indices in Chemoinformatics and Quantitative Structure-Activity Relationships§" in: Current Computer Aided-Drug Design 9.2 (June 2013), pp. 153-163. ISSN: 15734099. DOI: 10.2174/15734099113090200002. URL: http://www.eurekaselect.com/openurl/content.php?genre=article%7B%5C&%7Dissn=1573-4099%7B%5C&%7Dvolume=9%7B%5C&%7Dissue=2%7B%5C&%7Dspage=153.

[19] Charles R. Qi et al. "PointNet++: Deep Hierarchical Feature Learning on Point Sets in a Metric Space". In: (June 2017). ISSN: 10495258. arXiv: 1706.02413. URL: http://arxiv.org/abs/1706.02413.

[20] Yue Wang et al. "Dynamic Graph CNN for Learning on Point Clouds". In: (January 2018). arXiv: 1801.07829. URL: http://arxiv.org/abs/1801.07829.

[21] Steven R. White and Richard L. Martin. "Ab initio quantum chemistry using the density matrix renormalization group". In: Journal of Chemical Physics 110.9 (April 1999), pp. 4127-4130. ISSN: 00219606. DOI: 10.1063/1.478295. arXiv:9808118 [cond-mat]. URL: https://aip.scitation.org/doi/10.1063/1.478295.

[22] Sebastian Wouters. "Accurate variational electronic structure calculations with the density matrix renormalization group". In: Thesis (2014). arXiv: 1405.1225. URL: http://arxiv.org/abs/1405.1225.

[23] Stefan Knecht et al. "New Approaches for ab initio Calculations of Molecules with Strong Electron Correlation". In: CHIMIA International Journal for Chemistry 70.4 (May 2015), pp. 244-251. ISSN: 00094293. DOI: 10.2533/chimia.2016.244. arXiv: 1512.09267. URL: http://arxiv.org/abs/1512.09267%7B%5C%%7D0Ahttp://dx.doi.org/10.2533/chimia.2016.244.

[24] Sebastian Wouters and Dimitri Van Neck. "The density matrix renormalization group for ab initio quantum chemistry". In: European Physical Journal D 68.9 (April 2014). ISSN: 14346079. DOI: 10.1140/epjd/e2014-50500-1. arXiv:1407.2040. URL: http://arxiv.org/abs/1407.2040%20http://www.arxiv.org/pdf/1407.2040.pdf%20https://arxiv.org/abs/1407.2040.

[25] Garnet Kin-Lic Chan et al. "Frontiers in Quantum Systems in Chemistry and Physics". In: Progress in Theoretical Chemistry and Physics 18 (April 2008), pp. 49-65-65. ISSN: 1567-7354. DOI: 10.1007/978-1-4020-8707-3. arXiv: arXiv: 1011.1669v3. URL: http://link.springer.com/10.1007/978-1-4020-8707-3.

[26] Garnet Kin-Lic Chan and Sandeep Sharma. "The Density Matrix Renormalization Group in Quantum Chemistry". In: Annual Review of Physical Chemistry 62.1 (April 2011), pp. 465-481. ISSN: 0066-426X. DOI: 10.1146/annurev-physchem-032210-103338. URL: http://www.annualreviews.org/doi/10.1146/annurev-physchem-032210-103338.

[27] Roberto Olivares-Amaya et al. "The ab-initio density matrix renormalization group in practice". In: Journal of Chemical Physics 142.3 (April 2015), p. 34102. ISSN: 00219606. DOI: 10.1063/1.4905329. URL: https://aip.scitation.org/doi/10.1063/1.4905329.

[28] Garnet Kin-lic Chan. Ab initio DMRG and beyond for realistic systems. 2015. URL: http://www.iip.ufrn.br/media/pdf/dmrg%7B%5C_%7DGarnet Chan%7B%5C_%7D06%7B%5C_%7D2015.pdf.

[29] Christopher J. Stein and Markus Reiher. "Automated Selection of Active Orbital Spaces". In: Journal of Chemical Theory and Computation 12.4 (April 2016), pp. 1760-1771. ISSN: 15499626. DOI: 10.1021/acs.jctc.6b00156. arXiv:1602.03835. URL: http://arxiv.org/abs/1602.03835%20http://www.arxiv.org/pdf/1602.03835.pdf%20https://arxiv.org/abs/1602.03835.

[30] Naoki Nakatani and Garnet Kin Lic Chan. "Efficient tree tensor network states (TTNS) for quantum chemistry: Generalizations of the density matrix renormalization group algorithm". In: Journal of Chemical Physics 138.13 (April 2013), p. 134113. ISSN: 00219606. DOI: 10.1063/1.4798639. arXiv: 1302.2298. URL: http://arxiv.org/abs/1302.2298%20http://www.arxiv.org/pdf/1302.2298.pdf%20https://arxiv.org/abs/1302.2298.

[31] V. Murg et al. "Tree tensor network state with variable tensor order: An efficient multireference method for strongly correlated systems". en. In: Journal of Chemical Theory and Computation 11.3 (April 2015), pp. 1027-1036. ISSN: 15499626. DOI: 10.1021/ct501187j. URL: http://pubs.acs.org/doi/10.1021/ct501187j.

[32] Klaas Gunst et al. "T3NS: Three-Legged Tree Tensor Network States". In: Journal of Chemical Theory and Computation 14.4 (April 2018), pp. 2026-2033. ISSN: 15499626. DOI: 10.1021/acs.jctc.8b00098. arXiv: 1801.09998. URL: https://doi.org/10.1021/acs.jctc.8b00098%20https://pubs.acs.org/doi/pdfplus/10.1021/acs.jctc.8b00098%20https://pubs.acs.org/doi/full/10.1021/acs.jctc.8b00098.

[33] Konrad H. Marti et al. "Complete-graph tensor network states: A new fermionic wave function ansatz for molecules". In: New Journal of Physics 12.10 (April 2010), p. 103008. ISSN: 13672630. DOI: 10.1088/1367-2630/12/10/103008.arXiv: 1004.5303. URL: http://arxiv.org/abs/1004.5303%20http://www.arxiv.org/pdf/1004.5303.pdf%20https://arxiv.org/abs/1004.5303.

[34] Debashree Ghosh et al. "Orbital optimization in the density matrix renormalization group, with applications to polyenes and β-carotene". In: Journal of Chemical Physics 128.14 (April 2008), p. 144117. ISSN: 00219606. DOI: 10.1063/1.2883976. arXiv: 0712.2475v2. URL: http://arxiv.org/abs/0712.2475%20http://www.arxiv.org/pdf/0712.2475.pdf%20https://arxiv.org/abs/0712.2475.

[35] Jordi Poater et al. "The calculation of electron localization and delocalization indices at the Hartree-Fock, density functional and post-Hartree-Fock levels of theory". In: Theoretical Chemistry Accounts: Theory, Computation, and Modeling (Theoretica Chimica Acta) 107.6 (June 2002), pp. 362-371. ISSN: 1432-881X. DOI: 10.1007/s00214-002-0356-8. URL: http://link.springer.com/10.1007/s00214-002-0356-8.

[36] Ulf Ryde and Pär Söderhjelm. "Ligand-Binding Affinity Estimates Supported by Quantum-Mechanical Methods". In: Chemical Reviews 116.9 (May 2016), pp. 5520-5566. ISSN: 15206890. DOI: 10.1021/acs.chemrev.5b00630. URL: http://www.ncbi.nlm.nih.gov/pubmed/27077817%20http://pubs.acs.org/doi/10.1021/acs.chemrev.5b00630.

[37] Charles R. Qi et al. "PointNet: Deep Learning on Point Sets for 3D Classification and Segmentation". In: (December 2016). arXiv: 1612.00593. URL: http://arxiv.org/abs/1612.00593.

[38] Peter W. Battaglia et al. "Relational inductive biases, deep learning, and graph networks". In: (June 2018). arXiv: 1806.01261. URL: http://arxiv.org/abs/1806.01261.

[39] Matthew J. Timm et al. "The localization-delocalization matrix and the electrondensity-weighted connectivity matrix of a finite graphene nanoribbon reconstructed from kernel fragments". In: Journal of Physical Chemistry A 118.47 (November 2014), pp. 11304-11316. ISSN: 15205215. DOI: 10.1021/jp508490p. URL: http://pubs.acs.org/doi/10.1021/jp508490p.

[40] U. A. Chaudry and P. L. A. Popelier. "Estimation of pKa Using Quantum Topological Molecular Similarity Descriptors: Application to Carboxylic Acids, Anilines and Phenols". In: Journal of Organic Chemistry 69.2 (2004), pp. 233-241. ISSN: 00223263. DOI: 10.1021/jo0347415. URL: https://pubs.acs.org/doi/abs/10.1021/jo0347415.

[41] Ramon Carbó, Luis Leyda, and Mariano Arnau. "How similar is a molecule to another? An electron density measure of similarity between two molecular structures". In: International Journal of Quantum Chemistry 17.6 (June 1980), pp. 1185-1189. ISSN: 1097461X. DOI: 10.1002/qua.560170612. URL: http://doi.wiley.com/10.1002/qua.560170612.

[42] Elahe K. Astani, Nasser L. Hadipour, and Chun Jung Chen. "Molecular interactions investigated with DFT calculations of QTAIM and NBO analyses: An application to dimeric structures of rice A-amylase/subtilisin inhibitor". In: Chemical Physics Letters 672 (March 2017), pp. 80-88. ISSN: 00092614. DOI: 10.1016/j.cplett.2017.01.047. URL: https://www.sciencedirect.com/science/article/abs/pii/S0009261417300696.

[43] Rodrigo D. Tosso et al. "The electronic density obtained from a QTAIM analysis used as molecular descriptor. A study performed in a new series of DHFR inhibitors". In: Journal of Molecular Structure 1134 (April 2017), pp. 464-474. ISSN: 00222860. DOI: 10.1016/j.mol-

[44] E. Espinosa, E. Molins, and C. Lecomte. "Hydrogen bond strengths revealed by topological analyses of experimentally observed electron densities". In: Chemical Physics Letters 285.3-4 (March 1998), pp. 170-173. ISSN: 00092614. DOI:10.1016/S0009-2614(98)00036-0. URL: https://www.sciencedirect.com/science/article/abs/pii/S0009261498000360.

[45] Sebastian Kmiecik et al. "Coarse-Grained Protein Models and Their Applications". In: Chemical Reviews 116.14 (July 2016), pp. 7898-7936. ISSN: 15206890. DOI: 10.1021/acs.chemrev.6b00163. URL: http://pubs.acs.org/doi/10.1021/acs.chemrev.6b00163.

[46] F. Weinhold, C. R. Landis, and E. D. Glendening. "What is NBO analysis and how is it useful?" In: International Reviews in Physical Chemistry 35.3 (July 2016), pp. 399-440. ISSN: 1366591X. DOI: 10.1080/0144235X.2016.1192262. URL: https://www.tandfonline.com/doi/full/10.1080/0144235X.2016.1192262.

[47] Michael Schlichtkrull et al. "Modeling Relational Data with Graph Convolutional Networks". In: (March 2017). arXiv: 1703.06103. URL: http://arxiv.org/abs/1703.06103.

[48] Ismat Sumar et al. "AIMLDM: A program to generate and analyze electron localization-delocalization matrices (LDMs)". In: Computational and Theoretical Chemistry 1070 (October 2015), pp. 55-67. ISSN: 2210271X. DOI: 10.1016/j.comptc.2015.07.014. URL: https://www.sciencedirect.com/science/article/pii/S2210271X15002947?via%7B%5C%%7D3Dihub.

[49] Chérif F. Matta. "Special issue: Philosophical aspects and implications of the quantum theory of atoms in molecules (QTAIM)". In: Foundations of Chemistry 15.3 (October 2013), pp. 245-251. ISSN: 13864238. DOI: 10.1007/s10698-013-9194-0. URL: http://link.springer.com/10.1007/s10698-013-9194-0.

[50] Chérif F. Matta. "On the connections between the quantum theory of atoms in molecules (QTAIM) and density functional theory (DFT): a letter from Richard F. W. Bader to Lou Massa". In: Structural Chemistry 28.5 (October 2017), pp. 1591-1597. ISSN: 10400400. DOI: 10.1007/s11224-017-0946-7. URL: http://link.springer.com/10.1007/s11224-017-0946-7.

[51] S. Irie et al. "Electron Density and Chemical Bonding: The Shape of Independent Atoms in Molecules". In: Berichte der Bunsengesellschaft fur physikalische Chemie 96.11 (November 1992), pp. 1545-1551. ISSN: 00059021. DOI: 10.1002/bbpc.19920961106. URL: http://doi.wiley.com/10.1002/bbpc.19920961106.

[52] C. F. Matta and R. J. Gillespie. "Understanding and Interpreting Molecular Electron Density Distributions". In: Journal of Chemical Education 79.9 (September 2002), p. 1141. ISSN: 0021-9584. DOI: 10.1021/ed079p1141. URL: http://pubs.acs.org/doi/abs/10.1021/ed079p1141.

[53] Chérif F. Matta. "How dependent are molecular and atomic properties on the electronic structure method? comparison of hartree-fock, DFT, and MP2 on a biologically relevant set of molecules". In: Journal of Computational Chemistry 31.6 (April 2010), pp. 1297-1311. ISSN: 01928651. DOI: 10.1002/jcc.21417.arXiv: NIHMS150003. URL: http://www.ncbi.nlm.nih.gov/pubmed/19882732%20http://doi.wiley.com/10.1002/jcc.21417.

[54] Chérif F. Matta and Alya A. Arabi. "Electron-density descriptors as predictors in quantitative structure-activity/property relationships and drug design". In: Future Medicinal Chemistry 3.8 (June 2011), pp. 969-994. ISSN: 17568919. DOI:10.4155/fmc.11.65. URL: http://www.ncbi.nlm.nih.gov/pubmed/21707400%20http://www.future-science.com/doi/10.4155/fmc.11.65.

[55] Evan N. Feinberg et al. "Spatial Graph Convolutions for Drug Discovery". In: (March 2018). arXiv: 1803.04465. URL: http://arxiv.org/abs/1803.04465.

[56] Junying Li, Deng Cai, and Xiaofei He. "Learning Graph-Level Representation for Drug Discovery". In: (September 2017). arXiv: 1709.03741. URL: http://arxiv.org/abs/1709.03741.

[57] Joseph Gomes et al. "Atomic Convolutional Networks for Predicting Protein-Ligand Binding Affinity". In: (March 2017). ISSN: 0148396X. DOI: 10.18653/v1/P16-1228. arXiv: 1703.10603. URL: http://arxiv.org/abs/1703.10603.

[58] Chao Shang et al. "Edge Attention-based Multi-Relational Graph Convolutional Networks". In: (February 2018). arXiv: 1802.04944. URL: http://arxiv.org/abs/1802.04944.

[59] Adam Santoro et al. "Relational recurrent networks". In: (June 2018). ISSN: 9789537619084. DOI: arXiv: 1806.01822v1. arXiv: 1806.01822. URL: http://arxiv.org/abs/1806.01822.

[60] Vinicius Zambaldi et al. "Relational Deep Reinforcement Learning". In: (June 2018). arXiv: 1806.01830. URL: http://arxiv.org/abs/1806.01830.

[61] Wengong Jin, Regina Barzilay, and Tommi Jaakkola. "Junction Tree Variational Autoencoder for Molecular Graph Generation". In: (February 2018). arXiv: 1802.04364. URL: http://arxiv.org/abs/1802.04364.

[62] Tymofii Yu. Nikolaienko and Leonid A. Bulavin. "Localized orbitals for optimal decomposition of molecular properties". In: (April 2018). DOI: arXiv: 1804 0.03723v1. arXiv: 1804.03723. URL: http://arxiv.org/abs/1804.03723.

[63] Samo Turk et al. "Coupling Matched Molecular Pairs with Machine Learning for Virtual Compound Optimization". In: Journal of Chemical Information and Modeling 57.12 (December 2017), pp. 3079-3085. ISSN: 15205142. DOI: 10.1021/acs.jcim.7b00298. URL: http://pubs.acs.org/doi/10.1021/acs.jcim.7b00298.

[64] Leon Freitag et al. "Orbital entanglement and CASSCF analysis of the Ru—NO bond in a Ruthenium nitrosyl complex". In: Physical Chemistry Chemical Physics 17.22 (June 2015), pp. 14383-14392. ISSN: 14639076. DOI: 10.1039/c4cp05278a. URL: http://www.ncbi.nlm.nih.gov/pubmed/25767830%20http://www.pubmedcentral.nih.gov/articlerender.fcgi?artid=PMC4447059.

[65] Alex D. Gottlieb and Norbert J. Mauser. "New measure of electron correlation". In: Physical Review Letters 95.12 (September 2005), p. 123003. ISSN: 00319007. DOI:10.1103/PhysRevLett.95.123003. URL: https://link.aps.org/doi/10.1103/PhysRevLett.95.123003.

[66] Eric D. Glendening, Clark R. Landis, and Frank Weinhold. "Natural bond orbital methods". In: Wiley Interdisciplinary Reviews: Computational Molecular Science 2.1 (January 2012), pp. 1-42. ISSN: 17590876. DOI: 10.1002/wcms.51. URL: http://doi.wiley.com/10.1002/wcms.51.

[67] Frank Weinhold. "Natural bond orbital analysis: A critical overview of relationships to alternative bonding perspectives". In: Journal of Computational Chemistry 33.30 (November 2012), pp. 2363-2379. ISSN: 01928651. DOI: 10.1002/jcc.23060. URL: http://doi.wiley.com/10.1002/jcc.23060.

[68] Garnet Kin Lic Chan. "Low entanglement wavefunctions". en. In: Wiley Interdisciplinary Reviews: Computational Molecular Science 2.6 (April 2012), pp. 907-920. ISSN: 17590876. DOI: 10.1002/wcms.1095. URL: http://doi.wiley.com/10.1002/wcms.1095%20http://gaznevada.iq.usp.br/wp-content/uploads/2017/10/chan-12%7B%5C_%7DMPS%7B%5C_%7Dlow-entanglement.pdf.

[69] Szilárd Szalay et al. "The correlation theory of the chemical bond". en. In: Scientific Reports 7.1 (April 2017), p. 2237. ISSN: 20452322. DOI: 10.1038/s41598-017-02447-z. arXiv: 1605.06919. URL: https://www.nature.com/articles/s41598-017-02447-z%20https://www.nature.com/articles/s41598-017-02447-z.pdf.

[70] E. Fertitta et al. "Investigation of metal-insulator-like transition through the <i>ab initio</i> density matrix renormalization group approach". In: Physical Review B 90.24 (May 2014), p. 245129. ISSN: 1098-0121. DOI: 10.1103/PhysRevB.90.245129. URL: https://link.aps.org/doi/10.1103/PhysRevB. 90.245129.

[71] Christopher J. Stein and Markus Reiher. "Measuring multi-configurational character by orbital entanglement". In: Molecular Physics 115.17-18 (May 2017), pp. 2110-2119. ISSN: 13623028. DOI: 10.1080/00268976.2017.1288934. arXiv: 1609.02617. URL: https://doi.org/10.1080/00268976.2017.1288934%20https://www.tandfonline.com/doi/pdf/10.1080/00268976.2017.1288934%20https://www.tandfonline.com/doi/full/10.1080/00268976.2017.1288934?src=recsys.

[72] Corinne Duperrouzel et al. "A quantum informational approach for dissecting chemical reactions". In: Chemical Physics Letters 621 (May 2015), pp. 160-164. ISSN: 00092614. DOI: 10.1016/j.cplett.2015.01.005. arXiv: arXiv:1409.4867v1. URL: http://www.sciencedirect.com/science/article/pii/S0009261415000159%20https://www.sciencedirect.com/science/article/abs/pii/S0009261415000159.

[73] Garnet Kin Lic Chan and Martin Head-Gordon. "Highly correlated calculations with a polynomial cost algorithm: A study of the density matrix renormalization group". In: Journal of Chemical Physics 116.11 (April 2002), pp. 4462-4476. ISSN: 00219606. DOI: 10.1063/1.1449459. URL: https://aip.scitation.org/doi/10.1063/1.1449459.

[74] Rodney J. Bartlett and Monika Musial. "Coupled-cluster theory in quantum chemistry". In: Reviews of Modern Physics 79.1 (April 2007), pp. 291-352. ISSN: 00346861. DOI: 10.1103/RevModPhys.79.291. URL: https://link.aps.org/doi/10.1103/RevModPhys.79.291%20https://journals.aps.org/rmp/abstract/10.1103/RevModPhys.79.291.

[75] Dominika Zgid and Marcel Nooijen. "Obtaining the two-body density matrix in the density matrix renormalization group method". In: The Journal of Chemical Physics 128.14 (May 2008), p. 144115. ISSN: 0021-9606. DOI: 10.1063/1.2883980. URL: http://aip.scitation.org/doi/10.1063/1.2883980.

[76] Yingjin Ma and Haibo Ma. "Assessment of various natural orbitals as the basis of large active space density-matrix renormalization group calculations". In: Journal of Chemical Physics 138.22 (May 2013), p. 224105. ISSN: 00219606. DOI:10.1063/1.4809682. arXiv: 1303.0616. URL: https://aip.scitation.org/doi/full/10.1063/1.4809682%20https://aip.scitation.org/doi/full/10.1063/1.4809682?ver=pdfcov.

[77] Zhendong Li et al. "Localization of molecular orbitals: From fragments to molecule". In: Accounts of Chemical Research 47.9 (April 2014), pp. 2758-2767. ISSN: 15204898. DOI: 10.1021/ar500082t. URL: https://doi.org/10.1021/ar500082t%20https://pubs.acs.org/doi/full/10.1021/ar500082t.

[78] Sebastian F. Keller and Markus Reiher. "Determining Factors for the Accuracy of DMRG in Chemistry". en. In: CHIMIA International Journal for Chemistry 68.4 (April 2014), pp. 200-203. ISSN: 00094293. DOI: 10.2533/chimia.2014.200. arXiv: 1401.5497. URL: http://openurl.ingenta.com/content/xref?genre=article%7B%5C&%7Dissn=0009-4293%7B%5C&%7Dvolume=68%7B%5C&%7Dissue=4%7B%5C&%7Dspage=200.

[79] Sebastian Wouters et al. "Communication: DMRG-SCF study of the singlet, triplet, and quintet states of oxo-Mn (Salen)". en. In: Journal of Chemical Physics 140.24 (May 2014). ISSN: 00219606. DOI: 10.1063/1.4885815. URL: https://arxiv.org/abs/1405.5642%20http://arxiv.org/pdf/1405.5642.

[80] Arseny Kovyrshin and Markus Reiher. "Self-adaptive tensor network states with multi-site correlators". en. In: Journal of Chemical Physics 147.21 (April 2017), p. 214111. ISSN: 00219606. DOI: 10.1063/1.5004693. arXiv: 1709.04565. URL: http://aip.scitation.org/doi/10.1063/1.5004693.

[81] Katharina Boguslawski et al. "Entanglement measures for single- and multireference correlation effects". en. In: Journal of Physical Chemistry Letters 3.21 (April 2012), pp. 3129-3135. ISSN: 19487185. DOI: 10.1021/jz301319v. arXiv: arXiv:1208.6586v1. URL: http://pubs.acs.org/doi/10.1021/jz301319v.

[82] Katharina Boguslawski et al. "Orbital entanglement in bond-formation processes". In: Journal of Chemical Theory and Computation 9.7 (May 2013), pp. 2959-2973. ISSN: 15499618. DOI: 10.1021/ct400247p. arXiv: 1303.7207. URL: http://arxiv.org/abs/1303.7207%20http://www.arxiv.org/pdf/1303.7207.pdf%20https://arxiv.org/abs/1303.7207.

[83] Katharina Boguslawski et al. "Accurate ab initio spin densities". In: Journal of Chemical Theory and Computation 8.6 (May 2012), pp. 1970-1982. ISSN:15499618. DOI: 10.1021/ct300211j. arXiv: 1203.3888. URL: https://doi.org/10.1021/ct300211j%20https://pubs.acs.org/doi/pdfplus/10.1021/ct300211j%20https://pubs.acs.org/doi/full/10.1021/ct300211j.

[84] Markus Reiher. Three Lectures on DMRG in Quantum Chemistry Three Lectures on DMRG in Quantum Chemistry. en. Ed. by Markus Reiher. 2014. URL: https://static.uni-graz.at/fileadmin/tagung-theoretische-chemie/Dokumente/Workshop%7B%5C_%7D2014/reiher%7B%5C_%7Dmariapfarr2014.pdf.

[85] Markus Reiher. DMRG in Quantum Chemistry: From its relation to traditional methods to n-orbital density matrices and beyond. en. Ed. by Markus Reiher. 2016. URL: http://www.reiher.ethz.ch.

[86] Gerrit Moritz, Bernd Artur Hess, and Markus Reiher. "Convergence behavior of the density-matrix renormalization group algorithm for optimized orbital orderings". In: Journal of Chemical Physics 122.2 (May 2005), p. 24107. ISSN: 00219606. DOI: 10.1063/1.1824891. URL: https://aip.scitation.org/doi/10.1063/1.1824891.

[87] Yingjin Ma, Jing Wen, and Haibo Ma. "Density-matrix renormalization group algorithm with multi-level active space". In: Journal of Chemical Physics 143.3 (April 2015), p. 34105. ISSN: 00219606. DOI: 10.1063/1.4926833. arXiv: arXiv:1507.05264v1. URL: http://arxiv.org/abs/1507.05264%20 http://www.arxiv.org/pdf/1507.05264.pdf%20https://arxiv.org/abs/1507.05264.

[88] G. Barcza et al. "Entanglement patterns and generalized correlation functions in quantum many-body systems". In: Physical Review B 92.12 (May 2015), p. 125140. ISSN: 1098-0121. DOI: 10.1103/PhysRevB.92.125140. arXiv: 1406.6643. URL: http://arxiv.org/abs/1406.6643.

[89] Sebastian Keller et al. "Selection of active spaces for multiconfigurational wavefunctions".eng. In: Journal of Chemical Physics 142.24 (2015), p. 244104. ISSN: 00219606. DOI: 10.1063/1.4922352. URL: http://www.ncbi.nlm.nih.gov/pubmed/26133407.

[90] Katharina Boguslawski. "How quantum entanglement can promote the understanding of electronic structures of molecules". en. In: November (2013), p. 37. URL: http://math.unice.fr/%7B~%7Dcassam/Workshop13/Presentations/boguslawski.pdf.

[91] Markus Reiher, ed. The first second-generation DMRG program for quantum chemistry. en. 2014. URL: https://www.ethz.ch/content/dam/ethz/specialinterest/chab/physical-chemistry/reiher-dam/documents/Diverse/reiher%7B%5C_%7Dsqmc.pdf.

[92] Sandeep Sharma and Garnet Kin-Lic Chan. "Spin-adapted density matrix renormalization group algorithms for quantum chemistry". In: The Journal of Chemical Physics 136.12 (April 2012), p. 124121. ISSN: 0021-9606. DOI: 10.1063/1.3695642. URL: http://aip.scitation.org/doi/10.1063/1.3695642.

[93] C. Krumnow et al. "Fermionic orbital optimization in tensor network states". In: Physical Review Letters 117.21 (April 2016). ISSN: 10797114. DOI: 10.1103/PhysRevLett.117.210402. arXiv: 1504.00042. URL: http://arxiv.org/abs/1504.00042%20http://www.arxiv.org/pdf/1504.00042.pdf%20https://arxiv.org/abs/1504.00042.

[94] Fengyi Liu et al. "Multireference ab initio density matrix renormalization group (DMRG)-CASSCF and DMRG-CASPT2 study on the photochromic ring opening of spiropyran". In: Journal of Chemical Theory and Computation 9.10 (May 2013), pp. 4462-4469. ISSN: 15499618. DOI: 10.1021/ct400707k. URL: https://doi.org/10.1021/ct400707k%20https://pubs.acs.org/doi/full/10.1021/ct400707k.

[95] Konrad Heinrich Marti and Markus Reiher. "The density matrix renormalization group algorithm in quantum chemistry". In: Zeitschrift fur Physikalische Chemie 224.3-4 (April 2010), pp. 583-599. ISSN: 09429352. DOI: 10.1524/zpch.2010.6125. URL: https://www.degruyter.com/view/j/zpch.2010.224.issue-3-4/zpch.2010.6125/zpch.2010.6125.xml%20http://www.reiher.ethz.ch/content/dam/ethz/special-interest/chab/physical-chemistry/reiherdam/documents/Publications%7B%5C_%7DPDF/153%7B%5C_%7DReiher%7B%5C_%7DZPhys Chem%7B%5C_%7D2010%7B%5C_%7D224%7B%5C_%7D583.pdf.

[96] Christopher J. Stein, Vera Von Burg, and Markus Reiher. "The Delicate Balance of Static and Dynamic Electron Correlation". In: Journal of Chemical Theory and Computation 12.8 (April 2016), pp. 3764-3773. ISSN: 15499626. DOI: 10.1021/acs.jctc.6b00528. arXiv: 1605.07020. URL: http://arxiv.org/abs/1605.07020%20http://www.arxiv.org/pdf/1605.07020.pdf%20https://arxiv.org/abs/1605.07020.

[97] Michael W. Schmidt and Mark S. Gordon. "the Construction and Interpretation of Mcscf Wavefunctions". In: Annual Review of Physical Chemistry 49.1 (May 1998), pp. 233-266. ISSN: 0066-426X. DOI: 10.1146/annurev.physchem.49.1.233. URL: http://www.annualreviews.org/doi/10.1146/annurev.physchem.49.1.233.

[98] Frank Neese. Local Correlation Approaches. en. Ed. by Frank Neese. URL: http://www.esqc.org/static/lectures/ESQC-LocalCorrelation%7B%5C_%7Dfinal.pdf.

[99] John B Parkinson and Damian J J Farnell. "The Coupled Cluster Method". In: arXiv:1506.06914 [math-ph, physics:quant-ph] (April 2010), pp. 109-134. ISSN: 00758450. DOI: 10.1007/978-3-642-13290-2_10. arXiv: arXiv:1506.06914v1. URL: http://link.springer.com/10.1007/978-3-642-13290-2%7B%5C_%7D10.

[100] Garnet Kin-Lic Chan et al. "Matrix Product Operators, Matrix Product States, and ab initio Density Matrix Renormalization Group algorithms". In: arXiv: 1605.02611 [cond-mat, physics:physics, physics:quant-ph] (April 2016). ISSN: 00219606. DOI: 10.1063/1.4955108. arXiv: 1605.02611. URL: http://arxiv.org/abs/1605.02611.

[101] Jörg Rissler, Reinhard M. Noack, and Steven R. White. "Measuring orbital interaction using quantum information theory". In: Chemical Physics 323.2-3 (April 2006), pp. 519-531. ISSN: 03010104. DOI: 10.1016/j.chemphys.2005.10.018. arXiv: 0508524v1 [arXiv:cond-mat]. URL: http://arxiv.org/abs/cond-mat/0508524%20http://www.arxiv.org/pdf/cond-mat/0508524.pdf%20https://arxiv.org/abs/cond-mat/0508524.

[102] Legeza and J. Sólyom. "Optimizing the density-matrix renormalization group method using quantum information entropy". In: Physical Review B—Condensed Matter and Materials Physics 68.9 (May 2003), p. 195116. ISSN: 1550235X. DOI:10.1103/PhysRevB.68.195116. URL: https://link.aps.org/doi/10.1103/PhysRevB.68.195116%20https://journals.aps.org/prb/abstract/10.1103/PhysRevB.68.195116.

[103] G. Barcza et al. "Quantum information analysis of electronic states at different molecular structures". In: Physical Review A 83.1 (April 2010). ISSN: 1050-2947, 1094-1622. DOI: 10.1103/PhysRevA.83.012508. arXiv: 1008.4607. URL: http://arxiv.org/abs/1008.4607%7B%5C%%7D0Ahttp://dx.doi.org/10.1103/PhysRevA.83.012508.

[104] David A. Mazziotti. "Structure of Fermionic density matrices: Complete N-representability conditions". In: Physical Review Letters 108.26 (May 2012), p. 263002. ISSN:00319007. DOI: 10.1103/PhysRevLett.108.263002. arXiv: arXiv: 1112.5866v2. URL: https://link.aps.org/doi/10.1103/PhysRevLett.108.263002%20https://journals.aps.org/prl/abstract/10.1103/PhysRevLett.108.263002.

[105] Dongxia Ma, Giovanni Li Manni, and Laura Gagliardi. "The generalized active space concept in multiconfigurational self-consistent field methods". In: Journal of Chemical Physics 135.4 (May 2011), p. 44128. ISSN: 00219606. DOI: 10.1063/1.3611401. URL: https://aip.scitation.org/doi/10.1063/1.3611401.

[106] Dominika Zgid and Marcel Nooijen. "The density matrix renormalization group self-consistent field method: Orbital optimization with the density matrix renormalization group method in the active space". In: Journal of Chemical Physics 128.14 (May 2008), p.

144116. ISSN: 00219606. DOI: 10.1063/1.2883981. URL: https://aip.scitation.org/doi/10.1063/1.2883981.
[107] Libor Veis et al. "Coupled Cluster Method with Single and Double Excitations Tailored by Matrix Product State Wave Functions". In: Journal of Physical Chemistry Letters 7.20 (April 2016), pp. 4072-4078. ISSN: 19487185. DOI: 10.1021/acs.jpclett.6b01908. URL: http://arxiv.org/abs/1606.06002%20http://www.arxiv.org/pdf/1606.06002.pdf%20https://arxiv.org/abs/1606.06002.
[108] Sebastian Wouters et al. "CheMPS2: A free open-source spin-adapted implementation of the density matrix renormalization group for ab initio quantum chemistry". In: Computer Physics Communications 185.6 (April 2014), pp. 1501-1514. ISSN: 00104655. DOI: 10.1016/j.cpc.2014.01.019. arXiv: 1312.2415. URL: http://arxiv.org/abs/1312.2415%20http://www.arxiv.org/pdf/1312.2415.pdf%20https://arxiv.org/abs/1312.2415.
[109] Arseny Kovyrshin and Markus Reiher. "Tensor network states with three-site correlators". en. In: New Journal of Physics 18.11 (April 2016), p. 113001. ISSN: 13672630. DOI: 10.1088/1367-2630/18/11/113001. arXiv: 1311.6696. URL: http://stacks.iop.org/1367-2630/18/i=11/a=113001%20http://iopscience.iop.org/article/10.1088/1367-2630/18/11/113001/pdf.
[110] Katharina Boguslawski and Pawel Tecmer. "Orbital entanglement in quantum chemistry". In: International Journal of Quantum Chemistry 115.19 (April 2015), pp. 1289-1295. ISSN: 1097461X. DOI: 10.1002/qua.24832. arXiv: 1409.8017. URL: http://arxiv.org/abs/1409.8017%20http://www.arxiv.org/pdf/1409.8017.pdf%20https://arxiv.org/abs/1409.8017.
[111] Yuki Kurashige, Garnet Kin Lic Chan, and Takeshi Yanai. "Entangled quantum electronic wavefunctions of the Mn4CaO5 cluster in photosystem II". en. In: Nature Chemistry 5.8 (May 2013), pp. 660-666. ISSN: 17554330. DOI: 10.1038/nchem.1677. URL: https://www.nature.com/articles/nchem.1677.
[112] Sandeep Sharma et al. "Low-energy spectrum of iron-sulfur clusters directly from many-particle quantum mechanics". en. In: Nature Chemistry 6.10 (May 2014), pp. 927-933. ISSN: 17554349. DOI: 10.1038/nchem.2041. arXiv: 1408.5080. URL: https://www.nature.com/articles/nchem.2041%20https://www.nature.com/articles/nchem.2041%7B%5C#%7Dsupplementary-information.
[113] Szilárd Szalay et al. "Tensor product methods and entanglement optimization for ab initio quantum chemistry". In: International Journal of Quantum Chemistry 115.19 (December 2015), pp. 1342-1391. ISSN: 1097461X. DOI: 10.1002/qua.24898. arXiv: 1412.5829. URL: http://arxiv.org/abs/1412.5829.

Section 5: Structure Based Model Overview

The approach is relevant both for structure based models, i.e. models based on information about both the ligand and the target protein, but applies generically to an ML approach used to predict any quantity that is a function of a thermodynamic ensemble. While training on an ensemble is the theme that ties all the ideas together, the spectrum of ideas described below is pretty broad. Generalisation of Q-graph to weak force and electrostatic descriptors is provided, as well as a proposal how to input scalar fields obtained from quantum calculations directly using a point cloud ML network. In addition, a proposal for an ML approach where training is performed on synthetically generated datasets of increasing complexity (e.g. expectation values of increasingly complex quantum observables), with the aim of predicting an experimentally measured quantity. Put another way, the idea is that the most complex set of observables, at the top level of the hierarchy, are designed to correlate maximally well with the experimental observable, and the network hierarchically builds up to achieve an accurate representation of these.

Overview

1) The model is trained on a set of representative conformational poses. The poses are sampled from a physically relevant thermodynamic ensemble. E.g. for binding affinities this might include both the ensemble of ligands and protein in solution, and ensemble of the bound complex, at some fixed temperature. The training can be performed in a manner such that every pose is treated as a separate data point, associated with the same experimental value (in the above example, the same binding affinity). More accurately the idea is to mimic the actual thermodynamic calculation, as described in "Section 7: Machine learning on thermodynamic ensembles".

2) Ligand, protein and ligand plus protein poses are generated using molecular dynamics (MD), or in principle QM/MM or even pure QM methods. Schematic diagram is provided in FIG. 49.

3) As above, but the sampled poses are combined into a single descriptor.

4) Conformations are sampled at inference time. The mean provides the predicted value, and the standard deviation corresponds to the error estimate. More elaborate statistical analysis can clearly be performed.

Figure 48:
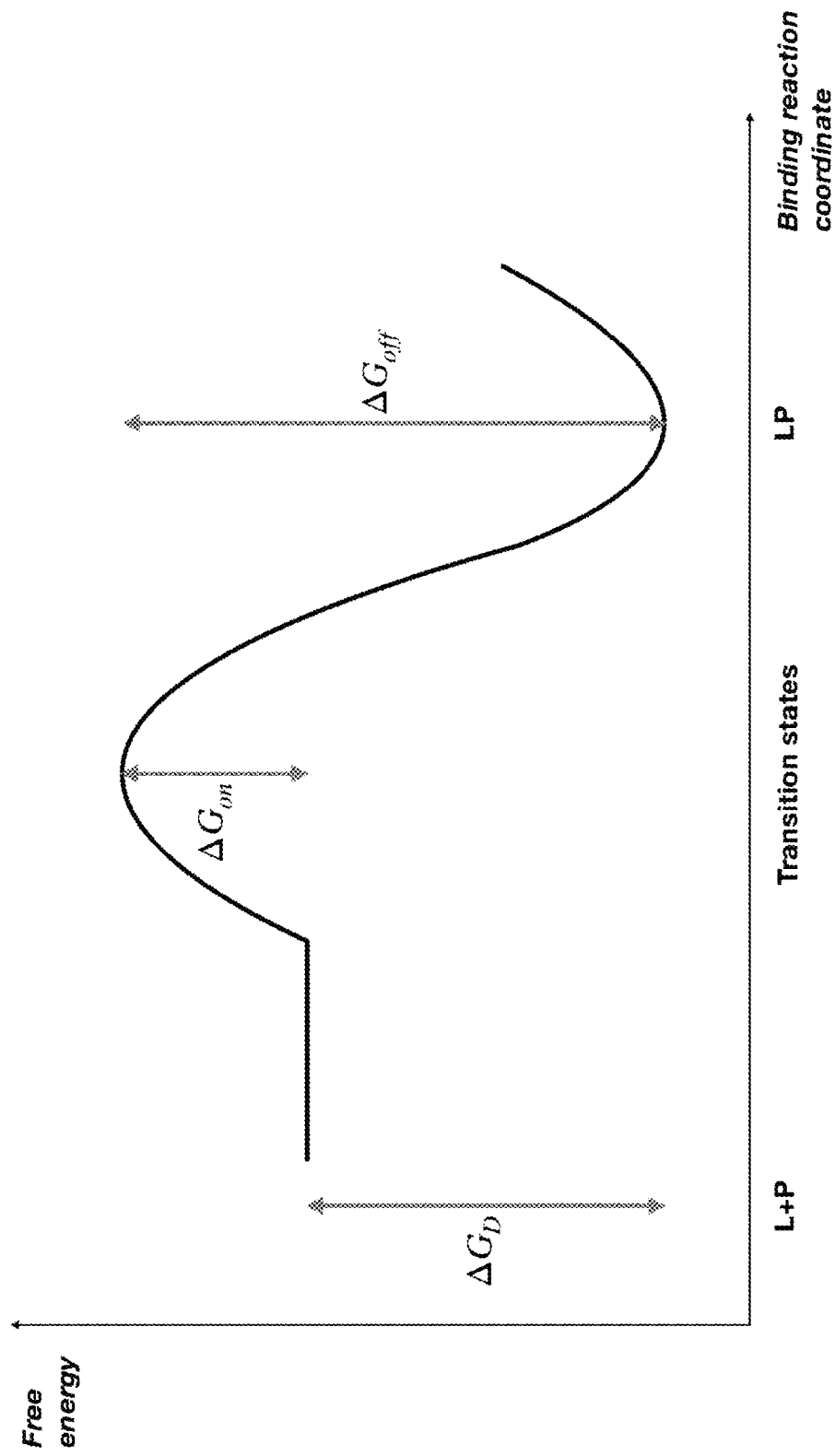
FIG. 48 shows a plot of free energy as a function of transition states.

5) Particular structure based architectures—The general structure based model architecture attempts to approximate the de novo physics expression for binding affinity $\Delta G = G_L + G_P - G_{LP}$ (see FIG. 48). The architecture is therefore split into three, in general independent networks: for the ligand in solution (L), for the isolated protein (P) in solution, and for the complex LP in solution. The architecture in [8] follows this prescription, but only for a single conformer per molecule and does not use convolutional layers with learnable weights.

6) Given enough data on conformations, a distribution over different conformations can be learned by a generative model that takes molecules as input and that outputs conformation samples for those molecules. The architecture is a graph-convolutional model that outputs atomic positions, and learning can be designed via GAN or VAE methods. Generative models for conformations do not yet exist to our knowledge.

7) For structure based models, in order to reduce the number of independent weights that need to be trained, in order to control over-fitting, one can use weight sharing, have a single architecture (as opposed to a sum of a number of independent networks), which takes both free and bound conformations as inputs.

8) In general, proteins are too large to efficiently input accurate information about all its constituents into the network. For many calculations, such as for structure based models defined as in 4), this isn't necessary, as away from the binding site, lots of terms in the expression for $\Delta G$ above are expected to cancel to high accuracy ($G_P$ away from the pocket can be expected to behave nearly identically to $G_{LP}$). In order to implement this at the level of ML models, one should, in the design of the networks, use the same weights both in $G_P$ and in $G_{LP}$. It follows that, given such an ML architecture, it isn't necessary to explicitly cut out the pocket from protein in order to make the ML algorithm feasible (as in [9])—this happens automatically. The cancellations need to be tracked in the algorithm and numerically dealt with in the optimal manner.

9) In the context of structure based models, docking can be used to generate a set of poses. These are unlikely to be accurate statistical representatives of the physically relevant thermodynamic ensemble, but are a good starting point for ML training. Docking can be improved by performing molecular dynamics runs on the docked poses, as well as analysis of the effect of water molecules.

10) For all model, and for both training and inference, we consider any suitable featurization of input molecules. In addition to featurisations, we introduce the weak-force and electrostatic versions of Q-graph. These descriptors can be considered in isolation, in solution, or obtained by considering the ligand in the presence of the pocket, treated either quantum mechanically or using empirical methods (most up-to-date details on Q-graph construction are given in "Section 4: Graph featurization and quantum chemistry".

11) Training models by sampling the scalar fields directly, using a point cloud architecture (as described in "Section 4: Graph featurization and quantum chemistry"). This can be done for each element in the ensemble separately, or across the ensemble at once.

12) Waters can be treated using semi-empirical methods, such as those in Waterflap, software or my more extensive QM/MM calculations.

13) Additional details which we combine from elsewhere include attention mechanism useful for chemistry (such as the one proposed in [11]), histogram description of distances, application of histogram stype binning [10] to current problem, non-bonding 'edges' in graphs.

14) Additional original algorithmic details: weights that depend on location, e.g. ligand/protein away from boundary, vs. boundary, and more. We propose a new structure-based model which computes a per-ligand-atom gating from the pocket. Coupling the pocket and ligand this way allows us to avoid graph-convolutional updates on the large graph constructed from the pocket-ligand complex, leading to a large increase in efficiency. The model is compatible with a principled form of ligand-based transfer learning, which is helpful given that ligand-based data is much more abundant than structure-based.

15) To take advantage of fixed protein structure when building a model against a single target, we propose a model where the locations of the ligand atoms relative to the pocket are encoded as node-features, and another where the locations are used to compute a gating.

16) Combine graph based models with standard fingerprints: SPLIF descriptors/salt bridge, H-bond terms, Pi-Pi cation Pi-Pi stacking (scalar fields+Q-graph methodologies), Mordred features.

17) Inclusion of descriptors for weak intermolecular forces in our graph models.

FIG. 48 shows a plot of free energy as a function of transition states. Binding affinities, as well as on- and, off-rates, are given by differences in free energies of different ensembles: Free ligand and protein (L+P), the bound ligand and protein complex (LP), and transition states. Note that this applies to chemical reactivity, and to calculations of transition state binding properties.

Figure 49:
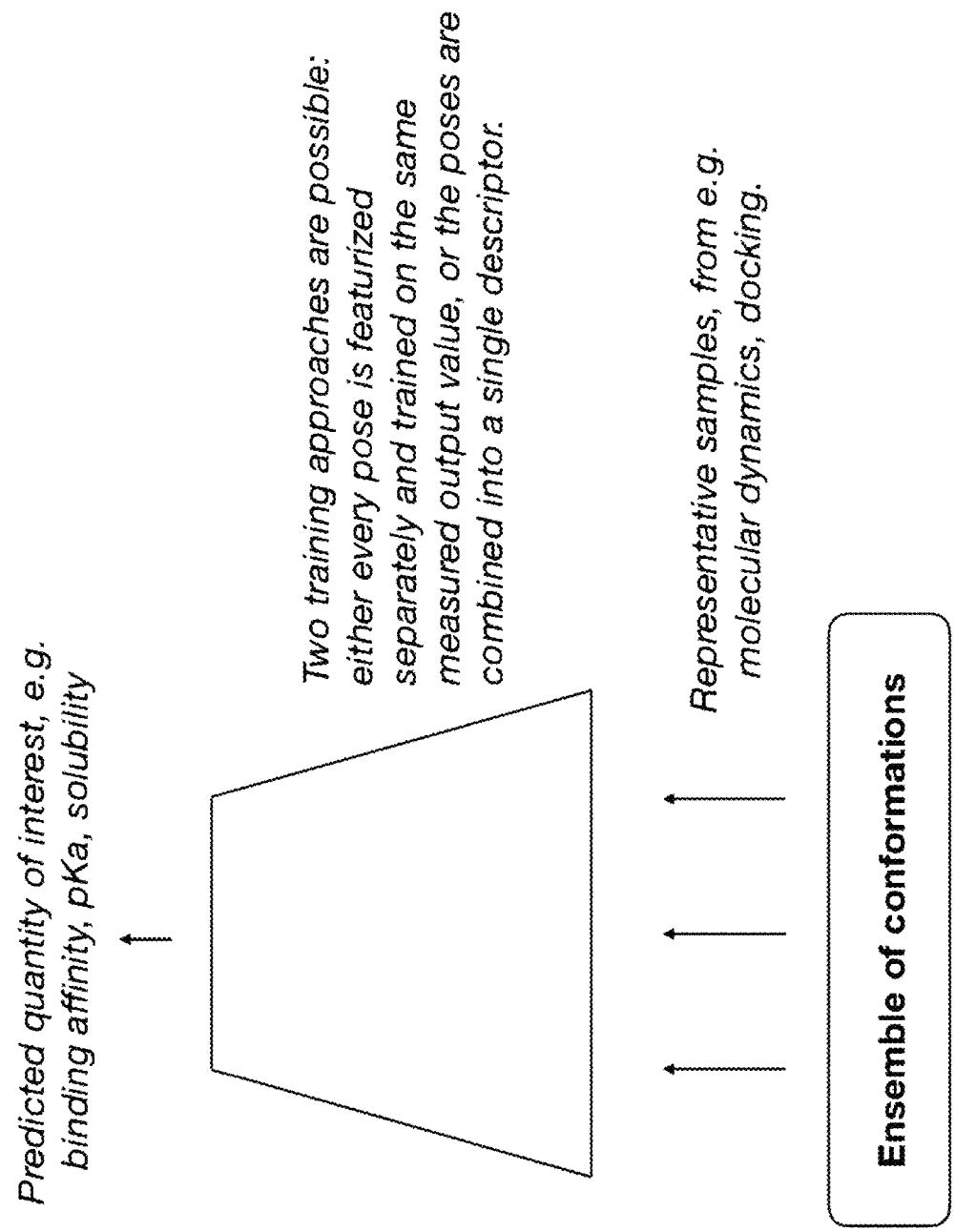
FIG. 49 shows a schematic diagram of a predictive model trained on an ensemble, schematic diagram.

FIG. 49 shows a schematic diagram of a predictive model trained on an ensemble, schematic diagram.

Model Details

In order to aid the ML process it is important to expose to the neural network the fundamental forces between the ligand and the protein pocket so as to cope with the lack of data from which these interactions could be in principle be learnt. It is expected that the ML process will be able to correlate the strength and topology of these interactions (see below) with the binding affinities.

For ligand-based models, for which the quantity to be predicted is understood to be closely correlated to a set of quantum mechanical or thermodynamic observables, we propose a general ML framework. In the simplest manifestation of this idea, QM data can be calculated on a synthetic dataset, and ML trained on this in order to create a ML model which can be queried quickly—so we are considering a two stage ML framework; given a molecule, the QM descriptors are obtained from the ML model, and these are then trained using another (usually simpler) ML architecture to reproduce experimentally measured values (see FIG. 50). In general, we propose a hierarchy, where models can be trained on increasingly complex set of quantum observables. For example, the first layer can be trained to generate a simple HF description of the molecule, the second trained on the HF descriptors to reproduce more complex DFT observables, and so on, with the final layer trained on experimentally derived data.

Figure 50:
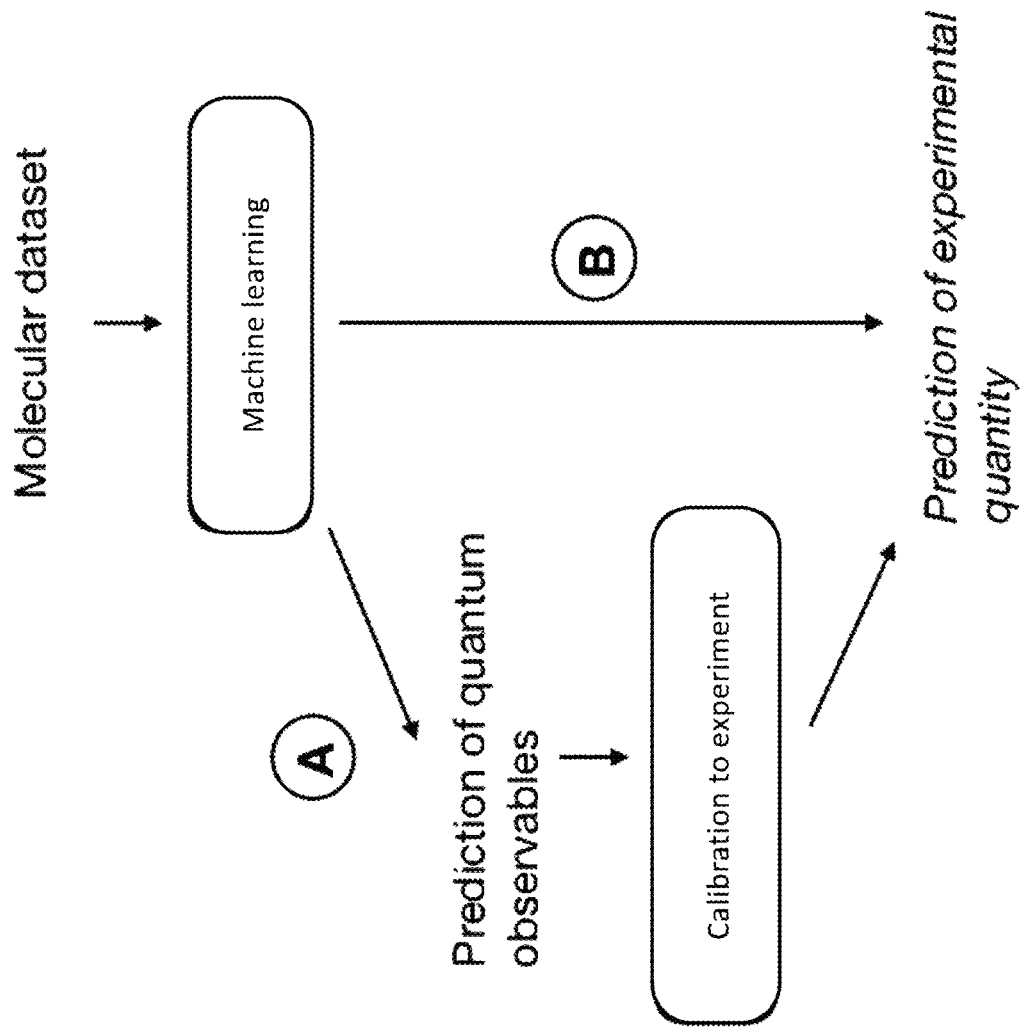
FIG. 50 shows a schematic diagram depicting two approaches for designing predictive models for physico-chemical properties.

FIG. 50 shows a schematic diagram depicting two approaches for designing predictive models for physico-chemical properties. For case A) the ML algorithm first predicts a set of quantum observables, which are then correlated to the experimental quantity of interest. In B) the model is trained on experimental data directly.

Generalisations of this idea: 1) Having trained the model, one then trains end to end, in order to improve results. 2) The observables need not be exclusively quantum mechanical, but can include classical, thermodynamic, or other quantities—this is the case for structure based models, as detailed below.

Aspects of this idea are described in more detail in the "Ligand based models", and "Structure based models" in "Section 1: Overview of small molecule drug discovery".

Data Augmentation

Data augmentation: FEP, TI, and other computationally heavier/less accurate methods [12, 13].

On the ligand model side we have some examples as well, like the perturbative pKa calculations. Perturbation theory more generally.

Docking approach to augment data, in our context, helped along with MD.

Featurization

Explicit hydrogens, with their positions optimised. Hydrogens are important for QM and/or QM/MM calculations but their positions might change a lot when waters are present. Good pKa predictors are ultimately very important, and pKa predictors can be used in order to advance structure based models for binding affinities. Accurate methods for modelling waters, obtained e.g. from simulations using software like Waterflap, are therefore essential.

Full Q-graph description of ligand, and proteins when appropriate. Q-graph can be generalised to mean not just an approximate graph description of the $\rho(x, x)$ and $\rho(x, x')$ density matrix (see "Section 4: Graph featurization and quantum chemistry"), but also a graph description obtained from any QM derived scalar field (and beyond, vector, tensor field).

Q-graph in presence of the protein pocket; Hamiltonian of the isolated ligand is modified with a term representing the overall effect of the pocket. In this QM/MM approach, the ligand and the pocket are not treated on an equal footing; the ligand is treated using QM while the rest of the system is treated using a classical force field. Thus, in this description only QM descriptors for the ligand can be extracted, while the rest of system only induces changes in the electronic structure of the ligand compared to the isolated (or solvated) ligand. The system is partitioned in the QM and MM regions and the energy of the total system can be expressed as $E_{tot}=E_{QM}+E_{MM}+E_{QM/MM}$ where the first, second and third terms represent the energy of the QM region (ligand), of the classical region (protein, solvent) and of the interaction terms between the two regions respectively. The electronic structure problem of the ligand will be modified in the presence of the pocket (and strictly speaking not only of the pocket but of all the classical subsystem) by introducing an interaction term $V_{int}$ in the ligand's gas-phase hamiltonian, i.e. $H=H_0+V_{int}$, where the precise form of the interaction will depend on the particular level of treatment employed. The electronic structure problem is solved in a self-consistent manner using a particular level of theory (e.g. DFT) and all the properties of the ligand can be subsequently computed from an analysis of the converged wavefunction or density. The Q-graph is derived by a topological analysis of the ligand's density [14, 15].

Q-graph with the ligand and pocket treated quantum mechanically. Here a QM/MM methodology is adopted but the QM part of the system now consists of the ligand and the pocket, the latter being defined as the protein residues that are within a radius of 10 Å away from the ligand. This is a more accurate description of the total system compared to the one above and it is expected that better correlation with the ligand binding affinities will be achieved [16]. The non-bonded interactions between the ligand and the pocket will be qualitatively be reproduced as well, by a topological analysis of the electron density (see below). The density can either be the fully converged SCF density (very extensive and expensive) or the promolecular densities (very fast but potentially inaccurate). For the latter, the superposition of atomic densities is recommended bibliographically but in our work the initial guess calculated by using polarized atomic densities as implemented in ORCA is used. The latter already give a density in accordance with the molecular shape and therefore are expected to contain correct information about the intermolecular forces.

Since the size of the system is prohibitively large for the employment of DFT methods, semi-empirical methods need to be employed (AM1, PM3, DFT Tight-Binding). Grimme's improved semi-empirical methods (hf-3c etc.) will also serve as an alternative, since they have been shown to be adequate for an estimation of the intermolecular forces between molecules [17].

Incorporate transition states. Here more advanced methods, including tensor network featurization becomes relevant, as transition states are generally highly entangled.

This is highly relevant for kinetics (on and off-rates), as well as chemical reactivity, and enzyme reactions, see "Section 1: Overview of small molecule drug discovery".

For structure based models, we consider both QM and thermodynamic quantities. From a strict QM perspective the separation of the system into ligand and pocket is not possible but using perturbation theory one can separate various intermolecular forces, assuming that the electron clouds of the two molecules do not overlap. The theory of intermolecular forces is based on perturbation theory in which the zeroth-order hamiltonian is the sum of the isolated hamiltonians of the two systems, i.e. $H_0=H_A+H_B$ while the total hamiltonian is $H_{tot}=H_A+H_B+H_{int}$ where the interaction term $H_{int}$ couples the two molecules and can be considered as a perturbation if the interaction is not too strong. The interaction hamiltonian can be setup easily and has the classical electrostatic interaction form for two sets of electric charges $q_A$ and $q_B$, each set belonging to molecules A and B, $$q^B V^A(B) = \Sigma_a q^B \frac{e_a}{4\pi\varepsilon_0|R-a|}$$

i.e. where the charge q of molecule B and the electrostatic potential of molecule A at the position of charge q were used. Employing perturbation theory, one can separate various contributions to the intermolecular interaction energy as provided in [18].

For our purposes, a more crude, less exact and rigorous classification of intermolecular forces can be made (ignoring the short-range ones which are difficult to reproduce because large amounts of electron-correlation must be included into a wavefunction-based method for their accurate estimation) as:

1) Bonding: Localized in space.
2) Electrostatic interactions: very important for molecular recognition and binding.
3) Non-electrostatic weak interactions: Weak per se but important in combination since they are numerous. Very important for molecular recognition and binding.

Obviously, both the atom types and bonding pattern of the ligand (chemical identity), and the non-covalent intermolecular interactions between the ligand and the pocket of the protein contribute significantly to molecular recognition and thus to the binding affinity. Despite the fact that the binding affinity is a thermodynamic quantity and requires a complete sampling of the configuration space of the total ligand+protein+solvent system for its accurate de novo determination, if one is determined to train the deep neural networks on a particular configuration of the system (or a sample of configurations from the thermodynamic ensemble) then it makes sense to include in the graph representation of the molecule, along with the various features (molecular properties etc.), a representation of the weak forces that are created when the ligand interacts with the pocket.

For the representation of the bonds between atoms and their order (single, double, triple) analysis based on the atoms-in-molecules (AIM) formalism [1-3] as well as the electron localization function (ELF) [4,5] are sufficient to represent the ligand in a graph-theoretical framework, see: "Section 4: Graph featurization and quantum chemistry".

For non-covalent interactions that are of electrostatic nature the ligand's electrostatic potential is routinely used, which is again a scalar field in three dimensions, and can be converted into a graph using a number of standard methods, similar to the ones used already for the Q-Graph. The electrostatic interactions, quantified by the ligand's electrostatic potential and charges (using a QM/MM description including the ligand in the QM only) should be estimated by using fully converged SCF results, because it is not know what the effect will be on these by using promolecular densities.

For the rest of the non-covalent interactions (e.g. pi-pi stacking, hydrogen bonding, steric repulsions, van der Waals interactions) an analysis based on the electron density and its gradient and the subsequent quantification in three dimensional physical space as scalar fields which are directional and localized is an attractive and a cost-effective method, quite similar to what is done in an AIM analysis of the electron density. Yan et al. [6,7] have described such an analysis, which can be done with the program NCIPLOT (and possibly Multiwfn), provided that an estimate of the electron density is given. The applicability of the methodology extends from semi-empirical methods (e.g. AM1, PM3, DFTB3) using promolecular (superposition of atomic densities or Hueckel-type) or SCF densities to more exact DFT or ab initio methods. Obviously the latter choice is more accurate since it takes into account among other things the mutual polarization of the ligand and the pocket but significantly more time consuming. This analysis can be extended to a QM/MM description of the total ligand+ protein+water system.

For a full description of the intermolecular forces a QM description of both the ligand and the pocket is mandatory, but is extremely resource heavy.

Most of the weak intermolecular forces that exist between the ligand and the pocket are represented as scalar fields that are much more delocalized in space than the ligands' bond descriptors which are sufficiently narrow so as to be represented as the edges of a graph. The representation of these weak forces in a graph-theoretic manner is therefore not straightforward. One could imagine integrating over all space the isosurface representations of the various interactions using a particular cutoff, and since these are sufficiently localized this will always result in a convergent numerical integration. A measure of the spatial extent of the field for the particular isosurface cutoff value must be introduced, as well as a measure for its directionality, in case it is not isotropic in space. The latter means that the field might exhibit a curvature along the line connecting any two atoms belonging to the ligand and the pocket. One way to include these requirements, without using point clouds (see "Section 4: Graph featurization and quantum chemistry") that would require significant adaptation of the ML algorithms, is to define the spatial position of the isosurfaces by introducing a vector having one end at the coordinate origin and the other end at a particular point of the surface, e.g. the maximum value of the scalar field. The direction of the vector is dictated by the curvature of the field. Thus, the relative position of the e.g. van der Waals interaction scalar field of two ligands interacting with a particular pocket can be defined and can be used for comparative purposes.

In addition, it is important to quantify the strength of the interactions, see «Section 4: Graph featurization and quantum chemistry».

Some Ensemble calculation details
  Conformations in solution can be approximated using MD [19] to explore the configuration space of the ligand in the presence of solvent (explicit or implicit) and taking into account the temperature (300K instead of absolute zero). QM featurization therefore can be done on each chosen conformation (Q-graph, QM descriptors) and the results be fed into the ML as inputs.
  MD can be also used in general, both to get poses in solution (either with implicit, or in principle, with explicit waters), as well as poses in the protein pocket without the need to adjust the computational methodology employed. If the available force fields prove to be inadequate for some ligands, then QM/MM MD simulations can be performed using semi-empirical methods.

Basic Structure-Based Model

The model is a graph-convolutional neural network, whose forward pass, on a single molecular input, we now describe (this generalises straight-forwardly to the thermodynamic ensemble models described in "Section 7: Machine learning on thermodynamic ensembles"). A feature vector for each ligand atom is computed using a series of graph-convolutional updates on the graph representing the isolated ligand, and similarly for each pocket atom. Here the ligand and pocket graph-convolutional layers do not share weights. Then, for each ligand atom, a subset of pocket nodes are selected based on their distance from the ligand atom, and their feature vectors are combined and fed through a non-linearity to form a gating vector, which multiplies the ligand node vector element-wise. The resulting ligand graph is reduced over the atom dimension and fed into a fully-connected network, whose output is a prediction of the target property (or properties). Ligand-based transfer-learning is achieved by using the graph-convolutional layers from a pre-trained ligand-based model in the first stage.

Fixed-Target Model

It may be that some regions of a given pocket accept certain atoms/ligand-fragments for reasons that are too complicated for a graph-convolutional neural network to unravel given limited data, but from several examples of ligands that occupy that region together with their binding affinities we can construct a simple empirical model of the effect on binding of filling that region with different atoms/ligand-fragments. This motivates a model where the location of the ligand relative to the pocket is explicitly taken into account when dealing with a fixed target. Given a perfectly fixed target we would simply chose four non-coplanar atoms to define a canonical coordinate system, which can be used to either augments the ligand atoms' feature vectors with their positions, or to determine via a fully-connected NN a per-ligand-atom gating that can be applied to ligand feature vectors at any stage during the graph-convolution process. When the pocket is somewhat flexible or contains mutations across the dataset, we can apply an alignment algorithm to all pairs in the set (or a random subset thereof if there are too many examples for this to be feasible), find four or more atoms whose positions are best preserved across the data (using more than four will lead to an over-complete description but one which is more robust to pocket movement) and use these to define our coordinate system.

Inclusion of Weak-Force Descriptors in Graph-Convolutional Models

Spatial characteristics of the weak interatomic forces arising in a protein-ligand complex can be captured by a scalar field S which, crudely, is given by the ratio of the DFT density with its gradient. When S takes a small value and the density is also sufficiently small, the presence of a weak interaction can be inferred. Thus, S can be used to partition 3D space into regions which do and do not "contain" weak interactions; regions where both S and p are sufficiently small are considered to contain a weak interaction, the rest of the space is assumed not to. We propose to use this partitioning to include weak interactions in pocket-ligand graphs. The interactions are captured in graph form in the same way as covalent interactions, i.e. as edges whose weights depend on the strength of the interaction. In the covalent case, strength takes a value in a small discrete set (single bond, double bond, etc); however with weak interactions strength is continuous. To determine this strength, we draw a straight line between the two atoms of interest, and compute the proportion of it that is contained within regions which contain a weak interaction. This value is then binned and fed through a fully connected NN whose output is a set of weights to be used in the graph-convolutional update. If the line does not pass through any weak-interaction region, we do not add an edge between that pair of atoms.

References from Section 5

[1] Bader, R. F. W. Chem. ReV. 1991, 91, 893-928.
[2] Bader, R. F. W. Atoms in Molecules: A Quantum Theory. International Series of Monographs on Chemistry 22; Oxford Science Publications: Oxford, 1990.
[3] Matta, C. F.; Boyd, R. J. In The Quantum Theory of Atoms in Molecules; Matta, C. F., Boyd, R. J., Eds.; Wiley-VCH: New York, 2007; pp 1-34.
[4] Becke, A. D.; Edgecombe, K. E. J. Chem. Phys. 1990, 92, 5397-5403.
[5] Silvi, B.; Savin, A. Nature 1994, 371, 683-686.
[6] Johnson, E. R.; Keinan, S.; Mori-Sanchez, P.; et al. J. Am. Chem. Soc. 2010, 132, 6498-6506.
[7] Contreras-Garcia, J.; Johnson, E. R.; Keinan, S. J. Chem. Theory Comput. 2011, 7, 625-632.
[8] {Gomes}, J. and {Ramsundar}, B. and {Feinberg}, E.~N. and {Pande}, V.~S., "Atomic Convolutional Networks for Predicting Protein-Ligand Binding Affinity", arXiv:1703.10603
[9] {Feinberg}, E.~N. and {Sur}, D. and {Husic}, B.~E. and {Mai}, D. and {Li}, Y. and {Yang}, J. and {Ramsundar}, B. and {Pande}, V.~S., "Spatial Graph Convolutions for Drug Discovery", arXiv:1803.04465
[10] {Kearnes}, S. and {McCloskey}, K. and {Berndl}, M. and {Pande}, V. and {Riley}, P., "Molecular graph convolutions: moving beyond fingerprints", arXiv: 1603.00856
[11] {Ryu}, S. and {Lim}, J. and {Kim}, W.~Y., "Deeply learning molecular structure-property relationships using graph attention neural network", arXiv:1805.10988
[12] Simonson, T. (2007). "Free Energy Calculations: Approximate Methods for Biological Macromolecules". C. Chipot, A. Pohorille (Eds.), *Free Energy Calculations: Theory and Applications in Chemistry and Biology*. Berlin Heidelberg: Springer.
[13] Brandsdal, B. O.; Österberg, F.; Almlöf, M. et al., *Adv. Protein Chem.*, 2003, 66, 123-158.
[14] Senn, H. M.; Thiel W., *Angew. Chem. Int. Ed.*, 2009, 48, 1198-1229.
[15] Bersuker, I. B., "Methods of Combined Quantum/Classical (QM/MM) Modeling for Large Organometallic and Metallobiochemical Systems". J. Leszcynski (Ed.), *Computational Chemistry: Review of Current Trends*, Vol 6, pp. 69-135.
[16] Thapa, B.; Beckett, D.; Erickson, J.; Raghavachari, K., *J. Chem. Theory Comput.*, xxxx, xxx, xxx-xxx, DOI: 10.1021/acs.jctc.8b00531.
[17] Bradenburg, J. A.; Hochheim, M.; Bredow, T.; Grimme, S., *J. Phys. Chem. Lett.*, 2014, 5, 4275-4284.
[18] Stone, A. J., *The Theory of Intermolecular Forces*, 2nd ed., 2013, Oxford University Press.
[19] De Vivo, M.; Masetti, M.; Bottegoni, G.; Cavalli, A., *J. Med. Chem.*, 2016, 59, 4035-4061.

Section 6: Conformations in Statistical Mechanics and Thermodynamics of Binding

1 Introduction

The purpose of the present document is not to be exhaustive nor even comprehensive in the coverage of the basics of conformational sampling in different thermodynamic ensembles and the description of the thermodynamics of binding and molecular recognition. Its purpose is to collect some ideas that have been identified as very important for the methodology of GTN and translate them in equations.

2 Conformations in Thermodynamic Ensembles, Molecular Dynamics and Boltzmann Averages The general notion of a thermodynamic ensemble is that of a collection of thermodynamic parameters such as the pressure P, the volume V or the number of molecules N that remain constant for the duration of a thermodynamic process under study. The process might be an alchemical transformation to estimate relative binding affinities, the study of phase equilibria and the estimation of solvation free energies of small organic molecules. The idea of a constant thermodynamic property is a tricky one: it does not imply the e.g. it should be constant throughout an MD simulation, but that its average value should be constant, i.e. it should fluctuate around a particular value. There are three well known and used thermodynamic ensembles, namely the microcanonical (NVE), the canonical ensemble (NVT) and the isothermal-isobaric ensemble (NPT). The thermodynamic parameters in parentheses imply that they are kept constant during the transformations under the corresponding ensemble.

Fundamental to the theory is the Hamiltonian of the system under study H(x,p) that governs its equilibrium properties and can parameterized with time H(x,p;t) and propagated according to Newtonian dynamics as done in MD simulations. The notion of time parametrization is crucial here: time enters in MD as a convenient way to explore the phase space (momenta and spatial coordinates) in computer simulations but in principle it is not needed for the computation of any thermodynamic average or observable property. Thus, the phase space {x, p} can be created on the fly by the Monte Carlo method and not MD or created by Newtonian dynamics. In the exact limit these two alternative methodologies should yield the same result for a property $f$, as $$\langle f \rangle = \overline{f(q_0, p_0)}, \langle f \rangle$$

$$= \int f(x, p) P_{ensemble}(x, p) dx dp, \overline{f(q_0, p_0)}$$

$$= \frac{1}{T} \int_0^T f[q(t), p(t)] dt$$

where the brackets designate ensemble averages, the overlined quantities time averages, $P_{ensemble}$ is the probability that the system is in phase space point (x, p) in the particular ensemble used (NPT, NVT etc.), $q_0$, $p_0$ are the initial conditions at time t=0 and q(t) and p(t) are the spatial coordinates and momenta of the system at time t. Note also that, strictly speaking, equality holds for T going to infinity only, and also that the equation doesn't work in microcanonical ensemble because there energy is conserved and one will never be able to explore phase space at other energies. The equation above does not only put the equivalence in strict mathematical form but also gives information on when the equivalence is to be expected. First of all, it implies that the time averages should not depend on the initial conditions $q_0$, $p_0$ since it must be always equal to the ensemble average. That gives a nice criterion for the robustness of MD calculations: many MD calculations starting from different initial conditions should result in the same observables if the results of the calculations are to be trusted. Secondly, the above equality implies that no matter where one starts, e.g. at $q_0$, $p_0$, the system will pass by every point in the phase space {x, p} at a later time during the simulation. For this to happen, a) sufficient time must be given to the system to sample all the phase space required to obtain an accurate estimate of the ensemble average $\langle f \rangle$ and b) the phase space points {x, p} should not be separated by large energetic barriers so that they can via visited during a finite time simulation (ergodicity) (Note: the problem with large energetic barriers exists only in classical mechanics or for finite T. For infinite T, a QM system will eventually tunnel through any potential barrier). To overcome the problem of nonergodicity of MD simulations enhanced sampling algorithms are devised that reduce the energetic barriers that separate the phase space points but do not lead to a large change in its topology.

So far, the probability distribution $P_{ensemble}$ has not been explained. For any system at thermodynamic equilibrium and at a particular ensemble the local probability density for any (x, p) point of phase space is given by a Boltzmann distribution as:

$$P_{ensemble}(x, p) = \frac{e^{-\beta H(x,p)}}{\int\int e^{-\beta H(x,p)} dxdp}$$

where all the variables have the same meaning as above. For a series of structures belonging to the particular thermodynamic ensemble and are compatible with the hamiltonian H(x,p), the average of an observable $f$ can be calculated easily using the Boltzmann weights as:

$$\langle f \rangle_{ensemble} = \frac{\int\int f(x,p) e^{-\beta H(x,p)} dxdp}{\int\int e^{-\beta H(x,p)} dxdp} = \int\int f^P_{ensemble} dxdp$$

The above equations are exact and no approximations have been introduced. In all the aforementioned equations the full hamiltonian for the system under study is used. Nonetheless, there are cases where either the property of interest does not depend on the momenta or the property definition is in such a form in which the integrations over momenta can be performed analytically and subsequently cancelled out. In this case the equations above still hold with the hamiltonian replaced by the potential energy of the system U(x) that depends on the spatial coordinates of the systems constituents. It is then that the notion of configuration averages is introduced. In these cases, the configurational partition function z can be studied instead of the full partition function Q for the corresponding ensemble (note: the partition function depends on the ensemble used and thus if it has to be learnt then the data used should be consistent with this ensemble).

Section 7: Machine Learning on Thermodynamic Ensembles

When we want to include conformational information in machine learning models, we are confronted with the fact that the different conformations are all states in a thermodynamic ensemble of the system. That means we cannot just assign a thermodynamic property to each individual pose, since it can only be observed as an expectation value over the entire ensemble.

Binding Affinity

In thermodynamics relative concentrations are directly linked to the magnitude of the partition function. For the problem of a ligand binding to a protein, the quantity of interest is the dissociation constant $$K_d = \frac{[C]_{ligand}[C]_{protein}}{[C]_{complex}},$$

which also is given by the ratio of off- and on-rate $$K_d = \frac{k_{off}}{k_{on}}.$$

When a ligand binding to a protein is inhibiting the function of the protein, the dissociation constant is also called the inhibition constant, so $$K_i = K_d.$$

In general we are interested in the scale of this quantity, which is best captured by taking the logarithm (also called pKd)

$$\log K_d = \log k_{off} - \log k_{on}.$$

The ratio of on- and off-rates $k_{on}$ and $k_{off}$ are by Arrhenius equation related to the binding affinity $$\log K_d = \beta \Delta G$$

where as usual $\beta = k_b T$.

We know that the binding affinity of a ligand to a protein is given by the change in Gibbs free energy between the unbound ligand and protein and the bound complex $$\Delta G = -\frac{1}{\beta} \log \frac{Q_{complex}}{Q_{ligand} Q_{protein}}.$$

Note that this equation is essentially the statistical mechanics version of the definition of the dissociation constant, where concentrations are simply replaced by partition functions.

The partition function Q is here just the weighted average over the ensemble, $$Q = \langle e^{-\beta H} \rangle.$$

In machine learning we approximate this expectation value by using a set of representative poses $p_i$ and let the neural network estimate the weight of each individual pose in the partition function so that the partition function is $$Q = \Sigma_i g_\theta(p_i),$$

and the neural network $g_\theta$ effectively estimates $$g_\theta(p_i) = e^{-\beta E_i + k_B S_i},$$

where $E_i$ is the effective energy and $S_i$ the effective entropy of each individual pose. It might be easier and computationally more stable for the neural network to just compute the exponent and exponentiate the results before aggregation. In other words, $$g_\theta(p_i) = -\beta E_i + k_B S_i \text{ and } Q = \sum_i e^{g_\theta(p_i)}.$$

Therefore the binding affinity effectively reduces to $$\Delta G = -\frac{1}{\beta}\left(\log \sum_{complex} e^{g_\theta^C(p)} - \log \sum_{ligand} e^{g_\theta^l(p)} - \log \sum_{protein} e^{g_\theta^p(p)}\right).$$

The three networks can in principle be the same, though we might want to choose them to be different from each other.

If there is only one target protein involved, we can replace the last term by a simple learnable bias. Moreover, it might be that the conformational information in solution does not change the binding affinity very much and that a network only acting on the complex is sufficient for estimation of binding affinity.

Inhibition Concentration

The half-maximal inhibitory concentration IC50 is an experimental quantity defined by the concentration of the ligand needed to inhibit the activity of the protein by 50%. In general there are a lot of factors that go into a specific IC50 value, but roughly one can relate it to the binding affinity in the following way.

Let us assume we are at the concentration for the ligand at which the activity of the protein is reduced by 50%. That means $$[C]_{ligand} + [C]_{complex} = IC50.$$

If we assume that the protein concentration and thereby the complex concentration is much lower than the ligand concentration, we can simplify this to $$[C]_{ligand} = IC50.$$

If we make the simplifying assumption that every unbound protein is active and every protein-ligand complex is inactive, then the activity of the protein is reduced by 50% at the point where $$[C]_{complex} = [C]_{protein}.$$

Inserting these relationships into the definition of the dissociation constant, we find $$K_d = IC50.$$

Though the above assumptions are very crude and do not reflect reality, it should serve as a justification why we can use the same network architecture.

It can be shown that for noncompetitive or uncompetitive kinetics this relationship is generally true. In the case of competitive inhibition kinetics (that means there are competing ligands), the Cheng-Prusoff equation describes the relationship of dissociation constant and IC50. That equation also shows that IC50 is usually higher than dissociation constant.

Lipophilicity

Things get slightly more challenging for quantities that are usually not defined in terms of ensembles of statistical mechanics. An easy example of this is lipophilicity, usually defined in terms of the quantities $$D = \frac{[C]_{octanol}}{[C]_{water}} \text{ and } P = \frac{[C]_{octanol}}{[C_{unionised}]_{water}},$$

where [C] denotes concentration in thermal equilibrium. Usually we are interested in the scale of D and P, and therefore focus on log D and log P.

Possibility for ionisation strongly impacts log D, which is therefore PH-dependent. The quantity log P is defined as a PH-independent quantity that serves as an upper bound for log D, i.e.

$$\log D \leq \log P.$$

Analogous to the case of binding affinity we can translate ratios in concentration in thermal equilibrium to ratios of partition functions. This means we can express log D and log P as $$\log D = \log \frac{Q_{molinoctanol}}{Q_{molinwater}} \text{ and } \log P = \log \frac{Q_{molinoctanol}}{Q_{unionisedmolinwater}}.$$

In octanol, the molecules are essentially always neutral (since if they are ionised they will always favor binding to water). Therefore we can write $$\log D = \log \frac{Q_{unionisedmolinoctanol}}{Q_{molinwater}} \text{ and } \log P = \log \frac{Q_{unionisedmolinoctanol}}{Q_{unionisedmolinwater}}.$$

Turning the computation of the partition function again into a neural network, we end up with $$\log D = \log \sum_{punionisedinoctanol} e^{g_\theta^O(p)} - \log \sum_{pinwater} e^{g_\theta^W(p)},$$

$$\log P = \log \sum_{punionisedinoctanol} e^{g_\theta^O(p)} - \log \sum_{punionisedinwater} e^{g_\theta^W(p)}.$$

Since the results in water and octanol are expected to be quite different, the two networks most likely should be networks with distinct weights. It seems that log P might be much easier to compute since we do not have to take ionised states into account at all.

Thermodynamic Solubility

Solubility S is measured by the saturation concentration (measured by their relative weight) between solvent and solute, or, in the case of organic chemistry, of water and the ligand molecule. Therefore, if the maximal concentration is one gram of the compound in each gram of water, one has S=1.

Thermodynamic solubility describes a thermodynamic equilibrium in which the chemical potential of the solid state and of the dissolved state are equal $$\mu_{solid} = \mu_{dissolved}.$$

In the thermodynamic limit $\mu_{dissolved}$ is the change in Gibbs free energy associated with adding a single compound into the solution (for a given concentration). The chemical potential of the ligand in solution is expressed in terms of its activity $a=\gamma x$ as $$\mu_{dissolved}=\lambda^0_{dissolved}+k_B T \log a = \mu^0_{dissolved}+k_B T \log \gamma x$$

where $\mu^0_{dissolved}$ is the chemical potential at infinitesimal concentration, $\gamma$ is the activity coefficient that describes the volatility of the compound and x is the mol fraction of the ligand, related to solubility by $$x = \frac{S}{S+1}.$$

In regimes where compounds are not highly soluble (i.e. $S<<1$), we can assume that x approximates S. In the same limit, the activity coefficient $\gamma$ can be approximated by one, and we find $$\log S = \beta(\mu_{solid} - \lambda^0_{dissolved}).$$

Both chemical potentials can be split into an internal energy and an entropic contribution, or alternative into a partition function for the internal degrees of freedom and the interaction energy of the compound with its environment. We can in general express $$\log S = \log Q^0_{dissolved} - \log Q^0_{solid},$$

Where we can evaluate each partition function in the usual (temperature-dependent) way. That means the neural networks predict solubility should compute $$\log S = \log \sum_{psolvedpose} e^{g_\theta^{solution}(p)} - \log \Sigma_{psolidpose} e^{g_\theta^{solid}(p)}.$$

Kinetic Solubility

Kinetic solubility is an experimental quantity that is defined by the experimental process that measures solubility in an automated and efficient way, but does not wait for thermodynamical equilibrium to be reached. The solution is in fact created by 'vigorous shaking or stirring'.

Kinetic solubility is suspected to measure concentration in a metastable solution, and in general measured results can be quite different from thermodynamic solubility: For compounds which form amorphous solids kinetic and thermodynamic solubility are correlated to some degree (differences are usually confined to half a log-unit, which might be close to experimental accuracy), while for compounds with crystalline solid phases kinetic solubility can massively overestimate over the thermodynamic solubility.

For practical purposes we can assume for predicting kinetic solubility that the solid phase is always in an amorphous phase, so that $$\log S_{kin} = \log Q^0_{dissolved} - \log Q^0_{amorphoussolid}.$$

In terms of a machine learning model, we can compute $$\log S = \log \sum_{psolvedpose} e^{g_\theta^{solution}(p)} - \log \Sigma_{pamorphouspose} e^{g_\theta^{amorphous}(p)}.$$

Melting Point

Melting point is interesting for drug discovery as it can serve as a predictor of thermodynamic solubility. The so-called general solubility equation has been derived empirically (i.e. fitting data) and reads:

$$\log_{10} S = 0.5 - \log_{10} P - 0.01(MP - 25),$$

where the melting point MP is measured in Kelvin. Note that this equation essentially says that the log of the solubility in octanol $S_{oct}$, which can be expressed as $$\log_{10} S_{oct} = \log_{10} S + \log_{10} P$$

is an affine function of the melting point. In practise we can treat melting point predictions synonymous for octanol solubility predictions, and compute $$\log S_{oct} = \log \sum_{pposeinoctanol} e^{g_\theta^{octanol}(p)} - \log \sum_{psolidpose} e^{g_\theta^{solid}(p)},$$

and express the melting point by $$MP = 75 - 100 \log_{10} S_{oct}.$$

Protonation

In principle we could use the same strategy as in the other cases, as pKa is defined completely analogously to pKd. The situation is however complicated by the fact that organic molecules can have various pKa values for protonation at different sites of the molecule. This means we have to estimate an entire pattern of pKa values, which might be less trivial.

An alternative would be to use the PH as an additional global input parameter based on which the model predicts the charge, ideally locally.

In General

If we want to compute a general thermodynamic quantity whose expression in terms of microscopic degrees of freedom is not known, we can add additional final layers $h_\phi$ to the neural network to figure out the relationship itself. This effectively leads to an expression of the form $$f_{\theta,\phi}(m) = h_\phi\left(\sum_{posesp} g_\theta(p(m))\right)$$

and similarly for quantities depending on several structures or molecules.

Section 8: Conformational Searching Methods for Machine Learning

1. Introduction

The problem of sampling all the conformation space of a drug-like molecule in different environments (e.g. solvent, binding pocket) and a particular temperature is equivalent to knowing the total partition function, a task that is computational infeasible but for the smallest systems. Therefore different methodologies are available for completing this task in a more ad hoc manner or more systematically and these are reviewed in the literature [V. Salmaso and S. Moro, *Frontiers in Pharmacology*, 9, 923 (2018).].

In terms of accuracy and physical rigor, on the one side of the spectrum of available methods lie the more approximate and less physically motivated computational methods falling under the umbrella of molecular docking. In these methods there are two components that are combined to deliver the docking poses: a) a conformations generator that produces the various conformers of the ligand and b) the use of empirical scoring functions that weight the likelihood of occurrence of the various previously calculated poses based on a function that was fitted to experimental data using least squares fitting. Obviously the function might give accurate results for some cases, and inaccurate ones for others and therefore their reliability is questionable. On the other side of the spectrum exist methods based on Molecular Dynamics that include in a classical way many of the physical interactions between the ligand and its environment, the relaxation of the environment as a response to the various conformational changes of the ligand and the presence of the solvent (in a discrete or continuous manner). The latter methods as well as their accelerate sampling analogous present an obvious rigorous way to sample the conformational space of the ligand by running long simulations and/or modifying the free energy landscape in order to improve sampling. Their drawbacks are the time consuming and heavy computations and their non ergodic nature for cases where certain parts of phase space are separated by high energetic barriers. Therefore, it can be argued that they are not the methods of choice if an exhaustive sampling of the phase space is required or even if there is need to produce many conformers in a quick and efficient way.

Herein we thus propose a divide-and-conquer hybrid methodology for creating conformers by combining both docking and short Molecular Dynamics simulations. This methodology is expected to produce many conformers that can be used as an input to the ML algorithms and also get a more realistic energetic estimated for each of them compared to the scoring functions by using MD. The strategy is briefly explained in the following sections.

2. Docking Methodology

The aim of docking is to create poses if the ligand docked inside the known pocket. The ligand is flexible, and poses can (will) have conformations different from the input structure. The pocket/protein is fixed (but can be made flexible when using AutoDockVina).

Let us consider a particular setup for an experiment we performed for a BRD4 target protein. All docking poses were obtained with AutoDockVina. One docking run was based docking one ligand, which created a maximum of 20 poses (AutoDockVina).

Datasets for docking BRD4 are:
1. PDBBind: 108 X-ray structures—38 refined dataset, 70 general dataset. These are being filtered to
2. dataset: 201 poses obtained by constraint docking in 4bjx (public structure, can be found in the PDBBind general data set). 4 of those poses cannot be converted to RDKit Chem.Mol objects.

Options used for input ligand structures for docking:
1. Using the X-ray structure (PDBBind dataset) or the pose that was obtained by constraint docking of the training set. So, one set of docking poses per PDBBind ID/ligand was obtained.
2. Converting the X-ray ligand/constraint-docked pose to a SMILES string. Then create conformers from scratch from that SMILES with RDKit (optimised with Force Fields and selected by a minimum RMSD to the energetic minimum), and dock the different conformers. The result was one set of poses per conformer. The number of conformers depends on the flexibility of the ligand, that is mainly the number of rotational bonds, since those will be distorted in the conformer search.

Both methods are tested for the quality of the results (RMSD to X-ray pose/constraint-docked ligand).

Docking took on average 1.5 min per conformer. The time for creating conformers from smiles is negligible compared to the time for docking. The number of conformers created per ligand is highly dependent on the number of rotational bonds, but it is also random. So, results could differ between calculations. Therefore, the best option was to calculate one set, and reuse that set if the ligand should be docked again. Timings for docking on a local Intel i5+Nvidia GForce GTX 1060 GPU machine:

1. PDBBind: 108 ligands*1.5 min=2 h 41 min, max. 2160 poses
2. PDBBind docking from smiles: between 1 and 68 conformers per ligand (average of 13). One outlier with 144 conformers (not included in the average, will most likely not be in the filtered set). Time for docking: 108 ligands*13 conformers*1.5 min=35 h, yielding maximum of 28080 poses.
3. (201-4) ligands*1.5 min=5 h, max. 3940
4. between 1 and 78 conformers per ligand (average of 12). (201-4) ligands*12 conformers*1.5 min=59 h=2.5 d, yielding max. 47280 poses.

Only a fraction of the poses have a low RMSD compared to the starting structure. Poses were filtered by RMSD.

3. Molecular Dynamics Methodology

After the initial conformers are computed using docking, a realistic estimate of the corresponding total energy of the system (protein+ligand+solvent) that goes beyond the scoring function estimates needs to be performed. The solvent is described as a continuum dielectric medium having the dielectric constant of water while the ligand and protein will retain their atomistic description. Very short MD runs are performed, of the order of tenths of a ps. The reason for the short MD runs is to allow the pocket to relax in the presence of the ligand conformer (docking is performed by assuming a rigid or semi rigid protein pocket) in the case of the complexed ligand, and for the ligand to adjust its conformation slightly when it is embedded in the pure solvent, without the protein. This methodology is expected to describe the various intermolecular interactions accurately and allow the environment to relax for each and every ligand conformation, leading thus to a better energy estimation. These relaxations are more important when explicit description of the solvent is adopted. This methodology has been adopted with slight alterations in at least one bibliographical study of the prediction of conformations of PDBBind ligands in solution (not in proteins) [O. Gürsoy and M. Smieško, *Journal of Cheminformatics*, 9, 29 (2017)].

The underlying theoretical reason for adopting the aforementioned strategy is that, in principle, the various conformations of a particular ligand in either the protein's pocket or in solution should be more or less the same, and only the probability of them occurring (or being of importance for the binding) and their related Boltzmann weights must differ. At the end of this methodology an ensemble of different conformers and accurate energies can be obtained which in turn can be fed to the ML algorithms, weighted appropriately for the thermodynamic ensemble chosen. The methodology is expected to be fast and efficient.

We performed experiments on following datasets:
a) PDBBind BRD4-containing systems: Refined Set (30 systems, variable number of conformers), General Set (76 systems, variable number of conformers produced). The systems can be found here. For this dataset, the timings depend on the number of conformers to be used.
b) BRD4 confidential data: Docked poses (200 training compounds and 400 compounds for the testing set, one conformer per compound). In total 600 conformers, and 7.15 min*600*1=3 days (the number of conformers for the test set is yet unknown and it is supposed that they are 4 per compound).
c) BRD4 confidential data: Extra poses from GTN's redocking methods (3-4 conformers per compound for each compound of b). 20 conformers in total. Quality assessment needed to choose the 3-4 best). 7.15 min*600*4=12 days, 7.15 min*600*20=60 days.

Section 9: DFTB Quantum Features
Quantum Features

Machine learning features calculated with quantum mechanics using an electronic structure package can be used to decorate a graph representation of a molecule or material. The input to an electronic structure algorithm is the atomic type (atomic number) and position of every atom in the system. No heuristic or chemical knowledge is needed as an input (i.e. nature of bonding, formal charge state). The output, within the limits of the accuracy and precision of the method, should include all of chemistry and materials science, as these interactions are fully specified within the Schrodinger equation.

Finite computer time requires approximate solutions. This leads to an approximate answer, and it is well known that some features are more accurate and/or more precise than others, with particular methods.

Typically these calculations make use of the Born-Oppenheimer approximation, and further assume that the nuclear degrees of freedom are classical and frozen. By doing multiple electronic structure calculations for snapshots taken from a molecular dynamics trajectory, or from an ensemble generated by a statistical mechanical analysis of a system's potential energy surface, one can integrate across a thermodynamic trajectory.

Here care must be taken that the representation of the molecule if calculated via a different method is compatible with the chemical Hamiltonian used in the single point calculation, e.g. if bond lengths are mismatched, a nonphysical answer will be produced.

The practical challenge of using electronic structure features in a machine learning pipeline is the computational cost, and latency, of the underlying calculations.

The standard approximate method used in materials modelling and quantum chemistry is Kohn-Sham Density Functional Theory (KS-DFT). This approximates the interacting electron problem as an independent electron problem in a mean-field, with an empirical exchange correlation functional which approximates the missing correlation interaction. This is an abinitio method, where an approximate solution of the exact chemical Hamiltonian is made. This method uses a finite basis, and scales with $O(N^3)$, expressed in the number of electrons (which correlates with the number of atoms). It is known to miss-predict the bandgap in material systems. This can be partially corrected by empirically mixing with a contribution from exact exchange calculated by Hartree-Fock, but the underlying cost of calculating two electron integrals increases the overall computational complexity to $O(N^4)$.

Typically, a KS-DFT calculation on a single drug-like molecule would be expected to take hours on a multiprocessor system.

Different electronic structure methods exist in an empirical hierarchy of computational complexity versus accuracy for a specific measure. This can naturally be combined in a machine learning framework, and active learning can be used to choose which calculations on which systems are required next to improve the accuracy of the machine learning models.

Density Functional Tight Binding

As an alternative to approximately solving the exact problem, we can construct an approximate model and solve this exactly. In doing this, one intentionally makes a model that is relatively lightweight to solve in a computer. This allows for far higher performance. These techniques are generally known as 'semi-empirical' in the materials modelling and quantum chemistry communities, as they rely on models where an a-priori choice of construction is made to reproduce empirical truth, either by reference to experimental measurements, or to higher level calculations. They are not necessarily less accurate than ab-initio models, as the model can be designed and fitted to make up for shortfalls of the computationally accessible ab-initio solutions.

We make use of density functional tight binding (DFTB).

Here the quantum mechanical model is that of tight binding, constructed in minimal quantum mechanical basis of linear combinations of atomic orbitals. DFTB is parameterised with the quantum mechanical overlaps between atoms specified by prior calculations on atomic dimers using Kohn-Sham density functional theory. A pair-wise interaction potential is added to reproduce the correct molecular dynamics. This can result in more accurate molecular dynamics than density functional theory, as van de Waals interactions are built into the model.

Using self-consistent charge (SCC) DFTB allows for partial oxidation and reduction of the atomic species, reproducing weak bonding interactions.

Practically, DFTB calculations on a single drug-like molecule take a fraction of a second. Partial charges The solution of self-consistent charge DFTB leads directly to a partial charge associated with each atom. The atomic orbital basis means there is no ambiguity about how to project electron density onto the atoms.

These partial charges are useful as a machine learning feature, as the non-bonded interaction between molecules and molecular fragments is normally considered to be composed of 1) electrostatic interactions (which vary with the partial charges) and 2) a pairwise interaction which is entirely determined by the atomic species involved.

Providing the machine learning with partial charges calculated for a particular arrangement of a molecule, provides it with the additional information needed to infer the overall forcefield.

Polarisation and Polarisability

Beyond the monopole approximation to the electrostatic interaction given by the partial charges, the dipole (polarisation) of the system can be calculated directly. This is a molecular level feature, and describes the dipole generated in the multipole expansion of the electrostatic interaction.

The response of a material or molecule to an applied electric field is described by the polarisability. Practically this can be calculated by applying a constant electric field to the DFTB calculation, and then measuring the response of the polarisation of the molecule. The resulting linear response describes how much of a back-reaction is generated by an applied electric field, an additional interaction.

Lattice Dynamics

Local distortions of a molecule around a particular conformation can be described by lattice dynamics. Here the molecular or material potential energy surface (a 3N dimensional object) is approximated by a 2nd order Taylor expansion. This describes the harmonic response to a perturbation. The Hessian (2nd order force constant matrix) can be calculated in the finite displacement method by perturbing each of the 3N degrees of freedom and then fitting the resulting change in energy to a quadratic. The resulting matrix, decorated with the squareroot of the atomic mass to make it unitless, is known as a Dynamic matrix. Diagonalisation of this matrix gives the normal modes of vibration (eigenvectors in the basis of Cartesian motions of the atoms), and the vibrational energies.

These modes can be used to generate a thermodynamic ensemble, correct for small displacements, by populating the modes with a randomly sampled thermal distribution for harmonic oscillators. This is most correctly a Bose-Einstein distribution reflecting the Boson nature of vibrational modes, but at high temperature (relative to the mode energy) this is indistinguishable from the (classical) Boltzmann distribution.

As well as generating individual samples of the thermodynamic distribution, which can be used for secondary electronic structure calculations, we can calculate features directly from the normal modes. As the modes are harmonic, the resulting probability distribution function both classical (with a Boltzmann distribution) and quantum mechanically (both with the individual expectation values of the quantum nuclear wavefunction, and when summing these across a thermodynamic Bose-Einstein ensemble) are Gaussian. For each individual mode, a one dimensional Gaussian distribution with a variance can be calculated which projects along the normal mode.

The Gaussian nature of these distributions makes them trivial to combine, assuming they are independent, by summing the variance in quadrature.

Combining these for different modes, at a certain temperature, results in a thermal ellipsoid defined for each atom.

From these thermal ellipsoids, we can define an atom-level feature of either the thermal ellipsoids specified as three Cartesian components (3 values), or a thermal-volume (1 value) which encompasses the standard variance of motion.

Edge-features can be calculated by projecting the summed variances from the thermal ellipsoids along the vector connecting the two atoms. The resulting distribution is defined as a Gaussian with inter-atomic mean and variance. This can be projected onto a histogram representation, by making use of knowledge that the cumulative distribution function for the Gaussian distribution is the error function.

Molecular Dynamics

DFTB has sufficient performance that molecular dynamics can be directly performed with the quantum-mechanical Hamiltonian. This has the particular benefit that any snapshots extracted from this trajectory (thermodynamic ensemble) can be directly used with the DFTB Hamiltonian to calculate observables of interest, such as partial charges and molecular orbitals.

Molecular Orbitals

The result of diagonalising a chemical Hamiltonian are the molecular orbital energies and eigenvectors (wavefunctions). These wavefunctions are large objects (matrices of 'mN', where m is the size of the atomic basis, and N is the number of atoms).

To generate a feature which is useful for understanding chemical reactivity, we can sum the orbital charge density of molecular orbitals within a specified window of interest. Of particular interest are the orbitals composed of the Highest Occupied Molecular Orbital (HOMO) and it's near orbitals. This is the molecular electron density closest to the vacuum level, and therefore closest to attack by an electron withdrawing agent (oxidation). This is of particular interest for metabolism of molecules.

By defining an energy window, collecting the molecular orbitals in this energy window, and then calculating their expectation value (electron density), we can produce an atomic feature in terms of the atomic orbital basis which describes where this electron density is, and where chemical reactions are most energetically favourable to take place.

Appendix A: GTN Models and Modules

This appendix contains an overview of GTN's models and modules. The idea is that these descriptions should give a quick understanding of the inner, technical workings of every model/module at a glance.

1. Basic Organization

Simple models come before complicated models, and if your model expands on an existing model, add it below that base model as a child using the correct title headings (so the outline to the left of your screen is useful).

The same rules apply to modules, which are smaller building blocks that can be used by other modules or be combined into elaborate predictive and/or generative models. Modules are included in this document because, thanks to the elegant PyTorch way of dynamically building computational graphs, you can easily swap a module in a model for a different, compatible one.

2. Modules 2.1 Message-Passing Graph Convolutions

Graph Convolutions mean that the feature vector of each node, possibly combined with the respective edge features, is used to compute a message that is then send to all neighbouring nodes. All messages incoming to a given node are aggregated, usually by summing them up (or averaging) and possibly adding the original node features. A specified non-linearity is applied to the resulting vector before outputting the new feature vector of that node.

GraphConvLayer

This is the basic graph-convolutional layer in a neural network acting on graphs, consisting only of node features. Message-passing graph convolutional network with node features. Messages to a target node are computed by acting with a matrix for the given edge type. There are no edge features.

EdgeGraphConvLayer

Message-passing graph convolutional network with node and edge features. Edge features are fed to a fully connected network that outputs a matrix similar to the weight matrix in the standard GraphConvLayer. Messages are computed by multiplying that matrix with the node feature vector.

PairMessageGraphConvLayer

Message-passing graph convolutional network with node and edge features. Messages to a target node are computed from a fully-connected neural network acting on both source atom and edge features of the connected nodes. Distance bin information can be incorporated via the edge features.

DualMessageGraphConvLayer

Message-passing graph convolutional network with node and edge features. Messages to a target node are computed from a fully-connected neural network acting on both source atom and edge features of the connected nodes. Subsequently edge features are updated by the new atom features of their end points. This model has more symmetry between atom and edge features and allows more for actual coarsegraining.

2.2 GraphGather

After applying graph-convolutional layers, a graph gather aggregates node features in a single feature vector for every molecule in a batch.

Simple Gather

Vanilla Gather

The gather layer we call 'vanilla' is aggregating both by max and sum independently and then concatenating the resulting feature vectors.

Ligand Gather

Identical to the vanilla gather, but only using node feature vectors that belong to the ligand molecule. For representations of the complex that are fully connected graphs, this type is important to focus on the different ligands, as the pocket alone has typically ten times more atoms than the ligand.

Set2vec Gather

A gather function that uses the set2vec module from the set2set model. It uses an LSTM network to learn a permutation invariant gather function.

2.3 PoolingLayers

Pooling layers are supposed to reduce the size of a graph to mimic coarse-graining, similar to pooling layers in convolutional networks. For graph-convolutional networks pooling layers are currently still a matter of research.

SimplePooling

The local graph pooling layer has a trainable projection vector that projects the input feature vectors to a score that decides which nodes are kept and which are erased. It also determines a gating prefactor, which is introduced to ensure the projection vector gets updated through backpropagation. That prefactor requires additional normalization in order to train well. Additional edges are created between kept nodes that were connected by at most two erased nodes, to keep the graph connected while not needing to run BFS or something similar. The edge features are simply aggregated to create effective edge features.

CoarseGrainGraphPooling

The local graph pooling layer has a trainable projection vector that projects the input feature vectors to a score that decides which nodes are kept and which are erased. It also determines a gating prefactor, which is introduced to ensure the projection vector gets updated through backpropagation. That prefactor requires additional normalization in order to train well. Additional edges are created between kept nodes that were connected by at most two erased nodes, to keep the graph connected while not needing to run BFS or something similar. The edge features are then processed through fully connected layers to create effective edge features.

3. Predictive Models

Baselines

Random Forest
    Type: predictive model
    Input: Molecular fingerprint
    Output: binding affinity prediction (regression)
    Random forest is a tree ensemble learning method that constructs multiple decision trees during training, outputting the mode of the classes (for classification) or the mean prediction (regression) of individual decision trees. This is a commonly used machine learning algorithm, and one that is quite common in pharma.

GraphConv (GC)
    Type: predictive model
    Input: ligand (single conformation), pocket (single conformation)
    Output: binding affinity prediction (regression)
    Overview: The pocket-ligand complex is treated as a single graph. Edges between pocket and ligand can be encoded by a different edge type on top of the edge types corresponding to covalent bonds or node degrees.

EdgeGraphConv (EGC)
    Type: predictive model
    Input: ligand (single conformation), pocket (single conformation)
    Output: binding affinity prediction (regression)
    Overview: Uses EdgeGraphConvLayer for message passing. The pocket-ligand complex is treated as a single graph. If there are edges and corresponding edge features between pocket and ligand, the information that might be important for binding will be passed around during the message passing.

PairMessageGraphConv (PMGC)
    Type: predictive model
    Input: ligand (single conformation), pocket (single conformation)
    Output: binding affinity prediction (regression)
    Overview: Uses PairMessageGraphConvLayer for message passing. The pocket-ligand complex is treated as a single graph. If there are edges and corresponding edge features between pocket and ligand, the information that might be important for binding will be passed around during the message passing.

DualMessageGraphConv (DMGC)
    Type: predictive model
    Input: ligand (single conformation), pocket (single conformation)
    Output: binding affinity prediction (regression)
    Overview: Uses PairMessageGraphConvLayer for message passing. The pocket-ligand complex is treated as a single graph. If there are edges and corresponding edge features between pocket and ligand, the information that might be important for binding will be passed around during the message passing.

PocketGatingGraphConv (PG*GC)
    Type: predictive model
    Input: ligand (single conformation), pocket (single conformation)
    Output: binding affinity prediction (regression)
    Overview: Incorporates the effect of the pocket via a gating mechanism acting on the ligand atoms after acting with a GCN on both pocket and ligand separately. The gating is calculated from the contributions of pocket-ligand neighbours which are connected by edges. Note that the ligand-GCN's task is very different from the pocket-GCN since the latter has to accommodate for whatever the gating operation thinks will lead to a better binding affinity prediction.
    The model can use PairMessage- or EdgeGraphConvLayers, and is named accordingly by replacing * by either PM or E.

PocketAttentionGraphConv (PAGC)
    Type: predictive model
    Input: ligand (single conformation), pocket (single conformation)
    Output: binding affinity prediction (regression)
    Overview: Incorporates the effect of the pocket via an attention mechanism acting on the ligand atoms after acting with a GCN on both pocket and ligand separately. The attention is calculated from the result of a fully-connected neural network acting on the atom and edge feature vectors of the pocket-ligand neighbours connected by edges. Note that the ligand-GCN's task is very different from the pocket-GCN since the latter has to accomodate for whatever the attention mechanism thinks will lead to a better binding affinity prediction.
    The model can use PairMessage- or EdgeGraphConvLayers, and is named accordingly.

Ensemble-Based Training
    Type: training procedure for predictive models
    Input: ligand (multiple conformations), pocket (optional, multiple conformations)
    Output: binding affinity or physchem property prediction (regression)
    Overview: Here we consider an ensemble of conformations as a single data point, associated with a single binding affinity (target). The target is assumed to be an aggregation over quantities that are calculated independently for each conformation. In the simplest case, we take a scalar function on conformations, and a prediction is obtained by summing outputs of this function when applied to a set of docked poses. We are free to learn the function with any of the models described above. As a more sophisticated realisation, we can obtain the ensembles from MD simulations and use a physics-based aggregation procedure. For instance, the thermodynamic equation for binding affinity involves a sum over energies of free-compound conformations and a sum over energies of in-complex conformations. We can use two neural networks to learn the energy functions, and aggregate their outputs on free and bound ensembles according to the physical expression to produce a prediction.

4. Generative Models and Multi-Parameter Optimization

RNN on SMILES

Type: generative model
Input: SMILES strings for training
Output: SMILES strings
Method: Recurrent Neural Network using LSTM cells Overview:

Recurrent Neural Networks (RNN) are a family of models that use an internal memory state to process input sequences. They are often used for modelling sequential data like time series prediction, speech recognition, and anomaly detection. RNNs process data by passing each element of the input (in our case each character in the SMILES string) through a series of gates and returns a hidden state. The hidden state passes from cell to cell, reflecting the information the RNN has previously seen. This allows the RNN to learn complex temporal dependencies.

We use a long short-term memory (LSTM) architecture for our model. First introduced by Hochreiter and Schmidhuber (1997), LSTMs are designed to learn long-term temporal dependencies from the input data. LSTMs control what information passes through to the next cell through the hidden state, allowing important information to pass through unaltered. The hidden state can be carefully altered using a series of control gates. LSTMs can be used to generate sequences by outputting a probability distribution over all possible characters/tokens for each time step. The model aims to predict the next character given the input. The loss is calculated for each position as the categorical cross-entropy between the predicted token and GT token from a training example. Additional references for RNNs, LSTMs, and their application to drug design (Gupta et al., 2018; Segler et al., 2018).

Transfer learning can also be performed using a generative RNN. In this case, the model is pretrained on a large dataset of drug-like molecules. Then a smaller set of molecules that have a particular characteristic (e.g. molecules scraped from patents that demonstrate activity against a particular target protein) can be used to fine-tune the generative model towards those characteristics (Segler et al., 2018).

Reinvent RL

Type: MPO
Input: Pretrained RNN with Reward function
Output: optimised molecules
Method: RL (Based on commonly used REINFORCE algorithm)

Overview:

Our implementation of this method is based on Olivecrona et al. (2017). The method involves first training a prior generative network to learn the distribution of the training set SMILES. Ideally the training set is a large, drug-like, and diverse dataset, resulting in similar generated molecules. A copy of this prior network (called the agent network) is then used for training using reinforcement learning. Specifically, the agent generates a batch of molecules and the reward function scores and returns a reward for each. The product of action probabilities associated with each step in generation represents the agent likehlihood for the sequence to have been generated. The goal is to update the agent policy from the prior policy to increase the expected reward, while keeping the agent policy anchored to the prior policy so as to not completely lose information regarding the sytnax of SMILES strings. To do this, an augmented likelihood is used, which calculates the prior likelihood of each sequence generated by the agent. The loss function is then the difference between the augmented likelihood and the agent likelihood. This agent's goal is then to maximize the expected reward return, which can be achieved by minimizing this loss. In practice this method tends to work well for optimising single parameters, but struggles optimising multiple parameters. This is likely because the agent struggles to learn the associations between sub-sections of SMILES and multiple parameters (i.e. pIC50 and Log P) simultaneously. Despite this, we have shown the model to be useful for optimising a single parameter, and when combined with a prior network that already has drug-like characteristics, can find potentially interesting scaffolds.

Hill-Climb Optimization

Type: MPO
Input: Pretrained RNN with Reward function
Output: optimised molecules
Method: Recurrent Neural Network using LSTM cells with appropriate reward function Overview:

Hill-Climb optimisation is a method that generates and scores a set of molecules, then retrained the generative model using the top rewarded molecules from the previous step. It continues this process until some preset condition is reached. Specifically, for each training step, a batch of molecules are generated.

Each molecule is then rewarded based on a pre-defined reward function. Then the generative model is fine-tuned using the top k molecules from the batch. Training stops when a predefined condition is achieved (i.e. average pIC50>7 per batch) (Neil et al., 2018).

GCPN (Graph-Convolutional Policy Network)

Type: generative model and MPO
Input: None (generative model)
Output: molecule (in rdkit molecule format)
Method: RL (PPO actor-critic learning) with GAN and expert Overview:

This model was developed by the Stanford groups around Pande and Leskovec[1806.02473]. It builds molecular graphs sequentially using reinforcement learning (RL). The policy network consists of two parts, a standard GCNN encoding in a "per-node" latent space that is similar to the constrained graph VAE, and fully connected layers that take those latent space representation of nodes as input and output probabilities for possible actions, which defines the policy of the reinforcement algorithm, and a state value prediction needed for the actor-critic model (see below).

While the state of the RL algorithm is determined by the (possibly incomplete) molecule, the possible actions are choice of the two atoms that should get connected by a bond, the bond type and the decision whether to finish the molecule. New atoms are added when the network decides to connect to a component, which comes from a given list. Currently those components are only individual atoms, but the algorithm is flexible enough to also allow larger building blocks, using the same "per-node" GCNN to parameterise such building blocks in latent space.

The reward structure features a GAN, whose discriminator is a standard GCNN that after a few graph convolutional layers sums over atom features and adds a few more fully connected layers. It is tasked to discriminate between the generated molecules and molecules in a given data set. Additional rewards (and penalties) are given for (not) obeying valence rules to steer the generator towards realistic molecules during generation, and other unrealistic features can be penalised at the end of episodes.

Tweaking the algorithm to generate molecules that optimise certain properties should be relatively simple, as relevant property scores can easily be implemented in the reward system as an incentive.

Policy updates are done using proximal policy optimisation (PPO), which is a RL gradient method that uses the actor-critic method. The critic is given by a trained state value prediction (with MSE loss) that has been mentioned above. PPO works on the basis of an advantage, that compares the return for the action to the state value that the critic network predicts.

Appendix B: Exploring Novel IP Space: New Candidates for CDK9

Cyclin-dependent kinase 9 (CDK9) has received broad interest as a target for cancer therapy due to its role as a key regulator of gene transcription in important pathways including MYC and MCL-1 (CDK9 biology; De Falco & Giordano, 2002, Cancer Biology and Therapy July-August; 1(4):342-7; Boffo et al., 2018, Journal of Experimental and Clinical Cancer Research doi: 10.1186/s13046-018-0704-8). A large number of publications and patents have described chemical series that inhibit CDK9 across a range of selectivities. Despite the significant amount of work and resources allocated to this problem, treatment with these drugs remains unsuccessful and is often accompanied with adverse side-effects. This is likely due to the fact that while many small molecules bind to CDK9, they are often lack selectivity and therefore bind to other members of the CDK family (e.g. CDK1 and CDK2). The difficulty of producing molecules that are selective for CDK9 using standard approaches makes it a prime target for assessing the power of the GTN platform.

We designed two experiments to demonstrate that the GTN platform is capable of producing interesting and novel candidates for CDK9 targeting. Each of these experiments utilised our platform's implementation of transfer learning applied to the generative model [52, 55], allowing us to fine-tune the model to produce molecules with a specific set of attributes (see FIG. 51), and was centered around splitting the data into train and test sets in a maximally challenging manner, in order to model the challenge of exploring novel IP space that one could encounter in a real-world setting.

Figure 51:
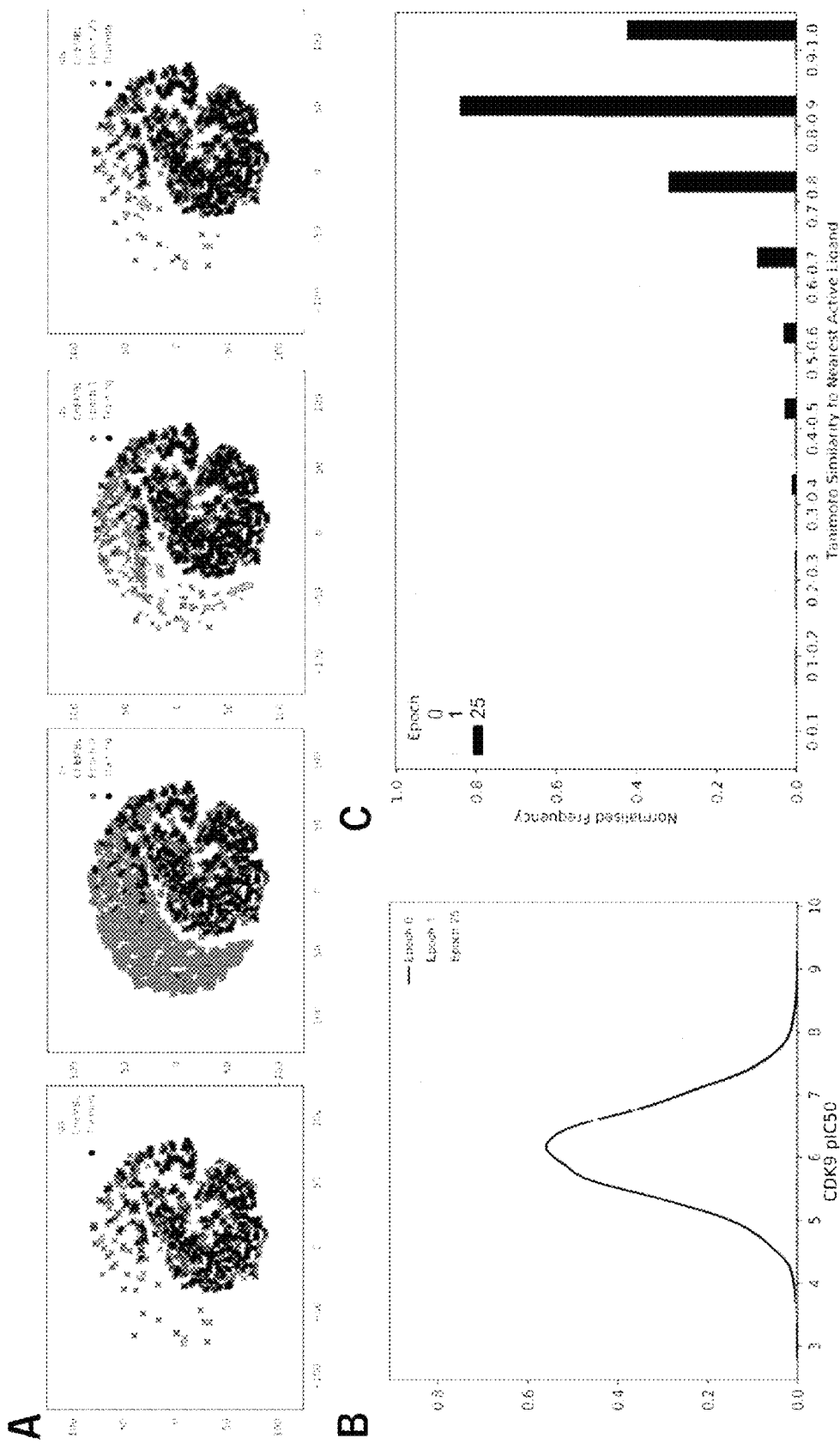
FIG. 51 shows a novel IP space for the CDK-9 molecule.

FIG. 51 shows a novel IP space for the CDK-9 molecule. A) t-SNE plots showing chemical space distribution of ChEMBL data, training data, and our generated molecules before (epoch 0) and after fine-tuning (epoch 1 and epoch 25). As fine-tuning progresses, the overlap between the generated molecules and the training data increase significantly. B) the distribution of CDK9 binding affinity of newly generated molecules before training (epoch 0) and after 1 and 25 epochs of training. Binding affinity with CDK9 increases as fine-tuning progresses. C) Normalised frequency of Tanimoto similarity between generated molecules and molecules from the training set: continued fine-tuning results in more generated compounds having high Tanimoto similarity with active molecules.

The dataset used for this purpose included small molecules and their activity values for CDK9 from 168 patents and published papers. In order to properly assess whether the molecules generated by our model would bind to CDK9 (and CDK1 for experiment 3), we first trained and optimised a predictive model. Our predictive models for CDK9 and CDK1 displayed high accuracy when applied to held-out test data, with $R^2$ values of 0.82 and 0.74, respectively.

The aim of the first experiment was to demonstrate that training our generative model with a subset of molecules is sufficient to reproduce molecules from held-out patent data. We split the CDK9 dataset by patent, by allocation 1280 molecules from 128 patents into the training set and 837 molecules from 40 patents into the test set. All considered molecules were active (Here we considered 'active' to mean $pIC_{50}>7$) against CDK9. The generative model was first trained on the ChEMBL dataset (comprised of 1.5 million compounds) and was then fine-tuned using the CDK9 training set, for a total of 25 epochs.

We were able to demonstrate the capacity of the generative model to effectively focus in on the desired area of chemical space (FIG. 51) from a number of different angles: 1) a t-SNE plot [van der Maaten, L. J. P.; Hinton, G. E. (November 2008). "Visualizing Data Using t-SNE" (PDF). Journal of Machine Learning Research. 9: 2579-2605.] was used to project and visualize six physicochemical descriptors into two dimensions in order to compare these properties between the training and generated dataset with those of active molecules, and 2) the convergence of Tanimoto similarity of generated molecules towards the active set was demonstrated—in both cases as a function of the number of training epochs.

As one can see in FIG. 51, fine-tuning the model resulted in generated molecules that closely reflect the physicochemical properties of the training set. Furthermore, it is evident that the number of training epochs can be used as a parameter that tunes the diversity of generative model. This is a powerful feature in a real-world setting, enabling one to balance the 'novelty' of new proposals with focus towards a specific area of chemical space, and was a useful feature when generating the proposals shown in FIG. 53.

The experiment showcased the capacity of the platform, by producing nine molecules that were in the held-out test set, demonstrating the capacity to produce molecules from separate chemical series. Furthermore, when the experiment was repeated using only a single patent in the training set, the generative model was still capable of producing two molecules from the held-out chemical series, showing that the GTN platform is capable of taking a small amount of data from a single chemical series and producing novel and diverse small molecules with a specific set of properties. It should be noted that without fine-tuning the model is not capable of reproducing any molecules from the held-out set, even after being run for hundreds of epochs.

The second experiment was aimed at producing molecules that have high selectivity for CDK9. To this end, we used the portion of our dataset that has measurements for both CDK9 and CDK1. To make this experiment particularly challenging, and to demonstrate the flexibility of the GTN platform, we split the data into CDK9 and CDK1 activity quadrants, removing the quadrant of interest (e.g. CDK9 active, CDK1 inactive) from our training set. This resulted in a total of 204 molecules in the training set and 93 molecules in the test set. Again, our results show that the GTN platform has the capacity to generate molecules from held out test data (FIG. 52) by 'learning' the desirable properties of the molecules in the training set, and generalising to novel chemical space. Even more interestingly, the experiment shows that, despite not being trained on molecules both active against CDK9 and inactive against CDK1, a subset of the generated molecules fit this profile (FIG. 51B). Thus, the platform is able to not only produce molecules with an activity profile of interest, but also possesses a flexibility and capacity to generate molecules with profiles it has not seen.

Figure 52:
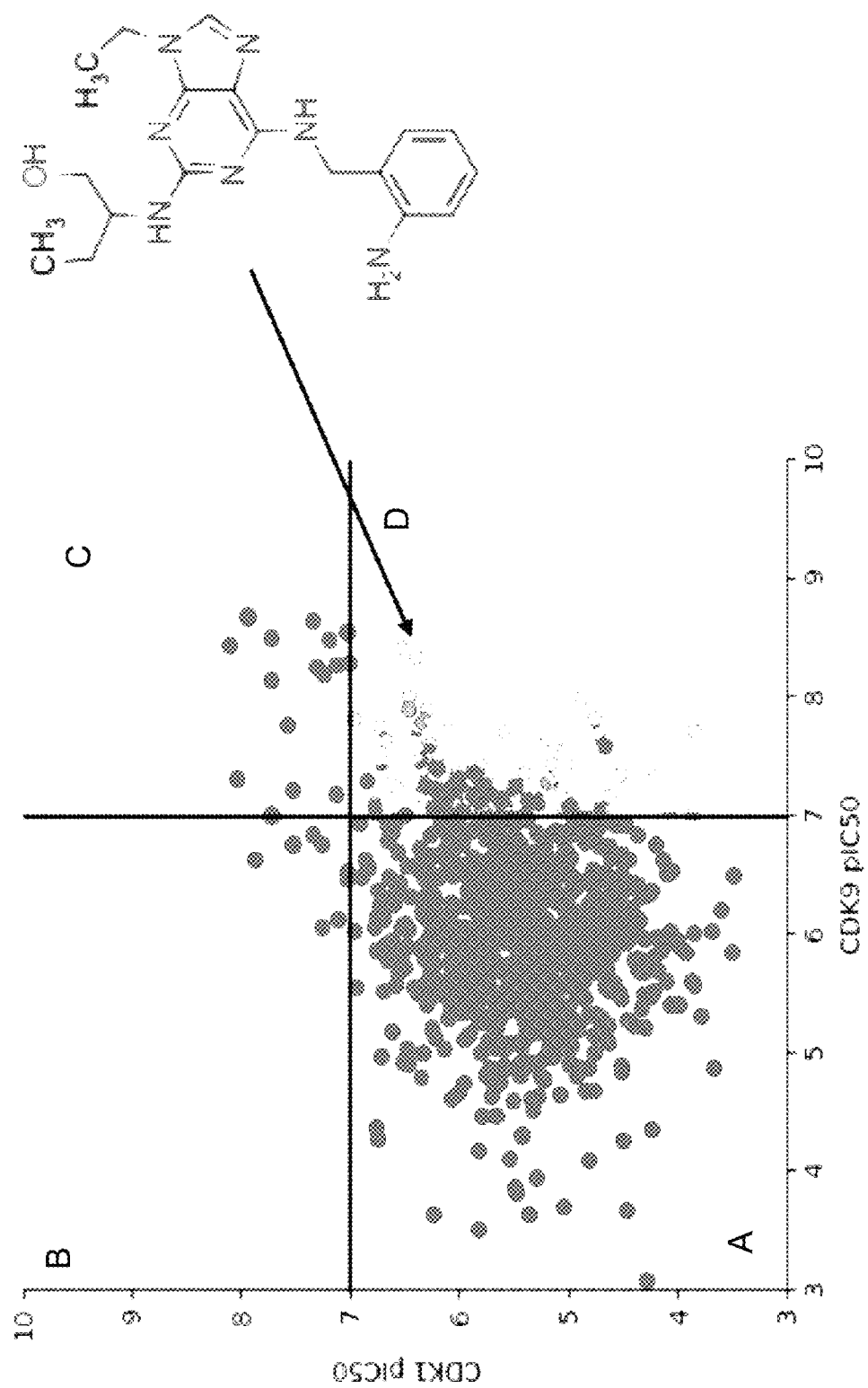
FIG. 52 shows a plot demonstrating the platform capabilities to generate molecules from held out test data.

FIG. 52 show the generalisation capabilities by seeing only part of the data in regions A, B and C and being able to generate compounds of interesting profile-active against CDK9 and inactive against CDK1 (in region D). The compound shown is found in one of the held-out patents.

Figure 53:
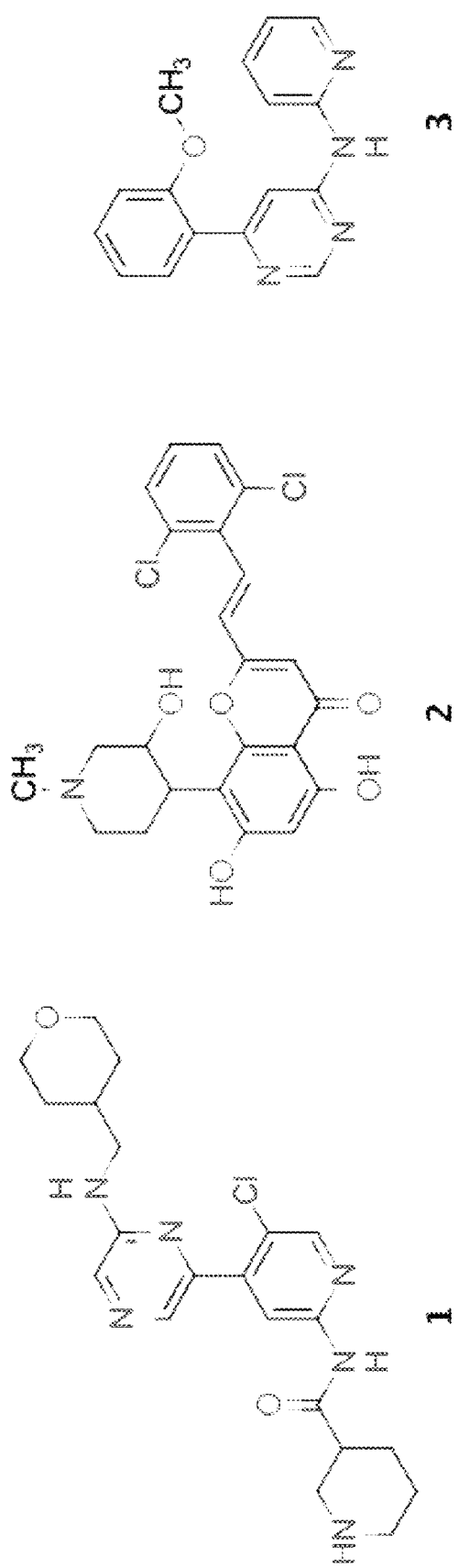
FIG. 53 shows examples of generated compounds not seen by the platform that are highly selective for CDK9.

FIG. 53 shows examples of generated compounds not seen by the platform that are highly selective for CDK9 (WO2011026904 A1, J. Med. Chem., 2018, 61 (4), 1664-1687, 3) Curr. Med. Chem., 2011, 18 (3), 342-358 DTNN reference: Schutt, K. T., Arbabzadah, F., Chmiela, S., Muller, K. R., & Tkatchenko, A. (2017). Quantum-chemical insights from deep tensor neural networks. Nature communications, 8, 13890). Compound 1 is a molecule from a lead series discovered by Novartis for the treatment of proliferative diseases. Compound 2 is a molecule with subtype selective CDK9 inhibitor activity with oral bioavailability and anti-proliferative properties proven in vivo (candidate quality). Compound 3 is a molecule with subtype selective CDK9 inhibitor activity (lead) for treatment of HIV. The molecule has good ligand efficiency and could be considered as a lead compound. These molecules are highly active, with measured pIC50 values of 8.05 (1), 8.70 (2), and 7.44 (3). Our predictive model showed excellent correlation with the measured activity.

Appendix C: Advanced Predictive Models from Quantum Observables

It is often the case that an experimental quantity can not be accurately modelled using de novo computational methods, for example due to the complexity of the system or effects of noise, but is nevertheless strongly correlated with a set of accessible quantum mechanical observables. As discussed in the context of GTN's predictive module, this is the case for a large number of properties relevant to both pharma and materials science. A two step machine learning process is then often the natural choice (depicted as path A in FIG. 3A (Section 1)). Because the QM calculations that need to be performed are in practice very costly (for certain highly entangled states these calculations become unfeasible, and require a quantum computational approach) in the first step a machine learning model is trained on as much synthetic data as is available, in order to predict the relevant QM observable, and in the second step these predictions are then correlated with experiment.

In such a scenario a machine learning method that is capable of accurately and quickly predicting relevant quantum observables becomes a crucial component of a predictive model pipeline. In this section we demonstrate the capacity of GTN's quantum featurization to go beyond what is possible with features based on standard chemical graphs, and to beat best-in-class models by a significant margin. For this purpose, we developed an experiment for our first series of proprietary Q-Graph descriptors, applied to a small subset of QM9 [R. Ramakrishnan, P. O. Dral, M. Rupp, O. A. von Lilienfeld, Quantum chemistry structures and properties of 134 kilo molecules, Scientific Data 1, 140022, 2014. [bibtex], WO2011026904 A1, J. Med. Chem., 2018, 61 (4), 1664-1687, 3) Curr. Med. Chem., 2011, 18 (3), 342-358 DTNN reference: Schutt, K. T., Arbabzadah, F., Chmiela, S., Muller, K. R., & Tkatchenko, A. (2017). Quantum-chemical insights from deep tensor neural networks. Nature communications, 8, 13890] (the QM9 dataset consists of 134,000 molecules from the GDB-17 database [L. Ruddigkeit, R. van Deursen, L. C. Blum, J.-L. Reymond, Enumeration of 166 billion organic small molecules in the chemical universe database GDB-17, J. Chem. Inf. Model. 52, 2864-2875, 2012.] containing up to nine heavy atoms. For each molecule, the QM9 dataset provides a conformation and 12 properties which have been determined using ab-initio density functional theory and coupled cluster methods. The multi-task training encompasses energetic properties, such as ground state energy and HOMO/LUMO eigenvalues, and electronic and thermodynamic properties.)

For ease of integration, the current Q-Graph formalism is implemented using standard graph convolutional networks. Descriptors associated with nodes and links of the Q-Graph serve as a proxy for the molecule's wavefunction (see FIG. 2 in "Section 1: Overview of small molecule drug discovery").

Figure 54:
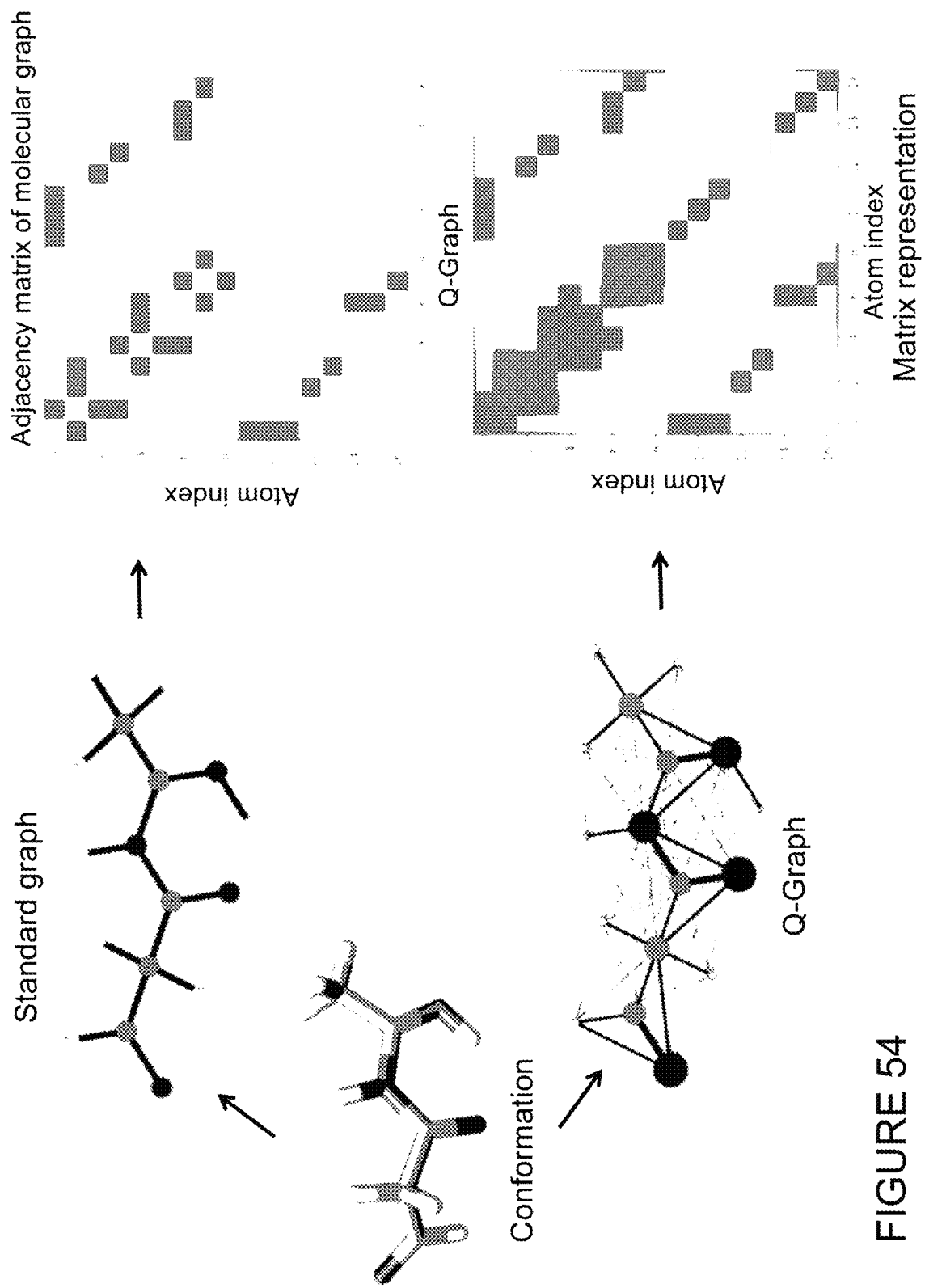
FIG. 54 shows a comparison of the standard chemical graph and the Q-Graph representation for a molecule in QM9.

FIG. 54 shows a comparison of the standard chemical graph and the Q-Graph representation for a molecule in QM9. The traditional molecular graph generally only contains information on the atomic connectivity, whereas our fully-connected Q-Graph contains additional links which can be thought of as encoding a coarse-grained representation of the delocalized nature of the molecule's electrons. The dominant weights of the edges of the Q-Graph recover the atomic connectivity of the molecular graph.

Figure 55:
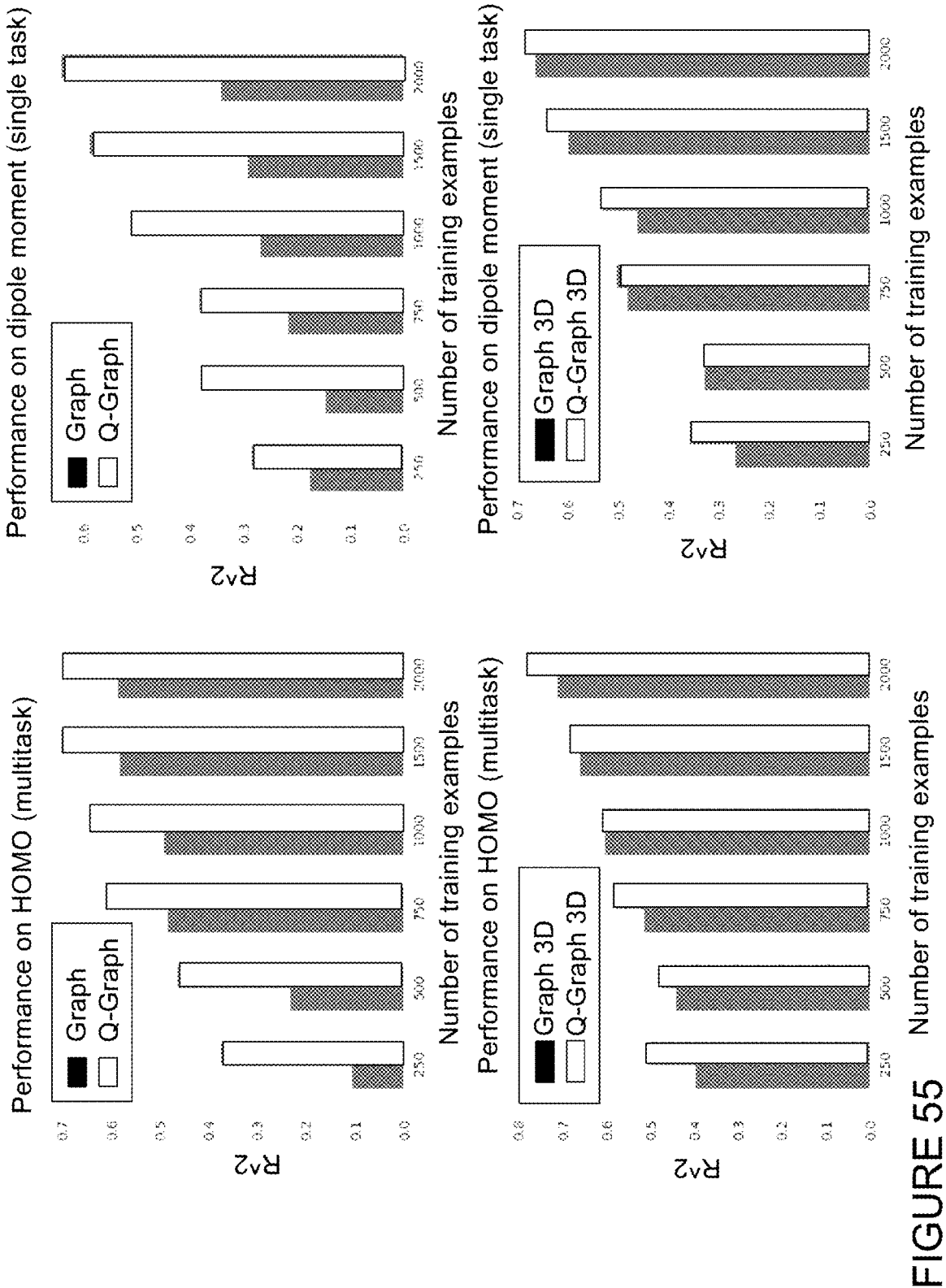
FIG. 55 shows a comparison of predictive model performances of total dipole moment, and HOMO energy values using different featurisations, both in a single- and multi-task setting.

We benchmarked how well our model would work on a small dataset, aiming to model a realistic scenario in which ab initio quantum calculations relevant for the data are too expensive to perform on a large number of molecules. We randomly picked small training datasets from QM9, ranging between 250 and 2000 molecules. Results of predictive model performances for the total dipole moment, and HOMO energies, which are among the hardest properties of the dataset to predict, are shown in FIG. 55 (these quantities are relevant for a number of physicochemical properties, like pKa, solubility and lipophilicity.) Incorporating Q-Graph features was seen to consistently improve upon graph models with familiar bond features. When comparing data represented in terms of Q-Graph vs. standard chemical graph features, the gains were huge, increasing the values of $R^2$ by up to 0.3. When comparing models for which conformational features are explicitly included, the Q-graph approach again consistently surpassed the current state-of-the-art model in this domain (reference 2) in [56]), for both HOMO and dipole moment tasks, by up to 10% for certain dataset sizes, and this without performing any systematic hyperparameter optimisation.

FIG. 55 shows a comparison of predictive model performances of total dipole moment, and HOMO energy values using different featurisations, both in a single- and multi-task setting. For the displayed experiments, data is presented to the model as respectively 1) Graph: a molecular graph with bond information (single, double, aromatic, . . . ), 2) $\mathcal{Q}$-Graph: a fully-connected molecular graph encoding a coarse-grained picture of electron correlations (see FIG. 2), 3) Graph 3D: A Graph together with conformational information, 4) $\mathcal{Q}$-Graph 3D: conformational information together with $\mathcal{Q}$-Graph features. The Q-Graph based model 4) consistently beats the model considered state-of-the-art 3), often by a considerable margin.

Figure 56:
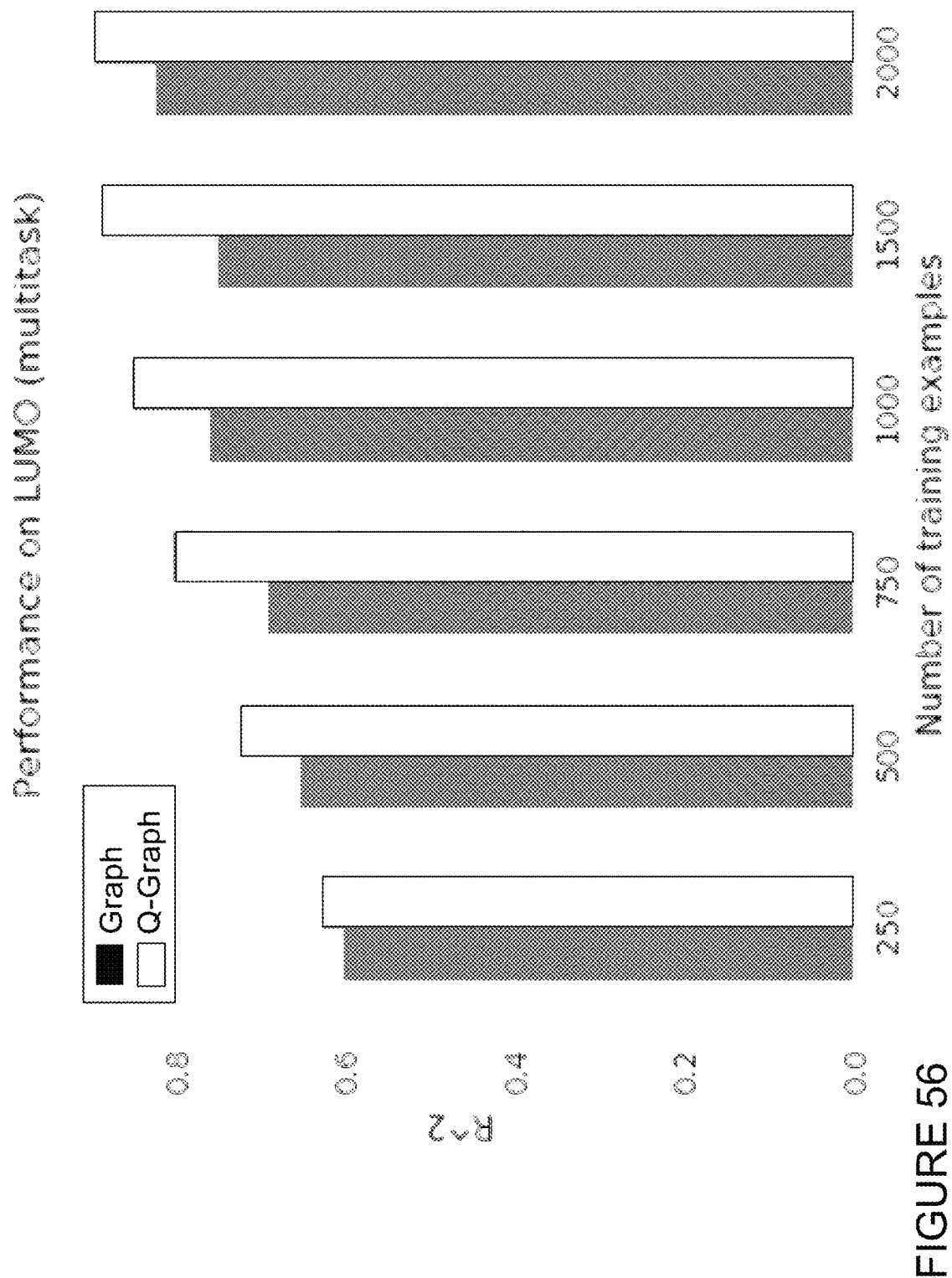
FIG. 56 shows a comparison of predictive model performances of LUMO using different featurisations.
Figure 57:
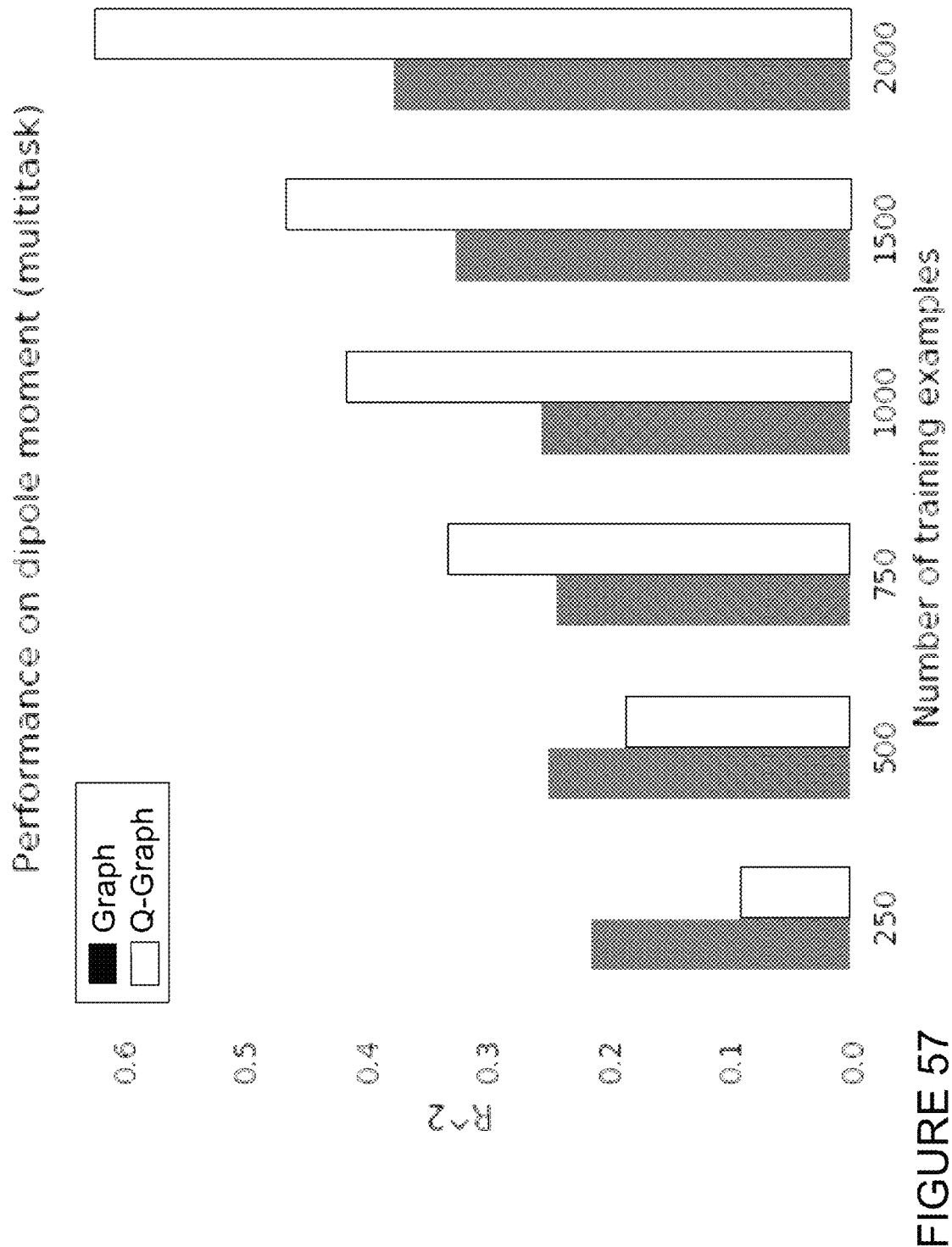
FIG. 57 shows a comparison of predictive model performances of dipole moment (multitask) using different featurisations.
Figure 58:
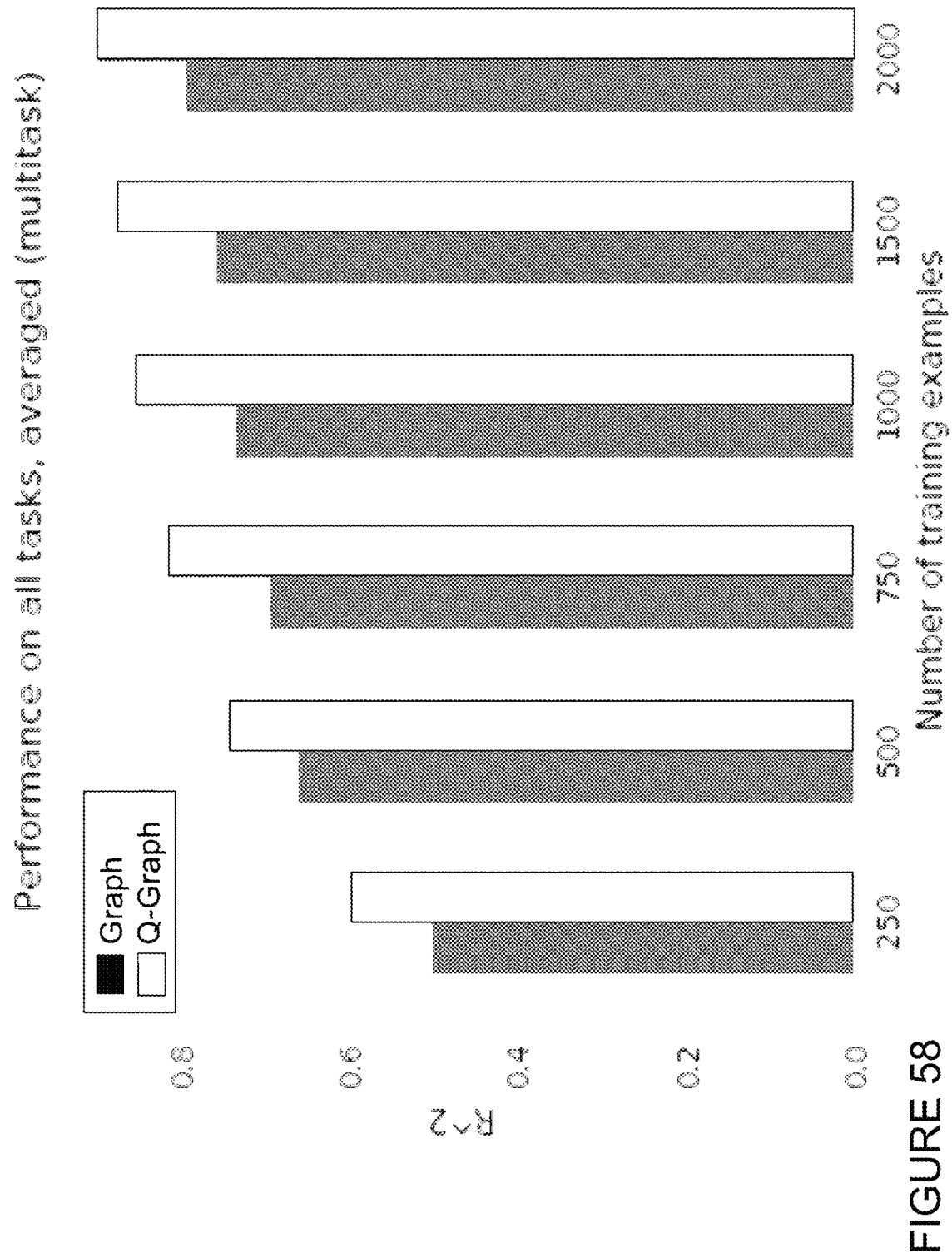
FIG. 58 shows a comparison of predictive model performances on multiple tasks, average (multitask) using different featurisations.
Figure 59:
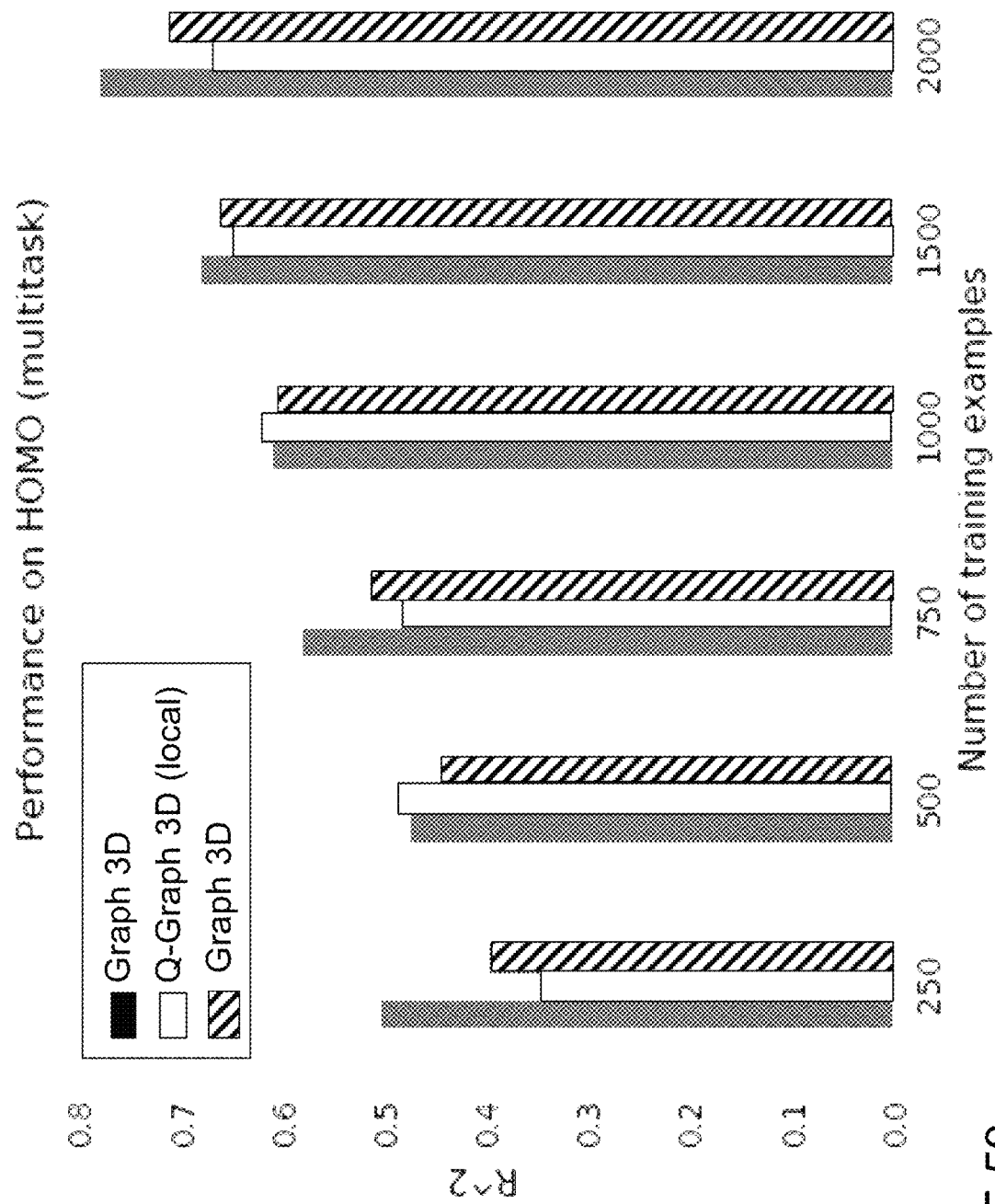
FIG. 59 shows a comparison of predictive model performances of performance on HOMO (multitask).
Figure 60:
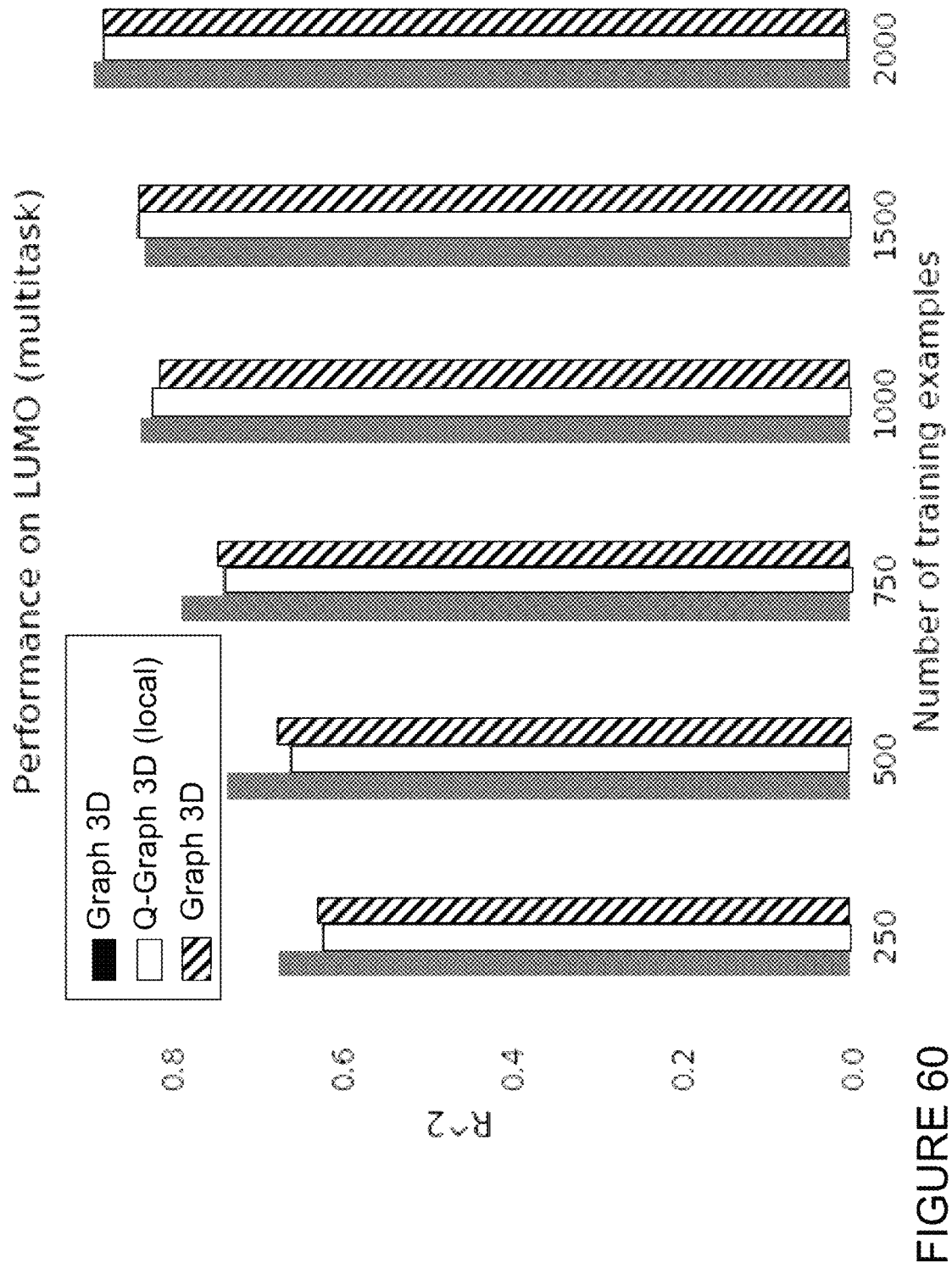
FIG. 60 shows a comparison of predictive model performances of performance on LUMO (multitask).
Figure 61:
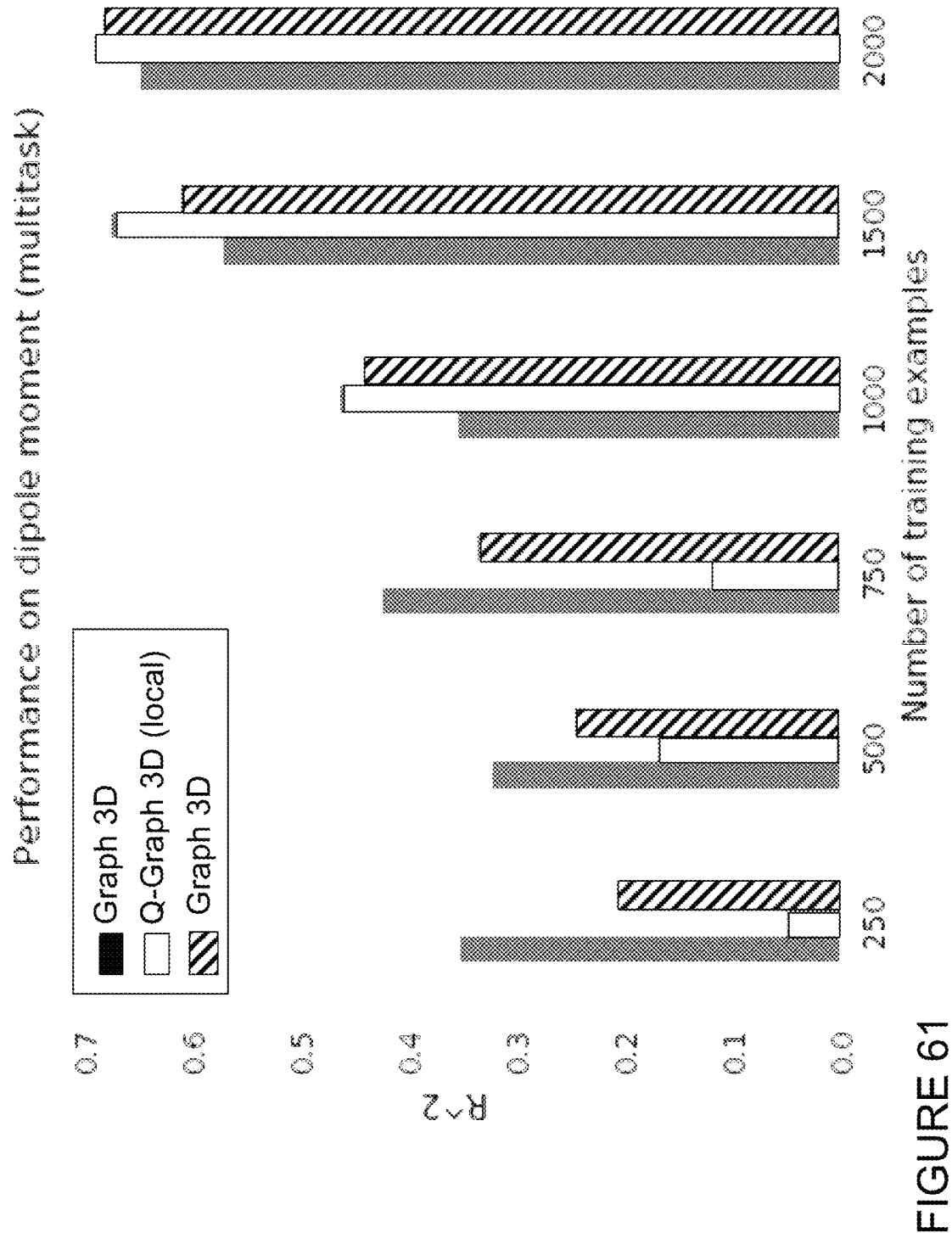
FIG. 61 shows a comparison of predictive model performances of performance on dipole moment (multitask).
Figure 62:
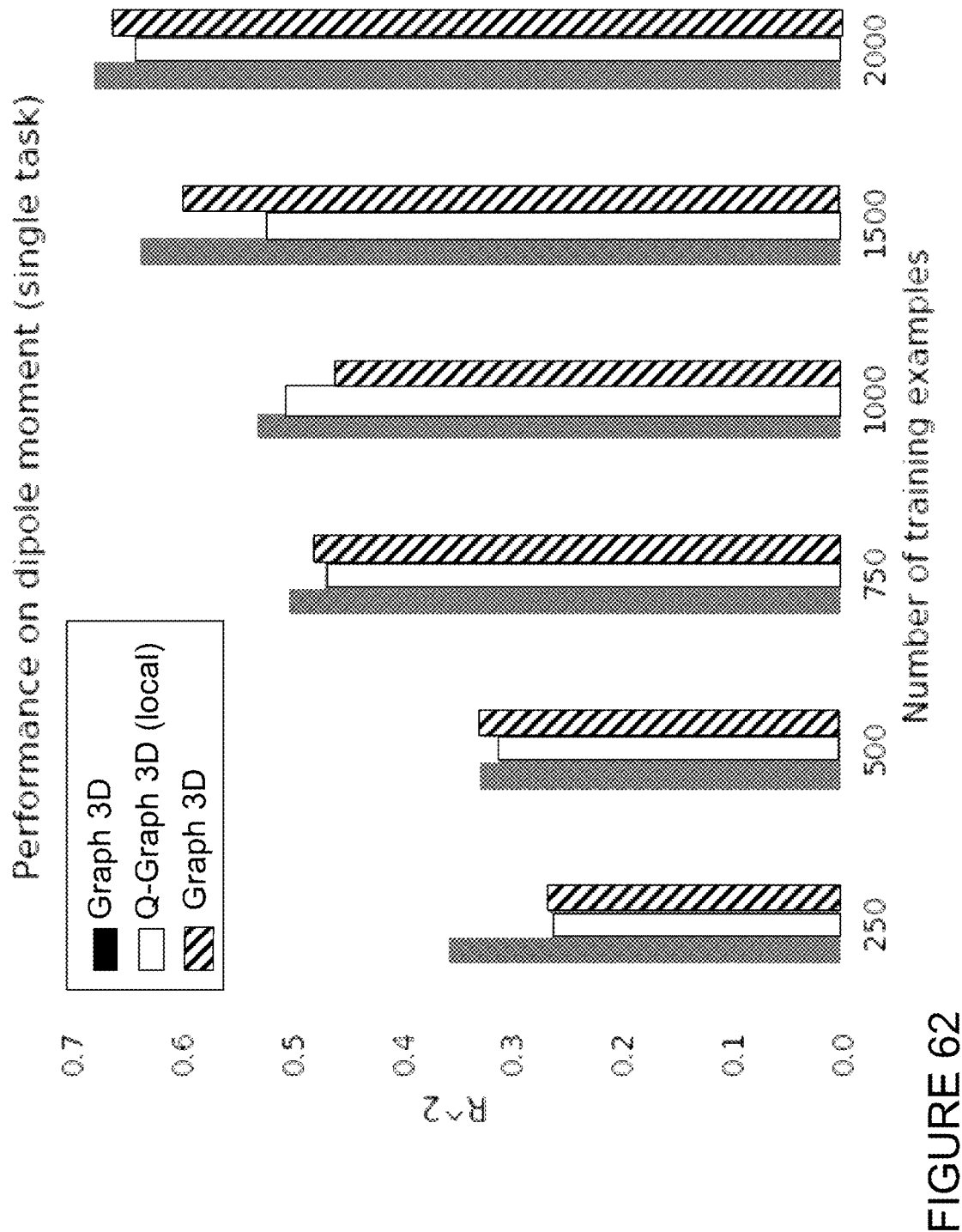
FIG. 62 shows a comparison of predictive model performances of performance on dipole moment (single task).
Figure 63:
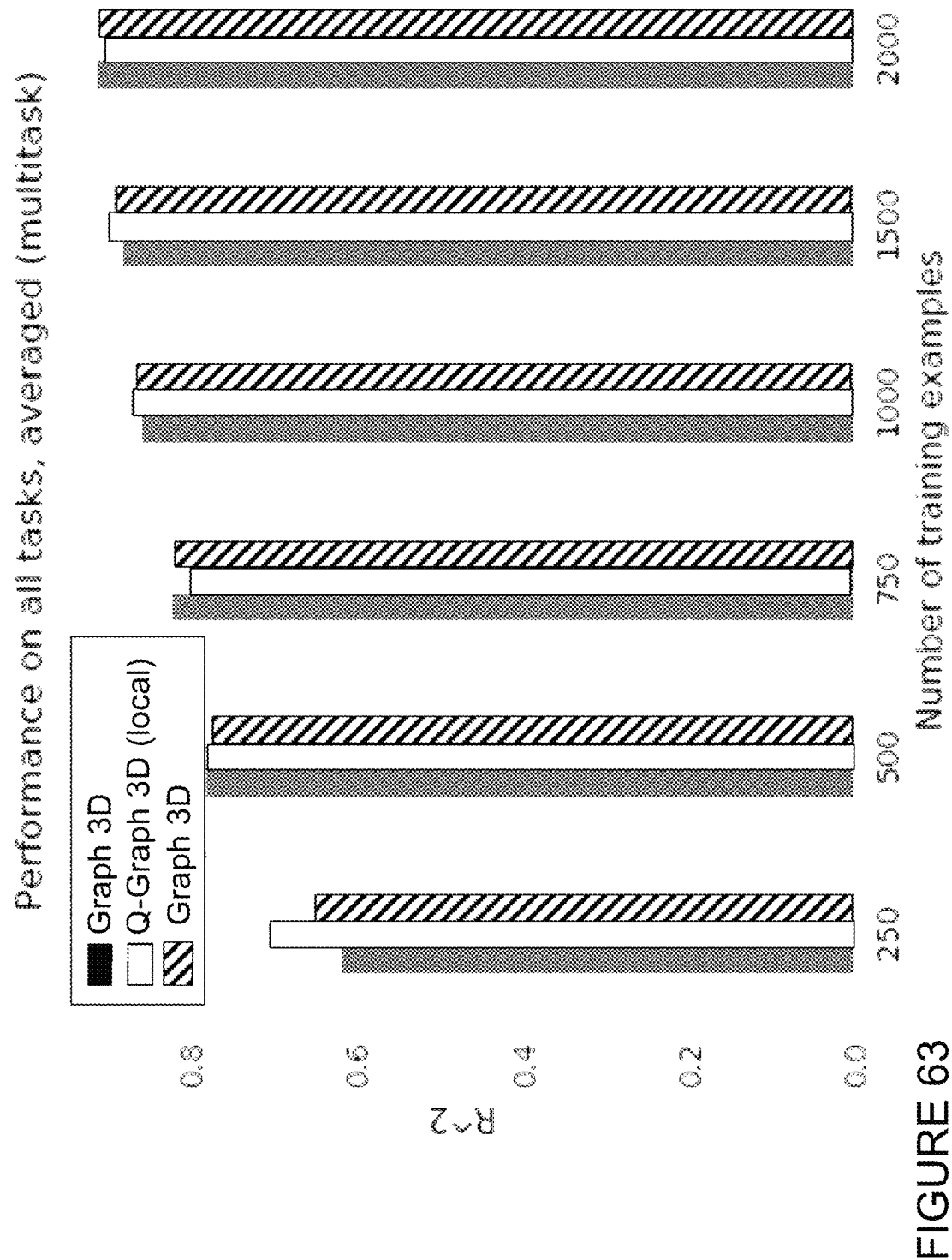
FIG. 63 shows a comparison of predictive model performances of performance on all tasks (FIG. 59-62), averaged (multitask).

FIG. 56 shows a comparison of predictive model performances of LUMO using different featurisations. FIG. 57 shows a comparison of predictive model performances of dipole moment (multitask) using different featurisations. FIG. 58 shows a comparison of predictive model performances on multiple tasks, average (multitask) using different featurisations. FIG. 59 shows a comparison of predictive model performances of performance on HOMO (multitask). FIG. 60 shows a comparison of predictive model performances of performance on LUMO (multitask). FIG. 61 shows a comparison of predictive model performances of performance on dipole moment (multitask). FIG. 62 shows a comparison of predictive model performances of performance on dipole moment (single task). FIG. 63 shows a comparison of predictive model performances of performance on all tasks (FIG. 59-62), averaged (multitask).

Appendix D: Experiment P450 Site of Metabolism

Background

Figure 64:
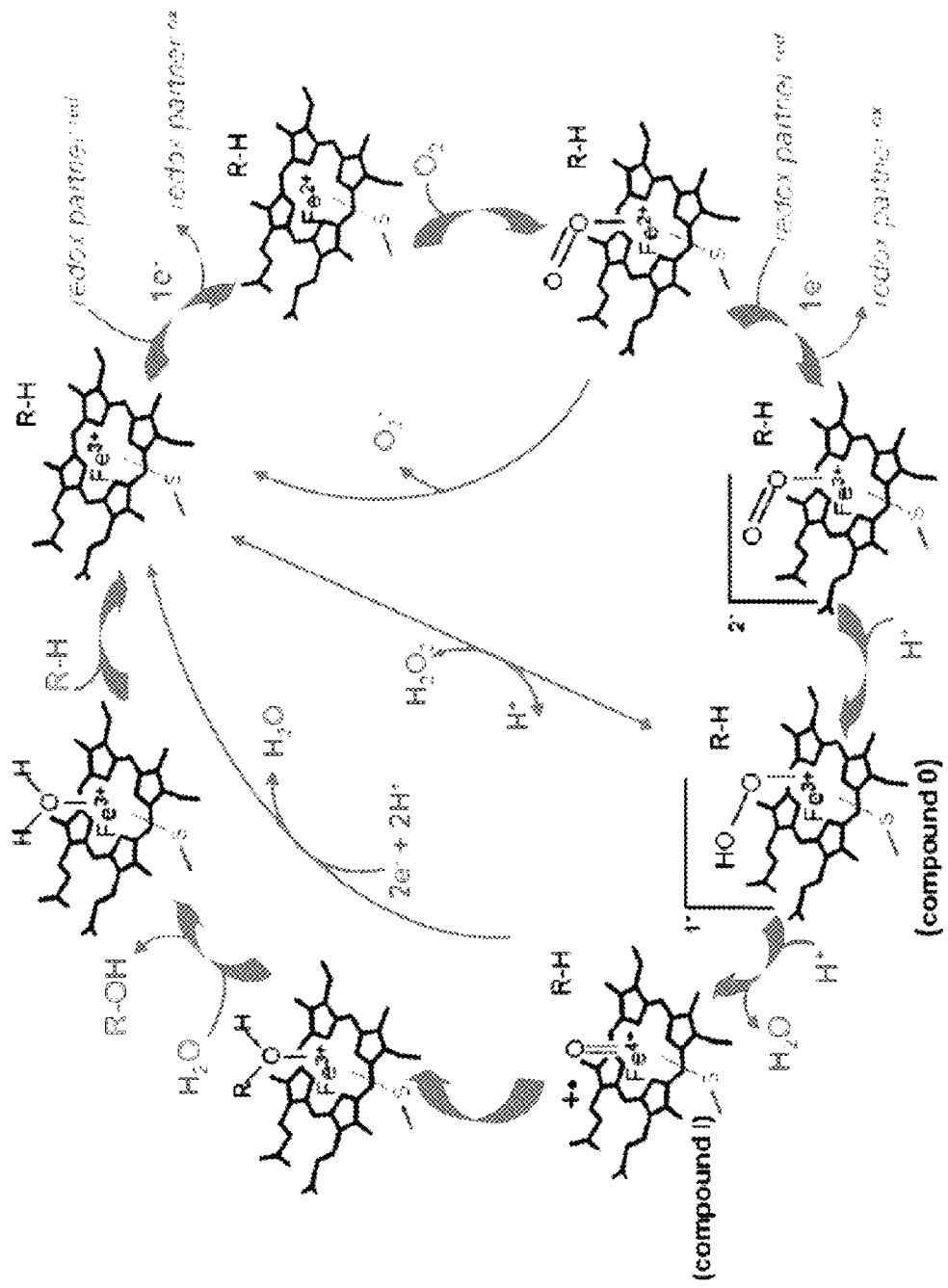
FIG. 64 shows an representation of P450.

As illustrated in FIG. 64, P450 is a superfamily of enzymes with Heme as a co-factor. Heme is an Iron containing porphyrin. P450 are a major driver of drug breakdown in animals. The chemical process is driven by Redox (electron transfer resulting in the change of a formal charge state) of the iron core of the Heme.

Dataset

Dataset was recovered from the supplementary information to: https://doi.org/10.1093/bioinformatics/btv100 Available at: https://bitbucket.org/swamidass/xenosite-region/wiki/Home Literature Models
FAME 2

Baselines & Atom Level Quantum Features
We were using roc as our metric.
P450 Site-of-Metabolism (SoM) Prediction
  Single-target (3A4, has 476 compounds):
    Zaretzki et al. 2015: ROC-AUC=0.855
    Fame 2 (QSAR model, best out of many): ROC-AUC=0.92
    Our baseline PairMessageGraphConv model: ROC-AUC=0.934±0.006
  Multi-target (9 targets, has 678 compounds)
    Zaretzki et al. 2015: ROC-AUC=0.87
    Fame 2 (QSAR model, best out of many): ROC-AUC=0.92
    Our baseline PairMessageGraphConv model: ROC-AUC=0.930±0.025
  Initial (by 16th May) molecular-orbital (MO) features, projected down onto graph nodes (as atom-level MO partial charges, and $\{s,px,py,pz\}$ MO orbital partial charges).
    ingle-target (1A2, 285 compounds), local runs w/o hyperparam optim
    PairMessageGraphConv baseline: ROC-AUC=0.945 (local run only, fixed split)
    +quantum molecular orbitals, atoms ROC-AUC=0.956 (local run only, fixed split)

Improved Quantum Features

Here (expensive) DFT calculations were carried out, and then analysis of the resulting charge density (with Multiwfn), using the exchange-correlation functional acting on the electron density, to provide an atoms-in-molecules model of bonding. This weighted graph (where the edges were specified by the degree of covalent bonding) was then used as an edge-feature in ML.

One of the key benefits of tight-binding (TB) methods of electronic structure, is that you are using a minimal (and therefore highly contracted) atomic basis. The spherical harmonics which make up the atomic basis are mutually orthogonal (i.e. between all $\{s, px,py,pz, dz2,dxy,dyz,dzx, dx2-y2\}$ located on an individual atom). The interactions overlap between these orbitals is parametrised by the TB code, generating the off diagonal (interacting) elements of the Hamiltonian and thereby the entire chemical nature of the molecule.

Solution of the time independent Schrodinger equation as a secular linear algebra equation produces a set of eigenvectors (in the basis of a linear combination of atomic $\{s,px,py,pz\}$ orbitals) corresponding to molecular orbitals with an energy of the corresponding eigenvalue.

Quantum Cloud Run 9-way binary classification on P450 SoM dataset {1A2, 2A6, 2B6, 2C8, 2C9, 2C19, 2D6, 2E1, 3A4}. 'Test' results, from result.json.

Baseline RDKIT:
  ROC_AUC_mean 0.934+−0.024
  "channels": [128, 128], "edge_channels": [128, 128], "message_edge_channels": [256], "message_nn_channels": [128], "linear_channels": 128

(Only) Quantum Edges, No Noise:
  ROC_AUC_mean 0.926+−0.035
  "channels": [64, 64], "edge_channels": [256, 256], "message_edge_channels": [64], "message_nn_channels": [64], "linear_channels": 256

(Only) Quantum Edges, with Noise:
  ROC_AUC_mean 0.925+−0.025
  "channels": [128, 128], "edge_channels": [256, 256], "message_edge_channels": [64, 64], "message_nn_channels": [64], "linear_channels": 256

Quantum Edges+RDKIT, No Noise:
  ROC_AUC_mean 0.922+−0.034
  "channels": [128, 128], "edge_channels": [64, 64], "message_edge_channels": [64, 64], "message_nn_channels": [128], "linear_channel": 12

Quantum Edges+RDKIT, with Noise:
  ROC_AUC_mean 0.935+−0.029
  "channels": [256, 256], "edge_channels": [64, 64], "message_edge_channels": [128], "message_nn_channels": [256], "linear_channels": 512

Appendix E: Experiments on Conformational Ensemble ML

The baseline we will compare with is our state-of-the-art structure-based model that we used before caring about different conformations. We compare the model in each experiment to that baseline to keep track of improvement. We assume for now that the protein remains fixed for those experiments.

General structure of our pipeline for one learning step on conformational ensembles is as follows (for one "data point"):
  a) Take molecule from dataset
  b) Create set of conformations of the molecule in the pocket, and possibly also just in solution
  c) If clustering on poses needs to be done, RMSD should be good enough for clustering.
  d) Run NN on each conformation separately.

e) Sum over different conformations (either weighted or unweighted). In any case we have to add a (learnable) bias to the sum, to include the contribution to dGby the protein.

In the case we have both conformations in pocket and in solution, we have to compute those two sums separately and divide them by each other, or first compute the log of each (see next point) and subtract them from each other.

f) Compute prediction (here: ΔG, which should be $-1/\beta \log(NNoutput)$)

g) Compute loss (MSE), backpropagate and train.

Different Scenarios:

How can the network learn:

Can the network learn entropy weights by itself: Create set of different conformations by clustering and compute (classical) Boltzmann probability weights (those weights are equal to the fraction of poses in each cluster, they correspond to $e^{-\beta E + S/k_b}$). [P0]

Compare how well the network does without giving it any weights, just giving it different representative poses.

Compare how well the network does with entropic probabilistic weights $e^{S/k_b}$. [P0]

How important are molecule conformations in solution?

Compare running including network computations on the both conformations in complex and in solution to training network only on conformations in complex. [P0]

How much accuracy do we gain from MD compared to docking:

Compare results from MD and docking (also scenarios where parts are done by docking and the rest by MD).

How well will a model will work on an imperfect set of conformers, when all we can do is dock at inference time. A model trained on ensembles is likely to be much more robust than one trained on single poses."

Find poses from MD:

Cranking up temperature for short time to a few hundred meV, then going down in temperature and getting to local minimum. Do this until there is confidence that all relevant poses have been found. Get entropy from harmonic analysis. There are crucial corrections from the waters that according to Jarvist can be incorporated.

Run MD longer around each minimum, use clustering in order to see if that improves entropy estimates $e^{S/k_b}$. It might be important to use clustering with low distance threshold first to eliminate identical poses before computing entropy weights.

Pure docking: Get poses from docking and use harmonic analysis around each pose to estimate entropic weights.

Summary of Ensemble Worked Examples

We performed two experiments, 1) binding affinity predictor for small datasets, 2) log P predictor.

The general structure of an algorithm is described in section above.

The general structure of the function predicting \Delta G for different experiments is described "Section 7: Machine learning on thermodynamic ensembles». For example, for binding affinity, there are three terms—so in the case of neural network algorithms, three different neural networks—the first describes the contribution form the complex (ligand+protein bond), second and third the contributions from the ligand and protein respectively.

The specific networks are designed to capture maximally well the particular contribution to Delta G. For particular examples the networks are designed to maximally capture the physics of the particular contribution to Delta G—see below.

Some examples of how actual docking poses are generated are described in "Section 8: Conformational searching methods for machine learning".

Experiment 1. Predictor for Binding Affinities on a Proprietary Dataset

Conformations were generated with MD in implicit water and in the pocket.

Figure 66:
FIG. 66 shows the edge complex results.
Figure 67:
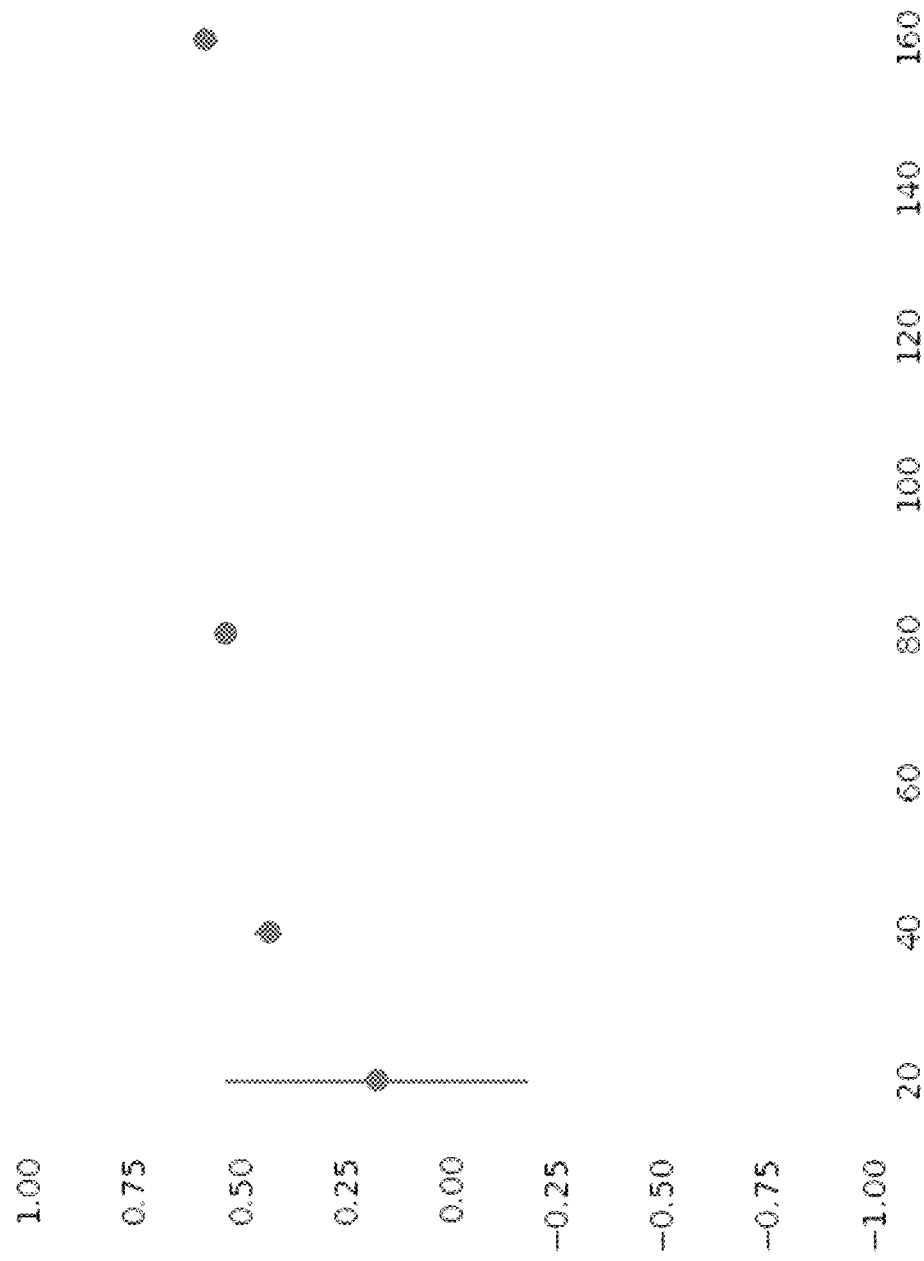
FIG. 67 shows the edge ligand based results.
Figure 68:
FIG. 68 shows the edge ligand only scatter max results.
Figure 69:
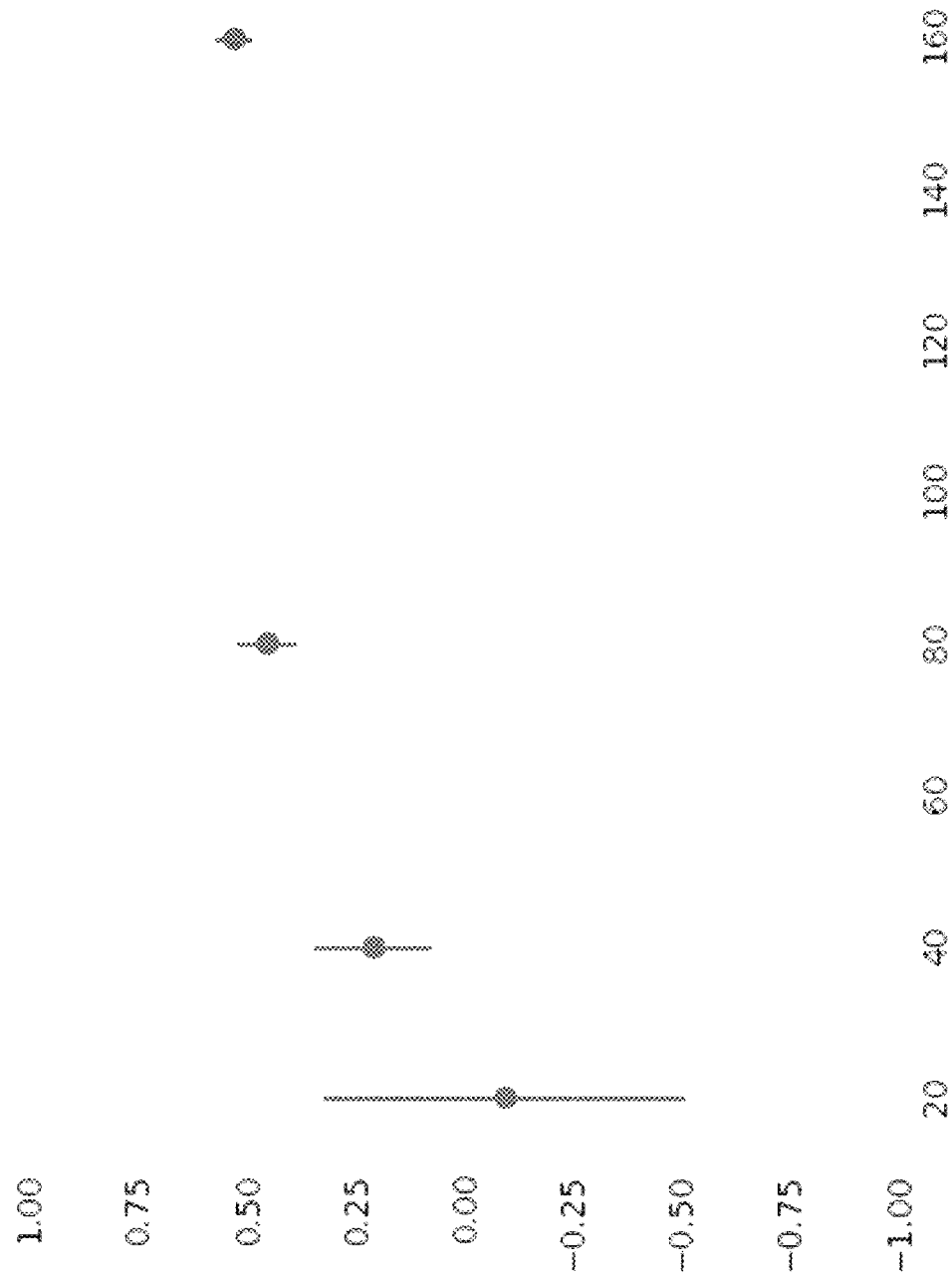
FIG. 69 shows the pocket attention pair message results.
Figure 70:
FIG. 70 shows the pocket gating pair message results.
Figure 71:
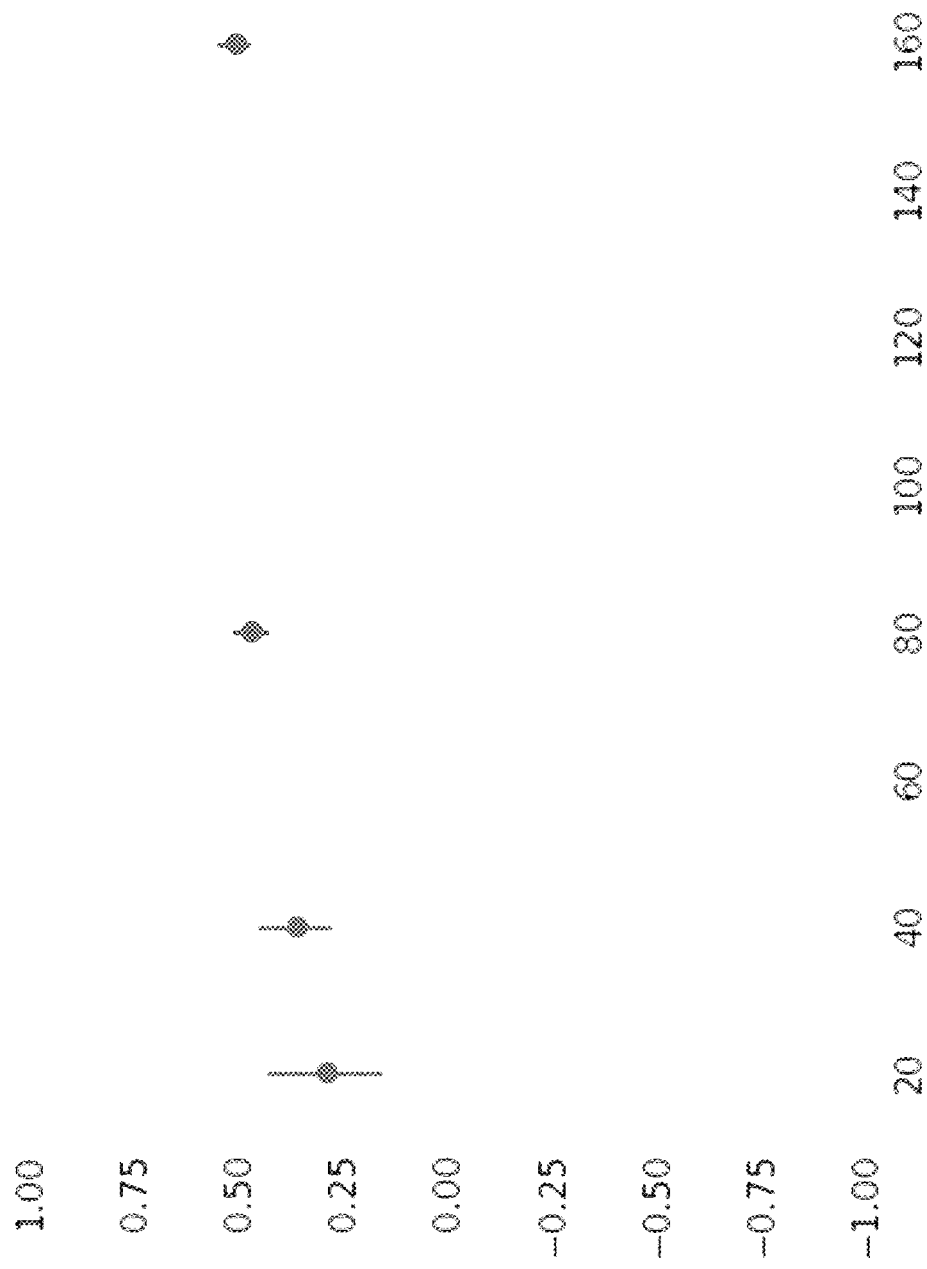
FIG. 71 shows the edge ensemble ligand only (10 per eg) results.
Figure 72:
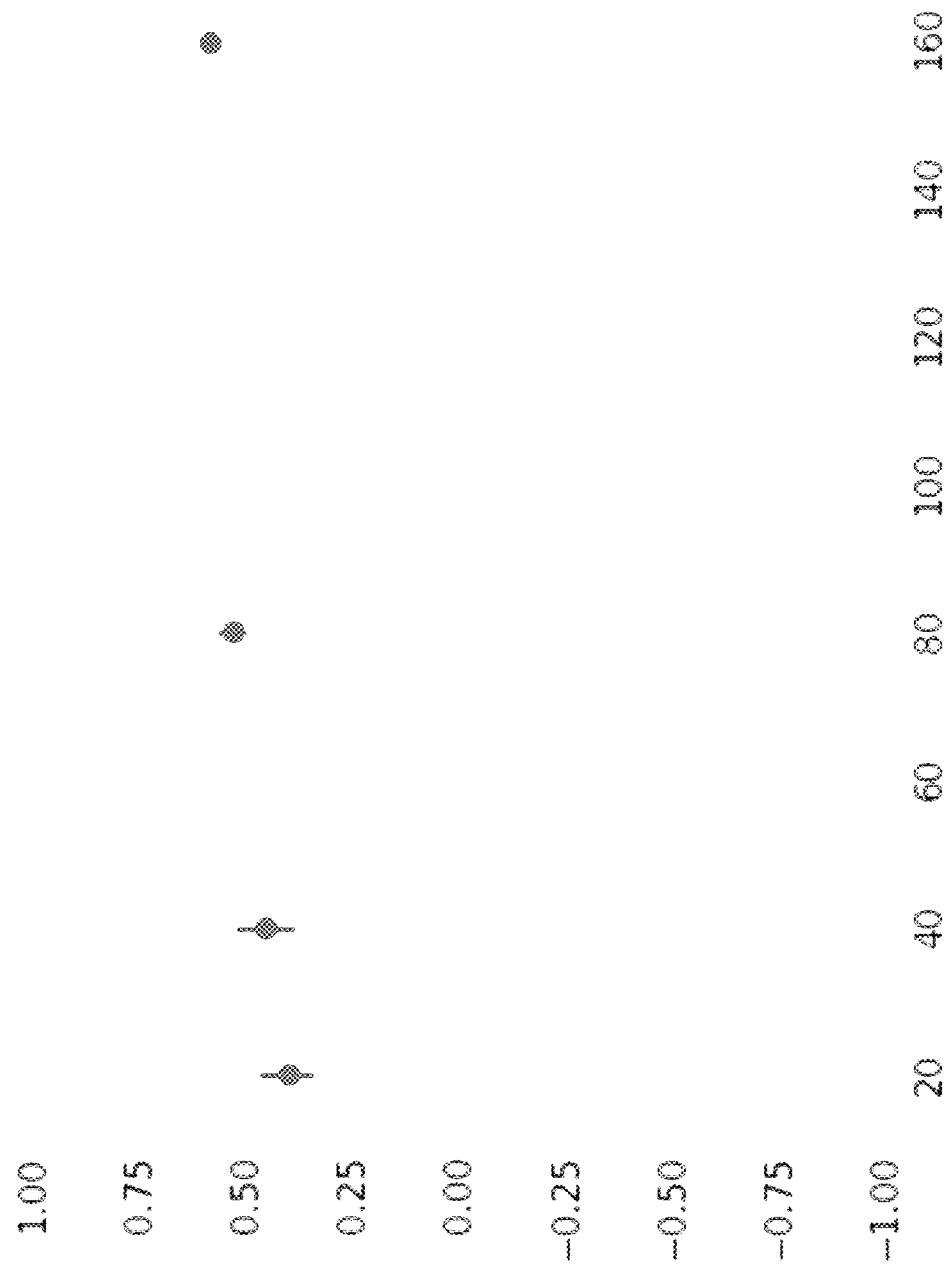
FIG. 72 shows the edge ensemble ligand only (2 per eg) results.

Results of the experiment 1 for random splits are summarised in FIG. 65. FIGS. 66 to 72 show plots of mean $r^2$ over 10 different splits as a function of the training set size. FIG. 66 shows the edge complex results. FIG. 67 shows the edge ligand based results. FIG. 68 shows the edge ligand only scatter max results. FIG. 69 shows the pocket attention pair message results. FIG. 70 shows the pocket gating pair message results. FIG. 71 shows the edge ensemble ligand only (10 per eg) results. FIG. 72 shows the edge ensemble ligand only (2 per eg) results.

Figure 74:
FIG. 74 shows the Edge ligand based results.
Figure 75:
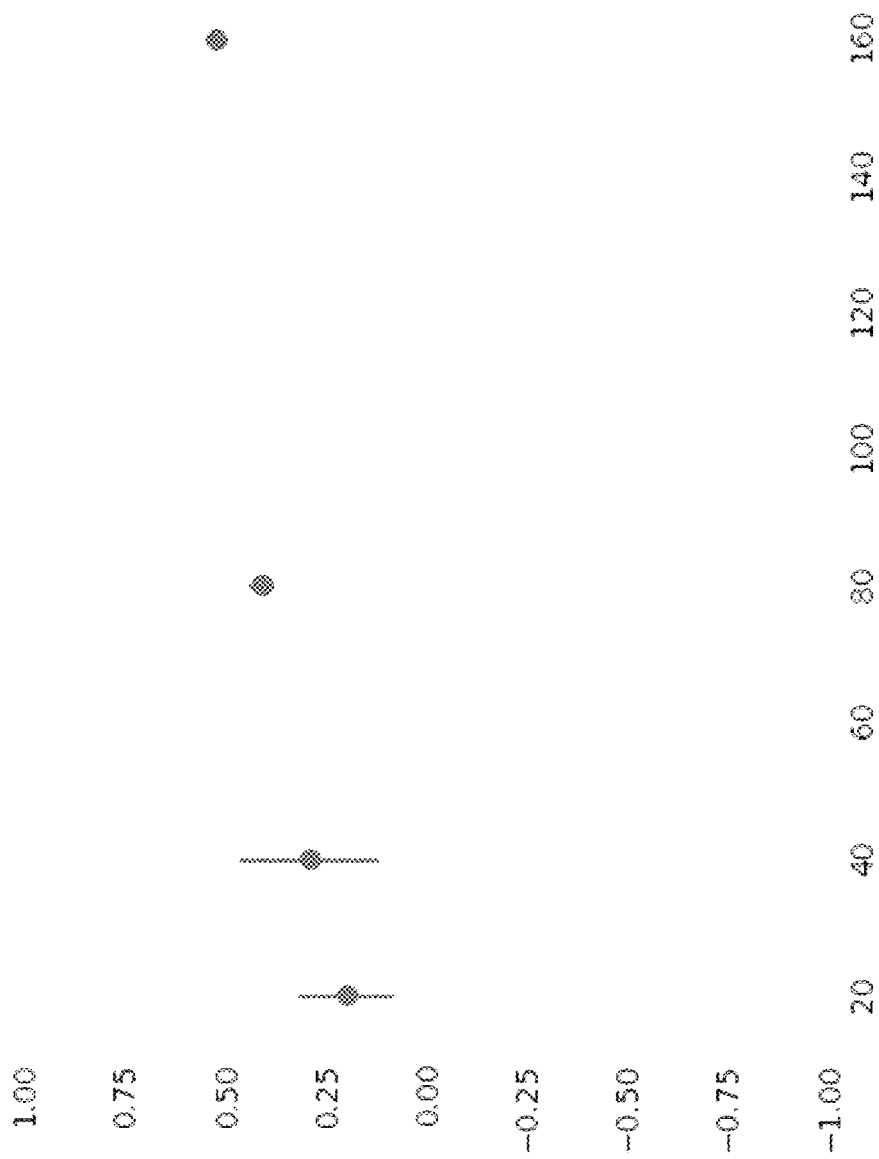
FIG. 75 shows the Edge ligand only results.
Figure 76:
FIG. 76 shows the pair message complex results.
Figure 77:
FIG. 77 shows the pocket attention pair message results.
Figure 78:
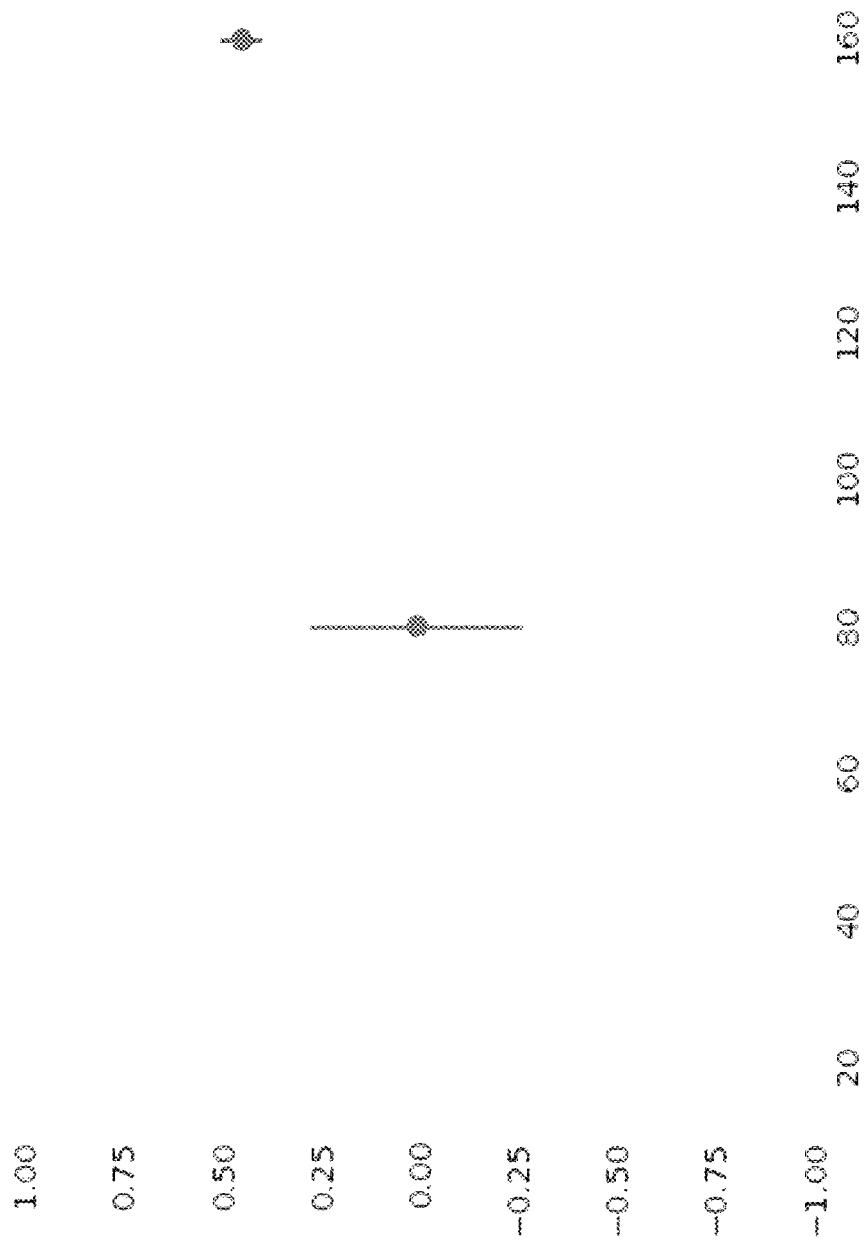
FIG. 78 shows the pocket gating pair message results.
Figure 79:
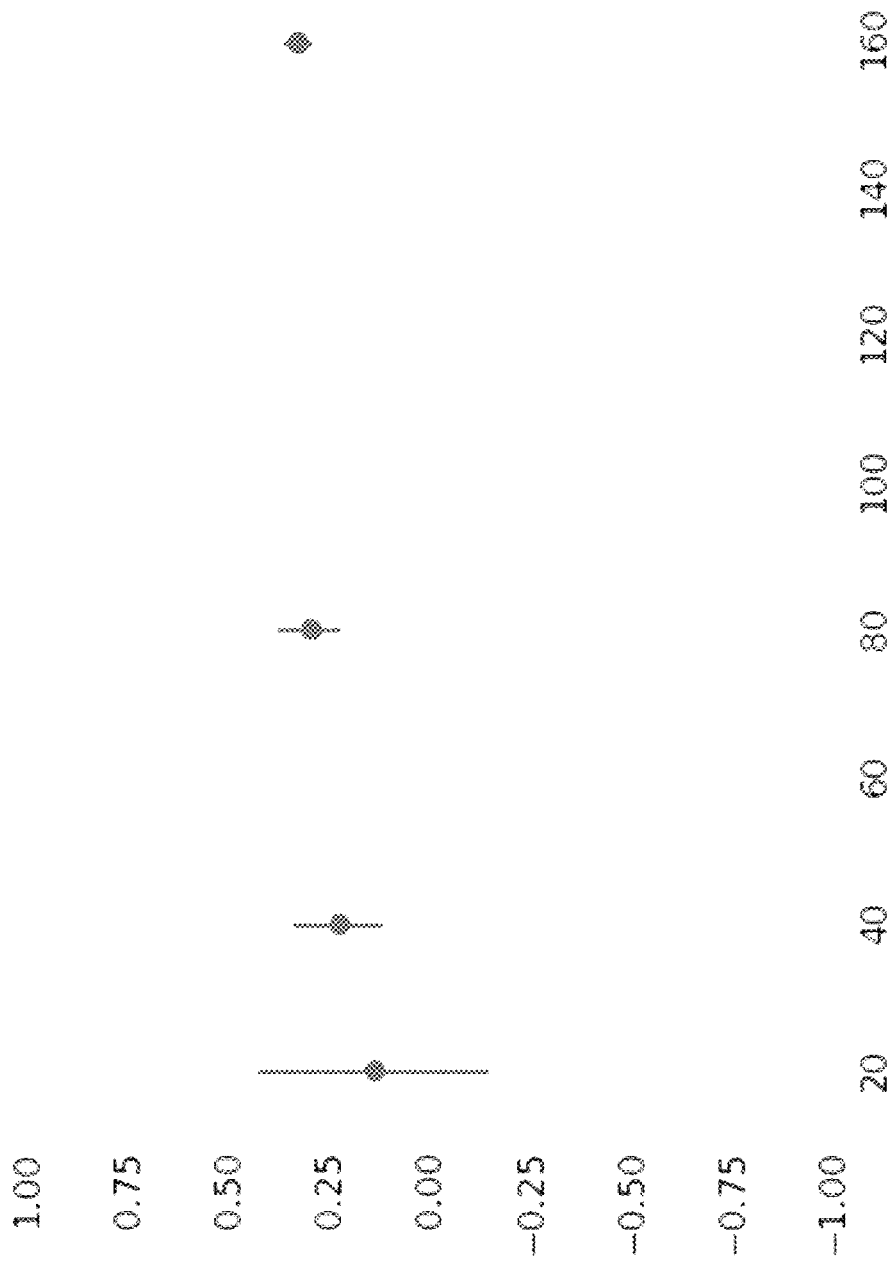
FIG. 79 shows the edge Ensemble Ligand Only (10 poses) results.
Figure 80:
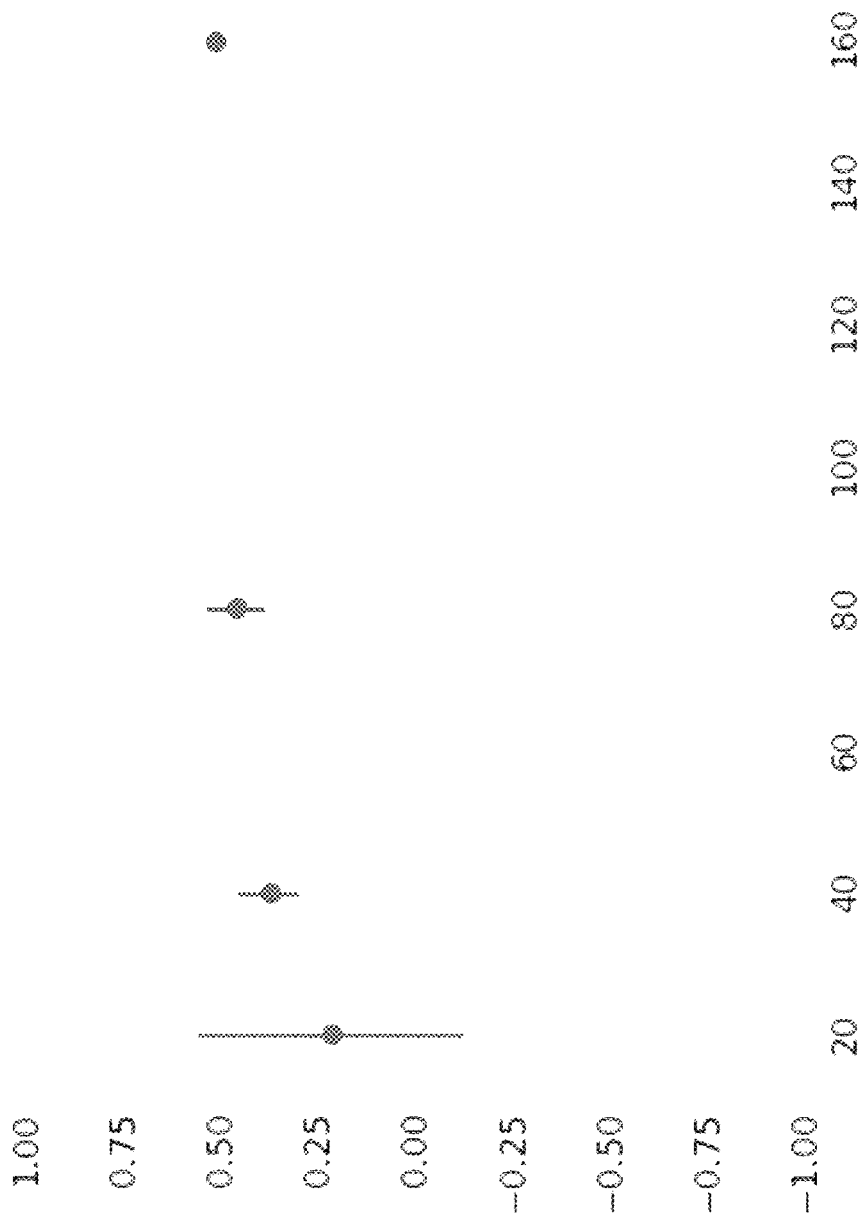
FIG. 80 shows the edge Ensemble Ligand Only (2 poses) results.
Figure 81:
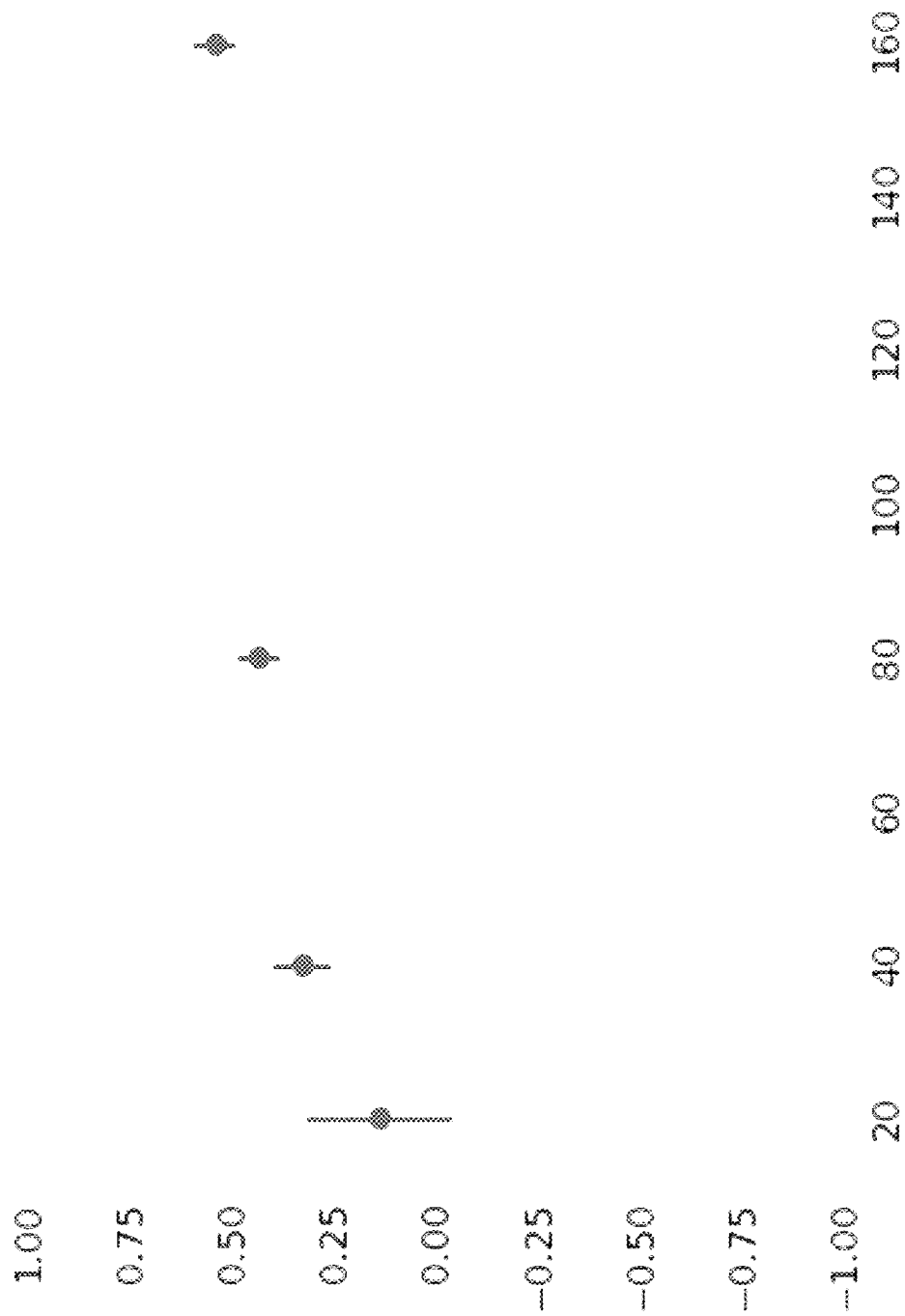
FIG. 81 shows the edge Ensemble Pocket (2 poses) results.

FIG. 73 shows another table of results for the experiment based on the client split. FIG. 74 shows the Edge ligand based results. FIG. 75 shows the Edge ligand only results. FIG. 76 shows the pair message complex results. FIG. 77 shows the pocket attention pair message results. FIG. 78 shows the pocket gating pair message results. FIG. 79 shows the edge Ensemble Ligand Only (10 poses) results. FIG. 80 shows the edge Ensemble Ligand Only (2 poses) results. FIG. 81 shows the edge Ensemble Pocket (2 poses) results.

FIG. 82 shows a table of results for the edge ligand only and edge ensemble ligand only experiments.

Experiment 2: Predictor for Log P

Results of the ensemble method, and other graph convolutional network models are now presented.

Conformations were generated:

1) with MD in implicit water and in implicit octanol;
2) with DFTB in vacuum.

Setup

Data set: the experiment was performed on the ChEMBL data set with 2782 compounds. Our validation and test sets contained 695 and 696 compounds, respectively, and left 1391 compounds for the training set. We selected the split randomly, after a manufactured split using fingerprint methods turned out to be counter productive and creating pathological problems where the training set was under-complex and led to much worse results. The most representative split turns out to be a random split.

Results

Baselines

Without hydrogens

PMGC: 0.79±0.01

Best hyperparameters:

Graph-cony channels: two layers with 512 channels

Message-passing within graph-cony: one fully connected layer with 256 channels

Linear channels: 512

PMGC (scaffold split): 0.776±0.008

Same hyperparameters as random split.

EGC: 0.78±0.01

Best hyperparameters:
- Graph-cony channels: three layers with 128 channels
- Message-passing: two fully connected layers with 64 and 128 channels
- Linear channels: 256

These baselines are already quite strong, and lead to RMSE of 0.66±0.01, which is very good compared to benchmarks.

With Hydrogens

In principle it can matter a lot whether hydrogens are included in the molecular graph or not. In order to examine that effect, we run the baselines also with hydrogens included in the graph.

PMGC:
Best hyperparameters: 0.79±0.01
- Graph-cony channels: two layers with 512 channels
- Message-passing within graph-cony: one fully connected layer with 64 channels
- Linear channels: 512

PMGC (scaffold split): 0.777±0.010
Same hyperparameters as random split.

The results are essentially identical to the results without hydrogens. Excluding the possibility that the effect could come from there.

Quantum Features

Models with DFTB quantum features by default include hydrogen atoms. Since both network architectures seem very comparable, we used the PMGC architecture in the following, as it has much less memory requirements:

Partial charges: 0.78±0.01
Best hyperparameters:
- Graph-cony channels: two layers with 512 channels
- Message-passing: one fully connected layer with 512 channels
- Linear channels: 512

Partial charges (scaffold split): 0.785±0.004
Same hyperparameters as random split.

Partial charges and vibrational atom features: 0.75±0.01
Best hyperparameters:
- Graph-cony channels: two layers with 256 channels
- Message-passing: a fully connected layer with 512 channels
- Linear channels: 256

Partial charges and vibrational atom features (scaffold split): 0.717±0.004
Same hyperparameters as random split.

Partial charges and vibrational edge features: 0.71±0.01
Best hyperparameters:
- Graph-cony channels: two layers with 512 channels
- Message-passing: two fully connected layers with 256 channels
- Linear channels: 512
- The distances were binned in 15 bins between 1 and 3 Angstrom, with a cutoff if the probability to be in that interval was less than 20% (for other configurations the results were even worse). With a shorter distance binning (up to 2 Angstrom) the performance dropped to 0.66, with longer distance binning (4 Angstrom) it dropped to 0.68

Partial charges and vibrational edge features (scaffold split): 0.729±0.014
Same hyperparameters as random split.

Ensemble Models

DFTB Single Ensemble Computation

PMGC: 0.783±0.007
Best hyperparameters:
- Graph-cony channels: two layers with 512 channels
- Message-passing within graph-cony: two fully connected layer with 256 channels
- Linear channels: 512

Classical MD double ensemble computation

The double-ensemble results on the octanol and water ensembles obtained from classical MD were a bit disappointing (essentially r2 of zero). Because of the additional complexity of multi-ensemble models running on multiple GPUs, we need to determine whether it is the data or an error in the model that is causing the bad performance. Since debugging and playing around with multi-ensemble models is painful in the cloud, we decided to first run the single-ensemble model model on both the octanol and water ensembles separately to see if the MD ensemble data might be the problem rather than the double-ensemble model.

Even without doing hyperparameter tuning, the single-ensemble runs on octanol and water data seemed fine. So the problem is likely with the more tricky tuning and hyperparameter optimization when using the double ensemble model.

RDKit Baselines for log P Datasets

As one of the baselines of our models, we calculated log P using the RDKit descriptor, which is an atom-based calculation of log P based on Wildman and Crippen *JCICS* 39:868-73 (1999). There are of course no standard deviations since the model is completely deterministic.

ChEMBL dataset:
- R2: 0.31677566
- MAE: 0.89926976
- RMSE: 1.1888

Avdeef dataset:
- R2: 0.1855524
- MAE: 0.89935718
- RMSE: 1.2995

Martel dataset:
- R2: −0.11930724
- MAE: 0.96409687
- RMSE: 1.2467

Training on scaffold split ChEMBL, evaluating RMSE on Avdeef and Martel:
{'logp_martel': {'PMGC_partial_vibr_edge_hs': 1.510725253798721, 'PMGC_baseline_hs': 1.5147464526182606, 'PMGC_baseline': 1.51557423614749, 'PMGC_partial_vibr_atom_hs': 1.496509719271568, 'PMGC_partial_hs': 1.4794899314132963}, 'logp_avdeef': {'PMGC_partial_vibr_edge_hs': 1.3315027614855663, 'PMGC_baseline_hs': 1.4605225162357198, 'PMGC_baseline': 1.3823966656466953, 'PMGC_partial_vibr_atom_hs': 1.4098072158965416, 'PMGC_partial_hs': 1.4372788549404134}}

Training on full ChEMBL, evaluating RMSE on Avdeef and Martel:
{'logp_avdeef': {'PMGC_baseline': 1.4478502418412211, 'PMGC_partial_hs': 1.4683983402100456, 'PMGC_baseline_hs': 1.4835298240191441, 'PMGC_partial_vibr_edge_hs': 1.3771074184248657, 'PMGC_partial_vibr_atom_hs': 1.47909453131065981, 'logp_martel': {'PMGC_baseline': 1.488645141649805, 'PMGC_partial_hs': 1.4289085142056153, 'PMGC_baseline_hs': 1.4820116603845626,
'PMGC_partial_vibr_edge_hs': 1.501741685605835,
'PMGC_partial_vibr_atom_hs':
    1.4667418041634208}}

Unsupervised Training

Figure 83:
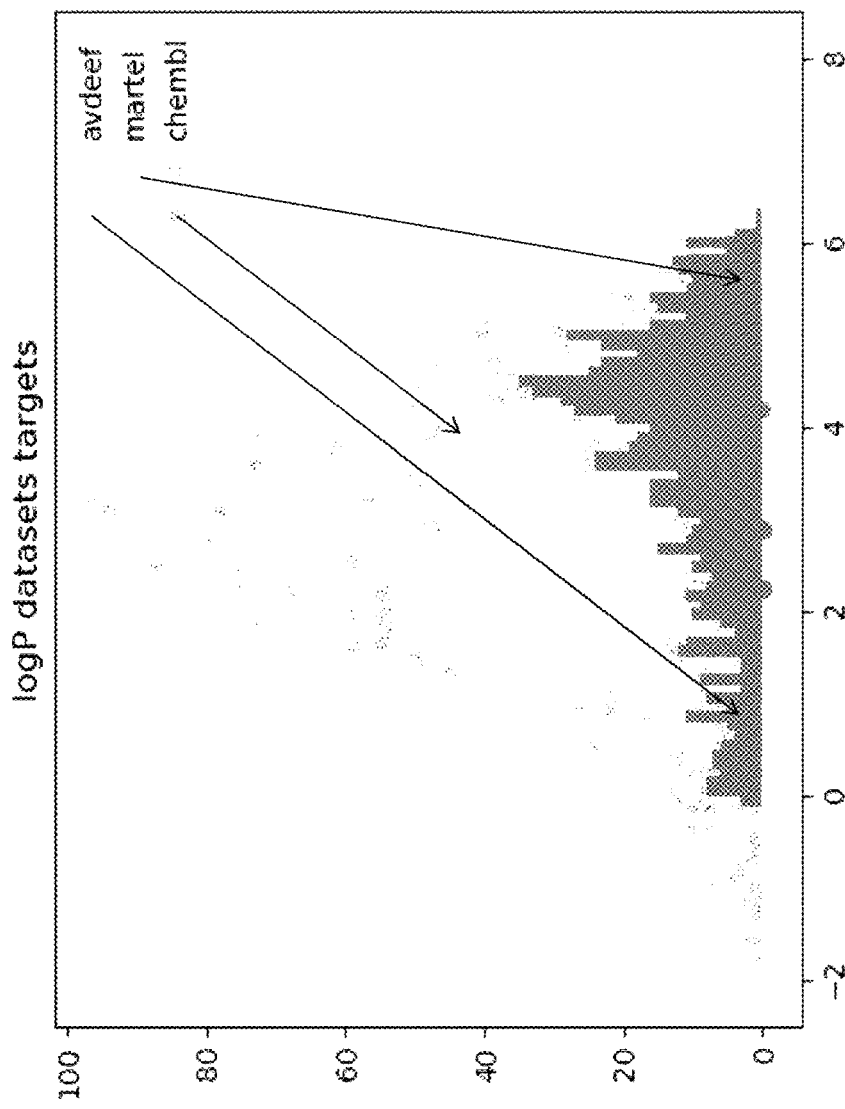
FIG. 83 shows a diagram with the log P datasets targets

FIG. 83 shows a diagram with the log P datasets targets. The combined log P dataset (A+B+C) we consider is comprised of A, which is our log P dataset (2780 compounds), B is Avdeef (290 compounds), and C is Martel (700 compounds). Features learned through unsupervised learning on the full dataset (A+B+C) do not seem to help significantly with the downstream out-of-distribution prediction task on B and C when training on A alone compared to random initialization. This might be explained by a) very different data and target distributions for the datasets b) graph convolutional networks not being expressive enough to come up with suitable representations c) the unsupervised learner needing more "in between" data to come up with robust representations.

When adding a small subset of REAL (10000 compounds) and the log D dataset (4200 compounds) to the unsupervised training set, RD Kit baseline script is shown in FIG. 84.
Filter other_dataset_results.json script is shown in FIG. 85.

Experiment 3: On Kinetic Solubility

Setup
Data Set

The experiment was performed on the PubChem data set with 55 k compounds. Our validation and test sets contained 5 k compounds each, and left 45 k compounds for the training set. We selected the split randomly.

Results
Baselines
  PMGC:

| On random splits: R2 = 0.540 ± 0.006, | RMSE = 13 |
| On scaffold splits: R2 = 0.526 ± 0.003, | |

Used hyperparameters:
  Graph-cony channels: three layers with 512 channels
  Message-passing within graph-cony: two fully connected layer with 256 channels
  Linear channels: 512
  Batch size: 64×4 workers=256
PMGC with log transformer:

| On random splits: R2 = 0.646 ± 0.002, | RMSE = 0.73 log units |
| On scaffold splits: R2 = 0.601 ± 0.006, | RMSE = 0.76 log units |

Used hyperparameters:
  Graph-cony channels: three layers with 512 channels
  Message-passing within graph-cony: two fully connected layer with 256 channels
  Linear channels: 512
  Batch size: 64×4 workers=256
PMGC with normalization transformer:

| On random splits: R2 = 0.605 ± 0.003, | RMSE = 12 |
| On scaffold splits: R2 = 0.559 ± 0.005, | RMSE = 12.5 |

Used hyperparameters:
  Graph-cony channels: three layers with 512 channels
  Message-passing within graph-cony: two fully connected layer with 256 channels
  Linear channels: 512
  Batch size: 64×4 workers=256
Quantum Features
  Partial charges:

| On random splits: R2 = 0.532 ± 0.005, | RMSE = 13 |
| On scaffold splits: R2 = 0.540 ± 0.004 | |

Best hyperparameters:
  Graph-cony channels: three layers with 512 channels
  Message-passing within graph-cony: two fully connected layer with 256 channels
  Linear channels: 512
  Batch size: 64×4 workers=256
Partial charges with log transformer:

| On random splits: R2 = 0.644 ± 0.002, | RMSE = 0.73 log units |
| On scaffold splits: R2 = 0.604 ± 0.007 | |

Best hyperparameters:
  Graph-cony channels: three layers with 512 channels
  Message-passing within graph-cony: two fully connected layer with 256 channels
  Linear channels: 512
  Batch size: 64×4 workers=256
Partial charges with normalization transformer:

| On random splits: R2 = 0.600 ± 0.007, | RMSE = 12 |
| On scaffold splits: R2 = 0.559 ± 0.004 | RMSE = 12.5 |

Best hyperparameters:
  Graph-cony channels: three layers with 512 channels
  Message-passing within graph-cony: two fully connected layer with 256 channels
  Linear channels: 512
  Batch size: 64×4 workers=256

Appendix F: Ligand-Based Models—Pharma Applications of Quantum and Conformational Features In pharma, this is the case for a large number of properties relevant to lead optimisation of high-quality, efficacious and safe clinical candidates. With reference to FIG. 86, for example properties relating to drug absorption (melting point [1], solubility [2], acidity (pKa)[3], lipophilicity[4], permeability[5]), distribution (non-specific binding to plasma proteins and tissue[6]), metabolism (oxidative metabolism[7]), excretion (drug transporter activity[8]) and toxicity (Ames mutagenicity[9], formation of reactive metabolites[10]) (ADMET) [11].

Pharma Problems—List of Datasets.

Mutagenicity/Carcinogenicity—complex process involving metabolism of drugs and irreversible binding to DNA causing mutations likely to lead to cancer. Measured in pharma industry using the Ames test—an in vitro assay which uses metabolism of drugs (using human or rat liver microsomes) in the presence of a bacterial strain which can only grow in the presence of histidine. In a histidine free environment they do not grow, so if the drug or metabolite causes mutation of the bacteria so that it can grow in the media, it is a mutagen and potential carcinogen.

Hansen data set has 6512 AMes results PAPER
Old paper from 1988 showing some correlation between MNDO-calculated molecular orbital features to predict mutagenicity/AMES.

Lipophilicity

Lipophilicty is a compound's affinity for fats and oils. More formally, we use log d (pH7.4) which is captured experimentally using the octan-1/water distribution coecient measured by the shake flask method. This is an important measure for scientists to have, because drugs that are not lipophilic enough frequently have poor permeability Khojasteh [2011]. Alternatively, highly lipophilic compounds are usually encumbered by low solubility, high clearance, high plasma protein binding, etc. Indeed, most drug discovery projects have a sweet spot for lipophilicity Khojasteh [2011]. This dataset is the largest of the three at 4200 compounds.

Solubility

Solubility is particularly important for drug discovery as drugs must be soluble in water in the blood but have a degree of lipophilicity which allows them to be permeable through membranes (cell, gut, CNS) and to bind to lipophilic pockets in proteins. Much of drug discovery involves a balance between optimising specific lipophilicity and solubility. Recent review on calculation of solvation free energies using a range of models—importance of water in drug discovery (Skyner, R. E., J. L. McDonagh, C. R. Groom, T. Van Mourik, and J. B. O. Mitchell. "A review of methods for the calculation of solution free energies and the modelling of systems in solution." *Physical Chemistry Chemical Physics* 17, no. 9 (2015): 6174-6191.)

Thermodynamic solubility (ie at equilibrium) is measured by shake-flask and is useful for understanding the dissolution of drug from the crystal state. Crystal packing of the molecule (and its associated salt) (indicated by melting point) and the lipophilicity of the molecule, as governed by the Yalkowsky equation, are relatively predictive here. However errors in measured values (0.6-0.7 log S units) are common making models less predictive.

Kinetic solubility looks at a more realistic situation in drug-discovery which is the non-equlibrium partitioning out of aqueous solution into a lipophilic environment e.g. for permeability. It does not take into account the salts present. This is measured in industry in particular using precipitation from a solution of drug in DMSO using water. A data set of 711 compounds (Kramer, Christian, Tilmann Heinisch, Thilo Fligge, Bernd Beck, and Timothy Clark. "A consistent dataset of kinetic solubilities for early-phase drug discovery." *ChemMedChem: Chemistry Enabling Drug Discovery* 4, no. 9 (2009): 1529-1536) is useful for building models.

Permeability

Permeability through biological barriers is a key part of drug discovery for small molecule drugs to pas through e.g. cell membranes to access intracellular targets, gut membrane to access the blood stream from an oral dose, blood-brain-barrier permeability to access the CNS.

Conformation plays an important role as displaying/hiding molecular functionality through intramolecular bonding in particular environments dramatically changes the interactions observed.

Melting Point

Important characteristic for predicting solubility—Yalkowsky defined a heuristic equation for solubility (log Saq.--0.01(MP-25)-log Poct/wat+0.5) which takes into account lipophilicity and melting point to measure aqueous solubility from solid (thermodynamic), and is often very accurate. Solubility is a major factor in ADME properties for drug discovery. Polarizability and dipole moment have been show n to be highly correlated with differences in melting point.

IR Spectra or Other Electronic Related Spectra—Chemical Shift/NMR

Interesting from a property prediction space, useful for molecular characterisation of purity and molecular identity.

Metabolic Stability

Clearance is the rate at which the human body removes circulating, unbound drug from the blood Lombardo [2014]. This is one of the key parameters to assess in drug discovery because low clearance will result in a longer residence time and a lower dose Khojasteh [2011]. In drug discovery, this property is assessed by measuring the metabolic stability of drugs in either human liver microsomes or hepatocytes Aliagas [2015]. This dataset includes 1102 examples of intrinsic clearance measured in human liver microsomes (µL/min/mg protein) following incubation at 37 C.

Plasma Protein Binding/Tissue Binding (e.g. Brain-Tissue, Peripheral Tissue)

Human Plasma Protein Binding assays measures the proportion of drug that is bound reversibly to proteins such as albumin and alpha-acid glycoprotein in the blood. Knowing the amount that is unbound/free is critical because it is that amount that can diffuse or actively taken up into tissues to exert its pharmacological activity or the liver to be cleared. Khojasteh [2011]. PPB is measured as bound to plasma by equilibrium dialysis after being incubated with whole human plasma at 37 C for >5 hrs. This measure is transformed using log(1-bound), so we can capture a measure more informative to scientists. The dataset contains measurements for 1614 compounds.

[1] Tetko, I. V., Sushko, Y., Novotarskyi, S., Patiny, L., Kondratov, I., Petrenko, A. E., Charochkina, L. and Asiri, A. M., 2014. How accurately can we predict the melting points of drug-like compounds?. *Journal of chemical information and modeling*, 54(12), pp. 3320-3329.

[2] Bergström, C. A., & Larsson, P. (2018). Computational prediction of drug solubility in water-based systems: Qualitative and quantitative approaches used in the current drug discovery and development setting. *International journal of pharmaceutics*, 540(1-2), 185-193.

[3] Jensen, J. H., Swain, C. J., & Olsen, L. (2017). Prediction of pKa Values for Druglike Molecules Using Semiempirical Quantum Chemical Methods. *The Journal of Physical Chemistry A*, 121(3), 699-707.

[4] Kujawski, J., Popielarska, H., Myka, A., Drabińska, B., & Bernard, M. K. (2012). The log P parameter as a molecular descriptor in the computer-aided drug design—an overview. Computational Methods in Science and Technology, 18(2), 81-88.

[5] Bennion, B. J., Be, N. A., McNerney, M. W., Lao, V., Carlson, E. M., Valdez, C. A., . . . & Carpenter, T. S. (2017). Predicting a drug's membrane permeability: a computational model validated with in vitro permeability assay data. *The Journal of Physical Chemistry B*, 121(20), 5228-5237.

[6] Rimac, H., Debeljak, ., Sakić, D., Weitner, T., Gabričevič, M., Vrček, V., ... & Bojič, M. (2016). Structural and electronic determinants of flavonoid binding to human serum albumin: an extensive ligand-based study. *RSC Advances,* 6(79), 75014-75022.

[7] Lonsdale, R., Fort, R. M., Rydberg, P., Harvey, J. N., & Mulholland, A. J. (2016). Quantum mechanics/molecular mechanics modeling of drug metabolism: Mexiletine N-hydroxylation by cytochrome P450 1A2. *Chemical research in toxicology,* 29(6), 963-971.

[8] Agrawal, M., Kumar, A., & Gupta, A. (2017). Conformational stability, spectroscopic signatures and biological interactions of proton pump inhibitor drug lansoprazole based on structural motifs. *RSC Advances,* 7(66), 41573-41584.

[9] McCarren, P., Springer, C., & Whitehead, L. (2011). An investigation into pharmaceutically relevant mutagenicity data and the influence on Ames predictive potential. *Journal of Cheminformatics,* 3, 51. http://doi.org/10.1186/1758-2946-3-51

[10] Hughes, T. B., Dang, N. L., Miller, G. P., & Swamidass, S. J. (2016). Modeling reactivity to biological macromolecules with a deep multitask network. *ACS central science,* 2(8), 529-537.

[11] F Silva-Júnior, E., M Aquino, T., & X Araujo-Junior, J. (2017). Quantum Mechanical (QM) Calculations Applied to ADMET Drug Prediction: A Review. *Current drug metabolism,* 18(6), 511-526.

Appendix G: QTAIM Code

Quantum Features: Electron Density Descriptors for Graphs
Overview
  Geometry (.xyz, .sdf, .mol2, ... )→Psi4/ORCA (quantum chemistry) Multiwfn (wavefunction analysis)→Features extracted from Multiwfn log files
Requisites
  To run the whole pipeline, you will need:
  Conda environment packages (conda install ... ): rdkit scipy
  System packages (sudo apt-get install ... ): parallel be
  Use tmux instead of screen for session preservation:
  https://askubuntu.com/questions/8653/how-to-keep-processes-running-after-ending-ssh-session. Activate conda environment only after entering a tmux session.
Overview
  This repo contains a mix of bash and Python scripts. There's a configuration file config.conf which contains paths and options you can define. The general workflow is as follows:
psi4_prep.sh→psi4_run.sh→multiwfn_run.sh→a shell script calling lidi_logfile.py for all log files
Step 1: Pre-Processing
  The bash script psi4_prep.sh calls data2psi4.py to load in the dataset and prepare the job files for Psi4 from a template file.
Step 2: Quantum Calculations
  After preparing the input files, psi4_run.sh launches the jobs in parallel by piping all of the Psi4 input files to GNU parallel. This is a pretty computationally expensive part. The number of jobs and cores can be set in config.conf.
Step 3: Wavefunction Analysis
  After the calculations, the bash script multiwfn_run.sh calls the wrapper multiwfn_wrapper.sh for every .fchk output file by piping all output files to GNU parallel. You should not edit the settings.ini file of Multiwfn unless you know what you are doing. The wrapper script automatically calls Multiwfn and executes the commands in multiwfn/templates/lidi.com to calculate, in this case, the localization indices and the delocalization indices from the electron density. This can be quite expensive since it involves a lot of numerical integrals (summing up contributions of small voxels), the cost of which depends on the MULTIWFN_GRID_SPACING set in config.conf. Some Multiwfn guidelines for grid space choice:
  Low quality grid, spacing=0.20 Bohr, cost: 1× [horrible]
  Medium quality grid, spacing=0.10 Bohr, cost: 8× [still a bit horrible]
  High quality grid, spacing=0.06 Bohr, cost: 36× [about right]
  Lunatic quality grid, spacing=0.04 Bohr, cost: 120× [too expensive]
  A measure for the accuracy of the overlap integrals required for the lidi descriptors is given in the log file after Error of BOM is which should be smaller than 0.001 according to the Multiwfn manual. A sanity check is implemented in the wrapper shell script multiwfn_wrapper.sh which checks this measure. check is implemented in the wrapper shell script multiwfn_wrapper.sh which checks this measure. You should lower the grid spacing if you get these warnings. I also check whether the number of attractors (from the QTAIM electron density analysis) equals the number of atoms (from the molecule's description) after the completion of every job and flag the log file if this is not the case. You should run Multiwfn manually on those files and restart the grid search from different points to find all attractors or deal with superfluous ones.
Step 4: Post-Processing
  The Multiwfn log files then have to be parsed to extract the descriptors (which are printed as human-readable text in the log file). This step is done by the lidi_logfile.py script, which extracts and converts the localization indices (vector) and delocalization indices (symmetric matrix) to numpy arrays from the log file. It also extracts the coordinates of the attractors. There is one additional caveat: Multiwfn picks an internal ordering for the attractors and associated basins which it finds numerically. This ordering generally does not correspond to the ordering of the atoms in your representation of the molecule in rdkit. So you might have to do additional permutations on the feature vectors and matrices. For this reason, a function lidi_attractors.py is included which compares the coordinates of the attractors and the atoms, matches them, and spits out the required permutation.
  The final output for every selected molecule of these descriptors calculated from integrals of functions of the electron density is
  a number for every node (localization index of the atom/attractor)
  a number for every bond (delocalization indices between atoms/attractors)
  With reference to FIG. 31, we thus get a fully-connected graph, where the signs of the dominant elements of the symmetric delocalization matrix correspond to the adjacency matrix of the associated 2D molecular graph. The edge weights are based on the DI and the nodes' sizes scale with the magnitude of the corresponding LI. Values of DI have been binned into 5 bins [>1>0.1>0.01>0.001>] from fat/black to thin/gray.
  As shown in FIG. 30, the values of the delocalization indices resemble the adjacency matrix but are all very different from unity. The "boxes" appearing in the plot on the lefthand side are due to the particular ordering of the ligand in the original geometry of the molecule, reflecting stronger correlations among neighbouring atoms or the atoms of functional groups (boxes before index 27 are the carbon/nitrogen rings in the molecule, starting at index 27-52 are all hydrogens attached to the rings).

These features represent a generalization which is a natural step beyond familiar bond features, with the values for the bonds beyond the molecular graph structure encoding a crude representation of the 'delocalization' of electrons.

Installation/Compilation

Installation of Multiwfn (Ubuntu 16.04 LTS)

Multiwfn is a free, open-source program for electronic wavefunction analysis, supporting almost all of the most important wavefunction analysis methods.

There's only one prerequisite on Ubuntu: install the libmotif library.

$sudo apt-get install libmotif-dev

Then download the binary from the Multiwfn website. Read relevant parts of the manual for set-up and configuration details. Do not use the "stable" 3.5 version since it tends to suffer from segmentation faults on Ubuntu when importing .fchk files with large basis sets or exporting large .cub files.

If you are getting ./Multiwfn: error while loading shared libraries: libGL.so.1: cannot open shared object file: No such file or directory on the cloud then sudo apt install libgl1-mesa-glx even though we are not going to use the GUI or visualization options.

Installation of Psi4 (+Add-on CheMPS2) (Ubuntu 16.04 LTS)

Psi4 is an open-source suite of ab initio quantum chemistry programs designed for efficient, high-accuracy simulations of a variety of molecular properties. It is easy to use and has an optional Python interface.

CheMPS2 is an open-source spin-adapted implementation of DMRG for ab initio quantum chemistry.

Make sure you have done sudo apt-get install build-essential if need be. Usually, most systems have cmake and a C/C++ compiler already installed. Then create a new conda environment with the required packages.

$ conda create--name qc-gtn cmake gxx_linux-64 gcc_linux-64 mkl-devel python numpy pytest zlib hdf5=1.10.1

The packages cmake gxx_linux-64 gcc_linux-64 are included because Psi4 requires a more recent compiler than the one provided by Ubuntu 16.04 LTS.

The last two packages (zlib hdf5=1.10.1) are for CheMPS2 and can be removed if only Psi4 is to be compiled. Additionally, you will need deepdiff at runtime, install with $ conda install deepdiff-c conda-forge Activate environment and clone the Psi4 and CheMPS2 source codes into ~ (in my case /home/mcbal).

```
$ source activate qc-gtn
$ git clone https://github.com/psi4/psi4.git
$ git clone https://github.com/SebWouters/CheMPS2.git
```

If we want to be able to modify both source codes, we want Psi4 to use our local clone of CheMPS2 and not download its own upstream copy automatically. To keep this from happening, modify the CMakeLists.txt governing the CheMPS2 add-on in psi4/external/upstream/chemps2 by commenting out GIT_REPOSITORY and GIT_TAG and adding DOWNLOAD_COMMAND and SOURCE_DIR keywords:

```
# GIT_REPOSITORY https://github.com/SebWouters/CheMPS2
# GIT_TAG v1.8.7
DOWNLOAD_COMMAND ""
SOURCE_DIR "/home/mcbal/CheMPS2"
```

Now navigate to the root directory of Psi4, create a build folder, and run cmake with these precise, magical options (you can change the installation directory CMAKE_INSTALL_PREFIX; the Python executable keyword assumes you are in a conda environment so it finds the right version).

```
$ cd psi4 && mkdir build
$ cmake -DENABLE_CheMPS2=ON                                -
DCMAKE_DISABLE_FIND_PACKAGE_CheMPS2=ON                     -
DBUILD_SHARED_LIBS=ON -DCMAKE_AR=/usr/bin/gcc-ar           -
DCMAKE_RANLIB=/usr/bin/gcc-ranlib -DPYTHON_EXECUTABLE=
'which python' -DCMAKE_INSTALL_PREFIX=/usr/local/psi4 -H.  -
B/home/mcbal/psi4/build
If only Psi4 is to be compiled, you can use
$ cmake -DPYTHON_EXECUTABLE= 'whichpython'
DCMAKE_INSTALL_PREFIX=/usr/local/psi4 -H.
-B/home/mcbal/psi4/build
```

Basically, run sudo apt-get install libstdc++6.

Now navigate to the build directory and make in parallel using N cores. Be careful with providing too many cores since the compilation sometimes stumbles when it tries to go too fast by building interdependent libraries all over the place.

$ cd build && make –j N

After a successful complication, run a small subset of tests.

$ make pytest or run ctest –j N for the complete test suite (this takes a very long time). If tests pass (no fails, skipped is OK since this just means that you did not enable these modules), install code with $ sudo make install which will copy some files to the CMAKE_INSTALL_PREFIX directory (here /usr/local/psi4 so sudo is required). A log of the installed files is kept in the file install_manifest.txt in the build directory. Uninstalling can be done with $ xargs rm<install_manifest.txt Finally, add the paths and set a local scratch directory (no network drive!) to use the executable file. When you do not set the scratch directory, Psi4 will use /tmp by default. Make sure there is enough hard disk space.

```
# sh, bash: add to shell or ~/.bashrc (Linux/Windows) or
~/.bash_profile (Mac) file
export PATH=/ usr/local/psi4/bin:$PATH
export PSL_SCRATCH=/path/ to/existing/writable/local-not-
network/directory/for/scratch/files
```

To use the Python wrapper, add relevant directories to path

```
$ export
PATH=/ path/to/dir/of/python/interpreter/against/which/psi4/compiled:
$PATH
$ export PYTHONPATH=/path/ to/dir/of/psi4/core-dot-so:$PYTHONPATH
```

The first path should point to the Python binary of your Conda environment which you used to compile Psi4. The second path should point to wherever the core.so file is located. Test the Python wrapper with
$ python-c "import psi4"
When modifying Psi4 code, you can just recompile. When modifying CheMPS2 code, remove the folders
$ rm-rf/home/mcbal/psi4/build/external/upstream/chemps2
$ rm-rf/home/mcbal/psi4/build/stage/usr/local/psi4/share/cmake/CheMPS2
to force a rebuild of CheMPS2 and its driver connection to the Psi4 core. If you change CheMPS2's file or directory structure, do not forget to also rm all traces of the previous structure in/home/mcbal/psi4/build/stage/usr/local/psi4/.
Running the CheMPS2 binary on its own, you might get an MKL-related linking error which can be fixed with
$ export LD_LIBRARY_PATH=/path/to/mkl/:$LD_LIBRARY_PATH

Appendix H: Quantum Mechanics and Entanglement

Accurate representations of quantum systems are in general exponentially costly in the number of basic constituents (e.g. the number atoms or electrons in a molecule). While problems in equilibrium can often—but not always—be analysed and simulated to high accuracy using efficient methods such as DFT or coupled cluster methods, non-equilibrium processes involved in chemical reactions or binding processes are often beyond the reach of classical computers.

A quantity called the entanglement is a useful measure of this complexity. (The term entanglement is more common in physics than in chemistry literature. In chemistry a highly entangled state is often characterised using a closely related concept of the state having multi-configurational character.) It is a generic feature of many particle systems that quantifies a type of collective behavior of its constituents entirely due to quantum mechanical effects, which is notoriously difficult to capture efficiently using classical computers. In the context of pharmaceutical and chemistry applications, molecular states in equilibrium can be said to have low entanglement in general, but transition states in chemical reactions or binding process are often highly entangled. Exploring the role of entanglement in quantum chemistry constitutes a major line of research [1-8].

The understanding of entanglement is crucial for addressing quantum problems effectively, and is behind technological ideas we are developing at GTN aimed to construct optimal representations for molecular data and use these in machine learning algorithms.

[1] J. Hachmann, J. J. Dorando, M. Aviles, and G. K.-L. Chan, The Journal of Chemical Physics 127, 134309 (2007).
[2] K. H. Marti, B. Bauer, M. Reiher, M. Troyer, and F. Verstraete, New Journal of Physics 12, 103008 (2010).
[3] G. K.-L. Chan and S. Sharma, Annual Review of Physical Chemistry 62, 465 (2011), pMID: 21219144.
[4] R. Orús, Annals of Physics 349, 117 (2014), arXiv: 1306.2164 [cond-mat.str-el].
[5] I. Kassal, J. D. Whitfield, A. Perdomo-Ortiz, M.-H. Yung, and A. Aspuru-Guzik, Annual Review of Physical Chemistry 62, 185 (2011), pMID: 21166541.
[6] P. J. D. Crowley, T. Duric, W. Vinci, P. A. Warburton, and A. G. Green, Phys. Rev. A 90, 042317 (2014), arXiv: 1405.5185 [quant-ph].
[7] S. Sharma and A. Alavi, J. Chem. Phys. 143, 102815 (2015), arXiv:1509.00216 [physics.chem-ph].
[8] Y. S. et al, Molecular Physics 113, 184 (2015).

Appendix I: Key Features

We will now formally re-state the high-level concepts underlying the GTN system that have been discussed in this specification, as well as a large number of implementation features. Note that any high-level concept may be combined with any other high level concept and any one or more features.

Concept A: Quantum Graph Candidate Molecular Models are Input to the ML Engine

A machine learning based method of analysing drug-like molecules by representing the molecular quantum states of each drug-like molecules as a quantum graph, and then feeding that quantum graph as an input to a machine learning system.

Optional Features:
- a quantum graph or Q-graph is a molecular graph representation of a drug-like molecule obtained from quantum mechanical calculations.
- a quantum graph is a molecular graph representation in which each node corresponds to an orbital and the edges correspond to a type of quantum correlation between these orbitals.
- a quantum graph depends on the conformational state of a drug-like molecule.
- quantum graphs for multiple conformational states or thermodynamic ensemble for each drug-like molecule are fed as an input to the machine learning system.
- for every conformational state of a drug-like molecule, a different Q-graph is created.
- for every conformational state in a thermodynamic ensemble of a drug-like molecule, a different Q-graph is created.
- Different quantum graphs can be combined, such as concatenated, or averaged over, in order to obtain a more expressive object that is fed into the machine learning system.
- a quantum graph represents conformations of ligands and protein pockets, and the machine learning system determines a specific property such as binding affinity binding affinity, lipophilicity, thermodynamic solubility, kinetic solubility, melting point or pKA, in order to identify candidate, small drug like molecules.
- in which the identified candidate, small drug like molecules are input to a machine learning platform that optimizes the selection of candidates across multiple parameters.
- the machine learning system is supervised, semi-supervised or unsupervised.
- the machine learning system is specifically a supervised system where the input consists of a set of Q-graph objects obtained from an ensemble of conformations of ligand in solution, ensemble of ligand in the protein pocket, where both pocket and ligand are represented as a large graph.

the large graph includes water molecules and/or other residues.

the machine learning system is one or more of the following: generative model, generative adversial network, GAN on graph data, autoencoder, RNN, GCPN, monte carlo tree search model, ising model, restricted Boltzmann machine trained in an unserpervised manner, graph model, graph to graph autoencoder.

a training dataset made up of multiple quantum graphs is used.

A system configured to perform any of the methods above.

A molecule or class of drug-like molecules identified using any of the methods above.

Concept B: Modeling a Thermodynamic Ensemble Using Synthetically Generated Graph Training Molecular Models.

A machine learning based method of modelling a thermodynamic ensemble or representation of a drug-like molecule, in which a sample of a thermodynamic ensemble or representation is synthetically generated and inputted into a machine learning system, the thermodynamic ensemble or representation being a molecular orbital representation or quantum graph representation of the drug-like molecule.

Optional Features:
every element of the thermodynamic ensemble can be represented as a quantum graph or tensor network, or molecular orbital representation.

a quantum graph is a molecular graph representation of a molecule obtained from quantum mechanical calculations.

a quantum graph is a molecular graph representation in which each node corresponds to a molecular orbital and the edges correspond to a type of quantum correlation between these orbitals.

a quantum graph depends on the conformational state of a molecule.

Molecular orbital representation is a tensor network representation of molecular quantum states of a drug like molecule.

the synthetic generation of one or more samples of thermodynamic ensembles or representations is based on a thermodynamic quantity.

the machine learning system is configured to output a thermodynamic quantity based on an approximate expectation value over the entire or a representative set of the modelled thermodynamic ensemble or representation.

the machine learning system is configured to learn the distribution of Boltzmann weights of the entire or a representative set of the thermodynamic ensemble or representation of the molecule.

determining the cost function or backpropagation of the machine learning system is based on a thermodynamic quantity to be outputted by the system.

the size of the synthetically generated sample of the thermodynamic ensemble or representation is tuned depending on a downstream application.

the machine learning system is a graph convolutional neural network.

the generated sample of thermodynamic ensemble or representation is inputted as a molecular graph such as a quantum graph.

the machine learning system is configured to output any quantity that is a function of a thermodynamic ensemble or representation, such as binding affinity, lipophilicity, thermodynamic solubility, kinetic solubility, melting point or protonation.

the machine learning system is used to predict ligand protein binding affinity, and in which synthetically generated samples of the thermodynamic ensemble or representation of the ligand in solution, of the protein in solution, and of the ligand-protein complex are inputted into the machine learning system.

the machine learning system is used to predict ligand protein inhibition concentration, and in which synthetically generated samples of the thermodynamic ensemble or representation of the ligand in solution and of the ligand-protein complex are inputted into the machine learning system.

the machine learning system is used to predict lipophilicity of a drug-like molecule, and in which synthetically generated samples of the thermodynamic ensemble or representation of the unionized and/or ionized state of the molecule in octanol, and in water are inputted into the machine learning system.

the machine learning system is used to predict thermodynamic solubility of the drug-like molecule, and in which synthetically generated samples of the thermodynamic ensemble or representation of the solid state of the molecule and of the dissolved state of the molecule are inputted into the machine learning.

the machine learning system is used to predict kinetic solubility of the drug-like molecule, and in which synthetically generated samples of the thermodynamic ensemble or representation of the amorphous solid state of the molecule and of the dissolved state of the molecule are inputted into the machine learning.

the machine learning system is used to predict melting point of the drug-like molecule, and in which synthetically generated samples of the thermodynamic ensemble or representation of the solid state of the molecule and of the molecule in octanol are inputted into the machine learning.

the machine learning system is used to predict pKa of the drug-like molecule and in which synthetically generated samples of the thermodynamic ensemble or representation of the small drug-like molecule in the appropriate environment, such as water or pocket on a target protein, are inputted into the machine learning.

the machine learning system uses GAN or VAE, or GCPN style models.

the machine learning system uses generative models to learn new thermodynamic ensemble or thermodynamic ensemble for which data is not available.

the machine learning system implements weight sharing method when multiple generated samples of thermodynamic ensembles or representations are inputted into the machine learning system.

docking is used to generate the sample of thermodynamic ensemble or representation.

docking enhanced by molecular dynamics is used to generate the sample of thermodynamic ensemble or representation.

A system configured to perform any of the methods above.

Concept C: The ML Engine Predicts Molecular Properties Using Graph Pooling Layers Trained for Relevance A graph-based machine learning method of predicting chemical properties of a molecule or class of molecules in which input graphs representing molecules are fed into a graph convolutional neural network that implements graph pooling layers that have been trained for usefulness or relevance with regards to the chemical properties.

Optional Features:
- the input graphs are represented with a sparse representation using node and edge feature vectors.
- Edge feature vectors represent different bond types or distances between atoms. input graphs are quantum graphs.
- a quantum graph is a molecular graph representation of a drug-like molecule obtained from quantum mechanical calculations.
- a quantum graph is a molecular graph representation of a molecule in which each node corresponds to a molecular orbital and the edges correspond to a type of quantum correlation between these orbitals.
- a quantum graph depends on the conformational state of a molecule.
- during a graph pooling step, the nodes in the input graphs are selected based on their usefulness or relevance with regards to the chemical property that is predicted.
- the convolutional neural network learns which nodes needs to be selected.
- during a graph pooling step, the nodes in the input graphs are selected by determining a gating for each node feature vector.
- In which effective edge feature vectors between selected nodes are updated or created using a pooling algorithm.
- effective edge feature vectors are updated or created based on atom features.
- the pooling algorithm computes an effective edge feature vector by summing all edge feature vectors along the paths connecting pairs of selected nodes and by reducing any overlapping effective edge feature vectors.
- the pooling algorithm uses multiple neural networks to compute effective edge-feature vectors.
- each convolutional layer apart from the final convolutional layer is followed by a pooling layer.
- a graph gathering layer is used following a pooling layer in order to map node and edge feature vectors into a global feature vector.
- a dual-message graph-convolutional layer that supports both node and edge feature vectors is implemented.
- an input graph representing a molecule encodes any chemical properties of the molecule such as atom type, node degree or bond type.
- the method is used to predict one or more of the following: binding affinity, lipophilicity, thermodynamic solubility, kinetic solubility, melting point or pKA.
- A system configured to perform any of the methods above.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. A machine learning based method of modelling a thermodynamic ensemble or representation of a drug-like molecule, in which a sample of the thermodynamic ensemble or representation is synthetically generated and inputted into a machine learning system, the thermodynamic ensemble or representation being a molecular orbital representation or a quantum graph representation of the drug-like molecule,
  and in which the quantum graph representation is a molecular graph representation in which each node corresponds to a molecular orbital and edges correspond to a type of quantum correlation between molecular orbitals.

2. The machine learning based method of claim 1, in which every element of the thermodynamic ensemble or representation can be represented as a Q-graph or tensor network, or the molecular orbital representation.

3. The machine learning based method of claim 1, in which the quantum graph representation is the molecular graph representation of the drug-like molecule obtained from quantum mechanical calculations.

4. The machine learning based method of claim 1, in which the quantum graph representation depends on a conformational state of the drug-like molecule.

5. The machine learning based method of claim 1, in which the molecular orbital representation is a tensor network representation of molecular quantum states of the drug-like molecule.

6. The machine learning based method of claim 1, in which synthetic generation of one or more samples of thermodynamic ensembles or representations is based on a thermodynamic quantity.

7. The machine learning based method of claim 1, in which the machine learning system is configured to output a thermodynamic quantity based on an approximate expectation value over an entire or a representative set of the thermodynamic ensemble or representation.

8. The machine learning based method of claim 1, in which the machine learning system is configured to learn a distribution of Boltzmann weights of an entire or a representative set of the thermodynamic ensemble or representation of the drug-like molecule.

9. The machine learning based method of claim 1, in which determining a cost function or backpropagation of the machine learning system is based on a thermodynamic quantity to be outputted by the machine learning system.

10. The machine learning based method of claim 1, in which a size of the synthetically generated sample of the thermodynamic ensemble or representation is tuned depending on a downstream application.

11. The machine learning based method of claim 1, in which the machine learning system is a graph convolutional neural network.

12. The machine learning based method of claim 1, in which the synthetically generated sample of the thermodynamic ensemble or representation is inputted as a molecular graph.

13. The machine learning based method of claim 1, in which the machine learning system is configured to output any quantity that is a function of the thermodynamic ensemble or representation.

14. The machine learning based method of claim 1, in which the machine learning system is used to predict ligand protein binding affinity, and in which synthetically generated samples of the thermodynamic ensemble or representation of a ligand in solution, of a protein in the solution, and of a ligand-protein complex are inputted into the machine learning system.

15. The machine learning based method of claim 1, in which the machine learning system is used to predict ligand protein inhibition concentration, and in which synthetically generated samples of the thermodynamic ensemble or representation of a ligand in solution and of a ligand-protein complex are inputted into the machine learning system.

16. The machine learning based method of claim 1, in which the machine learning system is used to predict lipophilicity of the drug-like molecule, and in which synthetically generated samples of the thermodynamic ensemble or representation of a unionized and/or ionized state of the drug-like molecule in octanol, and in water are inputted into the machine learning system.

17. The machine learning based method of claim 1, in which the machine learning system is used to predict thermodynamic solubility of the drug-like molecule, and in which synthetically generated samples of the thermodynamic ensemble or representation of a solid state of the drug-like molecule and of a dissolved state of the drug-like molecule are inputted into the machine learning system.

18. The machine learning based method of claim 1, in which the machine learning system is used to predict kinetic solubility of the drug-like molecule, and in which synthetically generated samples of the thermodynamic ensemble or representation of an amorphous solid state of the drug-like molecule and of a dissolved state of the drug-like molecule are inputted into the machine learning system.

19. The machine learning based method of claim 1, in which the machine learning system is used to predict melting point of the drug-like molecule, and in which synthetically generated samples of the thermodynamic ensemble or representation of a solid state of the drug-like molecule and of the drug-like molecule in octanol are inputted into the machine learning system.

20. The machine learning based method of claim 1, in which the machine learning system is used to predict acidity (pKa) of the drug-like molecule and in which synthetically generated samples of the thermodynamic ensemble or representation of the drug-like molecule in an appropriate environment are inputted into the machine learning system.

21. The machine learning based method of claim 1, in which the machine learning system uses Generative adversarial network (GAN) or Variational auto-encoder (VAE), or Graph-Convolutional Policy Network (GCPN) style models.

22. The machine learning based method of claim 1, in which the machine learning system uses generative models to learn new thermodynamic ensemble or thermodynamic ensemble for which data is not available.

23. The machine learning based method of claim 1, in which the machine learning system implements weight sharing method when multiple generated samples of thermodynamic ensembles or representations are inputted into the machine learning system.

24. The machine learning based method of claim 1, in which docking is used to generate the sample of the thermodynamic ensemble or representation.

25. The machine learning based method of claim 1, in which docking enhanced by molecular dynamics is used to generate the sample of the thermodynamic ensemble or representation.

26. A machine learning based system configured to model a thermodynamic ensemble or representation of a drug-like molecule, in which the machine learning based system is configured to receive and process a synthetically generated sample of the thermodynamic ensemble or representation, the thermodynamic ensemble or representation being a molecular orbital representation or a quantum graph representation of the drug-like molecule; and in which the quantum graph representation is a molecular graph representation in which each node corresponds to a molecular orbital and edges correspond to a type of quantum correlation between molecular orbitals.

27. A molecule or class of drug-like molecules identified using a machine learning based method of modelling a thermodynamic ensemble or representation of a drug-like molecule, in which a sample of the thermodynamic ensemble or representation is synthetically generated and inputted into a machine learning system, the thermodynamic ensemble or representation being a molecular orbital representation or a quantum graph representation of the drug-like molecule; and in which the quantum graph representation is a molecular graph representation in which each node corresponds to a molecular orbital and edges correspond to a type of quantum correlation between molecular orbitals.

* * * * *